(12) United States Patent
Zhang et al.

(10) Patent No.: US 9,089,522 B2
(45) Date of Patent: Jul. 28, 2015

(54) METHOD OF REDUCING TOTAL CHOLESTEROL LEVEL BY ADMINISTERING MATRILIN-2 POLYPEPTIDE

(75) Inventors: Qing Zhang, Short Hills, NJ (US); Nicholas J. Murgolo, Millington, NJ (US); Joseph A. Hedrick, South River, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 729 days.

(21) Appl. No.: 12/993,672

(22) PCT Filed: May 21, 2009

(86) PCT No.: PCT/US2009/044883
§ 371 (c)(1),
(2), (4) Date: Mar. 7, 2011

(87) PCT Pub. No.: WO2009/143367
PCT Pub. Date: Nov. 26, 2009

(65) Prior Publication Data
US 2011/0150875 A1  Jun. 23, 2011

Related U.S. Application Data

(60) Provisional application No. 61/055,266, filed on May 22, 2008.

(51) Int. Cl.
| | |
|---|---|
| *A61K 38/17* | (2006.01) |
| *A61K 47/48* | (2006.01) |
| *A61K 31/366* | (2006.01) |
| *A61K 31/397* | (2006.01) |
| *A61K 38/39* | (2006.01) |
| *A61K 45/06* | (2006.01) |
| *C07K 14/78* | (2006.01) |
| *G01N 33/573* | (2006.01) |

(52) U.S. Cl.
CPC ............ *A61K 38/1709* (2013.01); *A61K 31/366* (2013.01); *A61K 31/397* (2013.01); *A61K 38/39* (2013.01); *A61K 45/06* (2013.01); *C07K 14/78* (2013.01); *G01N 33/573* (2013.01); *G01N 2333/96433* (2013.01)

(58) Field of Classification Search
CPC ......................... A61K 38/1709; A61K 38/39
USPC .................................................. 514/1.1, 7.4
See application file for complete search history.

(56) References Cited

FOREIGN PATENT DOCUMENTS

| WO | WO03/062469 | 7/2003 |
|---|---|---|
| WO | WO 2005070965 A2 * | 8/2005 |
| WO | WO2006/128179 | 11/2006 |
| WO | WO2008/043753 | 4/2008 |
| WO | WO2008/057459 | 5/2008 |
| WO | WO2009/055783 | 4/2009 |
| WO | WO 2009055783 A2 * | 4/2009 |

OTHER PUBLICATIONS

Bowie et al. Deciphering the message in protein sequences:tolerance to amino acid substitutions. Science, 247:1306-1310, 1990.*
Whisstock et al. Prediction of protein function from protein sequence and structure.Quarterly Reviews in Biophysics. 36(3):307-340, 2003.*
Poirier et al. The proprotein convertase PCSK9 induces the degradation of low density lipoprotein receptor (LDLR) and its closet family members VLDLR and ApoER2. Journal of Biological Chemistry. 283(4), Nov. 26, 2007.*
Lo et al. High level expresiion and secretion of Fc-X fusion proteins in mammalian cells. Protein Engineering. 11(6):495-500, 1998.*
Genbank accession No. NP_002371.3 (IDS Oct. 3, 2012, Reference AG).*
Kwon et al. Molecular basis for LDL receptor recognition by PCSK9. PNAS. 105(6):1820-185, published online Feb. 4, 2008.*
Rader et al. Monogenic hypercholesterolemia: new insights in pathogenesis and treatment. Journal of Clinical Investigation. 111(12):1795-1803, 2003.*
Grigore et al. Combination therapy in cholesterol reduction: focus in ezetimibe and statins. Vascular Health and Risk Management. 4(2):267-278, May 5, 2008.*
Sheppherd. Prevention of coronary heart disease with prevastatin in men with hypercholesterolemia. New England Journal of Medicine. 333(2):1301-1307.*
Nissen et al. Effect of very high-intensity statin therapy on regression of coronary atherosclerosis. JAMA. 295(13):1556-1565, 2006.*
Wagner et al. The matrilins—adaptoer proteins in extracellular matrix. FEBS Letters. 579:3323-3329, 2005.*
Rader et al. Monogenic hypercholesterolemia: new insights in pathogenesis and treatment. Journal of Clinical Investigation. 111 (12):1795-1803, 2003.*
Muratoglu et al. Primary structure of human matrilin-2, chromosome location of the MATN2 gene and conservation of an AT-AC intron in matrilin genes. Cytogenes and Cell Genetics. 2000; 90(3-4): 323-327.*
Yoon et al. Comparison of effects of morning versus evening administration of ezetimibe/simvastatin on serum cholesterol in patients with primary hypercholesterolemia. Annals of Pharmacotherapy. 2011; 45 (7-8): 841-849).*
Stroes, E. et al., Anti-PCSK9 antibody effectively lowers cholesterol in patients with statin intolerance: the GAUSS-2 randomized, placebo-controlled phase 3 clinical trial of evolocumab, J. Am. Coll. Cardiol, Jun. 17, 2014;63(23):2541-8.
Bottomley et al. (2009) *J Biol Chem*. 284(2):1313-23 "Structural and biochemical characterization of the wild type PCSK9-EGF(AB) complex and natural familial hypercholesterolemia mutants".
Kurniawan et al. (2001) *J Mol Biol*. 311(2):341-56 "NMR structure and backbone dynamics of a concatemer of epidermal growth factor homology modules of the human low-density lipoprotein receptor".
Kwon et al. (2008) *Proc Nati Acad Sci U S A*. 105(6):1820-5 "Molecular basis for LDL receptor recognition by PCSK9".

(Continued)

*Primary Examiner* — Prema Mertz
(74) *Attorney, Agent, or Firm* — Immac J. Thampoe; Li Su

(57) ABSTRACT

The present invention provides, in part, methods and compositions for treating lipid disorders comprising administering a polypeptide that inhibits PCSK9. A novel method for identifying polypeptides that interact with PCSK9 is also provided.

18 Claims, 2 Drawing Sheets

(56) References Cited

OTHER PUBLICATIONS

Poirier et al. (2008) *J. Biol. Chem.* 283(4):2363-2372 "The Proprotein Convertase PCSK9 Induces the Degradation of Low Density Lipoprotein Receptor (LDLR) and Its Closest Family Members VLDLR and ApoER2".

Schmidt et al. (2008) *DNA Cell Biol.* 27(4):183-9 "A novel splicing variant of proprotein convertase subtilisin/kexin type 9".

Shan et al., (2008) *Biochemical and Biophysical Research Communications* 375(1):69-73 "PCSK9 binds to multiple receptors and can be functionally inhibited by an EGF-A peptide".

Wagener et al., (2005) *FEBS Letters* 579(15):3323-3329 "The matrilins—adaptor proteins in the extracellular matrix".

Wouters et al., (2005) *Protein Science* 14(4):1091-1103 "Evolution of distinct EGF domains with specific functions".

Zhang et al. (2007) *J Biol Chem.* 282(25):18602-12 "Binding of proprotein convertase subtilisin/kexin type 9 to epidermal growth factor-like repeat A of low density lipoprotein receptor decreases receptor recycling and increases degradation".

* cited by examiner

SEQUENCE LISTING

```
<160> NUMBER OF SEQ ID NOS: 46

<210> SEQ ID NO 1
<211> LENGTH: 23
<212> TYPE: PRT
<213> ORGANISM: Homo sapiens

<400> SEQUENCE: 1

Asn Tyr Cys Ala Leu Asn Lys Pro Gly Cys Glu His Glu Cys Val Asn
1               5                   10                  15

Met Glu Glu Ser Tyr Tyr Cys
            20

<210> SEQ ID NO 2
<211> LENGTH: 956
<212> TYPE: PRT
<213> ORGANISM: Homo sapiens

<400> SEQUENCE: 2

Met Glu Lys Met Leu Ala Gly Cys Phe Leu Leu Ile Leu Gly Gln Ile
1               5                   10                  15

Val Leu Leu Pro Ala Glu Ala Arg Glu Arg Ser Arg Gly Arg Ser Ile
```

-continued

```
                20                  25                  30
Ser Arg Gly Arg His Ala Arg Thr His Pro Gln Thr Ala Leu Leu Glu
            35                  40                  45
Ser Ser Cys Glu Asn Lys Arg Ala Asp Leu Val Phe Ile Ile Asp Ser
 50                  55                  60
Ser Arg Ser Val Asn Thr His Asp Tyr Ala Lys Val Lys Glu Phe Ile
 65                  70                  75                  80
Val Asp Ile Leu Gln Phe Leu Asp Ile Gly Pro Asp Val Thr Arg Val
                85                  90                  95
Gly Leu Leu Gln Tyr Gly Ser Thr Val Lys Asn Glu Phe Ser Leu Lys
            100                 105                 110
Thr Phe Lys Arg Lys Ser Glu Val Glu Arg Ala Val Lys Arg Met Arg
            115                 120                 125
His Leu Ser Thr Gly Thr Met Thr Gly Leu Ala Ile Gln Tyr Ala Leu
            130                 135                 140
Asn Ile Ala Phe Ser Glu Ala Glu Gly Ala Arg Pro Leu Arg Glu Asn
145                 150                 155                 160
Val Pro Arg Val Ile Met Ile Val Thr Asp Gly Arg Pro Gln Asp Ser
                165                 170                 175
Val Ala Glu Val Ala Ala Lys Ala Arg Asp Thr Gly Ile Leu Ile Phe
            180                 185                 190
Ala Ile Gly Val Gly Gln Val Asp Phe Asn Thr Leu Lys Ser Ile Gly
            195                 200                 205
Ser Glu Pro His Glu Asp His Val Phe Leu Val Ala Asn Phe Ser Gln
            210                 215                 220
Ile Glu Thr Leu Thr Ser Val Phe Gln Lys Lys Leu Cys Thr Ala His
225                 230                 235                 240
Met Cys Ser Thr Leu Glu His Asn Cys Ala His Phe Cys Ile Asn Ile
                245                 250                 255
Pro Gly Ser Tyr Val Cys Arg Cys Lys Gln Gly Tyr Ile Leu Asn Ser
            260                 265                 270
Asp Gln Thr Thr Cys Arg Ile Gln Asp Leu Cys Ala Met Glu Asp His
            275                 280                 285
Asn Cys Glu Gln Leu Cys Val Asn Val Pro Gly Ser Phe Val Cys Gln
            290                 295                 300
Cys Tyr Ser Gly Tyr Ala Leu Ala Glu Asp Gly Lys Arg Cys Val Ala
305                 310                 315                 320
Val Asp Tyr Cys Ala Ser Glu Asn His Gly Cys Glu His Glu Cys Val
                325                 330                 335
Asn Ala Asp Gly Ser Tyr Leu Cys Gln Cys His Glu Gly Phe Ala Leu
            340                 345                 350
Asn Pro Asp Lys Lys Thr Cys Thr Lys Ile Asp Tyr Cys Ala Ser Ser
            355                 360                 365
Asn His Gly Cys Gln His Glu Cys Val Asn Thr Asp Asp Ser Tyr Ser
            370                 375                 380
Cys His Cys Leu Lys Gly Phe Thr Leu Asn Pro Asp Lys Lys Thr Cys
385                 390                 395                 400
Arg Arg Ile Asn Tyr Cys Ala Leu Asn Lys Pro Gly Cys Glu His Glu
                405                 410                 415
Cys Val Asn Met Glu Glu Ser Tyr Tyr Cys Arg Cys His Arg Gly Tyr
            420                 425                 430
Thr Leu Asp Pro Asn Gly Lys Thr Cys Ser Arg Val Asp His Cys Ala
            435                 440                 445
```

```
Gln Gln Asp His Gly Cys Glu Gln Leu Cys Leu Asn Thr Glu Asp Ser
            450                 455                 460

Phe Val Cys Gln Cys Ser Glu Gly Phe Leu Ile Asn Glu Asp Leu Lys
465                 470                 475                 480

Thr Cys Ser Arg Val Asp Tyr Cys Leu Leu Ser Asp His Gly Cys Glu
                485                 490                 495

Tyr Ser Cys Val Asn Met Asp Arg Ser Phe Ala Cys Gln Cys Pro Glu
            500                 505                 510

Gly His Val Leu Arg Ser Asp Gly Lys Thr Cys Ala Lys Leu Asp Ser
        515                 520                 525

Cys Ala Leu Gly Asp His Gly Cys Glu His Ser Cys Val Ser Ser Glu
530                 535                 540

Asp Ser Phe Val Cys Gln Cys Phe Glu Gly Tyr Ile Leu Arg Glu Asp
545                 550                 555                 560

Gly Lys Thr Cys Arg Arg Lys Asp Val Cys Gln Ala Ile Asp His Gly
                565                 570                 575

Cys Glu His Ile Cys Val Asn Ser Asp Asp Ser Tyr Thr Cys Glu Cys
            580                 585                 590

Leu Glu Gly Phe Arg Leu Ala Glu Asp Gly Lys Arg Cys Arg Arg Lys
        595                 600                 605

Asp Val Cys Lys Ser Thr His His Gly Cys Glu His Ile Cys Val Asn
610                 615                 620

Asn Gly Asn Ser Tyr Ile Cys Lys Cys Ser Glu Gly Phe Val Leu Ala
625                 630                 635                 640

Glu Asp Gly Arg Arg Cys Lys Lys Cys Thr Glu Gly Pro Ile Asp Leu
                645                 650                 655

Val Phe Val Ile Asp Gly Ser Lys Ser Leu Gly Glu Glu Asn Phe Glu
            660                 665                 670

Val Val Lys Gln Phe Val Thr Gly Ile Ile Asp Ser Leu Thr Ile Ser
        675                 680                 685

Pro Lys Ala Ala Arg Val Gly Leu Leu Gln Tyr Ser Thr Gln Val His
690                 695                 700

Thr Glu Phe Thr Leu Arg Asn Phe Asn Ser Ala Lys Asp Met Lys Lys
705                 710                 715                 720

Ala Val Ala His Met Lys Tyr Met Gly Lys Gly Ser Met Thr Gly Leu
                725                 730                 735

Ala Leu Lys His Met Phe Glu Arg Ser Phe Thr Gln Gly Glu Gly Ala
            740                 745                 750

Arg Pro Leu Ser Thr Arg Val Pro Arg Ala Ala Ile Val Phe Thr Asp
        755                 760                 765

Gly Arg Ala Gln Asp Asp Val Ser Glu Trp Ala Ser Lys Ala Lys Ala
770                 775                 780

Asn Gly Ile Thr Met Tyr Ala Val Gly Val Gly Lys Ala Ile Glu Glu
785                 790                 795                 800

Glu Leu Gln Glu Ile Ala Ser Glu Pro Thr Asn Lys His Leu Phe Tyr
                805                 810                 815

Ala Glu Asp Phe Ser Thr Met Asp Glu Ile Ser Glu Lys Leu Lys Lys
            820                 825                 830

Gly Ile Cys Glu Ala Leu Glu Asp Ser Asp Gly Arg Gln Asp Ser Pro
        835                 840                 845

Ala Gly Glu Leu Pro Lys Thr Val Gln Gln Pro Thr Glu Ser Glu Pro
850                 855                 860
```

```
Val Thr Ile Asn Ile Gln Asp Leu Leu Ser Cys Ser Asn Phe Ala Val
865                 870                 875                 880

Gln His Arg Tyr Leu Phe Glu Glu Asp Asn Leu Leu Arg Ser Thr Gln
            885                 890                 895

Lys Leu Ser His Ser Thr Lys Pro Ser Gly Pro Leu Glu Glu Lys
        900                 905                 910

His Asp Gln Cys Lys Cys Glu Asn Leu Ile Met Phe Gln Asn Leu Ala
            915                 920                 925

Asn Glu Glu Val Arg Lys Leu Thr Gln Arg Leu Glu Met Thr Gln
        930                 935                 940

Arg Met Glu Ala Leu Glu Asn Arg Leu Arg Tyr Arg
945                 950                 955

<210> SEQ ID NO 3
<211> LENGTH: 937
<212> TYPE: PRT
<213> ORGANISM: Mus sp.

<400> SEQUENCE: 3

Met Glu Lys Met Leu Val Gly Cys Leu Leu Met Leu Gly Gln Leu Phe
1               5                   10                  15

Leu Val Leu Pro Val Asp Gly Arg Glu Arg Pro Gln Ala Arg Phe Pro
            20                  25                  30

Ser Arg Gly Arg His Val Arg Met Tyr Pro Gln Thr Ala Leu Leu Glu
        35                  40                  45

Ser Ser Cys Glu Asn Lys Arg Ala Asp Leu Val Phe Ile Ile Asp Ser
    50                  55                  60

Ser Arg Ser Val Asn Thr Tyr Asp Tyr Ala Lys Val Lys Glu Phe Ile
65                  70                  75                  80

Leu Asp Ile Leu Gln Phe Leu Asp Ile Gly Pro Asp Val Thr Arg Val
                85                  90                  95

Gly Leu Leu Gln Tyr Gly Ser Thr Val Lys Asn Glu Phe Ser Leu Lys
            100                 105                 110

Thr Phe Lys Arg Lys Ser Glu Val Glu Arg Ala Val Lys Arg Met Arg
        115                 120                 125

His Leu Ser Thr Gly Thr Met Thr Gly Leu Ala Ile Gln Tyr Ala Leu
    130                 135                 140

Asn Ile Ala Phe Ser Glu Ala Glu Gly Ala Arg Pro Leu Arg Glu Asn
145                 150                 155                 160

Val Pro Arg Ile Ile Met Ile Val Thr Asp Gly Arg Pro Gln Asp Ser
                165                 170                 175

Val Ala Glu Val Ala Ala Lys Ala Arg Asn Thr Gly Ile Leu Ile Phe
            180                 185                 190

Ala Ile Gly Val Gly Gln Val Asp Leu Asn Thr Leu Lys Ala Ile Gly
        195                 200                 205

Ser Glu Pro His Lys Asp His Val Phe Leu Val Ala Asn Phe Ser Gln
    210                 215                 220

Ile Glu Ser Leu Thr Ser Val Phe Gln Asn Lys Leu Cys Thr Val His
225                 230                 235                 240

Met Cys Ser Val Leu Glu His Asn Cys Ala His Phe Cys Leu Asn Thr
                245                 250                 255

Pro Gly Ser Tyr Ile Cys Lys Cys Lys Gln Gly Tyr Ile Leu Ser Thr
            260                 265                 270

Asp Gln Lys Thr Cys Arg Ile Gln Asp Leu Cys Ala Thr Glu Asp His
        275                 280                 285
```

```
Gly Cys Glu Gln Leu Cys Val Asn Met Leu Gly Ser Phe Val Cys Gln
290                 295                 300
Cys Tyr Ser Gly Tyr Thr Leu Ala Glu Asp Gly Lys Arg Cys Thr Ala
305                 310                 315                 320
Val Asp Tyr Cys Ala Ser Glu Asn His Gly Cys Glu His Glu Cys Val
                325                 330                 335
Asn Ala Glu Ser Ser Tyr Leu Cys Arg Cys His Glu Gly Phe Ala Leu
                340                 345                 350
Asn Ser Asp Lys Lys Thr Cys Ser Lys Ile Asp Tyr Cys Ala Ser Ser
        355                 360                 365
Asn His Gly Cys Gln His Glu Cys Val Asn Ala Gln Thr Ser Ala Leu
370                 375                 380
Cys Arg Cys Leu Lys Gly Phe Met Leu Asn Pro Asp Arg Lys Thr Cys
385                 390                 395                 400
Arg Arg Ile Asn Tyr Cys Ala Leu Asn Lys Pro Gly Cys Glu His Glu
                405                 410                 415
Cys Val Asn Thr Glu Glu Gly His Tyr Cys Arg Cys Arg Gln Gly Tyr
            420                 425                 430
Asn Leu Asp Pro Asn Gly Lys Thr Cys Ser Arg Val Asp His Cys Ala
        435                 440                 445
Gln Gln Asp His Gly Cys Glu Gln Leu Cys Leu Asn Thr Glu Glu Ser
450                 455                 460
Phe Val Cys Gln Cys Ser Glu Gly Phe Leu Ile Asn Asp Asp Leu Lys
465                 470                 475                 480
Thr Cys Ser Arg Ala Asp Tyr Cys Leu Leu Ser Asn His Gly Cys Glu
                485                 490                 495
Tyr Ser Cys Val Asn Thr Asp Lys Ser Phe Ala Cys Gln Cys Pro Glu
            500                 505                 510
Gly His Val Leu Arg Ser Asp Gly Lys Thr Cys Ala Lys Leu Asp Ser
        515                 520                 525
Cys Ala Leu Gly Asp His Gly Cys Glu His Ser Cys Val Ser Ser Glu
530                 535                 540
Asp Ser Phe Val Cys Gln Cys Phe Glu Gly Tyr Ile Leu Arg Asp Asp
545                 550                 555                 560
Gly Lys Thr Cys Arg Arg Lys Asp Val Cys Gln Asp Val Asn His Gly
                565                 570                 575
Cys Glu His Leu Cys Val Asn Ser Gly Glu Ser Tyr Val Cys Lys Cys
            580                 585                 590
Leu Glu Gly Phe Arg Leu Ala Glu Asp Gly Lys Arg Cys Arg Arg Lys
        595                 600                 605
Asn Val Cys Lys Ser Thr Gln His Gly Cys Glu His Met Cys Val Asn
610                 615                 620
Asn Gly Asn Ser Tyr Leu Cys Arg Cys Ser Glu Gly Phe Val Leu Ala
625                 630                 635                 640
Glu Asp Gly Lys His Cys Lys Arg Cys Thr Glu Gly Pro Ile Asp Leu
                645                 650                 655
Val Phe Val Ile Asp Gly Ser Lys Ser Leu Gly Glu Glu Asn Phe Glu
            660                 665                 670
Thr Val Lys His Phe Val Thr Gly Ile Ile Asp Ser Leu Ala Val Ser
        675                 680                 685
Pro Lys Ala Ala Arg Val Gly Leu Leu Gln Tyr Ser Thr Gln Val Arg
690                 695                 700
```

```
Thr Glu Phe Thr Leu Arg Gly Phe Ser Ser Ala Lys Glu Met Lys Lys
705                 710                 715                 720

Ala Val Thr His Met Lys Tyr Met Gly Lys Gly Ser Met Thr Gly Leu
            725                 730                 735

Ala Leu Lys His Met Phe Glu Arg Ser Phe Thr Gln Val Glu Gly Ala
            740                 745                 750

Arg Pro Pro Ser Thr Gln Val Pro Arg Val Ala Ile Val Phe Thr Asp
            755                 760                 765

Gly Arg Ala Gln Asp Asp Val Ser Glu Trp Ala Ser Lys Ala Lys Ala
            770                 775                 780

Asn Gly Ile Thr Met Tyr Ala Val Gly Val Gly Lys Ala Ile Glu Glu
785                 790                 795                 800

Glu Leu Gln Glu Ile Ala Ser Glu Pro Ile Asp Lys His Leu Phe Tyr
            805                 810                 815

Ala Glu Asp Phe Ser Thr Met Gly Glu Ile Ser Glu Lys Leu Lys Glu
            820                 825                 830

Gly Ile Cys Glu Ala Leu Glu Asp Ser Gly Gly Arg Gln Asp Ser Ala
            835                 840                 845

Ala Trp Asp Leu Pro Gln Gln Ala His Gln Pro Thr Val Gln His Arg
            850                 855                 860

Phe Leu Phe Glu Glu Asp Asn Leu Ser Arg Ser Thr Gln Lys Leu Phe
865                 870                 875                 880

His Ser Thr Lys Ser Ser Gly Asn Pro Leu Glu Ser Gln Asp Gln
            885                 890                 895

Cys Lys Cys Glu Asn Leu Ile Leu Phe Gln Asn Val Ala Asn Glu Glu
            900                 905                 910

Val Arg Lys Leu Thr Gln Arg Leu Glu Glu Met Thr Gln Arg Met Glu
            915                 920                 925

Ala Leu Glu Asn Arg Leu Lys Tyr Arg
            930                 935

<210> SEQ ID NO 4
<211> LENGTH: 23
<212> TYPE: PRT
<213> ORGANISM: Mus sp.

<400> SEQUENCE: 4

Asn Tyr Cys Ala Leu Asn Lys Pro Gly Cys Glu His Glu Cys Val Asn
1               5                   10                  15

Thr Glu Glu Gly His Tyr Cys
            20

<210> SEQ ID NO 5
<211> LENGTH: 227
<212> TYPE: PRT
<213> ORGANISM: Mus sp.

<400> SEQUENCE: 5

Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
            20                  25                  30

Ile Thr Leu Thr Pro Lys Val Thr Cys Val Val Val Asp Ile Ser Lys
            35                  40                  45

Asp Asp Pro Glu Val Gln Phe Ser Trp Phe Val Asp Asp Val Glu Val
        50                  55                  60
```

```
His Thr Ala Gln Thr Lys Pro Arg Glu Glu Gln Phe Asn Ser Thr Phe
 65                  70                  75                  80

Arg Ser Val Ser Glu Leu Pro Ile Met His Gln Asp Trp Leu Asn Gly
                 85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
        115                 120                 125

Tyr Thr Ile Pro Pro Lys Glu Gln Met Ala Lys Asp Lys Val Ser
    130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
    210                 215                 220

Pro Gly Lys
225

<210> SEQ ID NO 6
<211> LENGTH: 229
<212> TYPE: PRT
<213> ORGANISM: Homo sapiens

<400> SEQUENCE: 6

Glu Ser Lys Tyr Gly Pro Pro Cys Pro Ser Cys Pro Ala Pro Glu Phe
  1               5                  10                  15

Leu Gly Gly Pro Ser Val Phe Leu Phe Pro Pro Lys Pro Lys Asp Thr
                 20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
     50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205
```

-continued

Val Met His Glu Ala Leu His Asn His Tyr Thr Gln Lys Ser Leu Ser
    210                 215                 220

Leu Ser Leu Gly Lys
225

<210> SEQ ID NO 7
<211> LENGTH: 229
<212> TYPE: PRT
<213> ORGANISM: Homo sapiens

<400> SEQUENCE: 7

Glu Ser Lys Tyr Gly Pro Pro Ser Pro Ser Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 8
<211> LENGTH: 233
<212> TYPE: PRT
<213> ORGANISM: Homo sapiens

<400> SEQUENCE: 8

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
        50                  55                  60

```
Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 9
<211> LENGTH: 233
<212> TYPE: PRT
<213> ORGANISM: Homo sapiens

<400> SEQUENCE: 9

Val Glu Pro Lys Ser Ser Asp Lys Thr His Thr Ser Pro Pro Ser Pro
  1               5                  10                  15

Ala Pro Glu Leu Leu Gly Gly Pro Ser Val Phe Leu Phe Pro Pro Lys
                 20                  25                  30

Pro Lys Asp Thr Leu Met Ile Ser Arg Thr Pro Glu Val Thr Cys Val
             35                  40                  45

Val Val Asp Val Ser His Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
```

```
                195                 200                 205
Phe Ser Cys Ser Val Met His Glu Ala Leu His Asn His Tyr Thr Gln
    210                 215                 220
Lys Ser Leu Ser Leu Ser Pro Gly Lys
225                 230

<210> SEQ ID NO 10
<211> LENGTH: 692
<212> TYPE: PRT
<213> ORGANISM: Homo sapiens

<400> SEQUENCE: 10

Met Gly Thr Val Ser Ser Arg Arg Ser Trp Trp Pro Leu Pro Leu Leu
1               5                   10                  15
Leu Leu Leu Leu Leu Leu Leu Gly Pro Ala Gly Ala Arg Ala Gln Glu
                20                  25                  30
Asp Glu Asp Gly Asp Tyr Glu Glu Leu Val Leu Ala Leu Arg Ser Glu
            35                  40                  45
Glu Asp Gly Leu Ala Glu Ala Pro Glu His Gly Thr Thr Ala Thr Phe
        50                  55                  60
His Arg Cys Ala Lys Asp Pro Trp Arg Leu Pro Gly Thr Tyr Val Val
65                  70                  75                  80
Val Leu Lys Glu Glu Thr His Leu Ser Gln Ser Glu Arg Thr Ala Arg
                85                  90                  95
Arg Leu Gln Ala Gln Ala Ala Arg Arg Gly Tyr Leu Thr Lys Ile Leu
            100                 105                 110
His Val Phe His Gly Leu Leu Pro Gly Phe Leu Val Lys Met Ser Gly
        115                 120                 125
Asp Leu Leu Glu Leu Ala Leu Lys Leu Pro His Val Asp Tyr Ile Glu
130                 135                 140
Glu Asp Ser Ser Val Phe Ala Gln Ser Ile Pro Trp Asn Leu Glu Arg
145                 150                 155                 160
Ile Thr Pro Pro Arg Tyr Arg Ala Asp Glu Tyr Gln Pro Pro Asp Gly
                165                 170                 175
Gly Ser Leu Val Glu Val Tyr Leu Leu Asp Thr Ser Ile Gln Ser Asp
            180                 185                 190
His Arg Glu Ile Glu Gly Arg Val Met Val Thr Asp Phe Glu Asn Val
        195                 200                 205
Pro Glu Glu Asp Gly Thr Arg Phe His Arg Gln Ala Ser Lys Cys Asp
    210                 215                 220
Ser His Gly Thr His Leu Ala Gly Val Val Ser Gly Arg Asp Ala Gly
225                 230                 235                 240
Val Ala Lys Gly Ala Ser Met Arg Ser Leu Arg Val Leu Asn Cys Gln
                245                 250                 255
Gly Lys Gly Thr Val Ser Gly Thr Leu Ile Gly Leu Glu Phe Ile Arg
            260                 265                 270
Lys Ser Gln Leu Val Gln Pro Val Gly Pro Leu Val Val Leu Leu Pro
        275                 280                 285
Leu Ala Gly Gly Tyr Ser Arg Val Leu Asn Ala Ala Cys Gln Arg Leu
290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
```

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
        370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
        450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
        690

<210> SEQ ID NO 11
<211> LENGTH: 677
<212> TYPE: PRT
<213> ORGANISM: Pan troglodytes

<400> SEQUENCE: 11

Met Gly Thr Val Ser Ser Arg Arg Ser Trp Trp Pro Leu Pro Leu Leu
1               5                   10                  15

```
Leu Leu Leu Leu Leu Leu Leu Gly Pro Ala Gly Ala Arg Ala Gln Glu
                20                  25                  30

Asp Glu Asp Gly Leu Ala Glu Ala Pro Glu His Gly Thr Thr Ala Thr
    35                  40                  45

Phe His Arg Cys Ala Lys Asp Pro Trp Arg Leu Pro Gly Thr Tyr Val
50                  55                  60

Val Val Leu Lys Glu Glu Thr His Leu Ser Gln Ser Glu Arg Thr Ala
65                  70                  75                  80

Arg Arg Leu Gln Ala Gln Ala Ala Arg Gly Tyr Leu Thr Lys Ile
                85                  90                  95

Leu His Val Phe His Gly Leu Leu Pro Gly Phe Leu Val Lys Met Ser
                100                 105                 110

Gly Asp Leu Leu Glu Leu Ala Leu Lys Leu Pro His Val Asp Tyr Ile
            115                 120                 125

Glu Glu Asp Ser Ser Val Phe Ala Gln Ser Ile Pro Trp Asn Leu Glu
        130                 135                 140

Arg Ile Thr Pro Pro Arg Tyr Arg Ala Asp Glu Tyr Gln Pro Pro Asp
145                 150                 155                 160

Gly Gly Ser Leu Val Glu Val Tyr Leu Leu Asp Thr Ser Ile Gln Ser
                165                 170                 175

Asp His Arg Glu Ile Glu Gly Arg Val Met Val Thr Asp Phe Glu Asn
                180                 185                 190

Val Pro Glu Glu Asp Gly Thr Arg Phe His Arg Gln Ala Ser Lys Cys
            195                 200                 205

Asp Ser His Gly Thr His Leu Ala Gly Val Val Ser Gly Arg Asp Ala
        210                 215                 220

Gly Val Ala Lys Gly Ala Ser Met Arg Ser Leu Arg Val Leu Asn Cys
225                 230                 235                 240

Gln Gly Lys Gly Thr Val Ser Gly Thr Leu Ile Gly Leu Glu Phe Ile
                245                 250                 255

Arg Lys Ser Gln Leu Val Gln Pro Val Gly Pro Leu Val Val Leu Leu
                260                 265                 270

Pro Leu Ala Gly Gly Tyr Ser Arg Val Leu Asn Ala Ala Cys Gln Arg
            275                 280                 285

Leu Ala Arg Ala Gly Val Val Leu Val Thr Ala Ala Gly Asn Phe Arg
        290                 295                 300

Asp Asp Ala Cys Leu Tyr Ser Pro Ala Ser Ala Pro Glu Val Ile Thr
305                 310                 315                 320

Val Gly Ala Thr Asn Ala Gln Asp Gln Pro Val Thr Leu Gly Thr Leu
                325                 330                 335

Gly Thr Asn Phe Gly Arg Cys Val Asp Leu Phe Ala Pro Gly Glu Asp
            340                 345                 350

Ile Ile Gly Ala Ser Ser Asp Cys Ser Thr Cys Phe Val Ser Gln Ser
        355                 360                 365

Gly Thr Ser Gln Ala Ala Ala His Val Ala Gly Ile Ala Ala Met Met
    370                 375                 380

Leu Ser Ala Glu Pro Glu Leu Thr Leu Ala Glu Leu Arg Gln Arg Leu
385                 390                 395                 400

Ile His Phe Ser Ala Lys Asp Val Ile Asn Glu Ala Trp Phe Pro Glu
                405                 410                 415

Asp Gln Arg Val Leu Thr Pro Asn Leu Val Ala Ala Leu Pro Pro Ser
            420                 425                 430
```

```
Thr His Gly Ala Gly Trp Gln Leu Phe Cys Arg Thr Val Trp Ser Ala
            435                 440                 445

His Ser Gly Pro Thr Arg Met Ala Thr Ala Val Ala Arg Cys Ala Pro
450                 455                 460

Asp Glu Glu Leu Leu Ser Cys Ser Ser Phe Ser Arg Ser Gly Lys Arg
465                 470                 475                 480

Arg Gly Glu Arg Met Glu Ala Gln Gly Gly Lys Leu Val Cys Arg Ala
                485                 490                 495

His Asn Ala Phe Gly Gly Glu Gly Val Tyr Ala Ile Ala Arg Cys Cys
            500                 505                 510

Leu Leu Pro Gln Ala Asn Cys Ser Ile His Thr Ala Pro Pro Ala Glu
        515                 520                 525

Ala Gly Met Gly Thr Arg Val His Cys His Gln Gln Gly His Val Leu
    530                 535                 540

Thr Gly Cys Ser Ser His Trp Glu Val Glu Asp Leu Gly Thr His Lys
545                 550                 555                 560

Pro Pro Met Leu Arg Pro Arg Gly Gln Pro Asn Gln Cys Val Gly His
                565                 570                 575

Arg Glu Ala Ser Ile His Ala Ser Cys Cys Arg Ala Pro Gly Leu Glu
            580                 585                 590

Cys Lys Val Lys Glu His Gly Ile Pro Ala Pro Gln Glu Gln Val Thr
        595                 600                 605

Val Ala Cys Glu Glu Gly Trp Thr Leu Thr Gly Cys Ser Ala Leu Pro
    610                 615                 620

Gly Thr Ser His Val Leu Gly Ala Tyr Ala Val Asp Asn Thr Cys Val
625                 630                 635                 640

Val Arg Ser Arg Asp Val Ser Thr Ala Gly Ser Thr Ser Glu Glu Ala
                645                 650                 655

Val Ala Ala Val Ala Ile Cys Cys Arg Ser Arg His Leu Ala Gln Ala
            660                 665                 670

Ser Gln Glu Leu Gln
        675

<210> SEQ ID NO 12
<211> LENGTH: 694
<212> TYPE: PRT
<213> ORGANISM: Mus musculus

<400> SEQUENCE: 12

Met Gly Thr His Cys Ser Ala Trp Leu Arg Trp Pro Leu Leu Pro Leu
1               5                   10                  15

Leu Pro Pro Leu Leu Leu Leu Leu Leu Leu Cys Pro Thr Gly Ala
                20                  25                  30

Gly Ala Gln Asp Glu Asp Gly Asp Tyr Glu Glu Leu Met Leu Ala Leu
            35                  40                  45

Pro Ser Gln Glu Asp Gly Leu Ala Asp Glu Ala Ala His Val Ala Thr
        50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Arg Gly Tyr Val Ile
            100                 105                 110

Lys Val Leu His Ile Phe Tyr Asp Leu Phe Pro Gly Phe Leu Val Lys
        115                 120                 125
```

```
Met Ser Ser Asp Leu Leu Gly Leu Ala Leu Lys Leu Pro His Val Glu
    130                 135                 140

Tyr Ile Glu Glu Asp Ser Phe Val Phe Ala Gln Ser Ile Pro Trp Asn
145                 150                 155                 160

Leu Glu Arg Ile Ile Pro Ala Trp His Gln Thr Glu Glu Asp Arg Ser
                165                 170                 175

Pro Asp Gly Ser Ser Gln Val Glu Val Tyr Leu Leu Asp Thr Ser Ile
                180                 185                 190

Gln Gly Ala His Arg Glu Ile Glu Gly Arg Val Thr Ile Thr Asp Phe
            195                 200                 205

Asn Ser Val Pro Glu Glu Asp Gly Thr Arg Phe His Arg Gln Ala Ser
210                 215                 220

Lys Cys Asp Ser His Gly Thr His Leu Ala Gly Val Val Ser Gly Arg
225                 230                 235                 240

Asp Ala Gly Val Ala Lys Gly Thr Ser Leu His Ser Leu Arg Val Leu
                245                 250                 255

Asn Cys Gln Gly Lys Gly Thr Val Ser Gly Thr Leu Ile Gly Leu Glu
                260                 265                 270

Phe Ile Arg Lys Ser Gln Leu Ile Gln Pro Ser Gly Pro Leu Val Val
            275                 280                 285

Leu Leu Pro Leu Ala Gly Gly Tyr Ser Arg Ile Leu Asn Ala Ala Cys
290                 295                 300

Arg His Leu Ala Arg Thr Gly Val Val Leu Val Ala Ala Ala Gly Asn
305                 310                 315                 320

Phe Arg Asp Asp Ala Cys Leu Tyr Ser Pro Ala Ser Ala Pro Glu Val
                325                 330                 335

Ile Thr Val Gly Ala Thr Asn Ala Gln Asp Gln Pro Val Thr Leu Gly
                340                 345                 350

Thr Leu Gly Thr Asn Phe Gly Arg Cys Val Asp Leu Phe Ala Pro Gly
            355                 360                 365

Lys Asp Ile Ile Gly Ala Ser Ser Asp Cys Ser Thr Cys Phe Met Ser
370                 375                 380

Gln Ser Gly Thr Ser Gln Ala Ala Ala His Val Ala Gly Ile Val Ala
385                 390                 395                 400

Arg Met Leu Ser Arg Glu Pro Thr Leu Thr Leu Ala Glu Leu Arg Gln
                405                 410                 415

Arg Leu Ile His Phe Ser Thr Lys Asp Val Ile Asn Met Ala Trp Phe
                420                 425                 430

Pro Glu Asp Gln Gln Val Leu Thr Pro Asn Leu Val Ala Thr Leu Pro
            435                 440                 445

Pro Ser Thr His Glu Thr Gly Gly Gln Leu Leu Cys Arg Thr Val Trp
450                 455                 460

Ser Ala His Ser Gly Pro Thr Arg Thr Ala Thr Ala Thr Ala Arg Cys
465                 470                 475                 480

Ala Pro Glu Glu Glu Leu Leu Ser Cys Ser Ser Phe Ser Arg Ser Gly
                485                 490                 495

Arg Arg Arg Gly Asp Trp Ile Glu Ala Ile Gly Gly Gln Gln Val Cys
                500                 505                 510

Lys Ala Leu Asn Ala Phe Gly Gly Glu Gly Val Tyr Ala Val Ala Arg
            515                 520                 525

Cys Cys Leu Val Pro Arg Ala Asn Cys Ser Ile His Asn Thr Pro Ala
530                 535                 540
```

```
Ala Arg Ala Gly Leu Glu Thr His Val His Cys His Gln Lys Asp His
545                 550                 555                 560

Val Leu Thr Gly Cys Ser Phe His Trp Glu Val Glu Asp Leu Ser Val
            565                 570                 575

Arg Arg Gln Pro Ala Leu Arg Ser Arg Arg Gln Pro Gly Gln Cys Val
                580                 585                 590

Gly His Gln Ala Ala Ser Val Tyr Ala Ser Cys Cys His Ala Pro Gly
            595                 600                 605

Leu Glu Cys Lys Ile Lys Glu His Gly Ile Ser Gly Pro Ser Glu Gln
        610                 615                 620

Val Thr Val Ala Cys Glu Ala Gly Trp Thr Leu Thr Gly Cys Asn Val
625                 630                 635                 640

Leu Pro Gly Ala Ser Leu Thr Leu Gly Ala Tyr Ser Val Asp Asn Leu
                645                 650                 655

Cys Val Ala Arg Val His Asp Thr Ala Arg Ala Asp Arg Thr Ser Gly
                660                 665                 670

Glu Ala Thr Val Ala Ala Ile Cys Cys Arg Ser Arg Pro Ser Ala
            675                 680                 685

Lys Ala Ser Trp Val Gln
        690

<210> SEQ ID NO 13
<211> LENGTH: 691
<212> TYPE: PRT
<213> ORGANISM: Rattus norvegicus

<400> SEQUENCE: 13

Met Gly Ile Arg Cys Ser Thr Trp Leu Arg Trp Pro Leu Ser Pro Gln
1               5                   10                  15

Leu Leu Leu Leu Leu Leu Leu Cys Pro Thr Gly Ser Arg Ala Gln Asp
            20                  25                  30

Glu Asp Gly Asp Tyr Glu Glu Leu Met Leu Ala Leu Pro Ser Gln Glu
        35                  40                  45

Asp Ser Leu Val Asp Glu Ala Ser His Val Ala Thr Ala Thr Phe Arg
50                  55                  60

Arg Cys Ser Lys Glu Ala Trp Arg Leu Pro Gly Thr Tyr Val Val Val
65                  70                  75                  80

Leu Met Glu Glu Thr Gln Arg Leu Gln Val Glu Gln Thr Ala His Arg
                85                  90                  95

Leu Gln Thr Trp Ala Ala Arg Arg Gly Tyr Val Ile Lys Val Leu His
            100                 105                 110

Val Phe Tyr Asp Leu Phe Pro Gly Phe Leu Val Lys Met Ser Ser Asp
        115                 120                 125

Leu Leu Gly Leu Ala Leu Lys Leu Pro His Val Glu Tyr Ile Glu Glu
    130                 135                 140

Asp Ser Leu Val Phe Ala Gln Ser Ile Pro Trp Asn Leu Glu Arg Ile
145                 150                 155                 160

Ile Pro Ala Trp Gln Gln Thr Glu Glu Asp Ser Ser Pro Asp Gly Ser
                165                 170                 175

Ser Gln Val Glu Val Tyr Leu Leu Asp Thr Ser Ile Gln Ser Gly His
            180                 185                 190

Arg Glu Ile Glu Gly Arg Val Thr Ile Thr Asp Phe Asn Ser Val Pro
        195                 200                 205

Glu Glu Asp Gly Thr Arg Phe His Arg Gln Ala Ser Lys Cys Asp Ser
    210                 215                 220
```

```
His Gly Thr His Leu Ala Gly Val Val Ser Gly Arg Asp Ala Gly Val
225                 230                 235                 240

Ala Lys Gly Thr Ser Leu His Ser Leu Arg Val Leu Asn Cys Gln Gly
            245                 250                 255

Lys Gly Thr Val Ser Gly Thr Leu Ile Gly Leu Glu Phe Ile Arg Lys
        260                 265                 270

Ser Gln Leu Ile Gln Pro Ser Gly Pro Leu Val Val Leu Leu Pro Leu
    275                 280                 285

Ala Gly Gly Tyr Ser Arg Ile Leu Asn Thr Ala Cys Gln Arg Leu Ala
290                 295                 300

Arg Thr Gly Val Val Leu Val Ala Ala Gly Asn Phe Arg Asp Asp
305                 310                 315                 320

Ala Cys Leu Tyr Ser Pro Ala Ser Ala Pro Glu Val Ile Thr Val Gly
            325                 330                 335

Ala Thr Asn Ala Gln Asp Gln Pro Val Thr Leu Gly Thr Leu Gly Thr
        340                 345                 350

Asn Phe Gly Arg Cys Val Asp Leu Phe Ala Pro Gly Lys Asp Ile Ile
    355                 360                 365

Gly Ala Ser Ser Asp Cys Ser Thr Cys Tyr Met Ser Gln Ser Gly Thr
370                 375                 380

Ser Gln Ala Ala Ala His Val Ala Gly Ile Val Ala Met Met Leu Asn
385                 390                 395                 400

Arg Asp Pro Ala Leu Thr Leu Ala Glu Leu Arg Gln Arg Leu Ile Leu
            405                 410                 415

Phe Ser Thr Lys Asp Val Ile Asn Met Ala Trp Phe Pro Glu Asp Gln
        420                 425                 430

Arg Val Leu Thr Pro Asn Arg Val Ala Thr Leu Pro Pro Ser Thr Gln
    435                 440                 445

Glu Thr Gly Gly Gln Leu Leu Cys Arg Thr Val Trp Ser Ala His Ser
450                 455                 460

Gly Pro Thr Arg Thr Ala Thr Ala Thr Ala Arg Cys Ala Pro Glu Glu
465                 470                 475                 480

Glu Leu Leu Ser Cys Ser Ser Phe Ser Arg Ser Gly Arg Arg Gly
            485                 490                 495

Asp Arg Ile Glu Ala Ile Gly Gly Gln Gln Val Cys Lys Ala Leu Asn
        500                 505                 510

Ala Phe Gly Gly Glu Gly Val Tyr Ala Val Ala Arg Cys Cys Leu Leu
    515                 520                 525

Pro Arg Val Asn Cys Ser Ile His Asn Thr Pro Ala Ala Arg Ala Gly
530                 535                 540

Pro Gln Thr Pro Val His Cys His Gln Lys Asp His Val Leu Thr Gly
545                 550                 555                 560

Cys Ser Phe His Trp Glu Val Glu Asn Leu Arg Ala Gln Gln Pro
            565                 570                 575

Leu Leu Arg Ser Arg His Gln Pro Gly Gln Cys Val Gly His Gln Glu
        580                 585                 590

Ala Ser Val His Ala Ser Cys Cys His Ala Pro Gly Leu Glu Cys Lys
    595                 600                 605

Ile Lys Glu His Gly Ile Ala Gly Pro Ala Glu Gln Val Thr Val Ala
610                 615                 620

Cys Glu Ala Gly Trp Thr Leu Thr Gly Cys Asn Val Leu Pro Gly Ala
625                 630                 635                 640
```

```
Ser Leu Pro Leu Gly Ala Tyr Ser Val Asp Asn Val Cys Val Ala Arg
                645                 650                 655

Ile Arg Asp Ala Gly Arg Ala Asp Arg Thr Ser Glu Glu Ala Thr Val
            660                 665                 670

Ala Ala Ala Ile Cys Cys Arg Ser Arg Pro Ser Ala Lys Ala Ser Trp
        675                 680                 685

Val His Gln
    690

<210> SEQ ID NO 14
<211> LENGTH: 17
<212> TYPE: PRT
<213> ORGANISM: Homo sapiens

<400> SEQUENCE: 14

Asn Glu Cys Leu Asp Asn Asn Gly Gly Cys Ser His Val Cys Asn Asp
1               5                   10                  15

Leu

<210> SEQ ID NO 15
<211> LENGTH: 937
<212> TYPE: PRT
<213> ORGANISM: Homo sapiens

<400> SEQUENCE: 15

Met Glu Lys Met Leu Ala Gly Cys Phe Leu Leu Ile Leu Gly Gln Ile
1               5                   10                  15

Val Leu Leu Pro Ala Glu Ala Arg Glu Arg Ser Arg Gly Arg Ser Ile
            20                  25                  30

Ser Arg Gly Arg His Ala Arg Thr His Pro Gln Thr Ala Leu Leu Glu
        35                  40                  45

Ser Ser Cys Glu Asn Lys Arg Ala Asp Leu Val Phe Ile Ile Asp Ser
    50                  55                  60

Ser Arg Ser Val Asn Thr His Asp Tyr Ala Lys Val Lys Glu Phe Ile
65                  70                  75                  80

Val Asp Ile Leu Gln Phe Leu Asp Ile Gly Pro Asp Val Thr Arg Val
                85                  90                  95

Gly Leu Leu Gln Tyr Gly Ser Thr Val Lys Asn Glu Phe Ser Leu Lys
            100                 105                 110

Thr Phe Lys Arg Lys Ser Glu Val Glu Arg Ala Val Lys Arg Met Arg
        115                 120                 125

His Leu Ser Thr Gly Thr Met Thr Gly Leu Ala Ile Gln Tyr Ala Leu
    130                 135                 140

Asn Ile Ala Phe Ser Glu Ala Glu Gly Ala Arg Pro Leu Arg Glu Asn
145                 150                 155                 160

Val Pro Arg Val Ile Met Ile Val Thr Asp Gly Arg Pro Gln Asp Ser
                165                 170                 175

Val Ala Glu Val Ala Ala Lys Ala Arg Asp Thr Gly Ile Leu Ile Phe
            180                 185                 190

Ala Ile Gly Val Gly Gln Val Asp Phe Asn Thr Leu Lys Ser Ile Gly
        195                 200                 205

Ser Glu Pro His Glu Asp His Val Phe Leu Val Ala Asn Phe Ser Gln
    210                 215                 220

Ile Glu Thr Leu Thr Ser Val Phe Gln Lys Lys Leu Cys Thr Ala His
225                 230                 235                 240

Met Cys Ser Thr Leu Glu His Asn Cys Ala His Phe Cys Ile Asn Ile
```

-continued

```
                245                 250                 255
Pro Gly Ser Tyr Val Cys Arg Cys Lys Gln Gly Tyr Ile Leu Asn Ser
            260                 265                 270

Asp Gln Thr Thr Cys Arg Ile Gln Asp Leu Cys Ala Met Glu Asp His
        275                 280                 285

Asn Cys Glu Gln Leu Cys Val Asn Val Pro Gly Ser Phe Val Cys Gln
    290                 295                 300

Cys Tyr Ser Gly Tyr Ala Leu Ala Glu Asp Gly Lys Arg Cys Val Ala
305                 310                 315                 320

Val Asp Tyr Cys Ala Ser Glu Asn His Gly Cys Glu His Glu Cys Val
                325                 330                 335

Asn Ala Asp Gly Ser Tyr Leu Cys Gln Cys His Glu Gly Phe Ala Leu
            340                 345                 350

Asn Pro Asp Lys Lys Thr Cys Thr Lys Ile Asp Tyr Cys Ala Ser Ser
        355                 360                 365

Asn His Gly Cys Gln His Glu Cys Val Asn Thr Asp Asp Ser Tyr Ser
    370                 375                 380

Cys His Cys Leu Lys Gly Phe Thr Leu Asn Pro Asp Lys Lys Thr Cys
385                 390                 395                 400

Arg Arg Ile Asn Tyr Cys Ala Leu Asn Lys Pro Gly Cys Glu His Glu
                405                 410                 415

Cys Val Asn Met Glu Glu Ser Tyr Tyr Cys Arg Cys His Arg Gly Tyr
            420                 425                 430

Thr Leu Asp Pro Asn Gly Lys Thr Cys Ser Arg Val Asp His Cys Ala
        435                 440                 445

Gln Gln Asp His Gly Cys Glu Gln Leu Cys Leu Asn Thr Glu Asp Ser
    450                 455                 460

Phe Val Cys Gln Cys Ser Glu Gly Phe Leu Ile Asn Glu Asp Leu Lys
465                 470                 475                 480

Thr Cys Ser Arg Val Asp Tyr Cys Leu Leu Ser Asp His Gly Cys Glu
                485                 490                 495

Tyr Ser Cys Val Asn Met Asp Arg Ser Phe Ala Cys Gln Cys Pro Glu
            500                 505                 510

Gly His Val Leu Arg Ser Asp Gly Lys Thr Cys Ala Lys Leu Asp Ser
        515                 520                 525

Cys Ala Leu Gly Asp His Gly Cys Glu His Ser Cys Val Ser Ser Glu
    530                 535                 540

Asp Ser Phe Val Cys Gln Cys Phe Glu Gly Tyr Ile Leu Arg Glu Asp
545                 550                 555                 560

Gly Lys Thr Cys Arg Arg Lys Asp Val Cys Gln Ala Ile Asp His Gly
                565                 570                 575

Cys Glu His Ile Cys Val Asn Ser Asp Asp Ser Tyr Thr Cys Glu Cys
            580                 585                 590

Leu Glu Gly Phe Arg Leu Ala Glu Asp Gly Lys Arg Cys Arg Arg Lys
        595                 600                 605

Asp Val Cys Lys Ser Thr His His Gly Cys Glu His Ile Cys Val Asn
    610                 615                 620

Asn Gly Asn Ser Tyr Ile Cys Lys Cys Ser Glu Gly Phe Val Leu Ala
625                 630                 635                 640

Glu Asp Gly Arg Arg Cys Lys Lys Cys Thr Glu Gly Pro Ile Asp Leu
                645                 650                 655

Val Phe Val Ile Asp Gly Ser Lys Ser Leu Gly Glu Glu Asn Phe Glu
            660                 665                 670
```

Val Val Lys Gln Phe Val Thr Gly Ile Ile Asp Ser Leu Thr Ile Ser
            675                 680                 685

Pro Lys Ala Ala Arg Val Gly Leu Leu Gln Tyr Ser Thr Gln Val His
        690                 695                 700

Thr Glu Phe Thr Leu Arg Asn Phe Asn Ser Ala Lys Asp Met Lys Lys
705                 710                 715                 720

Ala Val Ala His Met Lys Tyr Met Gly Lys Gly Ser Met Thr Gly Leu
                725                 730                 735

Ala Leu Lys His Met Phe Glu Arg Ser Phe Thr Gln Gly Glu Gly Ala
            740                 745                 750

Arg Pro Leu Ser Thr Arg Val Pro Arg Ala Ala Ile Val Phe Thr Asp
        755                 760                 765

Gly Arg Ala Gln Asp Asp Val Ser Glu Trp Ala Ser Lys Ala Lys Ala
770                 775                 780

Asn Gly Ile Thr Met Tyr Ala Val Gly Val Gly Lys Ala Ile Glu Glu
785                 790                 795                 800

Glu Leu Gln Glu Ile Ala Ser Glu Pro Thr Asn Lys His Leu Phe Tyr
                805                 810                 815

Ala Glu Asp Phe Ser Thr Met Asp Glu Ile Ser Glu Lys Leu Lys Lys
            820                 825                 830

Gly Ile Cys Glu Ala Leu Glu Asp Ser Asp Gly Arg Gln Asp Ser Pro
        835                 840                 845

Ala Gly Glu Leu Pro Lys Thr Val Gln Gln Pro Thr Val Gln His Arg
850                 855                 860

Tyr Leu Phe Glu Glu Asp Asn Leu Leu Arg Ser Thr Gln Lys Leu Ser
865                 870                 875                 880

His Ser Thr Lys Pro Ser Gly Ser Pro Leu Glu Glu Lys His Asp Gln
                885                 890                 895

Cys Lys Cys Glu Asn Leu Ile Met Phe Gln Asn Leu Ala Asn Glu Glu
            900                 905                 910

Val Arg Lys Leu Thr Gln Arg Leu Glu Glu Met Thr Gln Arg Met Glu
        915                 920                 925

Ala Leu Glu Asn Arg Leu Arg Tyr Arg
    930                 935

<210> SEQ ID NO 16
<211> LENGTH: 999
<212> TYPE: PRT
<213> ORGANISM: Homo sapiens

<400> SEQUENCE: 16

Met Gly Val Ala Gly Arg Asn Arg Pro Gly Ala Ala Trp Ala Val Leu
1               5                   10                  15

Leu Leu Leu Leu Leu Leu Pro Pro Leu Leu Leu Ala Gly Ala Val
                20                  25                  30

Pro Pro Gly Arg Gly Arg Ala Ala Gly Pro Gln Glu Asp Val Asp Glu
            35                  40                  45

Cys Ala Gln Gly Leu Asp Asp Cys His Ala Asp Ala Leu Cys Gln Asn
        50                  55                  60

Thr Pro Thr Ser Tyr Lys Cys Ser Cys Lys Pro Gly Tyr Gln Gly Glu
65                  70                  75                  80

Gly Arg Gln Cys Glu Asp Ile Asp Glu Cys Gly Asn Glu Leu Asn Gly
                85                  90                  95

Gly Cys Val His Asp Cys Leu Asn Ile Pro Gly Asn Tyr Arg Cys Thr

-continued

```
              100                 105                 110
Cys Phe Asp Gly Phe Met Leu Ala His Asp Gly His Asn Cys Leu Asp
              115                 120                 125
Val Asp Glu Cys Leu Glu Asn Asn Gly Gly Cys Gln His Thr Cys Val
130                 135                 140
Asn Val Met Gly Ser Tyr Glu Cys Cys Lys Glu Gly Phe Phe Leu
145                 150                 155                 160
Ser Asp Asn Gln His Thr Cys Ile His Arg Ser Glu Glu Gly Leu Ser
                  165                 170                 175
Cys Met Asn Lys Asp His Gly Cys Ser His Ile Cys Lys Glu Ala Pro
              180                 185                 190
Arg Gly Ser Val Ala Cys Glu Cys Arg Pro Gly Phe Glu Leu Ala Lys
              195                 200                 205
Asn Gln Arg Asp Cys Ile Leu Thr Cys Asn His Gly Asn Gly Gly Cys
210                 215                 220
Gln His Ser Cys Asp Asp Thr Ala Asp Gly Pro Glu Cys Ser Cys His
225                 230                 235                 240
Pro Gln Tyr Lys Met His Thr Asp Gly Arg Ser Cys Leu Glu Arg Glu
                  245                 250                 255
Asp Thr Val Leu Glu Val Thr Glu Ser Asn Thr Thr Ser Val Val Asp
              260                 265                 270
Gly Asp Lys Arg Val Lys Arg Leu Leu Met Glu Thr Cys Ala Val
              275                 280                 285
Asn Asn Gly Gly Cys Asp Arg Thr Cys Lys Asp Thr Ser Thr Gly Val
290                 295                 300
His Cys Ser Cys Pro Val Gly Phe Thr Leu Gln Leu Asp Gly Lys Thr
305                 310                 315                 320
Cys Lys Asp Ile Asp Glu Cys Gln Thr Arg Asn Gly Gly Cys Asp His
                  325                 330                 335
Phe Cys Lys Asn Ile Val Gly Ser Phe Asp Cys Gly Cys Lys Lys Gly
              340                 345                 350
Phe Lys Leu Leu Thr Asp Glu Lys Ser Cys Gln Asp Val Asp Glu Cys
              355                 360                 365
Ser Leu Asp Arg Thr Cys Asp His Ser Cys Ile Asn His Pro Gly Thr
370                 375                 380
Phe Ala Cys Ala Cys Asn Arg Gly Tyr Thr Leu Tyr Gly Phe Thr His
385                 390                 395                 400
Cys Gly Asp Thr Asn Glu Cys Ser Ile Asn Asn Gly Gly Cys Gln Gln
                  405                 410                 415
Val Cys Val Asn Thr Val Gly Ser Tyr Glu Cys Gln Cys His Pro Gly
              420                 425                 430
Tyr Lys Leu His Trp Asn Lys Lys Asp Cys Val Glu Val Lys Gly Leu
              435                 440                 445
Leu Pro Thr Ser Val Ser Pro Arg Val Ser Leu His Cys Gly Lys Ser
450                 455                 460
Gly Gly Gly Asp Gly Cys Phe Leu Arg Cys His Ser Gly Ile His Leu
465                 470                 475                 480
Ser Ser Asp Val Thr Thr Ile Arg Thr Ser Val Thr Phe Lys Leu Asn
                  485                 490                 495
Glu Gly Lys Cys Ser Leu Lys Asn Ala Glu Leu Phe Pro Glu Gly Leu
              500                 505                 510
Arg Pro Ala Leu Pro Glu Lys His Ser Ser Val Lys Glu Ser Phe Arg
              515                 520                 525
```

```
Tyr Val Asn Leu Thr Cys Ser Ser Gly Lys Gln Val Pro Gly Ala Pro
    530                 535                 540
Gly Arg Pro Ser Thr Pro Lys Glu Met Phe Ile Thr Val Glu Phe Glu
545                 550                 555                 560
Leu Glu Thr Asn Gln Lys Glu Val Thr Ala Ser Cys Asp Leu Ser Cys
                565                 570                 575
Ile Val Lys Arg Thr Glu Lys Arg Leu Arg Lys Ala Ile Arg Thr Leu
            580                 585                 590
Arg Lys Ala Val His Arg Glu Gln Phe His Leu Gln Leu Ser Gly Met
        595                 600                 605
Asn Leu Asp Val Ala Lys Lys Pro Pro Arg Thr Ser Glu Arg Gln Ala
610                 615                 620
Glu Ser Cys Gly Val Gly Gln Gly His Ala Glu Asn Gln Cys Val Ser
625                 630                 635                 640
Cys Arg Ala Gly Thr Tyr Tyr Asp Gly Ala Arg Glu Arg Cys Ile Leu
                645                 650                 655
Cys Pro Asn Gly Thr Phe Gln Asn Glu Glu Gly Gln Met Thr Cys Glu
            660                 665                 670
Pro Cys Pro Arg Pro Gly Asn Ser Gly Ala Leu Lys Thr Pro Glu Ala
        675                 680                 685
Trp Asn Met Ser Glu Cys Gly Gly Leu Cys Gln Pro Gly Glu Tyr Ser
    690                 695                 700
Ala Asp Gly Phe Ala Pro Cys Gln Leu Cys Ala Leu Gly Thr Phe Gln
705                 710                 715                 720
Pro Glu Ala Gly Arg Thr Ser Cys Phe Pro Cys Gly Gly Gly Leu Ala
                725                 730                 735
Thr Lys His Gln Gly Ala Thr Ser Phe Gln Asp Cys Glu Thr Arg Val
            740                 745                 750
Gln Cys Ser Pro Gly His Phe Tyr Asn Thr Thr Thr His Arg Cys Ile
        755                 760                 765
Arg Cys Pro Val Gly Thr Tyr Gln Pro Glu Phe Gly Lys Asn Asn Cys
    770                 775                 780
Val Ser Cys Pro Gly Asn Thr Thr Thr Asp Phe Asp Gly Ser Thr Asn
785                 790                 795                 800
Ile Thr Gln Cys Lys Asn Arg Arg Cys Gly Gly Glu Leu Gly Asp Phe
                805                 810                 815
Thr Gly Tyr Ile Glu Ser Pro Asn Tyr Pro Gly Asn Tyr Pro Ala Asn
            820                 825                 830
Thr Glu Cys Thr Trp Thr Ile Asn Pro Pro Lys Arg Arg Ile Leu
        835                 840                 845
Ile Val Val Pro Glu Ile Phe Leu Pro Ile Glu Asp Asp Cys Gly Asp
    850                 855                 860
Tyr Leu Val Met Arg Lys Thr Ser Ser Asn Ser Val Thr Thr Tyr
865                 870                 875                 880
Glu Thr Cys Gln Thr Tyr Glu Arg Pro Ile Ala Phe Thr Ser Arg Ser
                885                 890                 895
Lys Lys Leu Trp Ile Gln Phe Lys Ser Asn Glu Gly Asn Ser Ala Arg
            900                 905                 910
Gly Phe Gln Val Pro Tyr Val Thr Tyr Asp Glu Asp Tyr Gln Glu Leu
        915                 920                 925
Ile Glu Asp Ile Val Arg Asp Gly Arg Leu Tyr Ala Ser Glu Asn His
    930                 935                 940
```

```
Gln Glu Ile Leu Lys Asp Lys Lys Leu Ile Lys Ala Leu Phe Asp Val
945                 950                 955                 960

Leu Ala His Pro Gln Asn Tyr Phe Lys Tyr Thr Ala Gln Glu Ser Arg
                965                 970                 975

Glu Met Phe Pro Arg Ser Phe Ile Arg Leu Leu Arg Ser Lys Val Ser
                980                 985                 990

Arg Phe Leu Arg Pro Tyr Lys
        995

<210> SEQ ID NO 17
<211> LENGTH: 545
<212> TYPE: PRT
<213> ORGANISM: Homo sapiens

<400> SEQUENCE: 17

Met Pro Pro Phe Leu Leu Leu Thr Cys Leu Phe Ile Thr Gly Thr Ser
1               5                   10                  15

Val Ser Pro Val Ala Leu Asp Pro Cys Ser Ala Tyr Ile Ser Leu Asn
            20                  25                  30

Glu Pro Trp Arg Asn Thr Asp His Gln Leu Asp Glu Ser Gln Gly Pro
        35                  40                  45

Pro Leu Cys Asp Asn His Val Asn Gly Glu Trp Tyr His Phe Thr Gly
    50                  55                  60

Met Ala Gly Asp Ala Met Pro Thr Phe Cys Ile Pro Glu Asn His Cys
65                  70                  75                  80

Gly Thr His Ala Pro Val Trp Leu Asn Gly Ser His Pro Leu Glu Gly
                85                  90                  95

Asp Gly Ile Val Gln Arg Gln Ala Cys Ala Ser Phe Asn Gly Asn Cys
            100                 105                 110

Cys Leu Trp Asn Thr Thr Val Glu Val Lys Ala Cys Pro Gly Gly Tyr
        115                 120                 125

Tyr Val Tyr Arg Leu Thr Lys Pro Ser Val Cys Phe His Val Tyr Cys
    130                 135                 140

Gly His Phe Tyr Asp Ile Cys Asp Glu Asp Cys His Gly Ser Cys Ser
145                 150                 155                 160

Asp Thr Ser Glu Cys Thr Cys Ala Pro Gly Thr Val Leu Gly Pro Asp
                165                 170                 175

Arg Gln Thr Cys Phe Asp Glu Asn Glu Cys Gln Asn Asn Gly Gly
            180                 185                 190

Cys Ser Glu Ile Cys Val Asn Leu Lys Asn Ser Tyr Arg Cys Glu Cys
        195                 200                 205

Gly Val Gly Arg Val Leu Arg Ser Asp Gly Lys Thr Cys Glu Asp Val
    210                 215                 220

Glu Gly Cys His Asn Asn Gly Gly Cys Ser His Ser Cys Leu Gly
225                 230                 235                 240

Ser Glu Lys Gly Tyr Gln Cys Glu Cys Pro Arg Gly Leu Val Leu Ser
                245                 250                 255

Glu Asp Asn His Thr Cys Gln Val Pro Val Leu Cys Lys Ser Asn Ala
            260                 265                 270

Ile Glu Val Asn Ile Pro Arg Glu Leu Val Gly Gly Leu Glu Leu Phe
        275                 280                 285

Leu Thr Asn Thr Ser Cys Arg Gly Val Ser Asn Gly Thr His Val Asn
    290                 295                 300

Ile Leu Phe Ser Leu Lys Thr Cys Gly Thr Val Val Asp Val Val Asn
305                 310                 315                 320
```

```
Asp Lys Ile Val Ala Ser Asn Leu Val Thr Gly Leu Pro Lys Gln Thr
                325                 330                 335

Pro Gly Ser Ser Gly Asp Phe Ile Ile Arg Thr Ser Lys Leu Leu Ile
            340                 345                 350

Pro Val Thr Cys Glu Phe Pro Arg Leu Tyr Thr Ile Ser Glu Gly Tyr
        355                 360                 365

Val Pro Asn Leu Arg Asn Ser Pro Leu Glu Ile Met Ser Arg Asn His
    370                 375                 380

Gly Ile Phe Pro Phe Thr Leu Glu Ile Phe Lys Asp Asn Glu Phe Glu
385                 390                 395                 400

Glu Pro Tyr Arg Glu Ala Leu Pro Thr Leu Lys Leu Arg Asp Ser Leu
                405                 410                 415

Tyr Phe Gly Ile Glu Pro Val Val His Val Ser Gly Leu Glu Ser Leu
            420                 425                 430

Val Glu Ser Cys Phe Ala Thr Pro Thr Ser Lys Ile Asp Glu Val Leu
        435                 440                 445

Lys Tyr Tyr Leu Ile Arg Asp Gly Cys Val Ser Asp Ser Val Lys
    450                 455                 460

Gln Tyr Thr Ser Arg Asp His Leu Ala Lys His Phe Gln Val Pro Val
465                 470                 475                 480

Phe Lys Phe Val Gly Lys Asp His Lys Glu Val Phe Leu His Cys Arg
                485                 490                 495

Val Leu Val Cys Gly Val Leu Asp Glu Arg Ser Arg Cys Ala Gln Gly
            500                 505                 510

Cys His Arg Arg Met Arg Arg Gly Ala Gly Gly Glu Asp Ser Ala Gly
        515                 520                 525

Leu Gln Gly Gln Thr Leu Thr Gly Gly Pro Ile Arg Ile Asp Trp Glu
    530                 535                 540

Asp
545

<210> SEQ ID NO 18
<211> LENGTH: 988
<212> TYPE: PRT
<213> ORGANISM: Homo sapiens

<400> SEQUENCE: 18

Met Gly Ala Ala Ala Val Arg Trp His Leu Cys Val Leu Leu Ala Leu
1               5                   10                  15

Gly Thr Arg Gly Arg Leu Ala Gly Gly Ser Gly Leu Pro Gly Ser Val
            20                  25                  30

Asp Val Asp Glu Cys Ser Glu Gly Thr Asp Asp Cys His Ile Asp Ala
        35                  40                  45

Ile Cys Gln Asn Thr Pro Lys Ser Tyr Lys Cys Leu Cys Lys Pro Gly
    50                  55                  60

Tyr Lys Gly Glu Gly Lys Gln Cys Glu Asp Ile Asp Glu Cys Glu Asn
65                  70                  75                  80

Asp Tyr Tyr Asn Gly Gly Cys Val His Glu Cys Ile Asn Ile Pro Gly
                85                  90                  95

Asn Tyr Arg Cys Thr Cys Phe Asp Gly Phe Met Leu Ala His Asp Gly
            100                 105                 110

His Asn Cys Leu Asp Val Asp Glu Cys Gln Asp Asn Asn Gly Gly Cys
        115                 120                 125

Gln Gln Ile Cys Val Asn Ala Met Gly Ser Tyr Glu Cys Gln Cys His
```

-continued

```
            130                 135                 140
Ser Gly Phe Phe Leu Ser Asp Asn Gln His Thr Cys Ile His Arg Ser
145                 150                 155                 160

Asn Glu Gly Met Asn Cys Met Asn Lys Asp His Gly Cys Ala His Ile
                165                 170                 175

Cys Arg Glu Thr Pro Lys Gly Gly Val Ala Cys Asp Cys Arg Pro Gly
            180                 185                 190

Phe Asp Leu Ala Gln Asn Gln Lys Asp Cys Thr Leu Thr Cys Asn Tyr
        195                 200                 205

Gly Asn Gly Gly Cys Gln His Ser Cys Glu Asp Thr Asp Thr Gly Pro
    210                 215                 220

Thr Cys Gly Cys His Gln Lys Tyr Ala Leu His Ser Asp Gly Arg Thr
225                 230                 235                 240

Cys Ile Glu Thr Cys Ala Val Asn Asn Gly Gly Cys Asp Arg Thr Cys
                245                 250                 255

Lys Asp Thr Ala Thr Gly Val Arg Cys Ser Cys Pro Val Gly Phe Thr
            260                 265                 270

Leu Gln Pro Asp Gly Lys Thr Cys Lys Asp Ile Asn Glu Cys Leu Val
        275                 280                 285

Asn Asn Gly Gly Cys Asp His Phe Cys Arg Asn Thr Val Gly Ser Phe
    290                 295                 300

Glu Cys Gly Cys Arg Lys Gly Tyr Lys Leu Leu Thr Asp Glu Arg Thr
305                 310                 315                 320

Cys Gln Asp Ile Asp Glu Cys Ser Phe Glu Arg Thr Cys Asp His Ile
                325                 330                 335

Cys Ile Asn Ser Pro Gly Ser Phe Gln Cys Leu Cys His Arg Gly Tyr
            340                 345                 350

Ile Leu Tyr Gly Thr Thr His Cys Gly Asp Val Asp Glu Cys Ser Met
        355                 360                 365

Ser Asn Gly Ser Cys Asp Gln Gly Cys Val Asn Thr Lys Gly Ser Tyr
    370                 375                 380

Glu Cys Val Cys Pro Pro Gly Arg Arg Leu His Trp Asn Gly Lys Asp
385                 390                 395                 400

Cys Val Glu Thr Gly Lys Cys Leu Ser Arg Ala Lys Thr Ser Pro Arg
                405                 410                 415

Ala Gln Leu Ser Cys Ser Lys Ala Gly Gly Val Glu Cys Phe Leu
            420                 425                 430

Ser Cys Pro Ala His Thr Leu Phe Val Pro Asp Ser Glu Asn Ser Tyr
        435                 440                 445

Val Leu Ser Cys Gly Val Pro Gly Pro Gln Gly Lys Ala Leu Gln Lys
    450                 455                 460

Arg Asn Gly Thr Ser Gly Leu Gly Pro Ser Cys Ser Asp Ala Pro
465                 470                 475                 480

Thr Thr Pro Ile Lys Gln Lys Ala Arg Phe Lys Ile Arg Asp Ala Lys
                485                 490                 495

Cys His Leu Arg Pro His Ser Gln Ala Arg Ala Lys Glu Thr Ala Arg
            500                 505                 510

Gln Pro Leu Leu Asp His Cys His Val Thr Phe Val Thr Leu Lys Cys
        515                 520                 525

Asp Ser Ser Lys Lys Arg Arg Arg Gly Arg Lys Ser Pro Ser Lys Glu
    530                 535                 540

Val Ser His Ile Thr Ala Glu Phe Glu Ile Glu Thr Lys Met Glu Glu
545                 550                 555                 560
```

```
Ala Ser Asp Thr Cys Glu Ala Asp Cys Leu Arg Lys Arg Ala Glu Gln
            565                 570                 575

Ser Leu Gln Ala Ala Ile Lys Thr Leu Arg Lys Ser Ile Gly Arg Gln
        580                 585                 590

Gln Phe Tyr Val Gln Val Ser Gly Thr Glu Tyr Glu Val Ala Gln Arg
        595                 600                 605

Pro Ala Lys Ala Leu Glu Gly Gln Gly Ala Cys Gly Ala Gly Gln Val
        610                 615                 620

Leu Gln Asp Ser Lys Cys Val Ala Cys Gly Pro Gly Thr His Phe Gly
625                 630                 635                 640

Gly Glu Leu Gly Gln Cys Val Ser Cys Met Pro Gly Thr Tyr Gln Asp
            645                 650                 655

Met Glu Gly Gln Leu Ser Cys Thr Pro Cys Pro Ser Ser Asp Gly Leu
            660                 665                 670

Gly Leu Pro Gly Ala Arg Asn Val Ser Glu Cys Gly Gly Gln Cys Ser
            675                 680                 685

Pro Gly Phe Phe Ser Ala Asp Gly Phe Lys Pro Cys Gln Ala Cys Pro
        690                 695                 700

Val Gly Thr Tyr Gln Pro Glu Pro Gly Arg Thr Gly Cys Phe Pro Cys
705                 710                 715                 720

Gly Gly Gly Leu Leu Thr Lys His Glu Gly Thr Thr Ser Phe Gln Asp
                725                 730                 735

Cys Glu Ala Lys Val His Cys Ser Pro Gly His His Tyr Asn Thr Thr
            740                 745                 750

Thr His Arg Cys Ile Arg Cys Pro Val Gly Thr Tyr Gln Pro Glu Phe
        755                 760                 765

Gly Gln Asn His Cys Ile Thr Cys Pro Gly Asn Thr Ser Thr Asp Phe
        770                 775                 780

Asp Gly Ser Thr Asn Val Thr His Cys Lys Asn Gln His Cys Gly Gly
785                 790                 795                 800

Glu Leu Gly Asp Tyr Thr Gly Tyr Ile Glu Ser Pro Asn Tyr Pro Gly
            805                 810                 815

Asp Tyr Pro Ala Asn Ala Glu Cys Val Trp His Ile Ala Pro Pro Pro
            820                 825                 830

Lys Arg Arg Ile Leu Ile Val Val Pro Glu Ile Phe Leu Pro Ile Glu
        835                 840                 845

Asp Glu Cys Gly Asp Val Leu Val Met Arg Lys Ser Ala Ser Pro Thr
        850                 855                 860

Ser Ile Thr Thr Tyr Glu Thr Cys Gln Thr Tyr Glu Arg Pro Ile Ala
865                 870                 875                 880

Phe Thr Ser Arg Ser Arg Lys Leu Trp Ile Gln Phe Lys Ser Asn Glu
                885                 890                 895

Gly Asn Ser Gly Lys Gly Phe Gln Val Pro Tyr Val Thr Tyr Asp Glu
                900                 905                 910

Asp Tyr Gln Gln Leu Ile Glu Asp Ile Val Arg Asp Gly Arg Leu Tyr
        915                 920                 925

Ala Ser Glu Asn His Gln Glu Ile Leu Lys Asp Lys Lys Leu Ile Lys
        930                 935                 940

Ala Leu Phe Asp Val Leu Ala His Pro Gln Asn Tyr Phe Lys Tyr Thr
945                 950                 955                 960

Ala Gln Glu Ser Lys Glu Met Phe Pro Arg Ser Phe Ile Lys Leu Leu
            965                 970                 975
```

```
Arg Ser Lys Val Ser Arg Phe Leu Arg Pro Tyr Lys
            980                 985
```

<210> SEQ ID NO 19
<211> LENGTH: 4544
<212> TYPE: PRT
<213> ORGANISM: Homo sapiens

<400> SEQUENCE: 19

```
Met Leu Thr Pro Pro Leu Leu Leu Leu Pro Leu Leu Ser Ala Leu
1               5                   10                  15

Val Ala Ala Ala Ile Asp Ala Pro Lys Thr Cys Ser Pro Lys Gln Phe
            20                  25                  30

Ala Cys Arg Asp Gln Ile Thr Cys Ile Ser Lys Gly Trp Arg Cys Asp
            35                  40                  45

Gly Glu Arg Asp Cys Pro Asp Gly Ser Asp Glu Ala Pro Glu Ile Cys
            50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
            115                 120                 125

Asp Gly Pro Thr Cys Tyr Cys Asn Ser Ser Phe Gln Leu Gln Ala Asp
            130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
            195                 200                 205

Ile Leu Ala Thr Tyr Leu Ser Gly Ala Gln Val Ser Thr Ile Thr Pro
            210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
            275                 280                 285

Trp Leu Thr Gly Asn Phe Tyr Phe Val Asp Asp Ile Asp Asp Arg Ile
            290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
            355                 360                 365
```

```
Pro His Gly Ile Thr Leu Asp Leu Val Ser Arg Leu Val Tyr Trp Ala
    370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
    450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
        515                 520                 525

Val Tyr Gly Lys Gly Arg Pro Gly Ile Ile Arg Gly Met Asp Met Gly
    530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
        595                 600                 605

Val Asp Trp Met Gly Asp Asn Leu Tyr Trp Thr Asp Asp Gly Pro Lys
    610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
        675                 680                 685

Arg Asp Ile Phe Val Thr Ser Lys Thr Val Leu Trp Pro Asn Gly Leu
    690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730                 735

Tyr Glu Gly Pro Glu Leu Asn His Ala Phe Gly Leu Cys His His Gly
            740                 745                 750

Asn Tyr Leu Phe Trp Thr Glu Tyr Arg Ser Gly Ser Val Tyr Arg Leu
        755                 760                 765

Glu Arg Gly Val Gly Gly Ala Pro Pro Thr Val Thr Leu Leu Arg Ser
    770                 775                 780
```

-continued

```
Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
            805                 810                 815

Leu Cys Leu Ala Thr Pro Gly Ser Arg Gln Cys Ala Cys Ala Glu Asp
        820                 825                 830

Gln Val Leu Asp Ala Asp Gly Val Thr Cys Leu Ala Asn Pro Ser Tyr
    835                 840                 845

Val Pro Pro Gln Cys Gln Pro Gly Glu Phe Ala Cys Ala Asn Ser
850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
            885                 890                 895

Ser Asp Arg Phe Lys Cys Glu Asn Asn Arg Cys Ile Pro Asn Arg Trp
        900                 905                 910

Leu Cys Asp Gly Asp Asn Asp Cys Gly Asn Ser Glu Asp Glu Ser Asn
    915                 920                 925

Ala Thr Cys Ser Ala Arg Thr Cys Pro Pro Asn Gln Phe Ser Cys Ala
930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
            965                 970                 975

Phe Pro Leu Thr Gln Phe Thr Cys Asn Asn Gly Arg Cys Ile Asn Ile
        980                 985                 990

Asn Trp Arg Cys Asp Asn Asp Asn Asp Cys Gly Asp Asn Ser Asp Glu
    995                 1000                1005

Ala Gly Cys Ser His Ser Cys Ser Ser Thr Gln Phe Lys Cys Asn
    1010                1015                1020

Ser Gly Arg Cys Ile Pro Glu His Trp Thr Cys Asp Gly Asp Asn
    1025                1030                1035

Asp Cys Gly Asp Tyr Ser Asp Glu Thr His Ala Asn Cys Thr Asn
    1040                1045                1050

Gln Ala Thr Arg Pro Pro Gly Gly Cys His Thr Asp Glu Phe Gln
    1055                1060                1065

Cys Arg Leu Asp Gly Leu Cys Ile Pro Leu Arg Trp Arg Cys Asp
    1070                1075                1080

Gly Asp Thr Asp Cys Met Asp Ser Ser Asp Glu Lys Ser Cys Glu
    1085                1090                1095

Gly Val Thr His Val Cys Asp Pro Ser Val Lys Phe Gly Cys Lys
    1100                1105                1110

Asp Ser Ala Arg Cys Ile Ser Lys Ala Trp Val Cys Asp Gly Asp
    1115                1120                1125

Asn Asp Cys Glu Asp Asn Ser Asp Glu Glu Asn Cys Glu Ser Leu
    1130                1135                1140

Ala Cys Arg Pro Pro Ser His Pro Cys Ala Asn Asn Thr Ser Val
    1145                1150                1155

Cys Leu Pro Pro Asp Lys Leu Cys Asp Gly Asn Asp Asp Cys Gly
    1160                1165                1170

Asp Gly Ser Asp Glu Gly Glu Leu Cys Asp Gln Cys Ser Leu Asn
    1175                1180                1185

Asn Gly Gly Cys Ser His Asn Cys Ser Val Ala Pro Gly Glu Gly
```

-continued

```
            1190                1195                1200
Ile Val Cys Ser Cys Pro Leu Gly Met Glu Leu Gly Pro Asp Asn
            1205                1210                1215
His Thr Cys Gln Ile Gln Ser Tyr Cys Ala Lys His Leu Lys Cys
            1220                1225                1230
Ser Gln Lys Cys Asp Gln Asn Lys Phe Ser Val Lys Cys Ser Cys
            1235                1240                1245
Tyr Glu Gly Trp Val Leu Glu Pro Asp Gly Glu Ser Cys Arg Ser
            1250                1255                1260
Leu Asp Pro Phe Lys Pro Phe Ile Ile Phe Ser Asn Arg His Glu
            1265                1270                1275
Ile Arg Arg Ile Asp Leu His Lys Gly Asp Tyr Ser Val Leu Val
            1280                1285                1290
Pro Gly Leu Arg Asn Thr Ile Ala Leu Asp Phe His Leu Ser Gln
            1295                1300                1305
Ser Ala Leu Tyr Trp Thr Asp Val Val Glu Asp Lys Ile Tyr Arg
            1310                1315                1320
Gly Lys Leu Leu Asp Asn Gly Ala Leu Thr Ser Phe Glu Val Val
            1325                1330                1335
Ile Gln Tyr Gly Leu Ala Thr Pro Glu Gly Leu Ala Val Asp Trp
            1340                1345                1350
Ile Ala Gly Asn Ile Tyr Trp Val Glu Ser Asn Leu Asp Gln Ile
            1355                1360                1365
Glu Val Ala Lys Leu Asp Gly Thr Leu Arg Thr Thr Leu Leu Ala
            1370                1375                1380
Gly Asp Ile Glu His Pro Arg Ala Ile Ala Leu Asp Pro Arg Asp
            1385                1390                1395
Gly Ile Leu Phe Trp Thr Asp Trp Asp Ala Ser Leu Pro Arg Ile
            1400                1405                1410
Glu Ala Ala Ser Met Ser Gly Ala Gly Arg Arg Thr Val His Arg
            1415                1420                1425
Glu Thr Gly Ser Gly Gly Trp Pro Asn Gly Leu Thr Val Asp Tyr
            1430                1435                1440
Leu Glu Lys Arg Ile Leu Trp Ile Asp Ala Arg Ser Asp Ala Ile
            1445                1450                1455
Tyr Ser Ala Arg Tyr Asp Gly Ser Gly His Met Glu Val Leu Arg
            1460                1465                1470
Gly His Glu Phe Leu Ser His Pro Phe Ala Val Thr Leu Tyr Gly
            1475                1480                1485
Gly Glu Val Tyr Trp Thr Asp Trp Arg Thr Asn Thr Leu Ala Lys
            1490                1495                1500
Ala Asn Lys Trp Thr Gly His Asn Val Thr Val Val Gln Arg Thr
            1505                1510                1515
Asn Thr Gln Pro Phe Asp Leu Gln Val Tyr His Pro Ser Arg Gln
            1520                1525                1530
Pro Met Ala Pro Asn Pro Cys Glu Ala Asn Gly Gly Gln Gly Pro
            1535                1540                1545
Cys Ser His Leu Cys Leu Ile Asn Tyr Asn Arg Thr Val Ser Cys
            1550                1555                1560
Ala Cys Pro His Leu Met Lys Leu His Lys Asp Asn Thr Thr Cys
            1565                1570                1575
Tyr Glu Phe Lys Lys Phe Leu Leu Tyr Ala Arg Gln Met Glu Ile
            1580                1585                1590
```

```
Arg Gly Val Asp Leu Asp Ala Pro Tyr Tyr Asn Tyr Ile Ile Ser
1595                1600                1605

Phe Thr Val Pro Asp Ile Asp Asn Val Thr Val Leu Asp Tyr Asp
1610                1615                1620

Ala Arg Glu Gln Arg Val Tyr Trp Ser Asp Val Arg Thr Gln Ala
1625                1630                1635

Ile Lys Arg Ala Phe Ile Asn Gly Thr Gly Val Glu Thr Val Val
1640                1645                1650

Ser Ala Asp Leu Pro Asn Ala His Gly Leu Ala Val Asp Trp Val
1655                1660                1665

Ser Arg Asn Leu Phe Trp Thr Ser Tyr Asp Thr Asn Lys Lys Gln
1670                1675                1680

Ile Asn Val Ala Arg Leu Asp Gly Ser Phe Lys Asn Ala Val Val
1685                1690                1695

Gln Gly Leu Glu Gln Pro His Gly Leu Val Val His Pro Leu Arg
1700                1705                1710

Gly Lys Leu Tyr Trp Thr Asp Gly Asp Asn Ile Ser Met Ala Asn
1715                1720                1725

Met Asp Gly Ser Asn Arg Thr Leu Leu Phe Ser Gly Gln Lys Gly
1730                1735                1740

Pro Val Gly Leu Ala Ile Asp Phe Pro Glu Ser Lys Leu Tyr Trp
1745                1750                1755

Ile Ser Ser Gly Asn His Thr Ile Asn Arg Cys Asn Leu Asp Gly
1760                1765                1770

Ser Gly Leu Glu Val Ile Asp Ala Met Arg Ser Gln Leu Gly Lys
1775                1780                1785

Ala Thr Ala Leu Ala Ile Met Gly Asp Lys Leu Trp Trp Ala Asp
1790                1795                1800

Gln Val Ser Glu Lys Met Gly Thr Cys Ser Lys Ala Asp Gly Ser
1805                1810                1815

Gly Ser Val Val Leu Arg Asn Ser Thr Thr Leu Val Met His Met
1820                1825                1830

Lys Val Tyr Asp Glu Ser Ile Gln Leu Asp His Lys Gly Thr Asn
1835                1840                1845

Pro Cys Ser Val Asn Asn Gly Asp Cys Ser Gln Leu Cys Leu Pro
1850                1855                1860

Thr Ser Glu Thr Thr Arg Ser Cys Met Cys Thr Ala Gly Tyr Ser
1865                1870                1875

Leu Arg Ser Gly Gln Gln Ala Cys Glu Gly Val Gly Ser Phe Leu
1880                1885                1890

Leu Tyr Ser Val His Glu Gly Ile Arg Gly Ile Pro Leu Asp Pro
1895                1900                1905

Asn Asp Lys Ser Asp Ala Leu Val Pro Val Ser Gly Thr Ser Leu
1910                1915                1920

Ala Val Gly Ile Asp Phe His Ala Glu Asn Asp Thr Ile Tyr Trp
1925                1930                1935

Val Asp Met Gly Leu Ser Thr Ile Ser Arg Ala Lys Arg Asp Gln
1940                1945                1950

Thr Trp Arg Glu Asp Val Val Thr Asn Gly Ile Gly Arg Val Glu
1955                1960                1965

Gly Ile Ala Val Asp Trp Ile Ala Gly Asn Ile Tyr Trp Thr Asp
1970                1975                1980
```

-continued

```
Gln Gly Phe Asp Val Ile Glu Val Ala Arg Leu Asn Gly Ser Phe
1985                1990                1995

Arg Tyr Val Val Ile Ser Gln Gly Leu Asp Lys Pro Arg Ala Ile
2000                2005                2010

Thr Val His Pro Glu Lys Gly Tyr Leu Phe Trp Thr Glu Trp Gly
2015                2020                2025

Gln Tyr Pro Arg Ile Glu Arg Ser Arg Leu Asp Gly Thr Glu Arg
2030                2035                2040

Val Val Leu Val Asn Val Ser Ile Ser Trp Pro Asn Gly Ile Ser
2045                2050                2055

Val Asp Tyr Gln Asp Gly Lys Leu Tyr Trp Cys Asp Ala Arg Thr
2060                2065                2070

Asp Lys Ile Glu Arg Ile Asp Leu Glu Thr Gly Glu Asn Arg Glu
2075                2080                2085

Val Val Leu Ser Ser Asn Asn Met Asp Met Phe Ser Val Ser Val
2090                2095                2100

Phe Glu Asp Phe Ile Tyr Trp Ser Asp Arg Thr His Ala Asn Gly
2105                2110                2115

Ser Ile Lys Arg Gly Ser Lys Asp Asn Ala Thr Asp Ser Val Pro
2120                2125                2130

Leu Arg Thr Gly Ile Gly Val Gln Leu Lys Asp Ile Lys Val Phe
2135                2140                2145

Asn Arg Asp Arg Gln Lys Gly Thr Asn Val Cys Ala Val Ala Asn
2150                2155                2160

Gly Gly Cys Gln Gln Leu Cys Leu Tyr Arg Gly Arg Gly Gln Arg
2165                2170                2175

Ala Cys Ala Cys Ala His Gly Met Leu Ala Glu Asp Gly Ala Ser
2180                2185                2190

Cys Arg Glu Tyr Ala Gly Tyr Leu Leu Tyr Ser Glu Arg Thr Ile
2195                2200                2205

Leu Lys Ser Ile His Leu Ser Asp Glu Arg Asn Leu Asn Ala Pro
2210                2215                2220

Val Gln Pro Phe Glu Asp Pro Glu His Met Lys Asn Val Ile Ala
2225                2230                2235

Leu Ala Phe Asp Tyr Arg Ala Gly Thr Ser Pro Gly Thr Pro Asn
2240                2245                2250

Arg Ile Phe Phe Ser Asp Ile His Phe Gly Asn Ile Gln Gln Ile
2255                2260                2265

Asn Asp Asp Gly Ser Arg Arg Ile Thr Ile Val Glu Asn Val Gly
2270                2275                2280

Ser Val Glu Gly Leu Ala Tyr His Arg Gly Trp Asp Thr Leu Tyr
2285                2290                2295

Trp Thr Ser Tyr Thr Thr Ser Thr Ile Thr Arg His Thr Val Asp
2300                2305                2310

Gln Thr Arg Pro Gly Ala Phe Glu Arg Glu Thr Val Ile Thr Met
2315                2320                2325

Ser Gly Asp Asp His Pro Arg Ala Phe Val Leu Asp Glu Cys Gln
2330                2335                2340

Asn Leu Met Phe Trp Thr Asn Trp Asn Glu Gln His Pro Ser Ile
2345                2350                2355

Met Arg Ala Ala Leu Ser Gly Ala Asn Val Leu Thr Leu Ile Glu
2360                2365                2370

Lys Asp Ile Arg Thr Pro Asn Gly Leu Ala Ile Asp His Arg Ala
```

```
            2375                2380                2385

Glu Lys Leu Tyr Phe Ser Asp Ala Thr Leu Asp Lys Ile Glu Arg
        2390                2395                2400

Cys Glu Tyr Asp Gly Ser His Arg Tyr Val Ile Leu Lys Ser Glu
        2405                2410                2415

Pro Val His Pro Phe Gly Leu Ala Val Tyr Gly Glu His Ile Phe
        2420                2425                2430

Trp Thr Asp Trp Val Arg Arg Ala Val Gln Arg Ala Asn Lys His
        2435                2440                2445

Val Gly Ser Asn Met Lys Leu Leu Arg Val Asp Ile Pro Gln Gln
        2450                2455                2460

Pro Met Gly Ile Ile Ala Val Ala Asn Asp Thr Asn Ser Cys Glu
        2465                2470                2475

Leu Ser Pro Cys Arg Ile Asn Asn Gly Gly Cys Gln Asp Leu Cys
        2480                2485                2490

Leu Leu Thr His Gln Gly His Val Asn Cys Ser Cys Arg Gly Gly
        2495                2500                2505

Arg Ile Leu Gln Asp Asp Leu Thr Cys Arg Ala Val Asn Ser Ser
        2510                2515                2520

Cys Arg Ala Gln Asp Glu Phe Glu Cys Ala Asn Gly Glu Cys Ile
        2525                2530                2535

Asn Phe Ser Leu Thr Cys Asp Gly Val Pro His Cys Lys Asp Lys
        2540                2545                2550

Ser Asp Glu Lys Pro Ser Tyr Cys Asn Ser Arg Cys Lys Lys
        2555                2560                2565

Thr Phe Arg Gln Cys Ser Asn Gly Arg Cys Val Ser Asn Met Leu
        2570                2575                2580

Trp Cys Asn Gly Ala Asp Asp Cys Gly Asp Gly Ser Asp Glu Ile
        2585                2590                2595

Pro Cys Asn Lys Thr Ala Cys Gly Val Gly Glu Phe Arg Cys Arg
        2600                2605                2610

Asp Gly Thr Cys Ile Gly Asn Ser Ser Arg Cys Asn Gln Phe Val
        2615                2620                2625

Asp Cys Glu Asp Ala Ser Asp Glu Met Asn Cys Ser Ala Thr Asp
        2630                2635                2640

Cys Ser Ser Tyr Phe Arg Leu Gly Val Lys Gly Val Leu Phe Gln
        2645                2650                2655

Pro Cys Glu Arg Thr Ser Leu Cys Tyr Ala Pro Ser Trp Val Cys
        2660                2665                2670

Asp Gly Ala Asn Asp Cys Gly Asp Tyr Ser Asp Glu Arg Asp Cys
        2675                2680                2685

Pro Gly Val Lys Arg Pro Arg Cys Pro Leu Asn Tyr Phe Ala Cys
        2690                2695                2700

Pro Ser Gly Arg Cys Ile Pro Met Ser Trp Thr Cys Asp Lys Glu
        2705                2710                2715

Asp Asp Cys Glu His Gly Glu Asp Glu Thr His Cys Asn Lys Phe
        2720                2725                2730

Cys Ser Glu Ala Gln Phe Glu Cys Gln Asn His Arg Cys Ile Ser
        2735                2740                2745

Lys Gln Trp Leu Cys Asp Gly Ser Asp Asp Cys Gly Asp Gly Ser
        2750                2755                2760

Asp Glu Ala Ala His Cys Glu Gly Lys Thr Cys Gly Pro Ser Ser
        2765                2770                2775
```

-continued

```
Phe Ser Cys Pro Gly Thr His Val Cys Val Pro Glu Arg Trp Leu
    2780            2785            2790

Cys Asp Gly Asp Lys Asp Cys Ala Asp Gly Ala Asp Glu Ser Ile
    2795            2800            2805

Ala Ala Gly Cys Leu Tyr Asn Ser Thr Cys Asp Asp Arg Glu Phe
    2810            2815            2820

Met Cys Gln Asn Arg Gln Cys Ile Pro Lys His Phe Val Cys Asp
    2825            2830            2835

His Asp Arg Asp Cys Ala Asp Gly Ser Asp Glu Ser Pro Glu Cys
    2840            2845            2850

Glu Tyr Pro Thr Cys Gly Pro Ser Glu Phe Arg Cys Ala Asn Gly
    2855            2860            2865

Arg Cys Leu Ser Ser Arg Gln Trp Glu Cys Asp Gly Glu Asn Asp
    2870            2875            2880

Cys His Asp Gln Ser Asp Glu Ala Pro Lys Asn Pro His Cys Thr
    2885            2890            2895

Ser Gln Glu His Lys Cys Asn Ala Ser Ser Gln Phe Leu Cys Ser
    2900            2905            2910

Ser Gly Arg Cys Val Ala Glu Ala Leu Leu Cys Asn Gly Gln Asp
    2915            2920            2925

Asp Cys Gly Asp Ser Ser Asp Glu Arg Gly Cys His Ile Asn Glu
    2930            2935            2940

Cys Leu Ser Arg Lys Leu Ser Gly Cys Ser Gln Asp Cys Glu Asp
    2945            2950            2955

Leu Lys Ile Gly Phe Lys Cys Arg Cys Arg Pro Gly Phe Arg Leu
    2960            2965            2970

Lys Asp Asp Gly Arg Thr Cys Ala Asp Val Asp Glu Cys Ser Thr
    2975            2980            2985

Thr Phe Pro Cys Ser Gln Arg Cys Ile Asn Thr His Gly Ser Tyr
    2990            2995            3000

Lys Cys Leu Cys Val Glu Gly Tyr Ala Pro Arg Gly Gly Asp Pro
    3005            3010            3015

His Ser Cys Lys Ala Val Thr Asp Glu Glu Pro Phe Leu Ile Phe
    3020            3025            3030

Ala Asn Arg Tyr Tyr Leu Arg Lys Leu Asn Leu Asp Gly Ser Asn
    3035            3040            3045

Tyr Thr Leu Leu Lys Gln Gly Leu Asn Asn Ala Val Ala Leu Asp
    3050            3055            3060

Phe Asp Tyr Arg Glu Gln Met Ile Tyr Trp Thr Asp Val Thr Thr
    3065            3070            3075

Gln Gly Ser Met Ile Arg Arg Met His Leu Asn Gly Ser Asn Val
    3080            3085            3090

Gln Val Leu His Arg Thr Gly Leu Ser Asn Pro Asp Gly Leu Ala
    3095            3100            3105

Val Asp Trp Val Gly Gly Asn Leu Tyr Trp Cys Asp Lys Gly Arg
    3110            3115            3120

Asp Thr Ile Glu Val Ser Lys Leu Asn Gly Ala Tyr Arg Thr Val
    3125            3130            3135

Leu Val Ser Ser Gly Leu Arg Glu Pro Arg Ala Leu Val Val Asp
    3140            3145            3150

Val Gln Asn Gly Tyr Leu Tyr Trp Thr Asp Trp Gly Asp His Ser
    3155            3160            3165
```

-continued

Leu Ile Gly Arg Ile Gly Met Asp Gly Ser Ser Arg Ser Val Ile
3170                3175                3180

Val Asp Thr Lys Ile Thr Trp Pro Asn Gly Leu Thr Leu Asp Tyr
3185                3190                3195

Val Thr Glu Arg Ile Tyr Trp Ala Asp Ala Arg Glu Asp Tyr Ile
3200                3205                3210

Glu Phe Ala Ser Leu Asp Gly Ser Asn Arg His Val Val Leu Ser
3215                3220                3225

Gln Asp Ile Pro His Ile Phe Ala Leu Thr Leu Phe Glu Asp Tyr
3230                3235                3240

Val Tyr Trp Thr Asp Trp Glu Thr Lys Ser Ile Asn Arg Ala His
3245                3250                3255

Lys Thr Thr Gly Thr Asn Lys Thr Leu Leu Ile Ser Thr Leu His
3260                3265                3270

Arg Pro Met Asp Leu His Val Phe His Ala Leu Arg Gln Pro Asp
3275                3280                3285

Val Pro Asn His Pro Cys Lys Val Asn Asn Gly Gly Cys Ser Asn
3290                3295                3300

Leu Cys Leu Leu Ser Pro Gly Gly Gly His Lys Cys Ala Cys Pro
3305                3310                3315

Thr Asn Phe Tyr Leu Gly Ser Asp Gly Arg Thr Cys Val Ser Asn
3320                3325                3330

Cys Thr Ala Ser Gln Phe Val Cys Lys Asn Asp Lys Cys Ile Pro
3335                3340                3345

Phe Trp Trp Lys Cys Asp Thr Glu Asp Asp Cys Gly Asp His Ser
3350                3355                3360

Asp Glu Pro Pro Asp Cys Pro Glu Phe Lys Cys Arg Pro Gly Gln
3365                3370                3375

Phe Gln Cys Ser Thr Gly Ile Cys Thr Asn Pro Ala Phe Ile Cys
3380                3385                3390

Asp Gly Asp Asn Asp Cys Gln Asp Asn Ser Asp Glu Ala Asn Cys
3395                3400                3405

Asp Ile His Val Cys Leu Pro Ser Gln Phe Lys Cys Thr Asn Thr
3410                3415                3420

Asn Arg Cys Ile Pro Gly Ile Phe Arg Cys Asn Gly Gln Asp Asn
3425                3430                3435

Cys Gly Asp Gly Glu Asp Glu Arg Asp Cys Pro Glu Val Thr Cys
3440                3445                3450

Ala Pro Asn Gln Phe Gln Cys Ser Ile Thr Lys Arg Cys Ile Pro
3455                3460                3465

Arg Val Trp Val Cys Asp Arg Asp Asn Asp Cys Val Asp Gly Ser
3470                3475                3480

Asp Glu Pro Ala Asn Cys Thr Gln Met Thr Cys Gly Val Asp Glu
3485                3490                3495

Phe Arg Cys Lys Asp Ser Gly Arg Cys Ile Pro Ala Arg Trp Lys
3500                3505                3510

Cys Asp Gly Glu Asp Asp Cys Gly Asp Gly Ser Asp Glu Pro Lys
3515                3520                3525

Glu Glu Cys Asp Glu Arg Thr Cys Glu Pro Tyr Gln Phe Arg Cys
3530                3535                3540

Lys Asn Asn Arg Cys Val Pro Gly Arg Trp Gln Cys Asp Tyr Asp
3545                3550                3555

Asn Asp Cys Gly Asp Asn Ser Asp Glu Glu Ser Cys Thr Pro Arg

```
              3560              3565              3570
Pro Cys Ser Glu Ser Glu Phe Ser Cys Ala Asn Gly Arg Cys Ile
    3575              3580              3585
Ala Gly Arg Trp Lys Cys Asp Gly Asp His Cys Ala Asp Gly
    3590              3595              3600
Ser Asp Glu Lys Asp Cys Thr Pro Arg Cys Asp Met Asp Gln Phe
    3605              3610              3615
Gln Cys Lys Ser Gly His Cys Ile Pro Leu Arg Trp Arg Cys Asp
    3620              3625              3630
Ala Asp Ala Asp Cys Met Asp Gly Ser Asp Glu Glu Ala Cys Gly
    3635              3640              3645
Thr Gly Val Arg Thr Cys Pro Leu Asp Glu Phe Gln Cys Asn Asn
    3650              3655              3660
Thr Leu Cys Lys Pro Leu Ala Trp Lys Cys Asp Gly Glu Asp Asp
    3665              3670              3675
Cys Gly Asp Asn Ser Asp Glu Asn Pro Glu Glu Cys Ala Arg Phe
    3680              3685              3690
Val Cys Pro Pro Asn Arg Pro Phe Arg Cys Lys Asn Asp Arg Val
    3695              3700              3705
Cys Leu Trp Ile Gly Arg Gln Cys Asp Gly Thr Asp Asn Cys Gly
    3710              3715              3720
Asp Gly Thr Asp Glu Glu Asp Cys Glu Pro Pro Thr Ala His Thr
    3725              3730              3735
Thr His Cys Lys Asp Lys Lys Glu Phe Leu Cys Arg Asn Gln Arg
    3740              3745              3750
Cys Leu Ser Ser Ser Leu Arg Cys Asn Met Phe Asp Asp Cys Gly
    3755              3760              3765
Asp Gly Ser Asp Glu Glu Asp Cys Ser Ile Asp Pro Lys Leu Thr
    3770              3775              3780
Ser Cys Ala Thr Asn Ala Ser Ile Cys Gly Asp Glu Ala Arg Cys
    3785              3790              3795
Val Arg Thr Glu Lys Ala Ala Tyr Cys Ala Cys Arg Ser Gly Phe
    3800              3805              3810
His Thr Val Pro Gly Gln Pro Gly Cys Gln Asp Ile Asn Glu Cys
    3815              3820              3825
Leu Arg Phe Gly Thr Cys Ser Gln Leu Cys Asn Asn Thr Lys Gly
    3830              3835              3840
Gly His Leu Cys Ser Cys Ala Arg Asn Phe Met Lys Thr His Asn
    3845              3850              3855
Thr Cys Lys Ala Glu Gly Ser Glu Tyr Gln Val Leu Tyr Ile Ala
    3860              3865              3870
Asp Asp Asn Glu Ile Arg Ser Leu Phe Pro Gly His Pro His Ser
    3875              3880              3885
Ala Tyr Glu Gln Ala Phe Gln Gly Asp Glu Ser Val Arg Ile Asp
    3890              3895              3900
Ala Met Asp Val His Val Lys Ala Gly Arg Val Tyr Trp Thr Asn
    3905              3910              3915
Trp His Thr Gly Thr Ile Ser Tyr Arg Ser Leu Pro Pro Ala Ala
    3920              3925              3930
Pro Pro Thr Thr Ser Asn Arg His Arg Arg Gln Ile Asp Arg Gly
    3935              3940              3945
Val Thr His Leu Asn Ile Ser Gly Leu Lys Met Pro Arg Gly Ile
    3950              3955              3960
```

```
Ala Ile Asp Trp Val Ala Gly Asn Val Tyr Trp Thr Asp Ser Gly
3965                3970                3975

Arg Asp Val Ile Glu Val Ala Gln Met Lys Gly Glu Asn Arg Lys
3980                3985                3990

Thr Leu Ile Ser Gly Met Ile Asp Glu Pro His Ala Ile Val Val
3995                4000                4005

Asp Pro Leu Arg Gly Thr Met Tyr Trp Ser Asp Trp Gly Asn His
4010                4015                4020

Pro Lys Ile Glu Thr Ala Ala Met Asp Gly Thr Leu Arg Glu Thr
4025                4030                4035

Leu Val Gln Asp Asn Ile Gln Trp Pro Thr Gly Leu Ala Val Asp
4040                4045                4050

Tyr His Asn Glu Arg Leu Tyr Trp Ala Asp Ala Lys Leu Ser Val
4055                4060                4065

Ile Gly Ser Ile Arg Leu Asn Gly Thr Asp Pro Ile Val Ala Ala
4070                4075                4080

Asp Ser Lys Arg Gly Leu Ser His Pro Phe Ser Ile Asp Val Phe
4085                4090                4095

Glu Asp Tyr Ile Tyr Gly Val Thr Tyr Ile Asn Asn Arg Val Phe
4100                4105                4110

Lys Ile His Lys Phe Gly His Ser Pro Leu Val Asn Leu Thr Gly
4115                4120                4125

Gly Leu Ser His Ala Ser Asp Val Val Leu Tyr His Gln His Lys
4130                4135                4140

Gln Pro Glu Val Thr Asn Pro Cys Asp Arg Lys Lys Cys Glu Trp
4145                4150                4155

Leu Cys Leu Leu Ser Pro Ser Gly Pro Val Cys Thr Cys Pro Asn
4160                4165                4170

Gly Lys Arg Leu Asp Asn Gly Thr Cys Val Pro Val Pro Ser Pro
4175                4180                4185

Thr Pro Pro Pro Asp Ala Pro Arg Pro Gly Thr Cys Asn Leu Gln
4190                4195                4200

Cys Phe Asn Gly Gly Ser Cys Phe Leu Asn Ala Arg Arg Gln Pro
4205                4210                4215

Lys Cys Arg Cys Gln Pro Arg Tyr Thr Gly Asp Lys Cys Glu Leu
4220                4225                4230

Asp Gln Cys Trp Glu His Cys Arg Asn Gly Gly Thr Cys Ala Ala
4235                4240                4245

Ser Pro Ser Gly Met Pro Thr Cys Arg Cys Pro Thr Gly Phe Thr
4250                4255                4260

Gly Pro Lys Cys Thr Gln Gln Val Cys Ala Gly Tyr Cys Ala Asn
4265                4270                4275

Asn Ser Thr Cys Thr Val Asn Gln Gly Asn Gln Pro Gln Cys Arg
4280                4285                4290

Cys Leu Pro Gly Phe Leu Gly Asp Arg Cys Gln Tyr Arg Gln Cys
4295                4300                4305

Ser Gly Tyr Cys Glu Asn Phe Gly Thr Cys Gln Met Ala Ala Asp
4310                4315                4320

Gly Ser Arg Gln Cys Arg Cys Thr Ala Tyr Phe Glu Gly Ser Arg
4325                4330                4335

Cys Glu Val Asn Lys Cys Ser Arg Cys Leu Glu Gly Ala Cys Val
4340                4345                4350
```

```
Val Asn Lys Gln Ser Gly Asp Val Thr Cys Asn Cys Thr Asp Gly
    4355                4360                4365

Arg Val Ala Pro Ser Cys Leu Thr Cys Val Gly His Cys Ser Asn
    4370                4375                4380

Gly Gly Ser Cys Thr Met Asn Ser Lys Met Met Pro Glu Cys Gln
    4385                4390                4395

Cys Pro Pro His Met Thr Gly Pro Arg Cys Glu Glu His Val Phe
    4400                4405                4410

Ser Gln Gln Gln Pro Gly His Ile Ala Ser Ile Leu Ile Pro Leu
    4415                4420                4425

Leu Leu Leu Leu Leu Leu Val Leu Val Ala Gly Val Val Phe Trp
    4430                4435                4440

Tyr Lys Arg Arg Val Gln Gly Ala Lys Gly Phe Gln His Gln Arg
    4445                4450                4455

Met Thr Asn Gly Ala Met Asn Val Glu Ile Gly Asn Pro Thr Tyr
    4460                4465                4470

Lys Met Tyr Glu Gly Gly Glu Pro Asp Asp Val Gly Gly Leu Leu
    4475                4480                4485

Asp Ala Asp Phe Ala Leu Asp Pro Asp Lys Pro Thr Asn Phe Thr
    4490                4495                4500

Asn Pro Val Tyr Ala Thr Leu Tyr Met Gly Gly His Gly Ser Arg
    4505                4510                4515

His Ser Leu Ala Ser Thr Asp Glu Lys Arg Glu Leu Leu Gly Arg
    4520                4525                4530

Gly Pro Glu Asp Glu Ile Gly Asp Pro Leu Ala
    4535                4540

<210> SEQ ID NO 20
<211> LENGTH: 4655
<212> TYPE: PRT
<213> ORGANISM: Homo sapiens

<400> SEQUENCE: 20

Met Asp Arg Gly Pro Ala Ala Val Ala Cys Thr Leu Leu Ala Leu
1               5                   10                  15

Val Ala Cys Leu Ala Pro Ala Ser Gly Gln Glu Cys Asp Ser Ala His
            20                  25                  30

Phe Arg Cys Gly Ser Gly His Cys Ile Pro Ala Asp Trp Arg Cys Asp
            35                  40                  45

Gly Thr Lys Asp Cys Ser Asp Asp Ala Asp Glu Ile Gly Cys Ala Val
    50                  55                  60

Val Thr Cys Gln Gln Gly Tyr Phe Lys Cys Gln Ser Glu Gly Gln Cys
65                  70                  75                  80

Ile Pro Asn Ser Trp Val Cys Asp Gln Asp Gln Asp Cys Asp Asp Gly
                85                  90                  95

Ser Asp Glu Arg Gln Asp Cys Ser Gln Ser Thr Cys Ser Ser His Gln
            100                 105                 110

Ile Thr Cys Ser Asn Gly Gln Cys Ile Pro Ser Glu Tyr Arg Cys Asp
            115                 120                 125

His Val Arg Asp Cys Pro Asp Gly Ala Asp Glu Asn Asp Cys Gln Tyr
            130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175
```

-continued

```
Ile Asn Cys Thr Glu Ile Cys Leu His Asn Glu Phe Ser Cys Gly Asn
            180                 185                 190
Gly Glu Cys Ile Pro Arg Ala Tyr Val Cys Asp His Asp Asn Asp Cys
        195                 200                 205
Gln Asp Gly Ser Asp Glu His Ala Cys Asn Tyr Pro Thr Cys Gly Gly
    210                 215                 220
Tyr Gln Phe Thr Cys Pro Ser Gly Arg Cys Ile Tyr Gln Asn Trp Val
225                 230                 235                 240
Cys Asp Gly Glu Asp Asp Cys Lys Asp Asn Gly Asp Glu Asp Gly Cys
            245                 250                 255
Glu Ser Gly Pro His Asp Val His Lys Cys Ser Pro Arg Glu Trp Ser
        260                 265                 270
Cys Pro Glu Ser Gly Arg Cys Ile Ser Ile Tyr Lys Val Cys Asp Gly
    275                 280                 285
Ile Leu Asp Cys Pro Gly Arg Glu Asp Glu Asn Asn Thr Ser Thr Gly
290                 295                 300
Lys Tyr Cys Ser Met Thr Leu Cys Ser Ala Leu Asn Cys Gln Tyr Gln
305                 310                 315                 320
Cys His Glu Thr Pro Tyr Gly Gly Ala Cys Phe Cys Pro Pro Gly Tyr
            325                 330                 335
Ile Ile Asn His Asn Asp Ser Arg Thr Cys Val Glu Phe Asp Asp Cys
        340                 345                 350
Gln Ile Trp Gly Ile Cys Asp Gln Lys Cys Glu Ser Arg Pro Gly Arg
    355                 360                 365
His Leu Cys His Cys Glu Glu Gly Tyr Ile Leu Glu Arg Gly Gln Tyr
370                 375                 380
Cys Lys Ala Asn Asp Ser Phe Gly Glu Ala Ser Ile Ile Phe Ser Asn
385                 390                 395                 400
Gly Arg Asp Leu Leu Ile Gly Asp Ile His Gly Arg Ser Phe Arg Ile
            405                 410                 415
Leu Val Glu Ser Gln Asn Arg Gly Val Ala Val Gly Val Ala Phe His
        420                 425                 430
Tyr His Leu Gln Arg Val Phe Trp Thr Asp Thr Val Gln Asn Lys Val
    435                 440                 445
Phe Ser Val Asp Ile Asn Gly Leu Asn Ile Gln Glu Val Leu Asn Val
450                 455                 460
Ser Val Glu Thr Pro Glu Asn Leu Ala Val Asp Trp Val Asn Asn Lys
465                 470                 475                 480
Ile Tyr Leu Val Glu Thr Lys Val Asn Arg Ile Asp Met Val Asn Leu
            485                 490                 495
Asp Gly Ser Tyr Arg Val Thr Leu Ile Thr Glu Asn Leu Gly His Pro
        500                 505                 510
Arg Gly Ile Ala Val Asp Pro Thr Val Gly Tyr Leu Phe Phe Ser Asp
    515                 520                 525
Trp Glu Ser Leu Ser Gly Glu Pro Lys Leu Glu Arg Ala Phe Met Asp
530                 535                 540
Gly Ser Asn Arg Lys Asp Leu Val Lys Thr Lys Leu Gly Trp Pro Ala
545                 550                 555                 560
Gly Val Thr Leu Asp Met Ile Ser Lys Arg Val Tyr Trp Val Asp Ser
            565                 570                 575
Arg Phe Asp Tyr Ile Glu Thr Val Thr Tyr Asp Gly Ile Gln Arg Lys
        580                 585                 590
```

```
Thr Val Val His Gly Gly Ser Leu Ile Pro His Pro Phe Gly Val Ser
            595                 600                 605

Leu Phe Glu Gly Gln Val Phe Phe Thr Asp Trp Thr Lys Met Ala Val
610                 615                 620

Leu Lys Ala Asn Lys Phe Thr Glu Thr Asn Pro Gln Val Tyr Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Asn Gly Gly Cys Glu Gln
            660                 665                 670

Val Cys Val Leu Ser His Arg Thr Asp Asn Asp Gly Leu Gly Phe Arg
            675                 680                 685

Cys Lys Cys Thr Phe Gly Phe Gln Leu Asp Thr Asp Glu Arg His Cys
690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
            740                 745                 750

Ser Thr Ile Phe Phe Ser Asp Met Ser Lys His Met Ile Phe Lys Gln
            755                 760                 765

Lys Ile Asp Gly Thr Gly Arg Glu Ile Leu Ala Ala Asn Arg Val Glu
770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
            820                 825                 830

Val His Pro Phe Ala Gly Tyr Leu Phe Phe Thr Asp Trp Phe Arg Pro
            835                 840                 845

Ala Lys Ile Met Arg Ala Trp Ser Asp Gly Ser His Leu Leu Pro Val
850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
                885                 890                 895

Ser Thr Phe Asp Gly Leu Asp Arg Arg Arg Leu Gly His Ile Glu Gln
            900                 905                 910

Met Thr His Pro Phe Gly Leu Ala Ile Phe Gly Glu His Leu Phe Phe
            915                 920                 925

Thr Asp Trp Arg Leu Gly Ala Ile Ile Arg Val Arg Lys Ala Asp Gly
930                 935                 940

Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
                965                 970                 975

Pro Thr His Pro Asn Gly Asp Cys Ser His Phe Cys Phe Pro Val Pro
            980                 985                 990

Asn Phe Gln Arg Val Cys Gly Cys Pro Tyr Gly Met Arg Leu Ala Ser
            995                 1000                1005

Asn His Leu Thr Cys Glu Gly Asp Pro Thr Asn Glu Pro Pro Thr
```

-continued

```
                1010                1015                1020
Glu Gln Cys Gly Leu Phe Ser Phe Pro Cys Lys Asn Gly Arg Cys
    1025                1030                1035

Val Pro Asn Tyr Tyr Leu Cys Asp Gly Val Asp Asp Cys His Asp
    1040                1045                1050

Asn Ser Asp Glu Gln Leu Cys Gly Thr Leu Asn Asn Thr Cys Ser
    1055                1060                1065

Ser Ser Ala Phe Thr Cys Gly His Gly Glu Cys Ile Pro Ala His
    1070                1075                1080

Trp Arg Cys Asp Lys Arg Asn Asp Cys Val Asp Gly Ser Asp Glu
    1085                1090                1095

His Asn Cys Pro Thr His Ala Pro Ala Ser Cys Leu Asp Thr Gln
    1100                1105                1110

Tyr Thr Cys Asp Asn His Gln Cys Ile Ser Lys Asn Trp Val Cys
    1115                1120                1125

Asp Thr Asp Asn Asp Cys Gly Asp Gly Ser Asp Glu Lys Asn Cys
    1130                1135                1140

Asn Ser Thr Glu Thr Cys Gln Pro Ser Gln Phe Asn Cys Pro Asn
    1145                1150                1155

His Arg Cys Ile Asp Leu Ser Phe Val Cys Asp Gly Asp Lys Asp
    1160                1165                1170

Cys Val Asp Gly Ser Asp Glu Val Gly Cys Val Leu Asn Cys Thr
    1175                1180                1185

Ala Ser Gln Phe Lys Cys Ala Ser Gly Asp Lys Cys Ile Gly Val
    1190                1195                1200

Thr Asn Arg Cys Asp Gly Val Phe Asp Cys Ser Asp Asn Ser Asp
    1205                1210                1215

Glu Ala Gly Cys Pro Thr Arg Pro Pro Gly Met Cys His Ser Asp
    1220                1225                1230

Glu Phe Gln Cys Gln Glu Asp Gly Ile Cys Ile Pro Asn Phe Trp
    1235                1240                1245

Glu Cys Asp Gly His Pro Asp Cys Leu Tyr Gly Ser Asp Glu His
    1250                1255                1260

Asn Ala Cys Val Pro Lys Thr Cys Pro Ser Ser Tyr Phe His Cys
    1265                1270                1275

Asp Asn Gly Asn Cys Ile His Arg Ala Trp Leu Cys Asp Arg Asp
    1280                1285                1290

Asn Asp Cys Gly Asp Met Ser Asp Glu Lys Asp Cys Pro Thr Gln
    1295                1300                1305

Pro Phe Arg Cys Pro Ser Trp Gln Trp Gln Cys Leu Gly His Asn
    1310                1315                1320

Ile Cys Val Asn Leu Ser Val Val Cys Asp Gly Ile Phe Asp Cys
    1325                1330                1335

Pro Asn Gly Thr Asp Glu Ser Pro Leu Cys Asn Gly Asn Ser Cys
    1340                1345                1350

Ser Asp Phe Asn Gly Gly Cys Thr His Glu Cys Val Gln Glu Pro
    1355                1360                1365

Phe Gly Ala Lys Cys Leu Cys Pro Leu Gly Phe Leu Leu Ala Asn
    1370                1375                1380

Asp Ser Lys Thr Cys Glu Asp Ile Asp Glu Cys Asp Ile Leu Gly
    1385                1390                1395

Ser Cys Ser Gln His Cys Tyr Asn Met Arg Gly Ser Phe Arg Cys
    1400                1405                1410
```

-continued

```
Ser Cys Asp Thr Gly Tyr Met Leu Glu Ser Asp Gly Arg Thr Cys
1415                1420                1425

Lys Val Thr Ala Ser Glu Ser Leu Leu Leu Leu Val Ala Ser Gln
1430                1435                1440

Asn Lys Ile Ile Ala Asp Ser Val Thr Ser Gln Val His Asn Ile
1445                1450                1455

Tyr Ser Leu Val Glu Asn Gly Ser Tyr Ile Val Ala Val Asp Phe
1460                1465                1470

Asp Ser Ile Ser Gly Arg Ile Phe Trp Ser Asp Ala Thr Gln Gly
1475                1480                1485

Lys Thr Trp Ser Ala Phe Gln Asn Gly Thr Asp Arg Arg Val Val
1490                1495                1500

Phe Asp Ser Ser Ile Ile Leu Thr Glu Thr Ile Ala Ile Asp Trp
1505                1510                1515

Val Gly Arg Asn Leu Tyr Trp Thr Asp Tyr Ala Leu Glu Thr Ile
1520                1525                1530

Glu Val Ser Lys Ile Asp Gly Ser His Arg Thr Val Leu Ile Ser
1535                1540                1545

Lys Asn Leu Thr Asn Pro Arg Gly Leu Ala Leu Asp Pro Arg Met
1550                1555                1560

Asn Glu His Leu Leu Phe Trp Ser Asp Trp Gly His His Pro Arg
1565                1570                1575

Ile Glu Arg Ala Ser Met Asp Gly Ser Met Arg Thr Val Ile Val
1580                1585                1590

Gln Asp Lys Ile Phe Trp Pro Cys Gly Leu Thr Ile Asp Tyr Pro
1595                1600                1605

Asn Arg Leu Leu Tyr Phe Met Asp Ser Tyr Leu Asp Tyr Met Asp
1610                1615                1620

Phe Cys Asp Tyr Asn Gly His His Arg Arg Gln Val Ile Ala Ser
1625                1630                1635

Asp Leu Ile Ile Arg His Pro Tyr Ala Leu Thr Leu Phe Glu Asp
1640                1645                1650

Ser Val Tyr Trp Thr Asp Arg Ala Thr Arg Arg Val Met Arg Ala
1655                1660                1665

Asn Lys Trp His Gly Gly Asn Gln Ser Val Val Met Tyr Asn Ile
1670                1675                1680

Gln Trp Pro Leu Gly Ile Val Ala Val His Pro Ser Lys Gln Pro
1685                1690                1695

Asn Ser Val Asn Pro Cys Ala Phe Ser Arg Cys Ser His Leu Cys
1700                1705                1710

Leu Leu Ser Ser Gln Gly Pro His Phe Tyr Ser Cys Val Cys Pro
1715                1720                1725

Ser Gly Trp Ser Leu Ser Pro Asp Leu Leu Asn Cys Leu Arg Asp
1730                1735                1740

Asp Gln Pro Phe Leu Ile Thr Val Arg Gln His Ile Ile Phe Gly
1745                1750                1755

Ile Ser Leu Asn Pro Glu Val Lys Ser Asn Asp Ala Met Val Pro
1760                1765                1770

Ile Ala Gly Ile Gln Asn Gly Leu Asp Val Glu Phe Asp Asp Ala
1775                1780                1785

Glu Gln Tyr Ile Tyr Trp Val Glu Asn Pro Gly Glu Ile His Arg
1790                1795                1800
```

```
Val Lys Thr Asp Gly Thr Asn Arg Thr Val Phe Ala Ser Ile Ser
    1805                1810                1815

Met Val Gly Pro Ser Met Asn Leu Ala Leu Asp Trp Ile Ser Arg
    1820                1825                1830

Asn Leu Tyr Ser Thr Asn Pro Arg Thr Gln Ser Ile Glu Val Leu
    1835                1840                1845

Thr Leu His Gly Asp Ile Arg Tyr Arg Lys Thr Leu Ile Ala Asn
    1850                1855                1860

Asp Gly Thr Ala Leu Gly Val Gly Phe Pro Ile Gly Ile Thr Val
    1865                1870                1875

Asp Pro Ala Arg Gly Lys Leu Tyr Trp Ser Asp Gln Gly Thr Asp
    1880                1885                1890

Ser Gly Val Pro Ala Lys Ile Ala Ser Ala Asn Met Asp Gly Thr
    1895                1900                1905

Ser Val Lys Thr Leu Phe Thr Gly Asn Leu Glu His Leu Glu Cys
    1910                1915                1920

Val Thr Leu Asp Ile Glu Glu Gln Lys Leu Tyr Trp Ala Val Thr
    1925                1930                1935

Gly Arg Gly Val Ile Glu Arg Gly Asn Val Asp Gly Thr Asp Arg
    1940                1945                1950

Met Ile Leu Val His Gln Leu Ser His Pro Trp Gly Ile Ala Val
    1955                1960                1965

His Asp Ser Phe Leu Tyr Tyr Thr Asp Glu Gln Tyr Glu Val Ile
    1970                1975                1980

Glu Arg Val Asp Lys Ala Thr Gly Ala Asn Lys Ile Val Leu Arg
    1985                1990                1995

Asp Asn Val Pro Asn Leu Arg Gly Leu Gln Val Tyr His Arg Arg
    2000                2005                2010

Asn Ala Ala Glu Ser Ser Asn Gly Cys Ser Asn Asn Met Asn Ala
    2015                2020                2025

Cys Gln Gln Ile Cys Leu Pro Val Pro Gly Gly Leu Phe Ser Cys
    2030                2035                2040

Ala Cys Ala Thr Gly Phe Lys Leu Asn Pro Asp Asn Arg Ser Cys
    2045                2050                2055

Ser Pro Tyr Asn Ser Phe Ile Val Val Ser Met Leu Ser Ala Ile
    2060                2065                2070

Arg Gly Phe Ser Leu Glu Leu Ser Asp His Ser Glu Thr Met Val
    2075                2080                2085

Pro Val Ala Gly Gln Gly Arg Asn Ala Leu His Val Asp Val Asp
    2090                2095                2100

Val Ser Ser Gly Phe Ile Tyr Trp Cys Asp Phe Ser Ser Ser Val
    2105                2110                2115

Ala Ser Asp Asn Ala Ile Arg Arg Ile Lys Pro Asp Gly Ser Ser
    2120                2125                2130

Leu Met Asn Ile Val Thr His Gly Ile Gly Glu Asn Gly Val Arg
    2135                2140                2145

Gly Ile Ala Val Asp Trp Val Ala Gly Asn Leu Tyr Phe Thr Asn
    2150                2155                2160

Ala Phe Val Ser Glu Thr Leu Ile Glu Val Leu Arg Ile Asn Thr
    2165                2170                2175

Thr Tyr Arg Arg Val Leu Leu Lys Val Thr Val Asp Met Pro Arg
    2180                2185                2190

His Ile Val Val Asp Pro Lys Asn Arg Tyr Leu Phe Trp Ala Asp
```

-continued

```
                2195                2200                2205

Tyr Gly Gln Arg Pro Lys Ile Glu Arg Ser Phe Leu Asp Cys Thr
        2210                2215                2220

Asn Arg Thr Val Leu Val Ser Glu Gly Ile Val Thr Pro Arg Gly
        2225                2230                2235

Leu Ala Val Asp Arg Ser Asp Gly Tyr Val Tyr Trp Val Asp Asp
        2240                2245                2250

Ser Leu Asp Ile Ile Ala Arg Ile Arg Ile Asn Gly Glu Asn Ser
        2255                2260                2265

Glu Val Ile Arg Tyr Gly Ser Arg Tyr Pro Thr Pro Tyr Gly Ile
        2270                2275                2280

Thr Val Phe Glu Asn Ser Ile Ile Trp Val Asp Arg Asn Leu Lys
        2285                2290                2295

Lys Ile Phe Gln Ala Ser Lys Glu Pro Glu Asn Thr Glu Pro Pro
        2300                2305                2310

Thr Val Ile Arg Asp Asn Ile Asn Trp Leu Arg Asp Val Thr Ile
        2315                2320                2325

Phe Asp Lys Gln Val Gln Pro Arg Ser Pro Ala Glu Val Asn Asn
        2330                2335                2340

Asn Pro Cys Leu Glu Asn Asn Gly Gly Cys Ser His Leu Cys Phe
        2345                2350                2355

Ala Leu Pro Gly Leu His Thr Pro Lys Cys Asp Cys Ala Phe Gly
        2360                2365                2370

Thr Leu Gln Ser Asp Gly Lys Asn Cys Ala Ile Ser Thr Glu Asn
        2375                2380                2385

Phe Leu Ile Phe Ala Leu Ser Asn Ser Leu Arg Ser Leu His Leu
        2390                2395                2400

Asp Pro Glu Asn His Ser Pro Pro Phe Gln Thr Ile Asn Val Glu
        2405                2410                2415

Arg Thr Val Met Ser Leu Asp Tyr Asp Ser Val Ser Asp Arg Ile
        2420                2425                2430

Tyr Phe Thr Gln Asn Leu Ala Ser Gly Val Gly Gln Ile Ser Tyr
        2435                2440                2445

Ala Thr Leu Ser Ser Gly Ile His Thr Pro Thr Val Ile Ala Ser
        2450                2455                2460

Gly Ile Gly Thr Ala Asp Gly Ile Ala Phe Asp Trp Ile Thr Arg
        2465                2470                2475

Arg Ile Tyr Tyr Ser Asp Tyr Leu Asn Gln Met Ile Asn Ser Met
        2480                2485                2490

Ala Glu Asp Gly Ser Asn Arg Thr Val Ile Ala Arg Val Pro Lys
        2495                2500                2505

Pro Arg Ala Ile Val Leu Asp Pro Cys Gln Gly Tyr Leu Tyr Trp
        2510                2515                2520

Ala Asp Trp Asp Thr His Ala Lys Ile Glu Arg Ala Thr Leu Gly
        2525                2530                2535

Gly Asn Phe Arg Val Pro Ile Val Asn Ser Ser Leu Val Met Pro
        2540                2545                2550

Ser Gly Leu Thr Leu Asp Tyr Glu Glu Asp Leu Leu Tyr Trp Val
        2555                2560                2565

Asp Ala Ser Leu Gln Arg Ile Glu Arg Ser Thr Leu Thr Gly Val
        2570                2575                2580

Asp Arg Glu Val Ile Val Asn Ala Ala Val His Ala Phe Gly Leu
        2585                2590                2595
```

```
Thr Leu Tyr Gly Gln Tyr Ile Tyr Trp Thr Asp Leu Tyr Thr Gln
    2600                2605                2610

Arg Ile Tyr Arg Ala Asn Lys Tyr Asp Gly Ser Gly Gln Ile Ala
    2615                2620                2625

Met Thr Thr Asn Leu Leu Ser Gln Pro Arg Gly Ile Asn Thr Val
    2630                2635                2640

Val Lys Asn Gln Lys Gln Gln Cys Asn Asn Pro Cys Glu Gln Phe
    2645                2650                2655

Asn Gly Gly Cys Ser His Ile Cys Ala Pro Gly Pro Asn Gly Ala
    2660                2665                2670

Glu Cys Gln Cys Pro His Glu Gly Asn Trp Tyr Leu Ala Asn Asn
    2675                2680                2685

Arg Lys His Cys Ile Val Asp Asn Gly Glu Arg Cys Gly Ala Ser
    2690                2695                2700

Ser Phe Thr Cys Ser Asn Gly Arg Cys Ile Ser Glu Glu Trp Lys
    2705                2710                2715

Cys Asp Asn Asp Asn Asp Cys Gly Asp Gly Ser Asp Glu Met Glu
    2720                2725                2730

Ser Val Cys Ala Leu His Thr Cys Ser Pro Thr Ala Phe Thr Cys
    2735                2740                2745

Ala Asn Gly Arg Cys Val Gln Tyr Ser Tyr Arg Cys Asp Tyr Tyr
    2750                2755                2760

Asn Asp Cys Gly Asp Gly Ser Asp Glu Ala Gly Cys Leu Phe Arg
    2765                2770                2775

Asp Cys Asn Ala Thr Thr Glu Phe Met Cys Asn Asn Arg Arg Cys
    2780                2785                2790

Ile Pro Arg Glu Phe Ile Cys Asn Gly Val Asp Asn Cys His Asp
    2795                2800                2805

Asn Asn Thr Ser Asp Glu Lys Asn Cys Pro Asp Arg Thr Cys Gln
    2810                2815                2820

Ser Gly Tyr Thr Lys Cys His Asn Ser Asn Ile Cys Ile Pro Arg
    2825                2830                2835

Val Tyr Leu Cys Asp Gly Asp Asn Asp Cys Gly Asp Asn Ser Asp
    2840                2845                2850

Glu Asn Pro Thr Tyr Cys Thr His Thr Cys Ser Ser Ser Glu
    2855                2860                2865

Phe Gln Cys Ala Ser Gly Arg Cys Ile Pro Gln His Trp Tyr Cys
    2870                2875                2880

Asp Gln Glu Thr Asp Cys Phe Asp Ala Ser Asp Glu Pro Ala Ser
    2885                2890                2895

Cys Gly His Ser Glu Arg Thr Cys Leu Ala Asp Glu Phe Lys Cys
    2900                2905                2910

Asp Gly Gly Arg Cys Ile Pro Ser Glu Trp Ile Cys Asp Gly Asp
    2915                2920                2925

Asn Asp Cys Gly Asp Met Ser Asp Glu Asp Lys Arg His Gln Cys
    2930                2935                2940

Gln Asn Gln Asn Cys Ser Asp Ser Glu Phe Leu Cys Val Asn Asp
    2945                2950                2955

Arg Pro Pro Asp Arg Arg Cys Ile Pro Gln Ser Trp Val Cys Asp
    2960                2965                2970

Gly Asp Val Asp Cys Thr Asp Gly Tyr Asp Glu Asn Gln Asn Cys
    2975                2980                2985
```

-continued

```
Thr Arg Arg Thr Cys Ser Glu Asn Glu Phe Thr Cys Gly Tyr Gly
2990                2995                3000
Leu Cys Ile Pro Lys Ile Phe Arg Cys Asp Arg His Asn Asp Cys
3005                3010                3015
Gly Asp Tyr Ser Asp Glu Arg Gly Cys Leu Tyr Gln Thr Cys Gln
3020                3025                3030
Gln Asn Gln Phe Thr Cys Gln Asn Gly Arg Cys Ile Ser Lys Thr
3035                3040                3045
Phe Val Cys Asp Glu Asp Asn Asp Cys Gly Asp Gly Ser Asp Glu
3050                3055                3060
Leu Met His Leu Cys His Thr Pro Glu Pro Thr Cys Pro Pro His
3065                3070                3075
Glu Phe Lys Cys Asp Asn Gly Arg Cys Ile Glu Met Met Lys Leu
3080                3085                3090
Cys Asn His Leu Asp Asp Cys Leu Asp Asn Ser Asp Glu Lys Gly
3095                3100                3105
Cys Gly Ile Asn Glu Cys His Asp Pro Ser Ile Ser Gly Cys Asp
3110                3115                3120
His Asn Cys Thr Asp Thr Leu Thr Ser Phe Tyr Cys Ser Cys Arg
3125                3130                3135
Pro Gly Tyr Lys Leu Met Ser Asp Lys Arg Thr Cys Val Asp Ile
3140                3145                3150
Asp Glu Cys Thr Glu Met Pro Phe Val Cys Ser Gln Lys Cys Glu
3155                3160                3165
Asn Val Ile Gly Ser Tyr Ile Cys Lys Cys Ala Pro Gly Tyr Leu
3170                3175                3180
Arg Glu Pro Asp Gly Lys Thr Cys Arg Gln Asn Ser Asn Ile Glu
3185                3190                3195
Pro Tyr Leu Ile Phe Ser Asn Arg Tyr Tyr Leu Arg Asn Leu Thr
3200                3205                3210
Ile Asp Gly Tyr Phe Tyr Ser Leu Ile Leu Glu Gly Leu Asp Asn
3215                3220                3225
Val Val Ala Leu Asp Phe Asp Arg Val Glu Lys Arg Leu Tyr Trp
3230                3235                3240
Ile Asp Thr Gln Arg Gln Val Ile Glu Arg Met Phe Leu Asn Lys
3245                3250                3255
Thr Asn Lys Glu Thr Ile Ile Asn His Arg Leu Pro Ala Ala Glu
3260                3265                3270
Ser Leu Ala Val Asp Trp Val Ser Arg Lys Leu Tyr Trp Leu Asp
3275                3280                3285
Ala Arg Leu Asp Gly Leu Phe Val Ser Asp Leu Asn Gly Gly His
3290                3295                3300
Arg Arg Met Leu Ala Gln His Cys Val Asp Ala Asn Asn Thr Phe
3305                3310                3315
Cys Phe Asp Asn Pro Arg Gly Leu Ala Leu His Pro Gln Tyr Gly
3320                3325                3330
Tyr Leu Tyr Trp Ala Asp Trp Gly His Arg Ala Tyr Ile Gly Arg
3335                3340                3345
Val Gly Met Asp Gly Thr Asn Lys Ser Val Ile Ile Ser Thr Lys
3350                3355                3360
Leu Glu Trp Pro Asn Gly Ile Thr Ile Asp Tyr Thr Asn Asp Leu
3365                3370                3375
Leu Tyr Trp Ala Asp Ala His Leu Gly Tyr Ile Glu Tyr Ser Asp
```

-continued

```
                3380                3385                3390

Leu Glu Gly His His Arg His Thr Val Tyr Asp Gly Ala Leu Pro
    3395                3400                3405

His Pro Phe Ala Ile Thr Ile Phe Glu Asp Thr Ile Tyr Trp Thr
    3410                3415                3420

Asp Trp Asn Thr Arg Thr Val Glu Lys Gly Asn Lys Tyr Asp Gly
    3425                3430                3435

Ser Asn Arg Gln Thr Leu Val Asn Thr Thr His Arg Pro Phe Asp
    3440                3445                3450

Ile His Val Tyr His Pro Tyr Arg Gln Pro Ile Val Ser Asn Pro
    3455                3460                3465

Cys Gly Thr Asn Asn Gly Gly Cys Ser His Leu Cys Leu Ile Lys
    3470                3475                3480

Pro Gly Gly Lys Gly Phe Thr Cys Glu Cys Pro Asp Asp Phe Arg
    3485                3490                3495

Thr Leu Gln Leu Ser Gly Ser Thr Tyr Cys Met Pro Met Cys Ser
    3500                3505                3510

Ser Thr Gln Phe Leu Cys Ala Asn Asn Glu Lys Cys Ile Pro Ile
    3515                3520                3525

Trp Trp Lys Cys Asp Gly Gln Lys Asp Cys Ser Asp Gly Ser Asp
    3530                3535                3540

Glu Leu Ala Leu Cys Pro Gln Arg Phe Cys Arg Leu Gly Gln Phe
    3545                3550                3555

Gln Cys Ser Asp Gly Asn Cys Thr Ser Pro Gln Thr Leu Cys Asn
    3560                3565                3570

Ala His Gln Asn Cys Pro Asp Gly Ser Asp Glu Asp Arg Leu Leu
    3575                3580                3585

Cys Glu Asn His His Cys Asp Ser Asn Glu Trp Gln Cys Ala Asn
    3590                3595                3600

Lys Arg Cys Ile Pro Glu Ser Trp Gln Cys Asp Thr Phe Asn Asp
    3605                3610                3615

Cys Glu Asp Asn Ser Asp Glu Asp Ser Ser His Cys Ala Ser Arg
    3620                3625                3630

Thr Cys Arg Pro Gly Gln Phe Arg Cys Ala Asn Gly Arg Cys Ile
    3635                3640                3645

Pro Gln Ala Trp Lys Cys Asp Val Asp Asn Asp Cys Gly Asp His
    3650                3655                3660

Ser Asp Glu Pro Ile Glu Cys Met Ser Ser Ala His Leu Cys
    3665                3670                3675

Asp Asn Phe Thr Glu Phe Ser Cys Lys Thr Asn Tyr Arg Cys Ile
    3680                3685                3690

Pro Lys Trp Ala Val Cys Asn Gly Val Asp Asp Cys Arg Asp Asn
    3695                3700                3705

Ser Asp Glu Gln Gly Cys Glu Arg Thr Cys His Pro Val Gly
    3710                3715                3720

Asp Phe Arg Cys Lys Asn His His Cys Ile Pro Leu Arg Trp Gln
    3725                3730                3735

Cys Asp Gly Gln Asn Asp Cys Gly Asp Asn Ser Asp Glu Glu Asn
    3740                3745                3750

Cys Ala Pro Arg Glu Cys Thr Glu Ser Glu Phe Arg Cys Val Asn
    3755                3760                3765

Gln Gln Cys Ile Pro Ser Arg Trp Ile Cys Asp His Tyr Asn Asp
    3770                3775                3780
```

```
Cys Gly Asp Asn Ser Asp Glu Arg Asp Cys Glu Met Arg Thr Cys
3785                3790                3795

His Pro Glu Tyr Phe Gln Cys Thr Ser Gly His Cys Val His Ser
    3800                3805                3810

Glu Leu Lys Cys Asp Gly Ser Ala Asp Cys Leu Asp Ala Ser Asp
3815                3820                3825

Glu Ala Asp Cys Pro Thr Arg Phe Pro Asp Gly Ala Tyr Cys Gln
3830                3835                3840

Ala Thr Met Phe Glu Cys Lys Asn His Val Cys Ile Pro Pro Tyr
3845                3850                3855

Trp Lys Cys Asp Gly Asp Asp Cys Gly Asp Gly Ser Asp Glu
3860                3865                3870

Glu Leu His Leu Cys Leu Asp Val Pro Cys Asn Ser Pro Asn Arg
3875                3880                3885

Phe Arg Cys Asp Asn Asn Arg Cys Ile Tyr Ser His Glu Val Cys
3890                3895                3900

Asn Gly Val Asp Asp Cys Gly Asp Gly Thr Asp Glu Thr Glu Glu
3905                3910                3915

His Cys Arg Lys Pro Thr Pro Lys Pro Cys Thr Glu Tyr Glu Tyr
3920                3925                3930

Lys Cys Gly Asn Gly His Cys Ile Pro His Asp Asn Val Cys Asp
3935                3940                3945

Asp Ala Asp Asp Cys Gly Asp Trp Ser Asp Glu Leu Gly Cys Asn
3950                3955                3960

Lys Gly Lys Glu Arg Thr Cys Ala Glu Asn Ile Cys Glu Gln Asn
3965                3970                3975

Cys Thr Gln Leu Asn Glu Gly Gly Phe Ile Cys Ser Cys Thr Ala
3980                3985                3990

Gly Phe Glu Thr Asn Val Phe Asp Arg Thr Ser Cys Leu Asp Ile
3995                4000                4005

Asn Glu Cys Glu Gln Phe Gly Thr Cys Pro Gln His Cys Arg Asn
4010                4015                4020

Thr Lys Gly Ser Tyr Glu Cys Val Cys Ala Asp Gly Phe Thr Ser
4025                4030                4035

Met Ser Asp Arg Pro Gly Lys Arg Cys Ala Ala Glu Gly Ser Ser
4040                4045                4050

Pro Leu Leu Leu Leu Pro Asp Asn Val Arg Ile Arg Lys Tyr Asn
4055                4060                4065

Leu Ser Ser Glu Arg Phe Ser Glu Tyr Leu Gln Asp Glu Glu Tyr
4070                4075                4080

Ile Gln Ala Val Asp Tyr Asp Trp Asp Pro Lys Asp Ile Gly Leu
4085                4090                4095

Ser Val Val Tyr Tyr Thr Val Arg Gly Glu Gly Ser Arg Phe Gly
4100                4105                4110

Ala Ile Lys Arg Ala Tyr Ile Pro Asn Phe Glu Ser Gly Arg Asn
4115                4120                4125

Asn Leu Val Gln Glu Val Asp Leu Lys Leu Lys Tyr Val Met Gln
4130                4135                4140

Pro Asp Gly Ile Ala Val Asp Trp Val Gly Arg His Ile Tyr Trp
4145                4150                4155

Ser Asp Val Lys Asn Lys Arg Ile Glu Val Ala Lys Leu Asp Gly
4160                4165                4170
```

-continued

```
Arg Tyr Arg Lys Trp Leu Ile Ser Thr Asp Leu Asp Gln Pro Ala
4175                4180                4185

Ala Ile Ala Val Asn Pro Lys Leu Gly Leu Met Phe Trp Thr Asp
4190                4195                4200

Trp Gly Lys Glu Pro Lys Ile Glu Ser Ala Trp Met Asn Gly Glu
4205                4210                4215

Asp Arg Asn Ile Leu Val Phe Glu Asp Leu Gly Trp Pro Thr Gly
4220                4225                4230

Leu Ser Ile Asp Tyr Leu Asn Asn Asp Arg Ile Tyr Trp Ser Asp
4235                4240                4245

Phe Lys Glu Asp Val Ile Glu Thr Ile Lys Tyr Asp Gly Thr Asp
4250                4255                4260

Arg Arg Val Ile Ala Lys Glu Ala Met Asn Pro Tyr Ser Leu Asp
4265                4270                4275

Ile Phe Glu Asp Gln Leu Tyr Trp Ile Ser Lys Glu Lys Gly Glu
4280                4285                4290

Val Trp Lys Gln Asn Lys Phe Gly Gln Gly Lys Lys Glu Lys Thr
4295                4300                4305

Leu Val Val Asn Pro Trp Leu Thr Gln Val Arg Ile Phe His Gln
4310                4315                4320

Leu Arg Tyr Asn Lys Ser Val Pro Asn Leu Cys Lys Gln Ile Cys
4325                4330                4335

Ser His Leu Cys Leu Leu Arg Pro Gly Gly Tyr Ser Cys Ala Cys
4340                4345                4350

Pro Gln Gly Ser Ser Phe Ile Glu Gly Ser Thr Thr Glu Cys Asp
4355                4360                4365

Ala Ala Ile Glu Leu Pro Ile Asn Leu Pro Pro Cys Arg Cys
4370                4375                4380

Met His Gly Gly Asn Cys Tyr Phe Asp Glu Thr Asp Leu Pro Lys
4385                4390                4395

Cys Lys Cys Pro Ser Gly Tyr Thr Gly Lys Tyr Cys Glu Met Ala
4400                4405                4410

Phe Ser Lys Gly Ile Ser Pro Gly Thr Thr Ala Val Ala Val Leu
4415                4420                4425

Leu Thr Ile Leu Leu Ile Val Val Ile Gly Ala Leu Ala Ile Ala
4430                4435                4440

Gly Phe Phe His Tyr Arg Arg Thr Gly Ser Leu Leu Pro Ala Leu
4445                4450                4455

Pro Lys Leu Pro Ser Leu Ser Ser Leu Val Lys Pro Ser Glu Asn
4460                4465                4470

Gly Asn Gly Val Thr Phe Arg Ser Gly Ala Asp Leu Asn Met Asp
4475                4480                4485

Ile Gly Val Ser Gly Phe Gly Pro Glu Thr Ala Ile Asp Arg Ser
4490                4495                4500

Met Ala Met Ser Glu Asp Phe Val Met Glu Met Gly Lys Gln Pro
4505                4510                4515

Ile Ile Phe Glu Asn Pro Met Tyr Ser Ala Arg Asp Ser Ala Val
4520                4525                4530

Lys Val Val Gln Pro Ile Gln Val Thr Val Ser Glu Asn Val Asp
4535                4540                4545

Asn Lys Asn Tyr Gly Ser Pro Ile Asn Pro Ser Glu Ile Val Pro
4550                4555                4560

Glu Thr Asn Pro Thr Ser Pro Ala Ala Asp Gly Thr Gln Val Thr
```

```
                    4565                4570                4575

Lys Trp Asn Leu Phe Lys Arg Lys Ser Lys Gln Thr Thr Asn Phe
    4580                4585                4590

Glu Asn Pro Ile Tyr Ala Gln Met Glu Asn Glu Gln Lys Glu Ser
    4595                4600                4605

Val Ala Ala Thr Pro Pro Ser Pro Ser Leu Pro Ala Lys Pro
    4610                4615                4620

Lys Pro Pro Ser Arg Arg Asp Pro Thr Pro Thr Tyr Ser Ala Thr
    4625                4630                4635

Glu Asp Thr Phe Lys Asp Thr Ala Asn Leu Val Lys Glu Asp Ser
    4640                4645                4650

Glu Val
    4655

<210> SEQ ID NO 21
<211> LENGTH: 1905
<212> TYPE: PRT
<213> ORGANISM: Homo sapiens

<400> SEQUENCE: 21

Met Arg Arg Gln Trp Gly Ala Leu Leu Gly Ala Leu Leu Cys Ala
1               5                   10                  15

His Gly Leu Ala Ser Ser Pro Glu Cys Ala Cys Gly Arg Ser His Phe
                20                  25                  30

Thr Cys Ala Val Ser Ala Leu Gly Glu Cys Thr Cys Ile Pro Ala Gln
                35                  40                  45

Trp Gln Cys Asp Gly Asp Asn Asp Cys Gly Asp His Ser Asp Glu Asp
50                  55                  60

Gly Cys Ile Leu Pro Thr Cys Ser Pro Leu Asp Phe His Cys Asp Asn
65                  70                  75                  80

Gly Lys Cys Ile Arg Arg Ser Trp Val Cys Asp Gly Asp Asn Asp Cys
                85                  90                  95

Glu Asp Asp Ser Asp Glu Gln Asp Cys Pro Pro Arg Glu Cys Glu Glu
                100                 105                 110

Asp Glu Phe Pro Cys Gln Asn Gly Tyr Cys Ile Arg Ser Leu Trp His
                115                 120                 125

Cys Asp Gly Asp Asn Asp Cys Gly Asp Asn Ser Asp Glu Gln Cys Asp
                130                 135                 140

Met Arg Lys Cys Ser Asp Lys Glu Phe Arg Cys Ser Asp Gly Ser Cys
145                 150                 155                 160

Ile Ala Glu His Trp Tyr Cys Asp Gly Asp Thr Asp Cys Lys Asp Gly
                165                 170                 175

Ser Asp Glu Glu Asn Cys Pro Ser Ala Val Pro Ala Pro Pro Cys Asn
                180                 185                 190

Leu Glu Glu Phe Gln Cys Ala Tyr Gly Arg Cys Ile Leu Asp Ile Tyr
                195                 200                 205

His Cys Asp Gly Asp Asp Cys Gly Asp Trp Ser Asp Glu Ser Asp
                210                 215                 220

Cys Ser Ser His Gln Pro Cys Arg Ser Gly Glu Phe Met Cys Asp Ser
225                 230                 235                 240

Gly Leu Cys Ile Asn Ala Gly Trp Arg Cys Asp Gly Asp Ala Asp Cys
                245                 250                 255

Asp Asp Gln Ser Asp Glu Arg Asn Cys Thr Thr Ser Met Cys Thr Ala
                260                 265                 270
```

```
Glu Gln Phe Arg Cys His Ser Gly Arg Cys Val Arg Leu Ser Trp Arg
            275                 280                 285
Cys Asp Gly Glu Asp Cys Ala Asp Asn Ser Asp Glu Glu Asn Cys
290                 295                 300
Glu Asn Thr Gly Ser Pro Gln Cys Ala Leu Asp Gln Phe Leu Cys Trp
305                 310                 315                 320
Asn Gly Arg Cys Ile Gly Gln Arg Lys Leu Cys Asn Gly Val Asn Asp
            325                 330                 335
Cys Gly Asp Ser Asp Glu Ser Pro Gln Gln Asn Cys Arg Pro Arg
            340                 345                 350
Thr Gly Glu Glu Asn Cys Asn Val Asn Asn Gly Gly Cys Ala Gln Lys
            355                 360                 365
Cys Gln Met Val Arg Gly Ala Val Gln Cys Thr Cys His Thr Gly Tyr
            370                 375                 380
Arg Leu Thr Glu Asp Gly His Thr Cys Gln Asp Val Asn Glu Cys Ala
385                 390                 395                 400
Glu Glu Gly Tyr Cys Ser Gln Gly Cys Thr Asn Ser Glu Gly Ala Phe
                405                 410                 415
Gln Cys Trp Cys Glu Thr Gly Tyr Glu Leu Arg Pro Asp Arg Arg Ser
            420                 425                 430
Cys Lys Ala Leu Gly Pro Glu Pro Val Leu Leu Phe Ala Asn Arg Ile
            435                 440                 445
Asp Ile Arg Gln Val Leu Pro His Arg Ser Glu Tyr Thr Leu Leu Leu
            450                 455                 460
Asn Asn Leu Glu Asn Ala Ile Ala Leu Asp Phe His His Arg Arg Glu
465                 470                 475                 480
Leu Val Phe Trp Ser Asp Val Thr Leu Asp Arg Ile Leu Arg Ala Asn
                485                 490                 495
Leu Asn Gly Ser Asn Val Glu Val Val Ser Thr Gly Leu Glu Ser
            500                 505                 510      Ser
Pro Gly Gly Leu Ala Val Asp Trp Val His Asp Lys Leu Tyr Trp Thr
            515                 520                 525
Asp Ser Gly Thr Ser Arg Ile Glu Val Ala Asn Leu Asp Gly Ala His
530                 535                 540
Arg Lys Val Leu Leu Trp Gln Asn Leu Glu Lys Pro Arg Ala Ile Ala
545                 550                 555                 560
Leu His Pro Met Glu Gly Thr Ile Tyr Trp Thr Asp Trp Gly Asn Thr
                565                 570                 575
Pro Arg Ile Glu Ala Ser Ser Met Asp Gly Ser Gly Arg Arg Ile Ile
            580                 585                 590
Ala Asp Thr His Leu Phe Trp Pro Asn Gly Leu Thr Ile Asp Tyr Ala
            595                 600                 605
Gly Arg Arg Met Tyr Trp Val Asp Ala Lys His His Val Ile Glu Arg
            610                 615                 620
Ala Asn Leu Asp Gly Ser His Arg Lys Ala Val Ile Ser Gln Gly Leu
625                 630                 635                 640
Pro His Pro Phe Ala Ile Thr Val Phe Glu Asp Ser Leu Tyr Trp Thr
                645                 650                 655
Asp Trp His Thr Lys Ser Ile Asn Ser Ala Asn Lys Phe Thr Gly Lys
            660                 665                 670
Asn Gln Glu Ile Ile Arg Asn Lys Leu His Phe Pro Met Asp Ile His
            675                 680                 685
Thr Leu His Pro Gln Arg Gln Pro Ala Gly Lys Asn Arg Cys Gly Asp
```

-continued

```
            690                 695                 700
Asn Asn Gly Gly Cys Thr His Leu Cys Leu Pro Ser Gly Gln Asn Tyr
705                 710                 715                 720
Thr Cys Ala Cys Pro Thr Gly Phe Arg Lys Ile Ser Ser His Ala Cys
                725                 730                 735
Ala Gln Ser Leu Asp Lys Phe Leu Leu Phe Ala Arg Arg Met Asp Ile
                740                 745                 750
Arg Arg Ile Ser Phe Asp Thr Glu Asp Leu Ser Asp Val Ile Pro
                755                 760                 765
Leu Ala Asp Val Arg Ser Ala Val Ala Leu Asp Trp Asp Ser Arg Asp
770                 775                 780
Asp His Val Tyr Trp Thr Asp Val Ser Thr Asp Thr Ile Ser Arg Ala
785                 790                 795                 800
Lys Trp Asp Gly Thr Gly Gln Glu Val Val Asp Thr Ser Leu Glu
                805                 810                 815
Ser Pro Ala Gly Leu Ala Ile Asp Trp Val Thr Asn Lys Leu Tyr Trp
                820                 825                 830
Thr Asp Ala Gly Thr Asp Arg Ile Glu Val Ala Asn Thr Asp Gly Ser
                835                 840                 845
Met Arg Thr Val Leu Ile Trp Glu Asn Leu Asp Arg Pro Arg Asp Ile
    850                 855                 860
Val Val Glu Pro Met Gly Gly Tyr Met Tyr Trp Thr Asp Trp Gly Ala
865                 870                 875                 880
Ser Pro Lys Ile Glu Arg Ala Gly Met Asp Ala Ser Gly Arg Gln Val
                885                 890                 895
Ile Ile Ser Ser Asn Leu Thr Trp Pro Asn Gly Leu Ala Ile Asp Tyr
                900                 905                 910
Gly Ser Gln Arg Leu Tyr Trp Ala Asp Ala Gly Met Lys Thr Ile Glu
                915                 920                 925
Phe Ala Gly Leu Asp Gly Ser Lys Arg Lys Val Leu Ile Gly Ser Gln
                930                 935                 940
Leu Pro His Pro Phe Gly Leu Thr Leu Tyr Gly Glu Arg Ile Tyr Trp
945                 950                 955                 960
Thr Asp Trp Gln Thr Lys Ser Ile Gln Ser Ala Asp Arg Leu Thr Gly
                965                 970                 975
Leu Asp Arg Glu Thr Leu Gln Glu Asn Leu Glu Asn Leu Met Asp Ile
                980                 985                 990
His Val Phe His Arg Arg Pro  Pro Val Ser Thr Pro  Cys Ala Met
                995                 1000                1005
Glu Asn  Gly Gly Cys Ser His  Leu Cys Leu Arg Ser  Pro Asn Pro
1010                1015                1020
Ser Gly  Phe Ser Cys Thr Cys  Pro Thr Gly Ile Asn  Leu Leu Ser
    1025                1030                1035
Asp Gly  Lys Thr Cys Ser Pro  Gly Met Asn Ser Phe  Leu Ile Phe
    1040                1045                1050
Ala Arg  Arg Ile Asp Ile Arg  Met Val Ser Leu Asp  Ile Pro Tyr
    1055                1060                1065
Phe Ala  Asp Val Val Pro  Ile Asn Ile Thr Met  Lys Asn Thr
    1070                1075                1080
Ile Ala  Ile Gly Val Asp Pro  Gln Glu Gly Lys Val  Tyr Trp Ser
    1085                1090                1095
Asp Ser  Thr Leu His Arg Ile  Ser Arg Ala Asn Leu  Asp Gly Ser
    1100                1105                1110
```

-continued

Gln His Glu Asp Ile Ile Thr Thr Gly Leu Gln Thr Thr Asp Gly
1115                1120                    1125

Leu Ala Val Asp Ala Ile Gly Arg Lys Val Tyr Trp Thr Asp Thr
1130                1135                    1140

Gly Thr Asn Arg Ile Glu Val Gly Asn Leu Asp Gly Ser Met Arg
1145                1150                    1155

Lys Val Leu Val Trp Gln Asn Leu Asp Ser Pro Arg Ala Ile Val
1160                1165                    1170

Leu Tyr His Glu Met Gly Phe Met Tyr Trp Thr Asp Trp Gly Glu
1175                1180                    1185

Asn Ala Lys Leu Glu Arg Ser Gly Met Asp Gly Ser Asp Arg Ala
1190                1195                    1200

Val Leu Ile Asn Asn Asn Leu Gly Trp Pro Asn Gly Leu Thr Val
1205                1210                    1215

Asp Lys Ala Ser Ser Gln Leu Leu Trp Ala Asp Ala His Thr Glu
1220                1225                    1230

Arg Ile Glu Ala Ala Asp Leu Asn Gly Ala Asn Arg His Thr Leu
1235                1240                    1245

Val Ser Pro Val Gln His Pro Tyr Gly Leu Thr Leu Leu Asp Ser
1250                1255                    1260

Tyr Ile Tyr Trp Thr Asp Trp Gln Thr Arg Ser Ile His Arg Ala
1265                1270                    1275

Asp Lys Gly Thr Gly Ser Asn Val Ile Leu Val Arg Ser Asn Leu
1280                1285                    1290

Pro Gly Leu Met Asp Met Gln Ala Val Asp Arg Ala Gln Pro Leu
1295                1300                    1305

Gly Phe Asn Lys Cys Gly Ser Arg Asn Gly Gly Cys Ser His Leu
1310                1315                    1320

Cys Leu Pro Arg Pro Ser Gly Phe Ser Cys Ala Cys Pro Thr Gly
1325                1330                    1335

Ile Gln Leu Lys Gly Asp Gly Lys Thr Cys Asp Pro Ser Pro Glu
1340                1345                    1350

Thr Tyr Leu Leu Phe Ser Ser Arg Gly Ser Ile Arg Arg Ile Ser
1355                1360                    1365

Leu Asp Thr Ser Asp His Thr Asp Val His Val Pro Val Pro Glu
1370                1375                    1380

Leu Asn Asn Val Ile Ser Leu Asp Tyr Asp Ser Val Asp Gly Lys
1385                1390                    1395

Val Tyr Tyr Thr Asp Val Phe Leu Asp Val Ile Arg Arg Ala Asp
1400                1405                    1410

Leu Asn Gly Ser Asn Met Glu Thr Val Ile Gly Arg Gly Leu Lys
1415                1420                    1425

Thr Thr Asp Gly Leu Ala Val Asp Trp Val Ala Arg Asn Leu Tyr
1430                1435                    1440

Trp Thr Asp Thr Gly Arg Asn Thr Ile Glu Ala Ser Arg Leu Asp
1445                1450                    1455

Gly Ser Cys Arg Lys Val Leu Ile Asn Asn Ser Leu Asp Glu Pro
1460                1465                    1470

Arg Ala Ile Ala Val Phe Pro Arg Lys Gly Tyr Leu Phe Trp Thr
1475                1480                    1485

Asp Trp Gly His Ile Ala Lys Ile Glu Arg Ala Asn Leu Asp Gly
1490                1495                    1500

```
Ser Glu Arg Lys Val Leu Ile Asn Thr Asp Leu Gly Trp Pro Asn
    1505                1510                1515
Gly Leu Thr Leu Asp Tyr Asp Thr Arg Arg Ile Tyr Trp Val Asp
    1520                1525                1530
Ala His Leu Asp Arg Ile Glu Ser Ala Asp Leu Asn Gly Lys Leu
    1535                1540                1545
Arg Gln Val Leu Val Ser His Val Ser His Pro Phe Ala Leu Thr
    1550                1555                1560
Gln Gln Asp Arg Trp Ile Tyr Trp Thr Asp Trp Gln Thr Lys Ser
    1565                1570                1575
Ile Gln Arg Val Asp Lys Tyr Ser Gly Arg Asn Lys Glu Thr Val
    1580                1585                1590
Leu Ala Asn Val Glu Gly Leu Met Asp Ile Ile Val Val Ser Pro
    1595                1600                1605
Gln Arg Gln Thr Gly Thr Asn Ala Cys Gly Val Asn Asn Gly Gly
    1610                1615                1620
Cys Thr His Leu Cys Phe Ala Arg Ala Ser Asp Phe Val Cys Ala
    1625                1630                1635
Cys Pro Asp Glu Pro Asp Ser Arg Pro Cys Ser Leu Val Pro Gly
    1640                1645                1650
Leu Val Pro Pro Ala Pro Arg Ala Thr Gly Met Ser Glu Lys Ser
    1655                1660                1665
Pro Val Leu Pro Asn Thr Pro Pro Thr Thr Leu Tyr Ser Ser Thr
    1670                1675                1680
Thr Arg Thr Arg Thr Ser Leu Glu Glu Val Glu Gly Arg Cys Ser
    1685                1690                1695
Glu Arg Asp Ala Arg Leu Gly Leu Cys Ala Arg Ser Asn Asp Ala
    1700                1705                1710
Val Pro Ala Ala Pro Gly Glu Gly Leu His Ile Ser Tyr Ala Ile
    1715                1720                1725
Gly Gly Leu Leu Ser Ile Leu Leu Ile Leu Val Val Ile Ala Ala
    1730                1735                1740
Leu Met Leu Tyr Arg His Lys Lys Ser Lys Phe Thr Asp Pro Gly
    1745                1750                1755
Met Gly Asn Leu Thr Tyr Ser Asn Pro Ser Tyr Arg Thr Ser Thr
    1760                1765                1770
Gln Glu Val Lys Ile Glu Ala Ile Pro Lys Pro Ala Met Tyr Asn
    1775                1780                1785
Gln Leu Cys Tyr Lys Lys Glu Gly Gly Pro Asp His Asn Tyr Thr
    1790                1795                1800
Lys Glu Lys Ile Lys Ile Val Glu Gly Ile Cys Leu Leu Ser Gly
    1805                1810                1815
Asp Asp Ala Glu Trp Asp Asp Leu Lys Gln Leu Arg Ser Ser Arg
    1820                1825                1830
Gly Gly Leu Leu Arg Asp His Val Cys Met Lys Thr Asp Thr Val
    1835                1840                1845
Ser Ile Gln Ala Ser Ser Gly Ser Leu Asp Asp Thr Glu Thr Glu
    1850                1855                1860
Gln Leu Leu Gln Glu Glu Gln Ser Glu Cys Ser Ser Val His Thr
    1865                1870                1875
Ala Ala Thr Pro Glu Arg Arg Gly Ser Leu Pro Asp Thr Gly Trp
    1880                1885                1890
Lys His Glu Arg Lys Leu Ser Ser Glu Ser Gln Val
```

<210> SEQ ID NO 22
<211> LENGTH: 993
<212> TYPE: PRT
<213> ORGANISM: Homo sapiens

<400> SEQUENCE: 22

```
Met Gly Ser Gly Arg Val Pro Gly Leu Cys Leu Leu Val Leu Leu Val
1               5                   10                  15

His Ala Arg Ala Ala Gln Tyr Ser Lys Ala Ala Gln Asp Val Asp Glu
            20                  25                  30

Cys Val Glu Gly Thr Asp Asn Cys His Ile Asp Ala Ile Cys Gln Asn
        35                  40                  45

Thr Pro Arg Ser Tyr Lys Cys Ile Cys Lys Ser Gly Tyr Thr Gly Asp
    50                  55                  60

Gly Lys His Cys Lys Asp Val Asp Glu Cys Glu Arg Glu Asp Asn Ala
65                  70                  75                  80

Gly Cys Val His Asp Cys Val Asn Ile Pro Gly Asn Tyr Arg Cys Thr
                85                  90                  95

Cys Tyr Asp Gly Phe His Leu Ala His Asp Gly His Asn Cys Leu Asp
            100                 105                 110

Val Asp Glu Cys Ala Glu Gly Asn Gly Gly Cys Gln Gln Ser Cys Val
        115                 120                 125

Asn Met Met Gly Ser Tyr Glu Cys His Cys Arg Glu Gly Phe Phe Leu
130                 135                 140

Ser Asp Asn Gln His Thr Cys Ile Gln Arg Pro Glu Glu Gly Met Asn
145                 150                 155                 160

Cys Met Asn Lys Asn His Gly Cys Ala His Ile Cys Arg Glu Thr Pro
                165                 170                 175

Lys Gly Gly Ile Ala Cys Glu Cys Arg Pro Gly Phe Glu Leu Thr Lys
            180                 185                 190

Asn Gln Arg Asp Cys Lys Leu Thr Cys Asn Tyr Gly Asn Gly Gly Cys
        195                 200                 205

Gln His Thr Cys Asp Asp Thr Glu Gln Gly Pro Arg Cys Gly Cys His
    210                 215                 220

Ile Lys Phe Val Leu His Thr Asp Gly Lys Thr Cys Ile Glu Thr Cys
225                 230                 235                 240

Ala Val Asn Asn Gly Gly Cys Asp Ser Lys Cys His Asp Ala Ala Thr
                245                 250                 255

Gly Val His Cys Thr Cys Pro Val Gly Phe Met Leu Gln Pro Asp Arg
            260                 265                 270

Lys Thr Cys Lys Asp Ile Asp Glu Cys Arg Leu Asn Asn Gly Gly Cys
        275                 280                 285

Asp His Ile Cys Arg Asn Thr Val Gly Ser Phe Glu Cys Ser Cys Lys
    290                 295                 300

Lys Gly Tyr Lys Leu Leu Ile Asn Glu Arg Asn Cys Gln Asp Ile Asp
305                 310                 315                 320

Glu Cys Ser Phe Asp Arg Thr Cys Asp His Ile Cys Val Asn Thr Pro
                325                 330                 335

Gly Ser Phe Gln Cys Leu Cys His Arg Gly Tyr Leu Leu Tyr Gly Ile
            340                 345                 350

Thr His Cys Gly Asp Val Asp Glu Cys Ser Ile Asn Arg Gly Gly Cys
        355                 360                 365
```

```
Arg Phe Gly Cys Ile Asn Thr Pro Gly Ser Tyr Gln Cys Thr Cys Pro
370                 375                 380

Ala Gly Gln Gly Arg Leu His Trp Asn Gly Lys Asp Cys Thr Glu Pro
385                 390                 395                 400

Leu Lys Cys Gln Gly Ser Pro Gly Ala Ser Lys Ala Met Leu Ser Cys
            405                 410                 415

Asn Arg Ser Gly Lys Lys Asp Thr Cys Ala Leu Thr Cys Pro Ser Arg
                420                 425                 430

Ala Arg Phe Leu Pro Glu Ser Glu Asn Gly Phe Thr Val Ser Cys Gly
    435                 440                 445

Thr Pro Ser Pro Arg Ala Ala Pro Ala Arg Ala Gly His Asn Gly Asn
450                 455                 460

Ser Thr Asn Ser Asn His Cys His Glu Ala Ala Val Leu Ser Ile Lys
465                 470                 475                 480

Gln Arg Ala Ser Phe Lys Ile Lys Asp Ala Lys Cys Arg Leu His Leu
                485                 490                 495

Arg Asn Lys Gly Lys Thr Glu Glu Ala Gly Arg Ile Thr Gly Pro Gly
                500                 505                 510

Gly Ala Pro Cys Ser Glu Cys Gln Val Thr Phe Ile His Leu Lys Cys
            515                 520                 525

Asp Ser Ser Arg Lys Gly Lys Gly Arg Arg Ala Arg Thr Pro Pro Gly
530                 535                 540

Lys Glu Val Thr Arg Leu Thr Leu Glu Leu Glu Ala Glu Val Arg Ala
545                 550                 555                 560

Glu Glu Thr Thr Ala Ser Cys Gly Leu Pro Cys Leu Arg Gln Arg Met
                565                 570                 575

Glu Arg Arg Leu Lys Gly Ser Leu Lys Met Leu Arg Lys Ser Ile Asn
        580                 585                 590

Gln Asp Arg Phe Leu Leu Arg Leu Ala Gly Leu Asp Tyr Glu Leu Ala
        595                 600                 605

His Lys Pro Gly Leu Val Ala Gly Glu Arg Ala Glu Pro Met Glu Ser
    610                 615                 620

Cys Arg Pro Gly Gln His Arg Ala Gly Thr Lys Cys Val Ser Cys Pro
625                 630                 635                 640

Gln Gly Thr Tyr Tyr His Gly Gln Thr Glu Gln Cys Val Pro Cys Pro
                645                 650                 655

Ala Gly Thr Phe Gln Glu Arg Glu Gly Gln Leu Ser Cys Asp Leu Cys
            660                 665                 670

Pro Gly Ser Asp Ala His Gly Pro Leu Gly Ala Thr Asn Val Thr Thr
        675                 680                 685

Cys Ala Gly Gln Cys Pro Pro Gly Gln His Ser Val Asp Gly Phe Lys
690                 695                 700

Pro Cys Gln Pro Cys Pro Arg Gly Thr Tyr Gln Pro Glu Ala Gly Arg
705                 710                 715                 720

Thr Leu Cys Phe Pro Cys Gly Gly Gly Leu Thr Thr Lys His Glu Gly
                725                 730                 735

Ala Ile Ser Phe Gln Asp Cys Asp Thr Lys Val Gln Cys Ser Pro Gly
            740                 745                 750

His Tyr Tyr Asn Thr Ser Ile His Arg Cys Ile Arg Cys Ala Met Gly
                755                 760                 765

Ser Tyr Gln Pro Asp Phe Arg Gln Asn Phe Cys Ser Arg Cys Pro Gly
770                 775                 780

Asn Thr Ser Thr Asp Phe Asp Gly Ser Thr Ser Val Ala Gln Cys Lys
```

```
              785                 790                 795                 800
Asn Arg Gln Cys Gly Gly Glu Leu Gly Glu Phe Thr Gly Tyr Ile Glu
                805                 810                 815

Ser Pro Asn Tyr Pro Gly Asn Tyr Pro Ala Gly Val Glu Cys Ile Trp
                820                 825                 830

Asn Ile Asn Pro Pro Lys Arg Lys Ile Leu Ile Val Pro Glu
            835                 840                 845

Ile Phe Leu Pro Ser Glu Asp Glu Cys Gly Asp Val Leu Val Met Arg
850                 855                 860

Lys Asn Ser Ser Pro Ser Ser Ile Thr Thr Tyr Glu Thr Cys Gln Thr
865                 870                 875                 880

Tyr Glu Arg Pro Ile Ala Phe Thr Ala Arg Ser Arg Lys Leu Trp Ile
                885                 890                 895

Asn Phe Lys Thr Ser Glu Ala Asn Ser Ala Arg Gly Phe Gln Ile Pro
            900                 905                 910

Tyr Val Thr Tyr Asp Glu Asp Tyr Glu Gln Leu Val Glu Asp Ile Val
            915                 920                 925

Arg Asp Gly Arg Leu Tyr Ala Ser Glu Asn His Gln Glu Ile Leu Lys
930                 935                 940

Asp Lys Lys Leu Ile Lys Ala Phe Phe Glu Val Leu Ala His Pro Gln
945                 950                 955                 960

Asn Tyr Phe Lys Tyr Thr Glu Lys His Lys Glu Met Leu Pro Lys Ser
                965                 970                 975

Phe Ile Lys Leu Leu Arg Ser Lys Val Ser Ser Phe Leu Arg Pro Tyr
                980                 985                 990

Lys

<210> SEQ ID NO 23
<211> LENGTH: 1615
<212> TYPE: PRT
<213> ORGANISM: Homo sapiens

<400> SEQUENCE: 23

Met Glu Ala Ala Pro Pro Gly Pro Pro Trp Pro Leu Leu Leu Leu Leu
1               5                   10                  15

Leu Leu Leu Ala Leu Cys Gly Cys Pro Ala Pro Ala Ala Ala Ser
                20                  25                  30

Pro Leu Leu Leu Phe Ala Asn Arg Arg Asp Val Arg Leu Val Asp Ala
            35                  40                  45

Gly Gly Val Lys Leu Glu Ser Thr Ile Val Val Ser Gly Leu Glu Asp
50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
            100                 105                 110

Leu Ala Cys Asp Trp Val Gly Lys Lys Leu Tyr Trp Thr Asp Ser Glu
            115                 120                 125

Thr Asn Arg Ile Glu Val Ala Asn Leu Asn Gly Thr Ser Arg Lys Val
            130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
```

```
            165                 170                 175
Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
            195                 200                 205

Leu Tyr Trp Ala Asp Ala Lys Leu Ser Phe Ile His Arg Ala Asn Leu
            210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
            245                 250                 255

Thr Arg Ser Ile His Ala Cys Asn Lys Arg Thr Gly Gly Lys Arg Lys
            260                 265                 270

Glu Ile Leu Ser Ala Leu Tyr Ser Pro Met Asp Ile Gln Val Leu Ser
            275                 280                 285

Gln Glu Arg Gln Pro Phe Phe His Thr Arg Cys Glu Glu Asp Asn Gly
            290                 295                 300

Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
            325                 330                 335

Lys Ala Gly Ala Glu Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
            355                 360                 365

Val Asp Asp Ile Arg His Ala Ile Ala Ile Asp Tyr Asp Pro Leu Glu
            370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
            405                 410                 415

Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
            435                 440                 445

Ser Arg Lys Ile Leu Val Ser Glu Asp Leu Asp Glu Pro Arg Ala Ile
            450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
            485                 490                 495

Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
            515                 520                 525

Val Ile Asn Val Asp Gly Thr Lys Arg Arg Thr Leu Leu Glu Asp Lys
            530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
            565                 570                 575

Ser Arg Asp Val Ile Ile Asp Gln Leu Pro Asp Leu Met Gly Leu Lys
            580                 585                 590
```

```
Ala Val Asn Val Ala Lys Val Val Gly Thr Asn Pro Cys Ala Asp Arg
            595                 600                 605

Asn Gly Gly Cys Ser His Leu Cys Phe Phe Thr Pro His Ala Thr Arg
        610                 615                 620

Cys Gly Cys Pro Ile Gly Leu Glu Leu Leu Ser Asp Met Lys Thr Cys
625                 630                 635                 640

Ile Val Pro Glu Ala Phe Leu Val Phe Thr Ser Arg Ala Ala Ile His
                645                 650                 655

Arg Ile Ser Leu Glu Thr Asn Asn Asp Val Ala Ile Pro Leu Thr
            660                 665                 670

Gly Val Lys Glu Ala Ser Ala Leu Asp Phe Asp Val Ser Asn Asn His
            675                 680                 685

Ile Tyr Trp Thr Asp Val Ser Leu Lys Thr Ile Ser Arg Ala Phe Met
        690                 695                 700

Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
                725                 730                 735

Thr Gly Thr Asn Arg Ile Glu Val Ala Arg Leu Asp Gly Gln Phe Arg
            740                 745                 750

Gln Val Leu Val Trp Arg Asp Leu Asp Asn Pro Arg Ser Leu Ala Leu
            755                 760                 765

Asp Pro Thr Lys Gly Tyr Ile Tyr Trp Thr Glu Trp Gly Gly Lys Pro
    770                 775                 780

Arg Ile Val Arg Ala Phe Met Asp Gly Thr Asn Cys Met Thr Leu Val
785                 790                 795                 800

Asp Lys Val Gly Arg Ala Asn Asp Leu Thr Ile Asp Tyr Ala Asp Gln
                805                 810                 815

Arg Leu Tyr Trp Thr Asp Leu Asp Thr Asn Met Ile Glu Ser Ser Asn
            820                 825                 830

Met Leu Gly Gln Glu Arg Val Val Ile Ala Asp Asp Leu Pro His Pro
        835                 840                 845

Phe Gly Leu Thr Gln Tyr Ser Asp Tyr Ile Tyr Trp Thr Asp Trp Asn
    850                 855                 860

Leu His Ser Ile Glu Arg Ala Asp Lys Thr Ser Gly Arg Asn Arg Thr
865                 870                 875                 880

Leu Ile Gln Gly His Leu Asp Phe Val Met Asp Ile Leu Val Phe His
                885                 890                 895

Ser Ser Arg Gln Asp Gly Leu Asn Asp Cys Met His Asn Asn Gly Gln
            900                 905                 910

Cys Gly Gln Leu Cys Leu Ala Ile Pro Gly His Arg Cys Gly Cys
        915                 920                 925

Ala Ser His Tyr Thr Leu Asp Pro Ser Ser Arg Asn Cys Ser Pro Pro
    930                 935                 940

Thr Thr Phe Leu Leu Phe Ser Gln Lys Ser Ala Ile Ser Arg Met Ile
945                 950                 955                 960

Pro Asp Asp Gln His Ser Pro Asp Leu Ile Leu Pro Leu His Gly Leu
                965                 970                 975

Arg Asn Val Lys Ala Ile Asp Tyr Asp Pro Leu Asp Lys Phe Ile Tyr
            980                 985                 990

Trp Val Asp Gly Arg Gln Asn Ile  Lys Arg Ala Lys Asp  Asp Gly Thr
            995                 1000                1005
```

```
Gln Pro Phe Val Leu Thr Ser Leu Ser Gln Gly Gln Asn Pro Asp
    1010                1015                1020

Arg Gln Pro His Asp Leu Ser Ile Asp Ile Tyr Ser Arg Thr Leu
    1025                1030                1035

Phe Trp Thr Cys Glu Ala Thr Asn Thr Ile Asn Val His Arg Leu
    1040                1045                1050

Ser Gly Glu Ala Met Gly Val Val Leu Arg Gly Asp Arg Asp Lys
    1055                1060                1065

Pro Arg Ala Ile Val Val Asn Ala Glu Arg Gly Tyr Leu Tyr Phe
    1070                1075                1080

Thr Asn Met Gln Asp Arg Ala Ala Lys Ile Glu Arg Ala Ala Leu
    1085                1090                1095

Asp Gly Thr Glu Arg Glu Val Leu Phe Thr Thr Gly Leu Ile Arg
    1100                1105                1110

Pro Val Ala Leu Val Val Asp Asn Thr Leu Gly Lys Leu Phe Trp
    1115                1120                1125

Val Asp Ala Asp Leu Lys Arg Ile Glu Ser Cys Asp Leu Ser Gly
    1130                1135                1140

Ala Asn Arg Leu Thr Leu Glu Asp Ala Asn Ile Val Gln Pro Leu
    1145                1150                1155

Gly Leu Thr Ile Leu Gly Lys His Leu Tyr Trp Ile Asp Arg Gln
    1160                1165                1170

Gln Gln Met Ile Glu Arg Val Glu Lys Thr Thr Gly Asp Lys Arg
    1175                1180                1185

Thr Arg Ile Gln Gly Arg Val Ala His Leu Thr Gly Ile His Ala
    1190                1195                1200

Val Glu Glu Val Ser Leu Glu Glu Phe Ser Ala His Pro Cys Ala
    1205                1210                1215

Arg Asp Asn Gly Gly Cys Ser His Ile Cys Ile Ala Lys Gly Asp
    1220                1225                1230

Gly Thr Pro Arg Cys Ser Cys Pro Val His Leu Val Leu Leu Gln
    1235                1240                1245

Asn Leu Leu Thr Cys Gly Glu Pro Pro Thr Cys Ser Pro Asp Gln
    1250                1255                1260

Phe Ala Cys Ala Thr Gly Glu Ile Asp Cys Ile Pro Gly Ala Trp
    1265                1270                1275

Arg Cys Asp Gly Phe Pro Glu Cys Asp Asp Gln Ser Asp Glu Glu
    1280                1285                1290

Gly Cys Pro Val Cys Ser Ala Ala Gln Phe Pro Cys Ala Arg Gly
    1295                1300                1305

Gln Cys Val Asp Leu Arg Leu Arg Cys Asp Gly Glu Ala Asp Cys
    1310                1315                1320

Gln Asp Arg Ser Asp Glu Ala Asp Cys Asp Ala Ile Cys Leu Pro
    1325                1330                1335

Asn Gln Phe Arg Cys Ala Ser Gly Gln Cys Val Leu Ile Lys Gln
    1340                1345                1350

Gln Cys Asp Ser Phe Pro Asp Cys Ile Asp Gly Ser Asp Glu Leu
    1355                1360                1365

Met Cys Glu Ile Thr Lys Pro Pro Ser Asp Asp Ser Pro Ala His
    1370                1375                1380

Ser Ser Ala Ile Gly Pro Val Ile Gly Ile Ile Leu Ser Leu Phe
    1385                1390                1395

Val Met Gly Gly Val Tyr Phe Val Cys Gln Arg Val Val Cys Gln
```

```
                1400                1405                1410
Arg Tyr Ala Gly Ala Asn Gly Pro Phe Pro His Glu Tyr Val Ser
        1415                1420                1425

Gly Thr Pro His Val Pro Leu Asn Phe Ile Ala Pro Gly Gly Ser
    1430                1435                1440

Gln His Gly Pro Phe Thr Gly Ile Ala Cys Gly Lys Ser Met Met
    1445                1450                1455

Ser Ser Val Ser Leu Met Gly Gly Arg Gly Gly Val Pro Leu Tyr
    1460                1465                1470

Asp Arg Asn His Val Thr Gly Ala Ser Ser Ser Ser Ser Ser Ser
    1475                1480                1485

Thr Lys Ala Thr Leu Tyr Pro Pro Ile Leu Asn Pro Pro Pro Ser
    1490                1495                1500

Pro Ala Thr Asp Pro Ser Leu Tyr Asn Met Asp Met Phe Tyr Ser
    1505                1510                1515

Ser Asn Ile Pro Ala Thr Ala Arg Pro Tyr Arg Pro Tyr Ile Ile
    1520                1525                1530

Arg Gly Met Ala Pro Pro Thr Thr Pro Cys Ser Thr Asp Val Cys
    1535                1540                1545

Asp Ser Asp Tyr Ser Ala Ser Arg Trp Lys Ala Ser Lys Tyr Tyr
    1550                1555                1560

Leu Asp Leu Asn Ser Asp Ser Asp Pro Tyr Pro Pro Pro Pro Thr
    1565                1570                1575

Pro His Ser Gln Tyr Leu Ser Ala Glu Asp Ser Cys Pro Pro Ser
    1580                1585                1590

Pro Ala Thr Glu Arg Ser Tyr Phe His Leu Phe Pro Pro Pro Pro
    1595                1600                1605

Ser Pro Cys Thr Asp Ser Ser
    1610                1615

<210> SEQ ID NO 24
<211> LENGTH: 1541
<212> TYPE: PRT
<213> ORGANISM: Homo sapiens

<400> SEQUENCE: 24

Met Ser Phe Leu Glu Glu Ala Arg Ala Ala Gly Arg Ala Val Val Leu
1               5                   10                  15

Ala Leu Val Leu Leu Leu Pro Ala Val Pro Val Gly Ala Ser Val
                20                  25                  30

Pro Pro Arg Pro Leu Leu Pro Leu Gln Pro Gly Met Pro His Val Cys
            35                  40                  45

Ala Glu Gln Glu Leu Thr Leu Val Gly Arg Arg Gln Pro Cys Val Gln
        50                  55                  60

Ala Leu Ser His Thr Val Pro Val Trp Lys Ala Gly Cys Gly Trp Gln
65                  70                  75                  80

Ala Trp Cys Val Gly His Glu Arg Arg Thr Val Tyr Tyr Met Gly Tyr
                85                  90                  95

Arg Gln Val Tyr Thr Thr Glu Ala Arg Thr Val Leu Arg Cys Cys Arg
                100                 105                 110

Gly Trp Met Gln Gln Pro Asp Glu Glu Gly Cys Leu Ser Ala Glu Cys
            115                 120                 125

Ser Ala Ser Leu Cys Phe His Gly Gly Arg Cys Val Pro Gly Ser Ala
        130                 135                 140
```

```
Gln Pro Cys His Cys Pro Gly Phe Gln Gly Pro Arg Cys Gln Tyr
145                 150                 155                 160

Asp Val Asp Glu Cys Arg Thr His Asn Gly Gly Cys Gln His Arg Cys
            165                 170                 175

Val Asn Thr Pro Gly Ser Tyr Leu Cys Glu Cys Lys Pro Gly Phe Arg
        180                 185                 190

Leu His Thr Asp Ser Arg Thr Cys Leu Ala Ile Asn Ser Cys Ala Leu
    195                 200                 205

Gly Asn Gly Gly Cys Gln His Cys Val Gln Leu Thr Ile Thr Arg
    210                 215                 220

His Arg Cys Gln Cys Arg Pro Gly Phe Gln Leu Gln Glu Asp Gly Arg
225                 230                 235                 240

His Cys Val Arg Arg Ser Pro Cys Ala Asn Arg Asn Gly Ser Cys Met
                245                 250                 255

His Arg Cys Gln Val Val Arg Gly Leu Ala Arg Cys Glu Cys His Val
                260                 265                 270

Gly Tyr Gln Leu Ala Ala Asp Gly Lys Ala Cys Glu Asp Val Asp Glu
        275                 280                 285

Cys Ala Ala Gly Leu Ala Gln Cys Ala His Gly Cys Leu Asn Thr Gln
290                 295                 300

Gly Ser Phe Lys Cys Val Cys His Ala Gly Tyr Glu Leu Gly Ala Asp
305                 310                 315                 320

Gly Arg Gln Cys Tyr Arg Ile Glu Met Glu Ile Val Asn Ser Cys Glu
                325                 330                 335

Ala Asn Asn Gly Gly Cys Ser His Gly Cys Ser His Thr Ser Ala Gly
                340                 345                 350

Pro Leu Cys Thr Cys Pro Arg Gly Tyr Glu Leu Asp Thr Asp Gln Arg
                355                 360                 365

Thr Cys Ile Asp Val Asp Cys Ala Asp Ser Pro Cys Cys Gln Gln
        370                 375                 380

Val Cys Thr Asn Asn Pro Gly Gly Tyr Glu Cys Gly Cys Tyr Ala Gly
385                 390                 395                 400

Tyr Arg Leu Ser Ala Asp Gly Cys Gly Cys Glu Asp Val Asp Glu Cys
                405                 410                 415

Ala Ser Ser Arg Gly Gly Cys Glu His His Cys Thr Asn Leu Ala Gly
                420                 425                 430

Ser Phe Gln Cys Ser Cys Glu Ala Gly Tyr Arg Leu His Glu Asp Arg
            435                 440                 445

Arg Gly Cys Ser Pro Leu Glu Glu Pro Met Val Asp Leu Asp Gly Glu
            450                 455                 460

Leu Pro Phe Val Arg Pro Leu Pro His Ile Ala Val Leu Gln Asp Glu
465                 470                 475                 480

Leu Pro Gln Leu Phe Gln Asp Asp Val Gly Ala Asp Glu Glu Glu
                485                 490                 495

Ala Glu Leu Arg Gly Glu His Thr Leu Thr Glu Lys Phe Val Cys Leu
            500                 505                 510

Asp Asp Ser Phe Gly His Asp Cys Ser Leu Thr Cys Asp Asp Cys Arg
            515                 520                 525

Asn Gly Gly Thr Cys Leu Leu Gly Leu Asp Gly Cys Asp Cys Pro Glu
            530                 535                 540

Gly Trp Thr Gly Leu Ile Cys Asn Glu Thr Cys Pro Pro Asp Thr Phe
545                 550                 555                 560

Gly Lys Asn Cys Ser Phe Ser Cys Ser Cys Gln Asn Gly Gly Thr Cys
```

```
            565                 570                 575
Asp Ser Val Thr Gly Ala Cys Arg Cys Pro Gly Val Ser Gly Thr
            580                 585                 590

Asn Cys Glu Asp Gly Cys Pro Lys Gly Tyr Tyr Gly Lys His Cys Arg
            595                 600                 605

Lys Lys Cys Asn Cys Ala Asn Arg Gly Arg Cys His Arg Leu Tyr Gly
610                 615                 620

Ala Cys Leu Cys Asp Pro Gly Leu Tyr Gly Arg Phe Cys His Leu Thr
625                 630                 635                 640

Cys Pro Pro Trp Ala Phe Gly Pro Gly Cys Ser Glu Cys Gln Cys
                645                 650                 655

Val Gln Pro His Thr Gln Ser Cys Asp Lys Arg Asp Gly Ser Cys Ser
            660                 665                 670

Cys Lys Ala Gly Phe Arg Gly Glu Arg Cys Gln Ala Glu Cys Glu Leu
            675                 680                 685

Gly Tyr Phe Gly Pro Gly Cys Trp Gln Ala Cys Thr Cys Pro Val Gly
            690                 695                 700

Val Ala Cys Asp Ser Val Ser Gly Glu Cys Gly Lys Arg Cys Pro Ala
705                 710                 715                 720

Gly Phe Gln Gly Glu Asp Cys Gly Gln Glu Cys Pro Val Gly Thr Phe
                725                 730                 735

Gly Val Asn Cys Ser Ser Cys Ser Cys Gly Ala Pro Cys His
            740                 745                 750

Gly Val Thr Gly Gln Cys Arg Cys Pro Pro Gly Arg Thr Gly Glu Asp
            755                 760                 765

Cys Glu Ala Asp Cys Pro Glu Gly Arg Trp Gly Leu Gly Cys Gln Glu
770                 775                 780

Ile Cys Pro Ala Cys Gln His Ala Ala Arg Cys Asp Pro Glu Thr Gly
785                 790                 795                 800

Ala Cys Leu Cys Leu Pro Gly Phe Val Gly Ser Arg Cys Gln Asp Val
                805                 810                 815

Cys Pro Ala Gly Trp Tyr Gly Pro Ser Cys Gln Thr Arg Cys Ser Cys
                820                 825                 830

Ala Asn Asp Gly His Cys His Pro Ala Thr Gly His Cys Ser Cys Ala
835                 840                 845

Pro Gly Trp Thr Gly Phe Ser Cys Gln Arg Ala Cys Asp Thr Gly His
    850                 855                 860

Trp Gly Pro Asp Cys Ser His Pro Cys Asn Cys Ser Ala Gly His Gly
865                 870                 875                 880

Ser Cys Asp Ala Ile Ser Gly Leu Cys Leu Cys Glu Ala Gly Tyr Val
                885                 890                 895

Gly Pro Arg Cys Glu Gln Gln Cys Pro Gln Gly His Phe Gly Pro Gly
                900                 905                 910

Cys Glu Gln Arg Cys Gln Cys Gln His Gly Ala Ala Cys Asp His Val
            915                 920                 925

Ser Gly Ala Cys Thr Cys Pro Ala Gly Trp Arg Gly Thr Phe Cys Glu
    930                 935                 940

His Ala Cys Pro Ala Gly Phe Phe Gly Leu Asp Cys Arg Ser Ala Cys
945                 950                 955                 960

Asn Cys Thr Ala Gly Ala Ala Cys Asp Ala Val Asn Gly Ser Cys Leu
            965                 970                 975

Cys Pro Ala Gly Arg Arg Gly Pro Arg Cys Ala Glu Thr Cys Pro Ala
            980                 985                 990
```

-continued

```
His Thr Tyr Gly His Asn Cys Ser  Gln Ala Cys Ala Cys Phe Asn Gly
        995               1000              1005

Ala Ser  Cys Asp Pro Val His  Gly Gln Cys His  Cys  Ala Pro Gly
    1010              1015             1020

Trp Met  Gly Pro Ser Cys Leu  Gln Ala Cys Pro  Ala  Gly Leu Tyr
    1025              1030             1035

Gly Asp  Asn Cys Arg His Ser  Cys Leu Cys Gln  Asn  Gly Gly Thr
    1040              1045             1050

Cys Asp  Pro Val Ser Gly His  Cys Ala Cys Pro  Glu  Gly Trp Ala
    1055              1060             1065

Gly Leu  Ala Cys Glu Lys Glu  Cys Leu Pro Arg  Asp  Val Arg Ala
    1070              1075             1080

Gly Cys  Arg His Ser Gly Gly  Cys Leu Asn Gly  Leu  Cys Asp
    1085              1090             1095

Pro His  Thr Gly Arg Cys Leu  Cys Pro Ala Gly  Trp  Thr Gly Asp
    1100              1105             1110

Lys Cys  Gln Ser Pro Cys Leu  Arg Gly Trp Phe  Gly  Glu Ala Cys
    1115              1120             1125

Ala Gln  Arg Cys Ser Cys Pro  Pro Gly Ala Ala  Cys  His His Val
    1130              1135             1140

Thr Gly  Ala Cys Arg Cys Pro  Pro Gly Phe Thr  Gly  Ser Gly Cys
    1145              1150             1155

Glu Gln  Ala Cys Pro Pro Gly  Ser Phe Gly Glu  Asp  Cys Ala Gln
    1160              1165             1170

Met Cys  Gln Cys Pro Gly Glu  Asn Pro Ala Cys  His  Pro Ala Thr
    1175              1180             1185

Gly Thr  Cys Ser Cys Ala Ala  Gly Tyr His Gly  Pro  Ser Cys Gln
    1190              1195             1200

Gln Arg  Cys Pro Pro Gly Arg  Tyr Gly Pro Gly  Cys  Glu Gln Leu
    1205              1210             1215

Cys Gly  Cys Leu Asn Gly Gly  Ser Cys Asp Ala  Ala  Thr Gly Ala
    1220              1225             1230

Cys Arg  Cys Pro Thr Gly Phe  Leu Gly Thr Asp  Cys  Asn Leu Thr
    1235              1240             1245

Cys Pro  Gln Gly Arg Phe Gly  Pro Asn Cys Thr  His  Val Cys Gly
    1250              1255             1260

Cys Gly  Gln Gly Ala Ala Cys  Asp Pro Val Thr  Gly  Thr Cys Leu
    1265              1270             1275

Cys Pro  Pro Gly Arg Ala Gly  Val Arg Cys Glu  Arg  Gly Cys Pro
    1280              1285             1290

Gln Asn  Arg Phe Gly Val Gly  Cys Glu His Thr  Cys  Ser Cys Arg
    1295              1300             1305

Asn Gly  Gly Leu Cys His Ala  Ser Asn Gly Ser  Cys  Ser Cys Gly
    1310              1315             1320

Leu Gly  Trp Thr Gly Arg His  Cys Glu Leu Ala  Cys  Pro Pro Gly
    1325              1330             1335

Arg Tyr  Gly Ala Ala Cys His  Leu Glu Cys Ser  Cys  His Asn Asn
    1340              1345             1350

Ser Thr  Cys Glu Pro Ala Thr  Gly Thr Cys Arg  Cys  Gly Pro Gly
    1355              1360             1365

Phe Tyr  Gly Gln Ala Cys Glu  His Pro Cys Pro  Pro  Gly Phe His
    1370              1375             1380
```

```
Gly Ala Gly Cys Gln Gly Leu Cys Trp Cys Gln His Gly Ala Pro
    1385            1390            1395

Cys Asp Pro Ile Ser Gly Arg Cys Leu Cys Pro Ala Gly Phe His
    1400            1405            1410

Gly His Phe Cys Glu Arg Gly Cys Glu Pro Gly Ser Phe Gly Glu
    1415            1420            1425

Gly Cys His Gln Arg Cys Asp Cys Gly Gly Ala Pro Cys Asp
    1430            1435            1440

Pro Val Thr Gly Leu Cys Leu Cys Pro Pro Gly Arg Ser Gly Ala
    1445            1450            1455

Thr Cys Asn Leu Asp Cys Arg Arg Gly Gln Phe Gly Pro Ser Cys
    1460            1465            1470

Thr Leu His Cys Asp Cys Gly Gly Ala Asp Cys Asp Pro Val
    1475            1480            1485

Ser Gly Gln Cys His Cys Val Asp Gly Tyr Met Gly Pro Thr Cys
    1490            1495            1500

Arg Glu Gly Gly Pro Leu Arg Leu Pro Glu Asn Pro Ser Leu Ala
    1505            1510            1515

Gln Gly Ser Ala Gly Thr Leu Pro Ala Ser Ser Arg Pro Thr Ser
    1520            1525            1530

Arg Ser Gly Gly Pro Ala Arg His
    1535            1540

<210> SEQ ID NO 25
<211> LENGTH: 1613
<212> TYPE: PRT
<213> ORGANISM: Homo sapiens

<400> SEQUENCE: 25

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Ala Val Asp Phe Val Phe Ser His Gly Leu
    50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
            85                  90                  95

Pro Asp Gly Leu Ala Cys Asp Trp Leu Gly Glu Lys Leu Tyr Trp Thr
        100                 105                 110

Asp Ser Glu Thr Asn Arg Ile Glu Val Ser Asn Leu Asp Gly Ser Leu
            115                 120                 125

Arg Lys Val Leu Phe Trp Gln Glu Leu Asp Gln Pro Arg Ala Ile Ala
        130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205
```

```
Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
                260                 265                 270

Ala Phe Ser Gln Gln Arg Gln Pro Asn Ala Thr Asn Pro Cys Gly Ile
            275                 280                 285

Asp Asn Gly Gly Cys Ser His Leu Cys Leu Met Ser Pro Val Lys Pro
290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
                325                 330                 335

Thr Asp Leu Arg Arg Ile Ser Leu Asp Thr Pro Asp Phe Thr Asp Ile
                340                 345                 350

Val Leu Gln Leu Glu Asp Ile Arg His Ala Ile Ala Ile Asp Tyr Asp
            355                 360                 365

Pro Val Glu Gly Tyr Ile Tyr Trp Thr Asp Asp Glu Val Arg Ala Ile
        370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
                420                 425                 430

Asn Gly Thr Met Arg Lys Ile Leu Ile Ser Glu Asp Leu Glu Glu Pro
            435                 440                 445

Arg Ala Ile Val Leu Asp Pro Met Val Gly Tyr Met Tyr Trp Thr Asp
        450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
                500                 505                 510

Lys Ile Glu Val Met Asn Thr Asp Gly Thr Gly Arg Arg Val Leu Val
            515                 520                 525

Glu Asp Lys Ile Pro His Ile Phe Gly Phe Thr Leu Leu Gly Asp Tyr
        530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
            580                 585                 590

Ala Glu Glu Asn Gly Gly Cys Ser His Leu Cys Leu Tyr Arg Pro Gln
        595                 600                 605

Gly Leu Arg Cys Ala Cys Pro Ile Gly Phe Glu Leu Ile Ser Asp Met
610                 615                 620
```

```
-continued

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Val Ala Ile
            645                 650                 655

Pro Leu Thr Gly Val Lys Glu Ala Ser Ala Leu Asp Phe Asp Val Thr
                660                 665                 670

Asp Asn Arg Ile Tyr Trp Thr Asp Ile Ser Leu Lys Thr Ile Ser Arg
            675                 680                 685

Ala Phe Met Asn Gly Ser Ala Leu Glu His Val Glu Phe Gly Leu
690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
            755                 760                 765

Gly Lys Pro Lys Ile Asp Arg Ala Ala Met Asp Gly Ser Glu Arg Thr
770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
            835                 840                 845

Asp Trp Ser Arg Arg Ser Ile Glu Arg Ala Asn Lys Thr Ser Gly Gln
850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
            915                 920                 925

Cys Ser Ala Pro Thr Thr Phe Leu Leu Phe Ser Gln Lys Ser Ala Ile
930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Val Ser Ser Val Pro
            995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
```

```
              1040                1045                1050
Gly Glu Gln Asp Arg Pro Arg  Ala Val Val Asn  Pro Glu Lys
        1055                1060                1065
Gly Tyr Met Tyr Phe Thr Asn  Leu Gln Glu Arg  Ser Pro Lys Ile
        1070                1075                1080
Glu Arg Ala Ala Leu Asp Gly  Thr Glu Arg Glu  Val Leu Phe Phe
        1085                1090                1095
Ser Gly Leu Ser Lys Pro Ile  Ala Leu Ala Leu  Asp Ser Arg Leu
        1100                1105                1110
Gly Lys Leu Phe Trp Ala Asp  Ser Asp Leu Arg  Arg Ile Glu Ser
        1115                1120                1125
Ser Asp Leu Ser Gly Ala Asn  Arg Ile Val Leu  Glu Asp Ser Asn
        1130                1135                1140
Ile Leu Gln Pro Val Gly Leu  Thr Val Phe Glu  Asn Trp Leu Tyr
        1145                1150                1155
Trp Ile Asp Lys Gln Gln Gln  Met Ile Glu Lys  Ile Asp Met Thr
        1160                1165                1170
Gly Arg Glu Gly Arg Thr Lys  Val Gln Ala Arg  Ile Ala Gln Leu
        1175                1180                1185
Ser Asp Ile His Ala Val Lys  Glu Leu Asn Leu  Gln Glu Tyr Arg
        1190                1195                1200
Gln His Pro Cys Ala Gln Asp  Asn Gly Gly Cys  Ser His Ile Cys
        1205                1210                1215
Leu Val Lys Gly Asp Gly Thr  Thr Arg Cys Ser  Cys Pro Met His
        1220                1225                1230
Leu Val Leu Leu Gln Asp Glu  Leu Ser Cys Gly  Glu Pro Pro Thr
        1235                1240                1245
Cys Ser Pro Gln Gln Phe Thr  Cys Phe Thr Gly  Glu Ile Asp Cys
        1250                1255                1260
Ile Pro Val Ala Trp Arg Cys  Asp Gly Phe Thr  Glu Cys Glu Asp
        1265                1270                1275
His Ser Asp Glu Leu Asn Cys  Pro Val Cys Ser  Glu Ser Gln Phe
        1280                1285                1290
Gln Cys Ala Ser Gly Gln Cys  Ile Asp Gly Ala  Leu Arg Cys Asn
        1295                1300                1305
Gly Asp Ala Asn Cys Gln Asp  Lys Ser Asp Glu  Lys Asn Cys Glu
        1310                1315                1320
Val Leu Cys Leu Ile Asp Gln  Phe Arg Cys Ala  Asn Gly Gln Cys
        1325                1330                1335
Ile Gly Lys His Lys Lys Cys  Asp His Asn Val  Asp Cys Ser Asp
        1340                1345                1350
Lys Ser Asp Glu Leu Asp Cys  Tyr Pro Thr Glu  Glu Pro Ala Pro
        1355                1360                1365
Gln Ala Thr Asn Thr Val Gly  Ser Val Ile Gly  Val Ile Val Thr
        1370                1375                1380
Ile Phe Val Ser Gly Thr Val  Tyr Phe Ile Cys  Gln Arg Met Leu
        1385                1390                1395
Cys Pro Arg Met Lys Gly Asp  Gly Glu Thr Met  Thr Asn Asp Tyr
        1400                1405                1410
Val Val His Gly Pro Ala Ser  Val Pro Leu Gly  Tyr Val Pro His
        1415                1420                1425
Pro Ser Ser Leu Ser Gly Ser  Leu Pro Gly Met  Ser Arg Gly Lys
        1430                1435                1440
```

```
Ser Met Ile Ser Ser Leu Ser Ile Met Gly Gly Ser Ser Gly Pro
    1445                1450                1455

Pro Tyr Asp Arg Ala His Val Thr Gly Ala Ser Ser Ser Ser Ser
    1460                1465                1470

Ser Ser Thr Lys Gly Thr Tyr Phe Pro Ala Ile Leu Asn Pro Pro
    1475                1480                1485

Pro Ser Pro Ala Thr Glu Arg Ser His Tyr Thr Met Glu Phe Gly
    1490                1495                1500

Tyr Ser Ser Asn Ser Pro Ser Thr His Arg Ser Tyr Ser Tyr Arg
    1505                1510                1515

Pro Tyr Ser Tyr Arg His Phe Ala Pro Pro Thr Thr Pro Cys Ser
    1520                1525                1530

Thr Asp Val Cys Asp Ser Asp Tyr Ala Pro Ser Arg Arg Met Thr
    1535                1540                1545

Ser Val Ala Thr Ala Lys Gly Tyr Thr Ser Asp Leu Asn Tyr Asp
    1550                1555                1560

Ser Glu Pro Val Pro Pro Pro Thr Pro Arg Ser Gln Tyr Leu
    1565                1570                1575

Ser Ala Glu Glu Asn Tyr Glu Ser Cys Pro Pro Ser Pro Tyr Thr
    1580                1585                1590

Glu Arg Ser Tyr Ser His His Leu Tyr Pro Pro Pro Ser Pro
    1595                1600                1605

Cys Thr Asp Ser Ser
    1610

<210> SEQ ID NO 26
<211> LENGTH: 4599
<212> TYPE: PRT
<213> ORGANISM: Homo sapiens

<400> SEQUENCE: 26

Met Ser Glu Phe Leu Leu Ala Leu Leu Thr Leu Ser Gly Leu Leu Pro
1               5                   10                  15

Ile Ala Arg Val Leu Thr Val Gly Ala Asp Arg Asp Gln Gln Leu Cys
            20                  25                  30

Asp Pro Gly Glu Phe Leu Cys His Asp His Val Thr Cys Val Ser Gln
        35                  40                  45

Ser Trp Leu Cys Asp Gly Asp Pro Asp Cys Pro Asp Asp Ser Asp Glu
    50                  55                  60

Ser Leu Asp Thr Cys Pro Glu Glu Val Glu Ile Lys Cys Pro Leu Asn
65                  70                  75                  80

His Ile Ala Cys Leu Gly Thr Asn Lys Cys Val His Leu Ser Gln Leu
                85                  90                  95

Cys Asn Gly Val Leu Asp Cys Pro Asp Gly Tyr Asp Glu Gly Val His
            100                 105                 110

Cys Gln Glu Leu Leu Ser Asn Cys Gln Gln Leu Asn Cys Gln Tyr Lys
        115                 120                 125

Cys Thr Met Val Arg Asn Ser Thr Arg Cys Tyr Cys Glu Asp Gly Phe
    130                 135                 140

Glu Ile Thr Glu Asp Gly Arg Ser Cys Lys Asp Gln Asp Glu Cys Ala
145                 150                 155                 160

Val Tyr Gly Thr Cys Ser Gln Thr Cys Arg Asn Thr His Gly Ser Tyr
                165                 170                 175

Thr Cys Ser Cys Val Glu Gly Tyr Leu Met Gln Pro Asp Asn Arg Ser
```

```
                180                 185                 190
Cys Lys Ala Lys Ile Glu Pro Thr Asp Arg Pro Ile Leu Leu Ile
            195                 200                 205

Ala Asn Phe Glu Thr Ile Glu Val Phe Tyr Leu Asn Gly Ser Lys Met
    210                 215                 220

Ala Thr Leu Ser Ser Val Asn Gly Asn Glu Ile His Thr Leu Asp Phe
225                 230                 235                 240

Ile Tyr Asn Glu Asp Met Ile Cys Trp Ile Glu Ser Arg Glu Ser Ser
                245                 250                 255

Asn Gln Leu Lys Cys Ile Gln Ile Thr Lys Ala Gly Gly Leu Thr Asp
            260                 265                 270

Glu Trp Thr Ile Asn Ile Leu Gln Ser Phe His Asn Val Gln Gln Met
        275                 280                 285

Ala Ile Asp Trp Leu Thr Arg Asn Leu Tyr Phe Val Asp His Val Gly
    290                 295                 300

Asp Arg Ile Phe Val Cys Asn Ser Asn Gly Ser Val Cys Val Thr Leu
305                 310                 315                 320

Ile Asp Leu Glu Leu His Asn Pro Lys Ala Ile Ala Val Asp Pro Ile
                325                 330                 335

Ala Gly Lys Leu Phe Phe Thr Asp Tyr Gly Asn Val Ala Lys Val Glu
            340                 345                 350

Arg Cys Asp Met Asp Gly Met Asn Arg Thr Arg Ile Ile Asp Ser Lys
        355                 360                 365

Thr Glu Gln Pro Ala Ala Leu Ala Leu Asp Leu Val Asn Lys Leu Val
    370                 375                 380

Tyr Trp Val Asp Leu Tyr Leu Asp Tyr Val Gly Val Val Asp Tyr Gln
385                 390                 395                 400

Gly Lys Asn Arg His Thr Val Ile Gln Gly Arg Gln Val Arg His Leu
                405                 410                 415

Tyr Gly Ile Thr Val Phe Glu Asp Tyr Leu Tyr Ala Thr Asn Ser Asp
            420                 425                 430

Asn Tyr Asn Ile Val Arg Ile Asn Arg Phe Asn Gly Thr Asp Ile His
        435                 440                 445

Ser Leu Ile Lys Ile Glu Asn Ala Trp Gly Ile Arg Ile Tyr Gln Lys
    450                 455                 460

Arg Thr Gln Pro Thr Val Arg Ser His Ala Cys Glu Val Asp Pro Tyr
465                 470                 475                 480

Gly Met Pro Gly Gly Cys Ser His Ile Cys Leu Leu Ser Ser Ser Tyr
                485                 490                 495

Lys Thr Arg Thr Cys Arg Cys Arg Thr Gly Phe Asn Leu Gly Ser Asp
            500                 505                 510

Gly Arg Ser Cys Lys Arg Pro Lys Asn Glu Leu Phe Leu Phe Tyr Gly
        515                 520                 525

Lys Gly Arg Pro Gly Ile Val Arg Gly Met Asp Leu Asn Thr Lys Ile
    530                 535                 540

Ala Asp Glu Tyr Met Ile Pro Ile Glu Asn Leu Val Asn Pro Arg Ala
545                 550                 555                 560

Leu Asp Phe His Ala Glu Thr Asn Tyr Ile Tyr Phe Ala Asp Thr Thr
                565                 570                 575

Ser Phe Leu Ile Gly Arg Gln Lys Ile Asp Gly Thr Glu Arg Glu Thr
            580                 585                 590

Ile Leu Lys Asp Asp Leu Asp Asn Val Glu Gly Ile Ala Val Asp Trp
        595                 600                 605
```

```
Ile Gly Asn Asn Leu Tyr Trp Thr Asn Asp Gly His Arg Lys Thr Ile
610                 615                 620

Asn Val Ala Arg Leu Glu Lys Ala Ser Gln Ser Arg Lys Thr Leu Leu
625                 630                 635                 640

Glu Gly Glu Met Ser His Pro Arg Gly Ile Val Val Asp Pro Val Asn
                645                 650                 655

Gly Trp Met Tyr Trp Thr Asp Trp Glu Glu Asp Glu Ile Asp Asp Ser
                660                 665                 670

Val Gly Arg Ile Glu Lys Ala Trp Met Asp Gly Phe Asn Arg Gln Ile
            675                 680                 685

Phe Val Thr Ser Lys Met Leu Trp Pro Asn Gly Leu Thr Leu Asp Phe
690                 695                 700

His Thr Asn Thr Leu Tyr Trp Cys Asp Ala Tyr Tyr Asp His Ile Glu
705                 710                 715                 720

Lys Val Phe Leu Asn Gly Thr His Arg Lys Ile Val Tyr Ser Gly Arg
                725                 730                 735

Glu Leu Asn His Pro Phe Gly Leu Ser His His Gly Asn Tyr Val Phe
                740                 745                 750

Trp Thr Asp Tyr Met Asn Gly Ser Ile Phe Gln Leu Asp Leu Ile Thr
            755                 760                 765

Ser Glu Val Thr Leu Leu Arg His Glu Arg Pro Pro Leu Phe Gly Leu
770                 775                 780

Gln Ile Tyr Asp Pro Arg Lys Gln Gln Gly Asp Asn Met Cys Arg Val
785                 790                 795                 800

Asn Asn Gly Gly Cys Ser Thr Leu Cys Leu Ala Ile Pro Gly Gly Arg
                805                 810                 815

Val Cys Ala Cys Ala Asp Asn Gln Leu Leu Asp Glu Asn Gly Thr Thr
            820                 825                 830

Cys Thr Phe Asn Pro Gly Glu Ala Leu Pro His Ile Cys Lys Ala Gly
                835                 840                 845

Glu Phe Arg Cys Lys Asn Arg His Cys Ile Gln Ala Arg Trp Lys Cys
850                 855                 860

Asp Gly Asp Asp Asp Cys Leu Asp Gly Ser Asp Glu Asp Ser Val Asn
865                 870                 875                 880

Cys Phe Asn His Ser Cys Pro Asp Asp Gln Phe Lys Cys Gln Asn Asn
                885                 890                 895

Arg Cys Ile Pro Lys Arg Trp Leu Cys Asp Gly Ala Asn Asp Cys Gly
                900                 905                 910

Ser Asn Glu Asp Glu Ser Asn Gln Thr Cys Thr Ala Arg Thr Cys Gln
            915                 920                 925

Val Asp Gln Phe Ser Cys Gly Asn Gly Arg Cys Ile Pro Arg Ala Trp
930                 935                 940

Leu Cys Asp Arg Glu Asp Asp Cys Gly Asp Gln Thr Asp Glu Met Ala
945                 950                 955                 960

Ser Cys Glu Phe Pro Thr Cys Glu Pro Leu Thr Gln Phe Val Cys Lys
                965                 970                 975

Ser Gly Arg Cys Ile Ser Ser Lys Trp His Cys Asp Ser Asp Asp Asp
            980                 985                 990

Cys Gly Asp Gly Ser Asp Glu Val Gly Cys Val His Ser Cys Phe Asp
            995                 1000                1005

Asn Gln Phe Arg Cys Ser Ser Gly Arg Cys Ile Pro Gly His Trp
    1010                1015                1020
```

```
Ala Cys Asp Gly Asp Asn Asp Cys Gly Asp Phe Ser Asp Glu Ala
1025                1030                1035

Gln Ile Asn Cys Thr Lys Glu Glu Ile His Ser Pro Ala Gly Cys
1040                1045                1050

Asn Gly Asn Glu Phe Gln Cys His Pro Asp Gly Asn Cys Val Pro
1055                1060                1065

Asp Leu Trp Arg Cys Asp Gly Glu Lys Asp Cys Glu Asp Gly Ser
1070                1075                1080

Asp Glu Lys Gly Cys Asn Gly Thr Ile Arg Leu Cys Asp His Lys
1085                1090                1095

Thr Lys Phe Ser Cys Trp Ser Thr Gly Arg Cys Ile Asn Lys Ala
1100                1105                1110

Trp Val Cys Asp Gly Asp Ile Asp Cys Glu Asp Gln Ser Asp Glu
1115                1120                1125

Asp Asp Cys Asp Ser Phe Leu Cys Gly Pro Pro Lys His Pro Cys
1130                1135                1140

Ala Asn Asp Thr Ser Val Cys Leu Gln Pro Glu Lys Leu Cys Asn
1145                1150                1155

Gly Lys Lys Asp Cys Pro Asp Gly Ser Asp Glu Gly Tyr Leu Cys
1160                1165                1170

Asp Glu Cys Ser Leu Asn Asn Gly Gly Cys Ser Asn His Cys Ser
1175                1180                1185

Val Val Pro Gly Arg Gly Ile Val Cys Ser Cys Pro Glu Gly Leu
1190                1195                1200

Gln Leu Asn Lys Asp Asn Lys Thr Cys Glu Ile Val Asp Tyr Cys
1205                1210                1215

Ser Asn His Leu Lys Cys Ser Gln Val Cys Glu Gln His Lys His
1220                1225                1230

Thr Val Lys Cys Ser Cys Tyr Glu Gly Trp Lys Leu Asp Val Asp
1235                1240                1245

Gly Glu Ser Cys Thr Ser Val Asp Pro Phe Glu Ala Phe Ile Ile
1250                1255                1260

Phe Ser Ile Arg His Glu Ile Arg Arg Ile Asp Leu His Lys Arg
1265                1270                1275

Asp Tyr Ser Leu Leu Val Pro Gly Leu Arg Asn Thr Ile Ala Leu
1280                1285                1290

Asp Phe His Phe Asn Gln Ser Leu Leu Tyr Trp Thr Asp Val Val
1295                1300                1305

Glu Asp Arg Ile Tyr Arg Gly Lys Leu Ser Glu Ser Gly Gly Val
1310                1315                1320

Ser Ala Ile Glu Val Val Val Glu His Gly Leu Ala Thr Pro Glu
1325                1330                1335

Gly Leu Thr Val Asp Trp Ile Ala Gly Asn Ile Tyr Trp Ile Asp
1340                1345                1350

Ser Asn Leu Asp Gln Ile Glu Val Ala Lys Leu Asp Gly Ser Leu
1355                1360                1365

Arg Thr Thr Leu Ile Ala Gly Ala Met Glu His Pro Arg Ala Ile
1370                1375                1380

Ala Leu Asp Pro Arg Tyr Gly Ile Leu Phe Trp Thr Asp Trp Asp
1385                1390                1395

Ala Asn Phe Pro Arg Ile Glu Ser Ala Ser Met Ser Gly Ala Gly
1400                1405                1410

Arg Lys Thr Ile Tyr Lys Asp Met Lys Thr Gly Ala Trp Pro Asn
```

```
                  1415                1420                1425

Gly Leu Thr Val Asp His Phe Glu Lys Arg Ile Val Trp Thr Asp
            1430                1435                1440

Ala Arg Ser Asp Ala Ile Tyr Ser Ala Leu Tyr Asp Gly Thr Asn
            1445                1450                1455

Met Ile Glu Ile Ile Arg Gly His Glu Tyr Leu Ser His Pro Phe
            1460                1465                1470

Ala Val Ser Leu Tyr Gly Ser Glu Val Tyr Trp Thr Asp Trp Arg
            1475                1480                1485

Thr Asn Thr Leu Ser Lys Ala Asn Lys Trp Thr Gly Gln Asn Val
            1490                1495                1500

Ser Val Ile Gln Lys Thr Ser Ala Gln Pro Phe Asp Leu Gln Ile
            1505                1510                1515

Tyr His Pro Ser Arg Gln Pro Gln Ala Pro Asn Pro Cys Ala Ala
            1520                1525                1530

Asn Asp Gly Lys Gly Pro Cys Ser His Met Cys Leu Ile Asn His
            1535                1540                1545

Asn Arg Ser Ala Ala Cys Ala Cys Pro His Leu Met Lys Leu Ser
            1550                1555                1560

Ser Asp Lys Lys Thr Cys Tyr Glu Met Lys Lys Phe Leu Leu Tyr
            1565                1570                1575

Ala Arg Arg Ser Glu Ile Arg Gly Val Asp Ile Asp Asn Pro Tyr
            1580                1585                1590

Phe Asn Phe Ile Thr Ala Phe Thr Val Pro Asp Ile Asp Asp Val
            1595                1600                1605

Thr Val Ile Asp Phe Asp Ala Ser Glu Glu Arg Leu Tyr Trp Thr
            1610                1615                1620

Asp Ile Lys Thr Gln Thr Ile Lys Arg Ala Phe Ile Asn Gly Thr
            1625                1630                1635

Gly Leu Glu Thr Val Ile Ser Arg Asp Ile Gln Ser Ile Arg Gly
            1640                1645                1650

Leu Ala Val Asp Trp Val Ser Arg Asn Leu Tyr Trp Ile Ser Ser
            1655                1660                1665

Glu Phe Asp Glu Thr Gln Ile Asn Val Ala Arg Leu Asp Gly Ser
            1670                1675                1680

Leu Lys Thr Ser Ile Ile His Gly Ile Asp Lys Pro Gln Cys Leu
            1685                1690                1695

Ala Ala His Pro Val Arg Gly Lys Leu Tyr Trp Thr Asp Gly Asn
            1700                1705                1710

Thr Ile Asn Met Ala Asn Met Asp Gly Ser Asn Ser Lys Ile Leu
            1715                1720                1725

Phe Gln Asn Gln Lys Glu Pro Val Gly Leu Ser Ile Asp Tyr Val
            1730                1735                1740

Glu Asn Lys Leu Tyr Trp Ile Ser Ser Gly Asn Gly Thr Ile Asn
            1745                1750                1755

Arg Cys Asn Leu Asp Gly Gly Asn Leu Glu Val Ile Glu Ser Met
            1760                1765                1770

Lys Glu Glu Leu Thr Lys Ala Thr Ala Leu Thr Ile Met Asp Lys
            1775                1780                1785

Lys Leu Trp Trp Ala Asp Gln Asn Leu Ala Gln Leu Gly Thr Cys
            1790                1795                1800

Ser Lys Arg Asp Gly Arg Asn Pro Thr Ile Leu Arg Asn Lys Thr
            1805                1810                1815
```

```
Ser Gly Val Val His Met Lys Val Tyr Asp Lys Glu Ala Gln Gln
    1820              1825                1830

Gly Ser Asn Ser Cys Gln Leu Asn Asn Gly Gly Cys Ser Gln Leu
    1835              1840                1845

Cys Leu Pro Thr Ser Glu Thr Thr Arg Thr Cys Met Cys Thr Val
    1850              1855                1860

Gly Tyr Tyr Leu Gln Lys Asn Arg Met Ser Cys Gln Gly Ile Glu
    1865              1870                1875

Ser Phe Leu Met Tyr Ser Val His Glu Gly Ile Arg Gly Ile Pro
    1880              1885                1890

Leu Glu Pro Ser Asp Lys Met Asp Ala Leu Met Pro Ile Ser Gly
    1895              1900                1905

Thr Ser Phe Ala Val Gly Ile Asp Phe His Ala Glu Asn Asp Thr
    1910              1915                1920

Ile Tyr Trp Thr Asp Met Gly Phe Asn Lys Ile Ser Arg Ala Lys
    1925              1930                1935

Arg Asp Gln Thr Trp Lys Glu Asp Ile Ile Thr Asn Gly Leu Gly
    1940              1945                1950

Arg Val Glu Gly Ile Ala Val Asp Trp Ile Ala Gly Asn Ile Tyr
    1955              1960                1965

Trp Thr Asp His Gly Phe Asn Leu Ile Glu Val Ala Arg Leu Asn
    1970              1975                1980

Gly Ser Phe Arg Tyr Val Ile Ile Ser Gln Gly Leu Asp Gln Pro
    1985              1990                1995

Arg Ser Ile Ala Val His Pro Glu Lys Gly Leu Leu Phe Trp Thr
    2000              2005                2010

Glu Trp Gly Gln Met Pro Cys Ile Gly Lys Ala Arg Leu Asp Gly
    2015              2020                2025

Ser Glu Lys Val Val Leu Val Ser Met Gly Ile Ala Trp Pro Asn
    2030              2035                2040

Gly Ile Ser Ile Asp Tyr Glu Glu Asn Lys Leu Tyr Trp Cys Asp
    2045              2050                2055

Ala Arg Thr Asp Lys Ile Glu Arg Ile Asp Leu Glu Thr Gly Gly
    2060              2065                2070

Asn Arg Glu Met Val Leu Ser Gly Ser Asn Val Asp Met Phe Ser
    2075              2080                2085

Val Ala Val Phe Gly Ala Tyr Ile Tyr Trp Ser Asp Arg Ala His
    2090              2095                2100

Ala Asn Gly Ser Val Arg Arg Gly His Lys Asn Asp Ala Thr Glu
    2105              2110                2115

Thr Ile Thr Met Arg Thr Gly Leu Gly Val Asn Leu Lys Glu Val
    2120              2125                2130

Lys Ile Phe Asn Arg Val Arg Glu Lys Gly Thr Asn Val Cys Ala
    2135              2140                2145

Arg Asp Asn Gly Gly Cys Lys Gln Leu Cys Leu Tyr Arg Gly Asn
    2150              2155                2160

Ser Arg Arg Thr Cys Ala Cys Ala His Gly Tyr Leu Ala Glu Asp
    2165              2170                2175

Gly Val Thr Cys Leu Arg His Glu Gly Tyr Leu Leu Tyr Ser Gly
    2180              2185                2190

Arg Thr Ile Leu Lys Ser Ile His Leu Ser Asp Glu Thr Asn Leu
    2195              2200                2205
```

```
Asn Ser Pro Ile Arg Pro Tyr Glu Asn Pro Arg Tyr Phe Lys Asn
    2210            2215            2220
Val Ile Ala Leu Ala Phe Asp Tyr Asn Gln Arg Arg Lys Gly Thr
    2225            2230            2235
Asn Arg Ile Phe Tyr Ser Asp Ala His Phe Gly Asn Ile Gln Leu
    2240            2245            2250
Ile Lys Asp Asn Trp Glu Asp Arg Gln Val Ile Val Glu Asn Val
    2255            2260            2265
Gly Ser Val Glu Gly Leu Ala Tyr His Arg Ala Trp Asp Thr Leu
    2270            2275            2280
Tyr Trp Thr Ser Ser Thr Thr Ser Ser Ile Thr Arg His Thr Val
    2285            2290            2295
Asp Gln Thr Arg Pro Gly Ala Phe Asp Arg Glu Ala Val Ile Thr
    2300            2305            2310
Met Ser Glu Asp Asp His Pro His Val Leu Ala Leu Asp Glu Cys
    2315            2320            2325
Gln Asn Leu Met Phe Trp Thr Asn Trp Asn Glu Gln His Pro Ser
    2330            2335            2340
Ile Met Arg Ser Thr Leu Thr Gly Lys Asn Ala Gln Val Val Val
    2345            2350            2355
Ser Thr Asp Ile Leu Thr Pro Asn Gly Leu Thr Ile Asp Tyr Arg
    2360            2365            2370
Ala Glu Lys Leu Tyr Phe Ser Asp Gly Ser Leu Gly Lys Ile Glu
    2375            2380            2385
Arg Cys Glu Tyr Asp Gly Ser Gln Arg His Val Ile Val Lys Ser
    2390            2395            2400
Gly Pro Gly Thr Phe Leu Ser Leu Ala Val Tyr Asp Asn Tyr Ile
    2405            2410            2415
Phe Trp Ser Asp Trp Gly Arg Arg Ala Ile Leu Arg Ser Asn Lys
    2420            2425            2430
Tyr Thr Gly Gly Asp Thr Lys Ile Leu Arg Ser Asp Ile Pro His
    2435            2440            2445
Gln Pro Met Gly Ile Ile Ala Val Ala Asn Asp Thr Asn Ser Cys
    2450            2455            2460
Glu Leu Ser Pro Cys Ala Leu Leu Asn Gly Gly Cys His Asp Leu
    2465            2470            2475
Cys Leu Leu Thr Pro Asn Gly Arg Val Asn Cys Ser Cys Arg Gly
    2480            2485            2490
Asp Arg Ile Leu Leu Glu Asp Asn Arg Cys Val Thr Lys Asn Ser
    2495            2500            2505
Ser Cys Asn Ala Tyr Ser Glu Phe Glu Cys Gly Asn Gly Glu Cys
    2510            2515            2520
Ile Asp Tyr Gln Leu Thr Cys Asp Gly Ile Pro His Cys Lys Asp
    2525            2530            2535
Lys Ser Asp Glu Lys Leu Leu Tyr Cys Glu Asn Arg Ser Cys Arg
    2540            2545            2550
Arg Gly Phe Lys Pro Cys Tyr Asn Arg Arg Cys Ile Pro His Gly
    2555            2560            2565
Lys Leu Cys Asp Gly Glu Asn Asp Cys Gly Asp Asn Ser Asp Glu
    2570            2575            2580
Leu Asp Cys Lys Val Ser Thr Cys Ala Thr Val Glu Phe Arg Cys
    2585            2590            2595
Ala Asp Gly Thr Cys Ile Pro Arg Ser Ala Arg Cys Asn Gln Asn
```

```
                    2600            2605              2610

Ile Asp Cys Ala Asp Ala Ser Asp Glu Lys Asn Cys Asn Asn Thr
    2615            2620              2625

Asp Cys Thr His Phe Tyr Lys Leu Gly Val Lys Thr Thr Gly Phe
    2630            2635              2640

Ile Arg Cys Asn Ser Thr Ser Leu Cys Val Leu Pro Thr Trp Ile
    2645            2650              2655

Cys Asp Gly Ser Asn Asp Cys Gly Asp Tyr Ser Asp Glu Leu Lys
    2660            2665              2670

Cys Pro Val Gln Asn Lys His Lys Cys Glu Glu Asn Tyr Phe Ser
    2675            2680              2685

Cys Pro Ser Gly Arg Cys Ile Leu Asn Thr Trp Ile Cys Asp Gly
    2690            2695              2700

Gln Lys Asp Cys Glu Asp Gly Arg Asp Glu Phe His Cys Asp Ser
    2705            2710              2715

Ser Cys Ser Trp Asn Gln Phe Ala Cys Ser Ala Gln Lys Cys Ile
    2720            2725              2730

Ser Lys His Trp Ile Cys Asp Gly Glu Asp Asp Cys Gly Asp Gly
    2735            2740              2745

Leu Asp Glu Ser Asp Ser Ile Cys Gly Ala Ile Thr Cys Ala Ala
    2750            2755              2760

Asp Met Phe Ser Cys Gln Gly Ser Arg Ala Cys Val Pro Arg His
    2765            2770              2775

Trp Leu Cys Asp Gly Glu Arg Asp Cys Pro Asp Gly Ser Asp Glu
    2780            2785              2790

Leu Ser Thr Ala Gly Cys Ala Pro Asn Asn Thr Cys Asp Glu Asn
    2795            2800              2805

Ala Phe Met Cys His Asn Lys Val Cys Ile Pro Lys Gln Phe Val
    2810            2815              2820

Cys Asp His Asp Asp Cys Gly Asp Gly Ser Asp Glu Ser Pro
    2825            2830              2835

Gln Cys Gly Tyr Arg Gln Cys Gly Thr Glu Glu Phe Ser Cys Ala
    2840            2845              2850

Asp Gly Arg Cys Leu Leu Asn Thr Gln Trp Gln Cys Asp Gly Asp
    2855            2860              2865

Phe Asp Cys Pro Asp His Ser Asp Glu Ala Pro Leu Asn Pro Lys
    2870            2875              2880

Cys Lys Ser Ala Glu Gln Ser Cys Asn Ser Ser Phe Phe Met Cys
    2885            2890              2895

Lys Asn Gly Arg Cys Ile Pro Ser Gly Gly Leu Cys Asp Asn Lys
    2900            2905              2910

Asp Asp Cys Gly Asp Gly Ser Asp Glu Arg Asn Cys His Ile Asn
    2915            2920              2925

Glu Cys Leu Ser Lys Lys Val Ser Gly Cys Ser Gln Asp Cys Gln
    2930            2935              2940

Asp Leu Pro Val Ser Tyr Lys Cys Lys Cys Trp Pro Gly Phe Gln
    2945            2950              2955

Leu Lys Asp Asp Gly Lys Thr Cys Val Asp Ile Asp Glu Cys Ser
    2960            2965              2970

Ser Gly Phe Pro Cys Ser Gln Gln Cys Ile Asn Thr Tyr Gly Thr
    2975            2980              2985

Tyr Lys Cys Leu Cys Thr Asp Gly Tyr Glu Ile Gln Pro Asp Asn
    2990            2995              3000
```

```
Pro Asn Gly Cys Lys Ser Leu Ser Asp Glu Pro Phe Leu Ile
    3005            3010            3015

Leu Ala Asp His His Glu Ile Arg Lys Ile Ser Thr Asp Gly Ser
    3020            3025            3030

Asn Tyr Thr Leu Leu Lys Gln Gly Leu Asn Asn Val Ile Ala Ile
    3035            3040            3045

Asp Phe Asp Tyr Arg Glu Glu Phe Ile Tyr Trp Ile Asp Ser Ser
    3050            3055            3060

Arg Pro Asn Gly Ser Arg Ile Asn Arg Met Cys Leu Asn Gly Ser
    3065            3070            3075

Asp Ile Lys Val Val His Asn Thr Ala Val Pro Asn Ala Leu Ala
    3080            3085            3090

Val Asp Trp Ile Gly Lys Asn Leu Tyr Trp Ser Asp Thr Glu Lys
    3095            3100            3105

Arg Ile Ile Glu Val Ser Lys Leu Asn Gly Leu Tyr Pro Thr Ile
    3110            3115            3120

Leu Val Ser Lys Arg Leu Lys Phe Pro Arg Asp Leu Ser Leu Asp
    3125            3130            3135

Pro Gln Ala Gly Tyr Leu Tyr Trp Ile Asp Cys Cys Glu Tyr Pro
    3140            3145            3150

His Ile Gly Arg Val Gly Met Asp Gly Thr Asn Gln Ser Val Val
    3155            3160            3165

Ile Glu Thr Lys Ile Ser Arg Pro Met Ala Leu Thr Ile Asp Tyr
    3170            3175            3180

Val Asn Arg Arg Leu Tyr Trp Ala Asp Glu Asn His Ile Glu Phe
    3185            3190            3195

Ser Asn Met Asp Gly Ser His Arg His Lys Val Pro Asn Gln Asp
    3200            3205            3210

Ile Pro Gly Val Ile Ala Leu Thr Leu Phe Glu Asp Tyr Ile Tyr
    3215            3220            3225

Trp Thr Asp Gly Lys Thr Lys Ser Leu Ser Arg Ala His Lys Thr
    3230            3235            3240

Ser Gly Ala Asp Arg Leu Ser Leu Ile Tyr Ser Trp His Ala Ile
    3245            3250            3255

Thr Asp Ile Gln Val Tyr His Ser Tyr Arg Gln Pro Asp Val Ser
    3260            3265            3270

Lys His Leu Cys Met Ile Asn Asn Gly Gly Cys Ser His Leu Cys
    3275            3280            3285

Leu Leu Ala Pro Gly Lys Thr His Thr Cys Ala Cys Pro Thr Asn
    3290            3295            3300

Phe Tyr Leu Ala Ala Asp Asn Arg Thr Cys Leu Ser Asn Cys Thr
    3305            3310            3315

Ala Ser Gln Phe Arg Cys Lys Thr Asp Lys Cys Ile Pro Phe Trp
    3320            3325            3330

Trp Lys Cys Asp Thr Val Asp Asp Cys Gly Asp Gly Ser Asp Glu
    3335            3340            3345

Pro Asp Asp Cys Pro Glu Phe Arg Cys Gln Pro Gly Arg Phe Gln
    3350            3355            3360

Cys Gly Thr Gly Leu Cys Ala Leu Pro Ala Phe Ile Cys Asp Gly
    3365            3370            3375

Glu Asn Asp Cys Gly Asp Asn Ser Asp Glu Leu Asn Cys Asp Thr
    3380            3385            3390
```

```
His Val Cys Leu Ser Gly Gln Phe Lys Cys Thr Lys Asn Gln Lys
3395                3400                3405

Cys Ile Pro Val Asn Leu Arg Cys Asn Gly Gln Asp Asp Cys Gly
3410                3415                3420

Asp Glu Glu Asp Glu Arg Asp Cys Pro Glu Asn Ser Cys Ser Pro
3425                3430                3435

Asp Tyr Phe Gln Cys Lys Thr Thr Lys His Cys Ile Ser Lys Leu
3440                3445                3450

Trp Val Cys Asp Glu Asp Pro Asp Cys Ala Asp Ala Ser Asp Glu
3455                3460                3465

Ala Asn Cys Asp Lys Lys Thr Cys Gly Pro His Glu Phe Gln Cys
3470                3475                3480

Lys Asn Asn Asn Cys Ile Pro Asp His Trp Arg Cys Asp Ser Gln
3485                3490                3495

Asn Asp Cys Ser Asp Asn Ser Asp Glu Glu Asn Cys Lys Pro Gln
3500                3505                3510

Thr Cys Thr Leu Lys Asp Phe Leu Cys Ala Asn Gly Asp Cys Val
3515                3520                3525

Ser Ser Arg Phe Trp Cys Asp Gly Asp Phe Asp Cys Ala Asp Gly
3530                3535                3540

Ser Asp Glu Arg Asn Cys Glu Thr Ser Cys Ser Lys Asp Gln Phe
3545                3550                3555

Arg Cys Ser Asn Gly Gln Cys Ile Pro Ala Lys Trp Lys Cys Asp
3560                3565                3570

Gly His Glu Asp Cys Lys Tyr Gly Glu Asp Glu Lys Ser Cys Glu
3575                3580                3585

Pro Ala Ser Pro Thr Cys Ser Arg Glu Tyr Ile Cys Ala Ser
3590                3595                3600

Asp Gly Cys Ile Ser Ala Ser Leu Lys Cys Asn Gly Glu Tyr Asp
3605                3610                3615

Cys Ala Asp Gly Ser Asp Glu Met Asp Cys Val Thr Glu Cys Lys
3620                3625                3630

Glu Asp Gln Phe Arg Cys Lys Asn Lys Ala His Cys Ile Pro Ile
3635                3640                3645

Arg Trp Leu Cys Asp Gly Ile His Asp Cys Val Asp Gly Ser Asp
3650                3655                3660

Glu Glu Asn Cys Glu Arg Gly Gly Asn Ile Cys Arg Ala Asp Glu
3665                3670                3675

Phe Leu Cys Asn Asn Ser Leu Cys Lys Leu His Phe Trp Val Cys
3680                3685                3690

Asp Gly Glu Asp Asp Cys Gly Asp Asn Ser Asp Glu Ala Pro Asp
3695                3700                3705

Met Cys Val Lys Phe Leu Cys Pro Ser Thr Arg Pro His Arg Cys
3710                3715                3720

Arg Asn Asn Arg Ile Cys Leu Gln Ser Glu Gln Met Cys Asn Gly
3725                3730                3735

Ile Asp Glu Cys Gly Asp Asn Ser Asp Glu Asp His Cys Gly Gly
3740                3745                3750

Lys Leu Thr Tyr Lys Ala Arg Pro Cys Lys Lys Asp Glu Phe Ala
3755                3760                3765

Cys Ser Asn Lys Lys Cys Ile Pro Met Asp Leu Gln Cys Asp Arg
3770                3775                3780

Leu Asp Asp Cys Gly Asp Gly Ser Asp Glu Gln Gly Cys Arg Ile
```

-continued

```
                3785                3790                3795
Ala Pro Thr Glu Tyr Thr Cys Glu Asp Asn Val Asn Pro Cys Gly
    3800                3805                3810
Asp Asp Ala Tyr Cys Asn Gln Ile Lys Thr Ser Val Phe Cys Arg
    3815                3820                3825
Cys Lys Pro Gly Phe Gln Arg Asn Met Lys Asn Arg Gln Cys Glu
    3830                3835                3840
Asp Leu Asn Glu Cys Leu Val Phe Gly Thr Cys Ser His Gln Cys
    3845                3850                3855
Ile Asn Val Glu Gly Ser Tyr Lys Cys Val Cys Asp Gln Asn Phe
    3860                3865                3870
Gln Glu Arg Asn Asn Thr Cys Ile Ala Glu Gly Ser Glu Asp Gln
    3875                3880                3885
Val Leu Tyr Ile Ala Asn Asp Thr Asp Ile Leu Gly Phe Ile Tyr
    3890                3895                3900
Pro Phe Asn Tyr Ser Gly Asp His Gln Gln Ile Ser His Ile Glu
    3905                3910                3915
His Asn Ser Arg Ile Thr Gly Met Asp Val Tyr Gln Arg Asp
    3920                3925                3930
Met Ile Ile Trp Ser Thr Gln Phe Asn Pro Gly Gly Ile Phe Tyr
    3935                3940                3945
Lys Arg Ile His Gly Arg Glu Lys Arg Gln Ala Asn Ser Gly Leu
    3950                3955                3960
Ile Cys Pro Glu Phe Lys Arg Pro Arg Asp Ile Ala Val Asp Trp
    3965                3970                3975
Val Ala Gly Asn Ile Tyr Trp Thr Asp His Ser Arg Met His Trp
    3980                3985                3990
Phe Ser Tyr Tyr Thr Thr His Trp Thr Ser Leu Arg Tyr Ser Ile
    3995                4000                4005
Asn Val Gly Gln Leu Asn Gly Pro Asn Cys Thr Arg Leu Leu Thr
    4010                4015                4020
Asn Met Ala Gly Glu Pro Tyr Ala Ile Ala Val Asn Pro Lys Arg
    4025                4030                4035
Gly Met Met Tyr Trp Thr Val Val Gly Asp His Ser His Ile Glu
    4040                4045                4050
Glu Ala Ala Met Asp Gly Thr Leu Arg Arg Ile Leu Val Gln Lys
    4055                4060                4065
Asn Leu Gln Arg Pro Thr Gly Leu Ala Val Asp Tyr Phe Ser Glu
    4070                4075                4080
Arg Ile Tyr Trp Ala Asp Phe Glu Leu Ser Ile Gly Ser Val
    4085                4090                4095
Leu Tyr Asp Gly Ser Asn Ser Val Val Ser Val Ser Ser Lys Gln
    4100                4105                4110
Gly Leu Leu His Pro His Arg Ile Asp Ile Phe Glu Asp Tyr Ile
    4115                4120                4125
Tyr Gly Ala Gly Pro Lys Asn Gly Val Phe Arg Val Gln Lys Phe
    4130                4135                4140
Gly His Gly Ser Val Glu Tyr Leu Ala Leu Asn Ile Asp Lys Thr
    4145                4150                4155
Lys Gly Val Leu Ile Ser His Arg Tyr Lys Gln Leu Asp Leu Pro
    4160                4165                4170
Asn Pro Cys Leu Asp Leu Ala Cys Glu Phe Leu Cys Leu Leu Asn
    4175                4180                4185
```

```
Pro Ser Gly Ala Thr Cys Val Cys Pro Glu Gly Lys Tyr Leu Ile
    4190                4195                4200

Asn Gly Thr Cys Asn Asp Asp Ser Leu Leu Asp Asp Ser Cys Lys
    4205                4210                4215

Leu Thr Cys Glu Asn Gly Gly Arg Cys Ile Leu Asn Glu Lys Gly
    4220                4225                4230

Asp Leu Arg Cys His Cys Trp Pro Ser Tyr Ser Gly Glu Arg Cys
    4235                4240                4245

Glu Val Asn His Cys Ser Asn Tyr Cys Gln Asn Gly Gly Thr Cys
    4250                4255                4260

Val Pro Ser Val Leu Gly Arg Pro Thr Cys Ser Cys Ala Leu Gly
    4265                4270                4275

Phe Thr Gly Pro Asn Cys Gly Lys Thr Val Cys Glu Asp Phe Cys
    4280                4285                4290

Gln Asn Gly Gly Thr Cys Ile Val Thr Ala Gly Asn Gln Pro Tyr
    4295                4300                4305

Cys His Cys Gln Pro Glu Tyr Thr Gly Asp Arg Cys Gln Tyr Tyr
    4310                4315                4320

Val Cys His His Tyr Cys Val Asn Ser Glu Ser Cys Thr Ile Gly
    4325                4330                4335

Asp Asp Gly Ser Val Glu Cys Val Cys Pro Thr Arg Tyr Glu Gly
    4340                4345                4350

Pro Lys Cys Glu Val Asp Lys Cys Val Arg His Gly Gly His
    4355                4360                4365

Cys Ile Ile Asn Lys Asp Ser Glu Asp Ile Phe Cys Asn Cys Thr
    4370                4375                4380

Asn Gly Lys Ile Ala Ser Ser Cys Gln Leu Cys Asp Gly Tyr Cys
    4385                4390                4395

Tyr Asn Gly Gly Thr Cys Gln Leu Asp Pro Glu Thr Asn Val Pro
    4400                4405                4410

Val Cys Leu Cys Ser Thr Asn Trp Ser Gly Thr Gln Cys Glu Arg
    4415                4420                4425

Pro Ala Pro Lys Ser Ser Lys Ser Asp His Ile Ser Thr Arg Ser
    4430                4435                4440

Ile Ala Ile Ile Val Pro Leu Val Leu Leu Val Thr Leu Ile Thr
    4445                4450                4455

Thr Leu Val Ile Gly Leu Val Leu Cys Lys Arg Lys Arg Arg Thr
    4460                4465                4470

Lys Thr Ile Arg Arg Gln Pro Ile Ile Asn Gly Gly Ile Asn Val
    4475                4480                4485

Glu Ile Gly Asn Pro Ser Tyr Asn Met Tyr Glu Val Asp His Asp
    4490                4495                4500

His Asn Asp Gly Gly Leu Leu Asp Pro Gly Phe Met Ile Asp Pro
    4505                4510                4515

Thr Lys Ala Arg Tyr Ile Gly Gly Gly Pro Ser Ala Phe Lys Leu
    4520                4525                4530

Pro His Thr Ala Pro Pro Ile Tyr Leu Asn Ser Asp Leu Lys Gly
    4535                4540                4545

Pro Leu Thr Ala Gly Pro Thr Asn Tyr Ser Asn Pro Val Tyr Ala
    4550                4555                4560

Lys Leu Tyr Met Asp Gly Gln Asn Cys Arg Asn Ser Leu Gly Ser
    4565                4570                4575
```

Val Asp Glu Arg Lys Glu Leu Leu Pro Lys Lys Ile Glu Ile Gly
4580                4585                     4590

Ile Arg Glu Thr Val Ala
    4595

<210> SEQ ID NO 27
<211> LENGTH: 676
<212> TYPE: PRT
<213> ORGANISM: Homo sapiens

<400> SEQUENCE: 27

Met Arg Val Leu Gly Gly Arg Cys Gly Ala Pro Leu Ala Cys Leu Leu
1               5                   10                  15

Leu Val Leu Pro Val Ser Glu Ala Asn Leu Leu Ser Lys Gln Gln Ala
            20                  25                  30

Ser Gln Val Leu Val Arg Lys Arg Ala Asn Ser Leu Leu Glu Glu
        35                  40                  45

Thr Lys Gln Gly Asn Leu Glu Arg Glu Cys Ile Glu Glu Leu Cys Asn
50                  55                  60

Lys Glu Glu Ala Arg Glu Val Phe Glu Asn Asp Pro Glu Thr Asp Tyr
65                  70                  75                  80

Phe Tyr Pro Lys Tyr Leu Val Cys Leu Arg Ser Phe Gln Thr Gly Leu
                85                  90                  95

Phe Thr Ala Ala Arg Gln Ser Thr Asn Ala Tyr Pro Asp Leu Arg Ser
            100                 105                 110

Cys Val Asn Ala Ile Pro Asp Gln Cys Ser Pro Leu Pro Cys Asn Glu
        115                 120                 125

Asp Gly Tyr Met Ser Cys Lys Asp Gly Lys Ala Ser Phe Thr Cys Thr
130                 135                 140

Cys Lys Pro Gly Trp Gln Gly Glu Lys Cys Glu Phe Asp Ile Asn Glu
145                 150                 155                 160

Cys Lys Asp Pro Ser Asn Ile Asn Gly Gly Cys Ser Gln Ile Cys Asp
                165                 170                 175

Asn Thr Pro Gly Ser Tyr His Cys Ser Cys Lys Asn Gly Phe Val Met
            180                 185                 190

Leu Ser Asn Lys Lys Asp Cys Lys Asp Val Asp Glu Cys Ser Leu Lys
        195                 200                 205

Pro Ser Ile Cys Gly Thr Ala Val Cys Lys Asn Ile Pro Gly Asp Phe
210                 215                 220

Glu Cys Glu Cys Pro Glu Gly Tyr Arg Tyr Asn Leu Lys Ser Lys Ser
225                 230                 235                 240

Cys Glu Asp Ile Asp Glu Cys Ser Glu Asn Met Cys Ala Gln Leu Cys
                245                 250                 255

Val Asn Tyr Pro Gly Gly Tyr Thr Cys Tyr Cys Asp Gly Lys Lys Gly
            260                 265                 270

Phe Lys Leu Ala Gln Asp Gln Lys Ser Cys Glu Val Val Ser Val Cys
        275                 280                 285

Leu Pro Leu Asn Leu Asp Thr Lys Tyr Glu Leu Leu Tyr Leu Ala Glu
290                 295                 300

Gln Phe Ala Gly Val Val Leu Tyr Leu Lys Phe Arg Leu Pro Glu Ile
305                 310                 315                 320

Ser Arg Phe Ser Ala Glu Phe Asp Phe Arg Thr Tyr Asp Ser Glu Gly
                325                 330                 335

Val Ile Leu Tyr Ala Glu Ser Ile Asp His Ser Ala Trp Leu Leu Ile
            340                 345                 350

Ala Leu Arg Gly Gly Lys Ile Glu Val Gln Leu Lys Asn Glu His Thr
        355                 360                 365

Ser Lys Ile Thr Thr Gly Gly Asp Val Ile Asn Asn Gly Leu Trp Asn
        370                 375                 380

Met Val Ser Val Glu Glu Leu Glu His Ser Ile Ser Ile Lys Ile Ala
385                 390                 395                 400

Lys Glu Ala Val Met Asp Ile Asn Lys Pro Gly Pro Leu Phe Lys Pro
                    405                 410                 415

Glu Asn Gly Leu Leu Glu Thr Lys Val Tyr Phe Ala Gly Phe Pro Arg
                420                 425                 430

Lys Val Glu Ser Glu Leu Ile Lys Pro Ile Asn Pro Arg Leu Asp Gly
            435                 440                 445

Cys Ile Arg Ser Trp Asn Leu Met Lys Gln Gly Ala Ser Gly Ile Lys
        450                 455                 460

Glu Ile Ile Gln Glu Lys Gln Asn Lys His Cys Leu Val Thr Val Glu
465                 470                 475                 480

Lys Gly Ser Tyr Tyr Pro Gly Ser Gly Ile Ala Gln Phe His Ile Asp
                    485                 490                 495

Tyr Asn Asn Val Ser Ser Ala Glu Gly Trp His Val Asn Val Thr Leu
                500                 505                 510

Asn Ile Arg Pro Ser Thr Gly Thr Gly Val Met Leu Ala Leu Val Ser
            515                 520                 525

Gly Asn Asn Thr Val Pro Phe Ala Val Ser Leu Val Asp Ser Thr Ser
        530                 535                 540

Glu Lys Ser Gln Asp Ile Leu Leu Ser Val Glu Asn Thr Val Ile Tyr
545                 550                 555                 560

Arg Ile Gln Ala Leu Ser Leu Cys Ser Asp Gln Gln Ser His Leu Glu
                    565                 570                 575

Phe Arg Val Asn Arg Asn Asn Leu Glu Leu Ser Thr Pro Leu Lys Ile
                580                 585                 590

Glu Thr Ile Ser His Glu Asp Leu Gln Arg Gln Leu Ala Val Leu Asp
            595                 600                 605

Lys Ala Met Lys Ala Lys Val Ala Thr Tyr Leu Gly Gly Leu Pro Asp
        610                 615                 620

Val Pro Phe Ser Ala Thr Pro Val Asn Ala Phe Tyr Asn Gly Cys Met
625                 630                 635                 640

Glu Val Asn Ile Asn Gly Val Gln Leu Asp Leu Asp Glu Ala Ile Ser
                    645                 650                 655

Lys His Asn Asp Ile Arg Ala His Ser Cys Pro Ser Val Trp Lys Lys
                660                 665                 670

Thr Lys Asn Ser
        675

<210> SEQ ID NO 28
<211> LENGTH: 678
<212> TYPE: PRT
<213> ORGANISM: Homo sapiens

<400> SEQUENCE: 28

Met Ala Pro Ser Leu Ser Pro Gly Pro Ala Ala Leu Arg Arg Ala Pro
1               5                   10                  15

Gln Leu Leu Leu Leu Leu Leu Ala Ala Glu Cys Ala Leu Ala Ala Leu
            20                  25                  30

Leu Pro Ala Arg Glu Ala Thr Gln Phe Leu Arg Pro Arg Gln Arg Arg

```
              35                  40                  45
Ala Phe Gln Val Phe Glu Glu Ala Lys Gln Gly His Leu Glu Arg Glu
             50                  55                  60

Cys Val Glu Glu Leu Cys Ser Arg Glu Glu Ala Arg Glu Val Phe Glu
 65                  70                  75                  80

Asn Asp Pro Glu Thr Asp Tyr Phe Tyr Pro Arg Tyr Leu Asp Cys Ile
                 85                  90                  95

Asn Lys Tyr Gly Ser Pro Tyr Thr Lys Asn Ser Gly Phe Ala Thr Cys
                100                 105                 110

Val Gln Asn Leu Pro Asp Gln Cys Thr Pro Asn Pro Cys Asp Arg Lys
            115                 120                 125

Gly Thr Gln Ala Cys Gln Asp Leu Met Gly Asn Phe Phe Cys Leu Cys
        130                 135                 140

Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
                180                 185                 190

Arg Thr Cys Gln Asp Ile Asp Glu Cys Ala Asp Ser Glu Ala Cys Gly
            195                 200                 205

Glu Ala Arg Cys Lys Asn Leu Pro Gly Ser Tyr Ser Cys Leu Cys Asp
        210                 215                 220

Glu Gly Phe Ala Tyr Ser Ser Gln Glu Lys Ala Cys Arg Asp Val Asp
225                 230                 235                 240

Glu Cys Leu Gln Gly Arg Cys Glu Gln Val Cys Val Asn Ser Pro Gly
                245                 250                 255

Ser Tyr Thr Cys His Cys Asp Gly Arg Gly Leu Lys Leu Ser Gln
                260                 265                 270

Asp Met Asp Thr Cys Glu Asp Ile Leu Pro Cys Val Pro Phe Ser Val
            275                 280                 285

Ala Lys Ser Val Lys Ser Leu Tyr Leu Gly Arg Met Phe Ser Gly Thr
        290                 295                 300

Pro Val Ile Arg Leu Arg Phe Lys Arg Leu Gln Pro Thr Arg Leu Val
305                 310                 315                 320

Ala Glu Phe Asp Phe Arg Thr Phe Asp Pro Glu Gly Ile Leu Leu Phe
                325                 330                 335

Ala Gly Gly His Gln Asp Ser Thr Trp Ile Val Leu Ala Leu Arg Ala
                340                 345                 350

Gly Arg Leu Glu Leu Gln Leu Arg Tyr Asn Gly Val Gly Arg Val Thr
        355                 360                 365

Ser Ser Gly Pro Val Ile Asn His Gly Met Trp Gln Thr Ile Ser Val
    370                 375                 380

Glu Glu Leu Ala Arg Asn Leu Val Ile Lys Val Asn Arg Asp Ala Val
385                 390                 395                 400

Met Lys Ile Ala Val Ala Gly Asp Leu Phe Gln Pro Glu Arg Gly Leu
                405                 410                 415

Tyr His Leu Asn Leu Thr Val Gly Gly Ile Pro Phe His Glu Lys Asp
                420                 425                 430

Leu Val Gln Pro Ile Asn Pro Arg Leu Asp Gly Cys Met Arg Ser Trp
        435                 440                 445

Asn Trp Leu Asn Gly Glu Asp Thr Thr Ile Gln Glu Thr Val Lys Val
    450                 455                 460
```

```
Asn Thr Arg Met Gln Cys Phe Ser Val Thr Glu Arg Gly Ser Phe Tyr
465                 470                 475                 480

Pro Gly Ser Gly Phe Ala Phe Tyr Ser Leu Asp Tyr Met Arg Thr Pro
            485                 490                 495

Leu Asp Val Gly Thr Glu Ser Thr Trp Glu Val Glu Val Ala His
        500                 505                 510

Ile Arg Pro Ala Ala Asp Thr Gly Val Leu Phe Ala Leu Trp Ala Pro
            515                 520                 525

Asp Leu Arg Ala Val Pro Leu Ser Val Ala Leu Val Asp Tyr His Ser
530                 535                 540

Thr Lys Lys Leu Lys Gln Leu Val Val Leu Ala Val Glu His Thr
545                 550                 555                 560

Ala Leu Ala Leu Met Glu Ile Lys Val Cys Asp Gly Gln Glu His Val
                565                 570                 575

Val Thr Val Ser Leu Arg Asp Gly Glu Ala Thr Leu Glu Val Asp Gly
            580                 585                 590

Thr Arg Gly Gln Ser Glu Val Ser Ala Ala Gln Leu Gln Glu Arg Leu
            595                 600                 605

Ala Val Leu Glu Arg His Leu Arg Ser Pro Val Leu Thr Phe Ala Gly
            610                 615                 620

Gly Leu Pro Asp Val Pro Val Thr Ser Ala Pro Val Thr Ala Phe Tyr
625                 630                 635                 640

Arg Gly Cys Met Thr Leu Glu Val Asn Arg Arg Leu Leu Asp Leu Asp
                645                 650                 655

Glu Ala Ala Tyr Lys His Ser Asp Ile Thr Ala His Ser Cys Pro Pro
                660                 665                 670

Val Glu Pro Ala Ala Ala
            675

<210> SEQ ID NO 29
<211> LENGTH: 1013
<212> TYPE: PRT
<213> ORGANISM: Homo sapiens

<400> SEQUENCE: 29

Met Gly Leu Gly Thr Leu Ser Pro Arg Met Leu Val Trp Leu Val Ala
1               5                   10                  15

Ser Gly Ile Val Phe Tyr Gly Glu Leu Trp Val Cys Ala Gly Leu Asp
            20                  25                  30

Tyr Asp Tyr Thr Phe Asp Gly Asn Glu Glu Asp Lys Thr Glu Thr Ile
        35                  40                  45

Asp Tyr Lys Asp Pro Cys Lys Ala Ala Val Phe Trp Gly Asp Ile Ala
    50                  55                  60

Leu Asp Asp Glu Asp Leu Asn Ile Phe Gln Ile Asp Arg Thr Ile Asp
65                  70                  75                  80

Leu Thr Gln Asn Pro Phe Gly Asn Leu Gly His Thr Thr Gly Gly Leu
                85                  90                  95

Gly Asp His Ala Met Ser Lys Lys Arg Gly Ala Leu Tyr Gln Leu Ile
            100                 105                 110

Asp Arg Ile Arg Arg Ile Gly Phe Gly Leu Glu Gln Asn Asn Thr Val
        115                 120                 125

Lys Gly Lys Val Pro Leu Gln Phe Ser Gly Gln Asn Glu Lys Asn Arg
    130                 135                 140

Val Pro Arg Ala Ala Thr Ser Arg Thr Glu Arg Ile Trp Pro Gly Gly
```

```
            145                 150                 155                 160
    Val Ile Pro Tyr Val Ile Gly Gly Asn Phe Thr Gly Ser Gln Arg Ala
                    165                 170                 175
    Met Phe Lys Gln Ala Met Arg His Trp Glu Lys His Thr Cys Val Thr
                    180                 185                 190
    Phe Ile Glu Arg Ser Asp Glu Ser Tyr Ile Val Phe Thr Tyr Arg
                    195                 200                 205
    Pro Cys Gly Cys Ser Tyr Val Gly Arg Arg Gly Asn Gly Pro Gln
                    210                 215                 220
    Ala Ile Ser Ile Gly Lys Asn Cys Asp Lys Phe Gly Ile Val Val His
    225                 230                 235                 240
    Glu Leu Gly His Val Ile Gly Phe Trp His Glu His Thr Arg Pro Asp
                    245                 250                 255
    Arg Asp Asn His Val Thr Ile Ile Arg Glu Asn Ile Gln Pro Gly Gln
                    260                 265                 270
    Glu Tyr Asn Phe Leu Lys Met Glu Pro Gly Glu Val Asn Ser Leu Gly
                    275                 280                 285
    Glu Arg Tyr Asp Phe Asp Ser Ile Met His Tyr Ala Arg Asn Thr Phe
                    290                 295                 300
    Ser Arg Gly Met Phe Leu Asp Thr Ile Leu Pro Ser Arg Asp Asp Asn
    305                 310                 315                 320
    Gly Ile Arg Pro Ala Ile Gly Gln Arg Thr Arg Leu Ser Lys Gly Asp
                    325                 330                 335
    Ile Ala Gln Ala Arg Lys Leu Tyr Arg Cys Pro Ala Cys Gly Glu Thr
                    340                 345                 350
    Leu Gln Glu Ser Asn Gly Asn Leu Ser Ser Pro Gly Phe Pro Asn Gly
                    355                 360                 365
    Tyr Pro Ser Tyr Thr His Cys Ile Trp Arg Val Ser Val Thr Pro Gly
                    370                 375                 380
    Glu Lys Ile Val Leu Asn Phe Thr Thr Met Asp Leu Tyr Lys Ser Ser
    385                 390                 395                 400
    Leu Cys Trp Tyr Asp Tyr Ile Glu Val Arg Asp Gly Tyr Trp Arg Lys
                    405                 410                 415
    Ser Pro Leu Leu Gly Arg Phe Cys Gly Asp Lys Leu Pro Glu Val Leu
                    420                 425                 430
    Thr Ser Thr Asp Ser Arg Met Trp Ile Glu Phe Arg Ser Ser Ser Asn
                    435                 440                 445
    Trp Val Gly Lys Gly Phe Ala Ala Val Tyr Glu Ala Ile Cys Gly Gly
                    450                 455                 460
    Glu Ile Arg Lys Asn Glu Gly Gln Ile Gln Ser Pro Asn Tyr Pro Asp
    465                 470                 475                 480
    Asp Tyr Arg Pro Met Lys Glu Cys Val Trp Lys Ile Thr Val Ser Glu
                    485                 490                 495
    Ser Tyr His Val Gly Leu Thr Phe Gln Ser Phe Glu Ile Glu Arg His
                    500                 505                 510
    Asp Asn Cys Ala Tyr Asp Tyr Leu Glu Val Arg Asp Gly Thr Ser Glu
                    515                 520                 525
    Asn Ser Pro Leu Ile Gly Arg Phe Cys Gly Tyr Asp Lys Pro Glu Asp
                    530                 535                 540
    Ile Arg Ser Thr Ser Asn Thr Leu Trp Met Lys Phe Val Ser Asp Gly
    545                 550                 555                 560
    Thr Val Asn Lys Ala Gly Phe Ala Ala Asn Phe Phe Lys Glu Glu Asp
                    565                 570                 575
```

```
Glu Cys Ala Lys Pro Asp Arg Gly Gly Cys Glu Gln Arg Cys Leu Asn
            580                 585                 590

Thr Leu Gly Ser Tyr Gln Cys Ala Cys Glu Pro Gly Tyr Glu Leu Gly
            595                 600                 605

Pro Asp Arg Arg Ser Cys Glu Ala Ala Cys Gly Gly Leu Leu Thr Lys
            610                 615                 620

Leu Asn Gly Thr Ile Thr Thr Pro Gly Trp Pro Lys Glu Tyr Pro Pro
625                 630                 635                 640

Asn Lys Asn Cys Val Trp Gln Val Val Ala Pro Thr Gln Tyr Arg Ile
            645                 650                 655

Ser Val Lys Phe Glu Phe Phe Glu Leu Glu Gly Asn Glu Val Cys Lys
            660                 665                 670

Tyr Asp Tyr Val Glu Ile Trp Ser Gly Leu Ser Ser Glu Ser Lys Leu
            675                 680                 685

His Gly Lys Phe Cys Gly Ala Glu Val Pro Glu Val Ile Thr Ser Gln
            690                 695                 700

Phe Asn Asn Met Arg Ile Glu Phe Lys Ser Asp Asn Thr Val Ser Lys
705                 710                 715                 720

Lys Gly Phe Lys Ala His Phe Phe Ser Asp Lys Asp Gly Cys Ser Lys
            725                 730                 735

Asp Asn Gly Gly Cys Gln His Glu Cys Val Asn Thr Met Gly Ser Tyr
            740                 745                 750

Met Cys Gln Cys Arg Asn Gly Phe Val Leu His Asp Asn Lys His Asp
            755                 760                 765

Cys Lys Glu Ala Glu Cys Glu Gln Lys Ile His Ser Pro Ser Gly Leu
            770                 775                 780

Ile Thr Ser Pro Asn Trp Pro Asp Lys Tyr Pro Ser Arg Lys Glu Cys
785                 790                 795                 800

Thr Trp Glu Ile Ser Ala Thr Pro Gly His Arg Ile Lys Leu Ala Phe
            805                 810                 815

Ser Glu Phe Glu Ile Glu Gln His Gln Glu Cys Ala Tyr Asp His Leu
            820                 825                 830

Glu Val Phe Asp Gly Glu Thr Glu Lys Ser Pro Ile Leu Gly Arg Leu
            835                 840                 845

Cys Gly Asn Lys Ile Pro Asp Pro Leu Val Ala Thr Gly Asn Lys Met
850                 855                 860

Phe Val Arg Phe Val Ser Asp Ala Ser Val Gln Arg Lys Gly Phe Gln
865                 870                 875                 880

Ala Thr His Ser Thr Glu Cys Gly Gly Arg Leu Lys Ala Glu Ser Lys
            885                 890                 895

Pro Arg Asp Leu Tyr Ser His Ala Gln Phe Gly Asp Asn Asn Tyr Pro
            900                 905                 910

Gly Gln Val Asp Cys Glu Trp Leu Leu Val Ser Glu Arg Gly Ser Arg
            915                 920                 925

Leu Glu Leu Ser Phe Gln Thr Phe Glu Val Glu Glu Ala Asp Cys
            930                 935                 940

Gly Tyr Asp Tyr Val Glu Leu Phe Asp Gly Leu Asp Ser Thr Ala Val
945                 950                 955                 960

Gly Leu Gly Arg Phe Cys Gly Ser Gly Pro Pro Glu Glu Ile Tyr Ser
            965                 970                 975

Ile Gly Asp Ser Val Leu Ile His Phe His Thr Asp Asp Thr Ile Asn
            980                 985                 990
```

```
Lys Lys Gly Phe His Ile Arg Tyr Lys Ser Ile Arg Tyr Pro Asp Thr
            995                 1000                1005

Thr His  Thr Lys Lys
    1010

<210> SEQ ID NO 30
<211> LENGTH: 1247
<212> TYPE: PRT
<213> ORGANISM: Homo sapiens

<400> SEQUENCE: 30

Met Leu Ala Ser Ser Arg Ile Arg Ala Ala Trp Thr Arg Ala Leu
1               5                   10                  15

Leu Leu Pro Leu Leu Leu Ala Gly Pro Val Gly Cys Leu Ser Arg Gln
                20                  25                  30

Glu Leu Phe Pro Phe Gly Pro Gly Gln Gly Asp Leu Glu Leu Glu Asp
                35                  40                  45

Gly Asp Asp Phe Val Ser Pro Ala Leu Glu Leu Ser Gly Ala Leu Arg
        50                  55                  60

Phe Tyr Asp Arg Ser Asp Ile Asp Ala Val Tyr Val Thr Thr Asn Gly
65                  70                  75                  80

Ile Ile Ala Thr Ser Glu Pro Pro Ala Lys Glu Ser His Pro Gly Leu
                85                  90                  95

Phe Pro Pro Thr Phe Gly Ala Val Ala Pro Phe Leu Ala Asp Leu Asp
                100                 105                 110

Thr Thr Asp Gly Leu Gly Lys Val Tyr Tyr Arg Glu Asp Leu Ser Pro
                115                 120                 125

Ser Ile Thr Gln Arg Ala Ala Glu Cys Val His Arg Gly Phe Pro Glu
        130                 135                 140

Ile Ser Phe Gln Pro Ser Ser Ala Val Val Val Thr Trp Glu Ser Val
145                 150                 155                 160

Ala Pro Tyr Gln Gly Pro Ser Arg Asp Pro Asp Gln Lys Gly Lys Arg
                165                 170                 175

Asn Thr Phe Gln Ala Val Leu Ala Ser Ser Asp Ser Ser Ser Tyr Ala
                180                 185                 190

Ile Phe Leu Tyr Pro Glu Asp Gly Leu Gln Phe His Thr Thr Phe Ser
        195                 200                 205

Lys Lys Glu Asn Asn Gln Val Pro Ala Val Val Ala Phe Ser Gln Gly
210                 215                 220

Ser Val Gly Phe Leu Trp Lys Ser Asn Gly Ala Tyr Asn Ile Phe Ala
225                 230                 235                 240

Asn Asp Arg Glu Ser Val Glu Asn Leu Ala Lys Ser Ser Asn Ser Gly
                245                 250                 255

Gln Gln Gly Val Trp Val Phe Glu Ile Gly Ser Pro Ala Thr Thr Asn
                260                 265                 270

Gly Val Val Pro Ala Asp Val Ile Leu Gly Thr Glu Asp Gly Ala Glu
                275                 280                 285

Tyr Asp Asp Glu Asp Glu Asp Tyr Asp Leu Ala Thr Thr Arg Leu Gly
        290                 295                 300

Leu Glu Asp Val Gly Thr Thr Pro Phe Ser Tyr Lys Ala Leu Arg Arg
305                 310                 315                 320

Gly Gly Ala Asp Thr Tyr Ser Val Pro Ser Val Leu Ser Pro Arg Arg
                325                 330                 335

Ala Ala Thr Glu Arg Pro Leu Gly Pro Pro Thr Glu Arg Thr Arg Ser
                340                 345                 350
```

Phe Gln Leu Ala Val Glu Thr Phe His Gln His Pro Gln Val Ile
            355                 360                 365

Asp Val Asp Glu Val Glu Thr Gly Val Val Phe Ser Tyr Asn Thr
370                 375                 380

Asp Ser Arg Gln Thr Cys Ala Asn Asn Arg His Gln Cys Ser Val His
385                 390                 395                 400

Ala Glu Cys Arg Asp Tyr Ala Thr Gly Phe Cys Cys Ser Cys Val Ala
                405                 410                 415

Gly Tyr Thr Gly Asn Gly Arg Gln Cys Val Ala Glu Gly Ser Pro Gln
                420                 425                 430

Arg Val Asn Gly Lys Val Lys Gly Arg Ile Phe Val Gly Ser Ser Gln
            435                 440                 445

Val Pro Ile Val Phe Glu Asn Thr Asp Leu His Ser Tyr Val Val Met
            450                 455                 460

Asn His Gly Arg Ser Tyr Thr Ala Ile Ser Thr Ile Pro Glu Thr Val
465                 470                 475                 480

Gly Tyr Ser Leu Leu Pro Leu Ala Pro Val Gly Ile Ile Gly Trp
                485                 490                 495

Met Phe Ala Val Glu Gln Asp Gly Phe Lys Asn Gly Phe Ser Ile Thr
                500                 505                 510

Gly Gly Glu Phe Thr Arg Gln Ala Glu Val Thr Phe Val Gly His Pro
            515                 520                 525

Gly Asn Leu Val Ile Lys Gln Arg Phe Ser Gly Ile Asp Glu His Gly
            530                 535                 540

His Leu Thr Ile Asp Thr Glu Leu Glu Gly Arg Val Pro Gln Ile Pro
545                 550                 555                 560

Phe Gly Ser Ser Val His Ile Glu Pro Tyr Thr Glu Leu Tyr His Tyr
                565                 570                 575

Ser Thr Ser Val Ile Thr Ser Ser Thr Arg Glu Tyr Thr Val Thr
                580                 585                 590

Glu Pro Glu Arg Asp Gly Ala Ser Pro Ser Arg Ile Tyr Thr Tyr Gln
            595                 600                 605

Trp Arg Gln Thr Ile Thr Phe Gln Glu Cys Val His Asp Asp Ser Arg
            610                 615                 620

Pro Ala Leu Pro Ser Thr Gln Gln Leu Ser Val Asp Ser Val Phe Val
625                 630                 635                 640

Leu Tyr Asn Gln Glu Glu Lys Ile Leu Arg Tyr Ala Leu Ser Asn Ser
                645                 650                 655

Ile Gly Pro Val Arg Glu Gly Ser Pro Asp Ala Leu Gln Asn Pro Cys
                660                 665                 670

Tyr Ile Gly Thr His Gly Cys Asp Thr Asn Ala Ala Cys Arg Pro Gly
                675                 680                 685

Pro Arg Thr Gln Phe Thr Cys Glu Cys Ser Ile Gly Phe Arg Gly Asp
            690                 695                 700

Gly Arg Thr Cys Tyr Asp Ile Asp Glu Cys Ser Glu Gln Pro Ser Val
705                 710                 715                 720

Cys Gly Ser His Thr Ile Cys Asn Asn His Pro Gly Thr Phe Arg Cys
                725                 730                 735

Glu Cys Val Glu Gly Tyr Gln Phe Ser Asp Glu Gly Thr Cys Val Ala
                740                 745                 750

Val Val Asp Gln Arg Pro Ile Asn Tyr Cys Glu Thr Gly Leu His Asn
            755                 760                 765

```
Cys Asp Ile Pro Gln Arg Ala Gln Cys Ile Tyr Thr Gly Gly Ser Ser
770                 775                 780

Tyr Thr Cys Ser Cys Leu Pro Gly Phe Ser Gly Asp Gly Gln Ala Cys
785                 790                 795                 800

Gln Asp Val Asp Glu Cys Gln Pro Ser Arg Cys His Pro Asp Ala Phe
                805                 810                 815

Cys Tyr Asn Thr Pro Gly Ser Phe Thr Cys Gln Cys Lys Pro Gly Tyr
                820                 825                 830

Gln Gly Asp Gly Phe Arg Cys Val Pro Gly Glu Val Glu Lys Thr Arg
                835                 840                 845

Cys Gln His Glu Arg Glu His Ile Leu Gly Ala Ala Gly Ala Thr Asp
850                 855                 860

Pro Gln Arg Pro Ile Pro Pro Gly Leu Phe Val Pro Glu Cys Asp Ala
865                 870                 875                 880

His Gly His Tyr Ala Pro Thr Gln Cys His Gly Ser Thr Gly Tyr Cys
                885                 890                 895

Trp Cys Val Asp Arg Asp Gly Arg Glu Val Glu Gly Thr Arg Thr Arg
                900                 905                 910

Pro Gly Met Thr Pro Pro Cys Leu Ser Thr Val Ala Pro Pro Ile His
                915                 920                 925

Gln Gly Pro Ala Val Pro Thr Ala Val Ile Pro Leu Pro Pro Gly Thr
930                 935                 940

His Leu Leu Phe Ala Gln Thr Gly Lys Ile Glu Arg Leu Pro Leu Glu
945                 950                 955                 960

Gly Asn Thr Met Arg Lys Thr Glu Ala Lys Ala Phe Leu His Val Pro
                965                 970                 975

Ala Lys Val Ile Ile Gly Leu Ala Phe Asp Cys Val Asp Lys Met Val
                980                 985                 990

Tyr Trp Thr Asp Ile Thr Glu Pro Ser Ile Gly Arg Ala Ser Leu His
                995                 1000                1005

Gly Gly Glu Pro Thr Thr Ile Ile Arg Gln Asp Leu Gly Ser Pro
    1010                1015                1020

Glu Gly Ile Ala Val Asp His Leu Gly Arg Asn Ile Phe Trp Thr
    1025                1030                1035

Asp Ser Asn Leu Asp Arg Ile Glu Val Ala Lys Leu Asp Gly Thr
    1040                1045                1050

Gln Arg Arg Val Leu Phe Glu Thr Asp Leu Val Asn Pro Arg Gly
    1055                1060                1065

Ile Val Thr Asp Ser Val Arg Gly Asn Leu Tyr Trp Thr Asp Trp
    1070                1075                1080

Asn Arg Asp Asn Pro Lys Ile Glu Thr Ser Tyr Met Asp Gly Thr
    1085                1090                1095

Asn Arg Arg Ile Leu Val Gln Asp Asp Leu Gly Leu Pro Asn Gly
    1100                1105                1110

Leu Thr Phe Asp Ala Phe Ser Ser Gln Leu Cys Trp Val Asp Ala
    1115                1120                1125

Gly Thr Asn Arg Ala Glu Cys Leu Asn Pro Ser Gln Pro Ser Arg
    1130                1135                1140

Arg Lys Ala Leu Glu Gly Leu Gln Tyr Pro Phe Ala Val Thr Ser
    1145                1150                1155

Tyr Gly Lys Asn Leu Tyr Phe Thr Asp Trp Lys Met Asn Ser Val
    1160                1165                1170

Val Ala Leu Asp Leu Ala Ile Ser Lys Glu Thr Asp Ala Phe Gln
```

-continued

```
            1175                1180                1185

Pro His Lys Gln Thr Arg Leu Tyr Gly Ile Thr Thr Ala Leu Ser
        1190                1195                1200

Gln Cys Pro Gln Gly His Asn Tyr Cys Ser Val Asn Asn Gly Gly
        1205                1210                1215

Cys Thr His Leu Cys Leu Ala Thr Pro Gly Ser Arg Thr Cys Arg
        1220                1225                1230

Cys Pro Asp Asn Thr Leu Gly Val Asp Cys Ile Glu Gln Lys
        1235                1240                1245

<210> SEQ ID NO 31
<211> LENGTH: 1015
<212> TYPE: PRT
<213> ORGANISM: Homo sapiens

<400> SEQUENCE: 31

Met Pro Arg Ala Thr Ala Leu Gly Ala Leu Val Ser Leu Leu Leu
1               5                   10                  15

Leu Pro Leu Pro Arg Gly Ala Gly Leu Gly Glu Arg Pro Asp Ala
                20                  25                  30

Thr Ala Asp Tyr Ser Glu Leu Asp Gly Glu Gly Thr Glu Gln Gln
            35                  40                  45

Leu Glu His Tyr His Asp Pro Cys Lys Ala Ala Val Phe Trp Gly Asp
50                  55                  60

Ile Ala Leu Asp Glu Asp Asp Leu Lys Leu Phe His Ile Asp Lys Ala
65                  70                  75                  80

Arg Asp Trp Thr Lys Gln Thr Val Gly Ala Thr Gly His Ser Thr Gly
                85                  90                  95

Gly Leu Glu Glu Gln Ala Ser Glu Ser Ser Pro Asp Thr Thr Ala Met
            100                 105                 110

Asp Thr Gly Thr Lys Glu Ala Gly Lys Asp Gly Arg Glu Asn Thr Thr
            115                 120                 125

Leu Leu His Ser Pro Gly Thr Leu His Ala Ala Ala Lys Thr Phe Ser
            130                 135                 140

Pro Arg Val Arg Arg Ala Thr Thr Ser Arg Thr Glu Arg Ile Trp Pro
145                 150                 155                 160

Gly Gly Val Ile Pro Tyr Val Ile Gly Gly Asn Phe Thr Gly Ser Gln
                165                 170                 175

Arg Ala Ile Phe Lys Gln Ala Met Arg His Trp Glu Lys His Thr Cys
            180                 185                 190

Val Thr Phe Ile Glu Arg Thr Asp Glu Glu Ser Phe Ile Val Phe Ser
            195                 200                 205

Tyr Arg Thr Cys Gly Cys Cys Ser Tyr Val Gly Arg Arg Gly Gly Gly
210                 215                 220

Pro Gln Ala Ile Ser Ile Gly Lys Asn Cys Asp Lys Phe Gly Ile Val
225                 230                 235                 240

Ala His Glu Leu Gly His Val Val Gly Phe Trp His Glu His Thr Arg
                245                 250                 255

Pro Asp Arg Asp Gln His Val Thr Ile Ile Arg Glu Asn Ile Gln Pro
            260                 265                 270

Gly Gln Glu Tyr Asn Phe Leu Lys Met Glu Ala Gly Glu Val Ser Ser
            275                 280                 285

Leu Gly Glu Thr Tyr Asp Phe Asp Ser Ile Met His Tyr Ala Arg Asn
            290                 295                 300
```

-continued

```
Thr Phe Ser Arg Gly Val Phe Leu Asp Thr Ile Leu Pro Arg Gln Asp
305                 310                 315                 320

Asp Asn Gly Val Arg Pro Thr Ile Gly Gln Arg Val Arg Leu Ser Gln
            325                 330                 335

Gly Asp Ile Ala Gln Ala Arg Lys Leu Tyr Lys Cys Pro Ala Cys Gly
            340                 345                 350

Glu Thr Leu Gln Asp Thr Thr Gly Asn Phe Ser Ala Pro Gly Phe Pro
            355                 360                 365

Asn Gly Tyr Pro Ser Tyr Ser His Cys Val Trp Arg Ile Ser Val Thr
370                 375                 380

Pro Gly Glu Lys Ile Val Leu Asn Phe Thr Ser Met Asp Leu Phe Lys
385                 390                 395                 400

Ser Arg Leu Cys Trp Tyr Asp Tyr Val Glu Val Arg Asp Gly Tyr Trp
                405                 410                 415

Arg Lys Ala Pro Leu Leu Gly Arg Phe Cys Gly Asp Lys Ile Pro Glu
                420                 425                 430

Pro Leu Val Ser Thr Asp Ser Arg Leu Trp Val Glu Phe Arg Ser Ser
            435                 440                 445

Ser Asn Ile Leu Gly Lys Gly Phe Ala Ala Tyr Glu Ala Thr Cys
450                 455                 460

Gly Gly Asp Met Asn Lys Asp Ala Gly Gln Ile Gln Ser Pro Asn Tyr
465                 470                 475                 480

Pro Asp Asp Tyr Arg Pro Ser Lys Glu Cys Val Trp Arg Ile Thr Val
                485                 490                 495

Ser Glu Gly Phe His Val Gly Leu Thr Phe Gln Ala Phe Glu Ile Glu
            500                 505                 510

Arg His Asp Ser Cys Ala Tyr Asp Tyr Leu Glu Val Arg Asp Gly Pro
            515                 520                 525

Thr Glu Glu Ser Ala Leu Ile Gly His Phe Cys Gly Tyr Glu Lys Pro
530                 535                 540

Glu Asp Val Lys Ser Ser Asn Arg Leu Trp Met Lys Phe Val Ser
545                 550                 555                 560

Asp Gly Ser Ile Asn Lys Ala Gly Phe Ala Ala Asn Phe Phe Lys Glu
                565                 570                 575

Val Asp Glu Cys Ser Trp Pro Asp His Gly Gly Cys Glu His Arg Cys
            580                 585                 590

Val Asn Thr Leu Gly Ser Tyr Lys Cys Ala Cys Asp Pro Gly Tyr Glu
            595                 600                 605

Leu Ala Ala Asp Lys Lys Met Cys Glu Val Ala Cys Gly Gly Phe Ile
610                 615                 620

Thr Lys Leu Asn Gly Thr Ile Thr Ser Pro Gly Trp Pro Lys Glu Tyr
625                 630                 635                 640

Pro Thr Asn Lys Asn Cys Val Trp Gln Val Val Ala Pro Ala Gln Tyr
                645                 650                 655

Arg Ile Ser Leu Gln Phe Glu Val Phe Glu Leu Glu Gly Asn Asp Val
            660                 665                 670

Cys Lys Tyr Asp Phe Val Glu Val Arg Ser Gly Leu Ser Pro Asp Ala
            675                 680                 685

Lys Leu His Gly Arg Phe Cys Gly Ser Glu Thr Pro Glu Val Ile Thr
            690                 695                 700

Ser Gln Ser Asn Asn Met Arg Val Glu Phe Lys Ser Asp Asn Thr Val
705                 710                 715                 720

Ser Lys Arg Gly Phe Arg Ala His Phe Phe Ser Asp Lys Asp Glu Cys
```

```
                725                 730                 735
Ala Lys Asp Asn Gly Gly Cys Gln His Glu Cys Val Asn Thr Phe Gly
            740                 745                 750

Ser Tyr Leu Cys Arg Cys Arg Asn Gly Tyr Trp Leu His Glu Asn Gly
            755                 760                 765

His Asp Cys Lys Glu Ala Gly Cys Ala His Lys Ile Ser Ser Val Glu
    770                 775                 780

Gly Thr Leu Ala Ser Pro Asn Trp Pro Asp Lys Tyr Pro Ser Arg Arg
785                 790                 795                 800

Glu Cys Thr Trp Asn Ile Ser Ser Thr Ala Gly His Arg Val Lys Leu
                805                 810                 815

Thr Phe Asn Glu Phe Glu Ile Glu Gln His Gln Glu Cys Ala Tyr Asp
            820                 825                 830

His Leu Glu Met Tyr Asp Gly Pro Asp Ser Leu Ala Pro Ile Leu Gly
        835                 840                 845

Arg Phe Cys Gly Ser Lys Lys Pro Asp Pro Thr Val Ala Ser Gly Ser
    850                 855                 860

Ser Met Phe Leu Arg Phe Tyr Ser Asp Ala Ser Val Gln Arg Lys Gly
865                 870                 875                 880

Phe Gln Ala Val His Ser Thr Glu Cys Gly Gly Arg Leu Lys Ala Glu
                885                 890                 895

Val Gln Thr Lys Glu Leu Tyr Ser His Ala Gln Phe Gly Asp Asn Asn
            900                 905                 910

Tyr Pro Ser Glu Ala Arg Cys Asp Trp Val Ile Val Ala Glu Asp Gly
        915                 920                 925

Tyr Gly Val Glu Leu Thr Phe Arg Thr Phe Glu Val Glu Glu Glu Ala
    930                 935                 940

Asp Cys Gly Tyr Asp Tyr Met Glu Ala Tyr Asp Gly Tyr Asp Ser Ser
945                 950                 955                 960

Ala Pro Arg Leu Gly Arg Phe Cys Gly Ser Gly Pro Leu Glu Glu Ile
                965                 970                 975

Tyr Ser Ala Gly Asp Ser Leu Met Ile Arg Phe Arg Thr Asp Asp Thr
            980                 985                 990

Ile Asn Lys Lys Gly Phe His Ala  Arg Tyr Thr Ser Thr Lys Phe Gln
        995                 1000                1005

Asp Ala  Leu His Met Lys Lys
    1010                1015

<210> SEQ ID NO 32
<211> LENGTH: 1207
<212> TYPE: PRT
<213> ORGANISM: Homo sapiens

<400> SEQUENCE: 32

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80
```

-continued

```
Phe His Tyr Asn Glu Lys Arg Ile Tyr Trp Val Asp Leu Glu Arg Gln
                 85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
            180                 185                 190

Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
    210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
            260                 265                 270

Asn Lys His Thr Gly Lys Asp Met Val Arg Ile Asn Leu His Ser Ser
        275                 280                 285

Phe Val Pro Leu Gly Glu Leu Lys Val Val His Pro Leu Ala Gln Pro
    290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
            340                 345                 350

Tyr Cys Glu Asp Val Asn Glu Cys Ala Phe Trp Asn His Gly Cys Thr
        355                 360                 365

Leu Gly Cys Lys Asn Thr Pro Gly Ser Tyr Tyr Cys Thr Cys Pro Val
    370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
            420                 425                 430

Gly Lys Thr Cys Ser Gly Cys Ser Ser Pro Asp Asn Gly Gly Cys Ser
        435                 440                 445

Gln Leu Cys Val Pro Leu Ser Pro Val Ser Trp Glu Cys Asp Cys Phe
    450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
```

```
            500             505             510
Met Val Tyr Ala Leu Asp His Asp Pro Val Glu Asn Lys Ile Tyr Phe
            515             520             525

Ala His Thr Ala Leu Lys Trp Ile Glu Arg Ala Asn Met Asp Gly Ser
            530             535             540

Gln Arg Glu Arg Leu Ile Glu Glu Gly Val Asp Val Pro Glu Gly Leu
545             550             555             560

Ala Val Asp Trp Ile Gly Arg Arg Phe Tyr Trp Thr Asp Arg Gly Lys
                565             570             575

Ser Leu Ile Gly Arg Ser Asp Leu Asn Gly Lys Arg Ser Lys Ile Ile
            580             585             590

Thr Lys Glu Asn Ile Ser Gln Pro Arg Gly Ile Ala Val His Pro Met
            595             600             605

Ala Lys Arg Leu Phe Trp Thr Asp Thr Gly Ile Asn Pro Arg Ile Glu
            610             615             620

Ser Ser Ser Leu Gln Gly Leu Gly Arg Leu Val Ile Ala Ser Ser Asp
625             630             635             640

Leu Ile Trp Pro Ser Gly Ile Thr Ile Asp Phe Leu Thr Asp Lys Leu
                645             650             655

Tyr Trp Cys Asp Ala Lys Gln Ser Val Ile Glu Met Ala Asn Leu Asp
                660             665             670

Gly Ser Lys Arg Arg Leu Thr Gln Asn Asp Val Gly His Pro Phe
            675             680             685

Ala Val Ala Val Phe Glu Asp Tyr Val Trp Phe Ser Asp Trp Ala Met
            690             695             700

Pro Ser Val Met Arg Val Asn Lys Arg Thr Gly Lys Asp Arg Val Arg
705             710             715             720

Leu Gln Gly Ser Met Leu Lys Pro Ser Ser Leu Val Val Val His Pro
                725             730             735

Leu Ala Lys Pro Gly Ala Asp Pro Cys Leu Tyr Gln Asn Gly Gly Cys
                740             745             750

Glu His Ile Cys Lys Lys Arg Leu Gly Thr Ala Trp Cys Ser Cys Arg
            755             760             765

Glu Gly Phe Met Lys Ala Ser Asp Gly Lys Thr Cys Leu Ala Leu Asp
            770             775             780

Gly His Gln Leu Leu Ala Gly Gly Glu Val Asp Leu Lys Asn Gln Val
785             790             795             800

Thr Pro Leu Asp Ile Leu Ser Lys Thr Arg Val Ser Glu Asp Asn Ile
                805             810             815

Thr Glu Ser Gln His Met Leu Val Ala Glu Ile Met Val Ser Asp Gln
            820             825             830

Asp Asp Cys Ala Pro Val Gly Cys Ser Met Tyr Ala Arg Cys Ile Ser
            835             840             845

Glu Gly Glu Asp Ala Thr Cys Gln Cys Leu Lys Gly Phe Ala Gly Asp
            850             855             860

Gly Lys Leu Cys Ser Asp Ile Asp Glu Cys Glu Met Gly Val Pro Val
865             870             875             880

Cys Pro Pro Ala Ser Ser Lys Cys Ile Asn Thr Glu Gly Gly Tyr Val
                885             890             895

Cys Arg Cys Ser Glu Gly Tyr Gln Gly Asp Gly Ile His Cys Leu Asp
                900             905             910

Ile Asp Glu Cys Gln Leu Gly Glu His Ser Cys Gly Glu Asn Ala Ser
            915             920             925
```

```
Cys Thr Asn Thr Glu Gly Gly Tyr Thr Cys Met Cys Ala Gly Arg Leu
930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
            965                 970                 975

Pro Leu Ser His Asp Gly Tyr Cys Leu His Asp Gly Val Cys Met Tyr
            980                 985                 990

Ile Glu Ala Leu Asp Lys Tyr Ala Cys Asn Cys Val Val Gly Tyr Ile
        995                 1000                1005

Gly Glu Arg Cys Gln Tyr Arg Asp Leu Lys Trp Trp Glu Leu Arg
    1010                1015                1020

His Ala Gly His Gly Gln Gln Gln Lys Val Ile Val Ala Val
    1025                1030                1035

Cys Val Val Val Leu Val Met Leu Leu Leu Ser Leu Trp Gly
    1040                1045                1050

Ala His Tyr Tyr Arg Thr Gln Lys Leu Leu Ser Lys Asn Pro Lys
    1055                1060                1065

Asn Pro Tyr Glu Glu Ser Ser Arg Asp Val Arg Ser Arg Arg Pro
    1070                1075                1080

Ala Asp Thr Glu Asp Gly Met Ser Ser Cys Pro Gln Pro Trp Phe
    1085                1090                1095

Val Val Ile Lys Glu His Gln Asp Leu Lys Asn Gly Gly Gln Pro
    1100                1105                1110

Val Ala Gly Glu Asp Gly Gln Ala Ala Asp Gly Ser Met Gln Pro
    1115                1120                1125

Thr Ser Trp Arg Gln Glu Pro Gln Leu Cys Gly Met Gly Thr Glu
    1130                1135                1140

Gln Gly Cys Trp Ile Pro Val Ser Ser Asp Lys Gly Ser Cys Pro
    1145                1150                1155

Gln Val Met Glu Arg Ser Phe His Met Pro Ser Tyr Gly Thr Gln
    1160                1165                1170

Thr Leu Glu Gly Gly Val Glu Lys Pro His Ser Leu Leu Ser Ala
    1175                1180                1185

Asn Pro Leu Trp Gln Gln Arg Ala Leu Asp Pro His Gln Met
    1190                1195                1200

Glu Leu Thr Gln
    1205

<210> SEQ ID NO 33
<211> LENGTH: 2912
<212> TYPE: PRT
<213> ORGANISM: Homo sapiens

<400> SEQUENCE: 33

Met Gly Arg Arg Arg Arg Leu Cys Leu Gln Leu Tyr Phe Leu Trp Leu
1               5                   10                  15

Gly Cys Val Val Leu Trp Ala Gln Gly Thr Ala Gly Gln Pro Gln Pro
                20                  25                  30

Pro Pro Pro Lys Pro Pro Arg Pro Gln Pro Pro Gln Val Arg
            35                  40                  45

Ser Ala Thr Ala Gly Ser Glu Gly Gly Phe Leu Ala Pro Glu Tyr Arg
        50                  55                  60

Glu Glu Gly Ala Ala Val Ala Ser Arg Val Arg Arg Arg Gly Gln Gln
```

```
            65                  70                  75                  80
Asp Val Leu Arg Gly Pro Asn Val Cys Gly Ser Arg Phe His Ser Tyr
                85                  90                  95
Cys Cys Pro Gly Trp Lys Thr Leu Pro Gly Gly Asn Gln Cys Ile Val
            100                 105                 110
Pro Ile Cys Arg Asn Ser Cys Gly Asp Gly Phe Cys Ser Arg Pro Asn
            115                 120                 125
Met Cys Thr Cys Ser Ser Gly Gln Ile Ser Ser Thr Cys Gly Ser Lys
        130                 135                 140
Ser Ile Gln Gln Cys Ser Val Arg Cys Met Asn Gly Gly Thr Cys Ala
145                 150                 155                 160
Asp Asp His Cys Gln Cys Gln Lys Gly Tyr Ile Gly Thr Tyr Cys Gly
                165                 170                 175
Gln Pro Val Cys Glu Asn Gly Cys Gln Asn Gly Gly Arg Cys Ile Gly
            180                 185                 190
Pro Asn Arg Cys Ala Cys Val Tyr Gly Phe Thr Gly Pro Gln Cys Glu
        195                 200                 205
Arg Asp Tyr Arg Thr Gly Pro Cys Phe Thr Gln Val Asn Asn Gln Met
    210                 215                 220
Cys Gln Gly Gln Leu Thr Gly Ile Val Cys Thr Lys Thr Leu Cys Cys
225                 230                 235                 240
Ala Thr Ile Gly Arg Ala Trp Gly His Pro Cys Glu Met Cys Pro Ala
                245                 250                 255
Gln Pro Gln Pro Cys Arg Arg Gly Phe Ile Pro Asn Ile Arg Thr Gly
            260                 265                 270
Ala Cys Gln Asp Val Asp Glu Cys Gln Ala Ile Pro Gly Ile Cys Gln
        275                 280                 285
Gly Gly Asn Cys Ile Asn Thr Val Gly Ser Phe Glu Cys Arg Cys Pro
    290                 295                 300
Ala Gly His Lys Gln Ser Glu Thr Thr Gln Lys Cys Glu Asp Ile Asp
305                 310                 315                 320
Glu Cys Ser Ile Ile Pro Gly Ile Cys Glu Thr Gly Glu Cys Ser Asn
                325                 330                 335
Thr Val Gly Ser Tyr Phe Cys Val Cys Pro Arg Gly Tyr Val Thr Ser
            340                 345                 350
Thr Asp Gly Ser Arg Cys Ile Asp Gln Arg Thr Gly Met Cys Phe Ser
        355                 360                 365
Gly Leu Val Asn Gly Arg Cys Ala Gln Glu Leu Pro Gly Arg Met Thr
    370                 375                 380
Lys Met Gln Cys Cys Cys Glu Pro Gly Arg Cys Trp Gly Ile Gly Thr
385                 390                 395                 400
Ile Pro Glu Ala Cys Pro Val Arg Gly Ser Glu Glu Tyr Arg Arg Leu
                405                 410                 415
Cys Met Asp Gly Leu Pro Met Gly Gly Ile Pro Gly Ser Ala Gly Ser
            420                 425                 430
Arg Pro Gly Gly Thr Gly Gly Asn Gly Phe Ala Pro Ser Gly Asn Gly
            435                 440                 445
Asn Gly Tyr Gly Pro Gly Gly Thr Gly Phe Ile Pro Ile Pro Gly Gly
        450                 455                 460
Asn Gly Phe Ser Pro Gly Val Gly Gly Ala Gly Val Gly Ala Gly Gly
465                 470                 475                 480
Gln Gly Pro Ile Ile Thr Gly Leu Thr Ile Leu Asn Gln Thr Ile Asp
                485                 490                 495
```

-continued

```
Ile Cys Lys His His Ala Asn Leu Cys Leu Asn Gly Arg Cys Ile Pro
            500                 505                 510

Thr Val Ser Ser Tyr Arg Cys Glu Cys Asn Met Gly Tyr Lys Gln Asp
            515                 520                 525

Ala Asn Gly Asp Cys Ile Asp Val Asp Glu Cys Thr Ser Asn Pro Cys
530                 535                 540

Thr Asn Gly Asp Cys Val Asn Thr Pro Gly Ser Tyr Tyr Cys Lys Cys
545                 550                 555                 560

His Ala Gly Phe Gln Arg Thr Pro Thr Lys Gln Ala Cys Ile Asp Ile
            565                 570                 575

Asp Glu Cys Ile Gln Asn Gly Val Leu Cys Lys Asn Gly Arg Cys Val
            580                 585                 590

Asn Thr Asp Gly Ser Phe Gln Cys Ile Cys Asn Ala Gly Phe Glu Leu
            595                 600                 605

Thr Thr Asp Gly Lys Asn Cys Val Asp His Asp Glu Cys Thr Thr Thr
            610                 615                 620

Asn Met Cys Leu Asn Gly Met Cys Ile Asn Glu Asp Gly Ser Phe Lys
625                 630                 635                 640

Cys Ile Cys Lys Pro Gly Phe Val Leu Ala Pro Asn Gly Arg Tyr Cys
            645                 650                 655

Thr Asp Val Asp Glu Cys Gln Thr Pro Gly Ile Cys Met Asn Gly His
            660                 665                 670

Cys Ile Asn Ser Glu Gly Ser Phe Arg Cys Asp Cys Pro Pro Gly Leu
            675                 680                 685

Ala Val Gly Met Asp Gly Arg Val Cys Val Asp Thr His Met Arg Ser
            690                 695                 700

Thr Cys Tyr Gly Gly Ile Lys Lys Gly Val Cys Val Arg Pro Phe Pro
705                 710                 715                 720

Gly Ala Val Thr Lys Ser Glu Cys Cys Cys Ala Asn Pro Asp Tyr Gly
            725                 730                 735

Phe Gly Glu Pro Cys Gln Pro Cys Pro Ala Lys Asn Ser Ala Glu Phe
            740                 745                 750

His Gly Leu Cys Ser Ser Gly Val Gly Ile Thr Val Asp Gly Arg Asp
            755                 760                 765

Ile Asn Glu Cys Ala Leu Asp Pro Asp Ile Cys Ala Asn Gly Ile Cys
            770                 775                 780

Glu Asn Leu Arg Gly Ser Tyr Arg Cys Asn Cys Asn Ser Gly Tyr Glu
785                 790                 795                 800

Pro Asp Ala Ser Gly Arg Asn Cys Ile Asp Ile Asp Glu Cys Leu Val
            805                 810                 815

Asn Arg Leu Leu Cys Asp Asn Gly Leu Cys Arg Asn Thr Pro Gly Ser
            820                 825                 830

Tyr Ser Cys Thr Cys Pro Pro Gly Tyr Val Phe Arg Thr Glu Thr Glu
            835                 840                 845

Thr Cys Glu Asp Ile Asn Glu Cys Glu Ser Asn Pro Cys Val Asn Gly
            850                 855                 860

Ala Cys Arg Asn Asn Leu Gly Ser Phe Asn Cys Glu Cys Ser Pro Gly
865                 870                 875                 880

Ser Lys Leu Ser Ser Thr Gly Leu Ile Cys Ile Asp Ser Leu Lys Gly
            885                 890                 895

Thr Cys Trp Leu Asn Ile Gln Asp Ser Arg Cys Glu Val Asn Ile Asn
            900                 905                 910
```

Gly Ala Thr Leu Lys Ser Glu Cys Cys Ala Thr Leu Gly Ala Ala Trp
            915                 920                 925

Gly Ser Pro Cys Glu Arg Cys Glu Leu Asp Thr Ala Cys Pro Arg Gly
            930                 935                 940

Leu Ala Arg Ile Lys Gly Val Thr Cys Glu Asp Val Asn Glu Cys Glu
945                 950                 955                 960

Val Phe Pro Gly Val Cys Pro Asn Gly Arg Cys Val Asn Ser Lys Gly
                965                 970                 975

Ser Phe His Cys Glu Cys Pro Glu Gly Leu Thr Leu Asp Gly Thr Gly
            980                 985                 990

Arg Val Cys Leu Asp Ile Arg Met Glu Gln Cys Tyr Leu Lys Trp Asp
            995                 1000                1005

Glu Asp Glu Cys Ile His Pro Val Pro Gly Lys Phe Arg Met Asp
    1010                1015                1020

Ala Cys Cys Cys Ala Val Gly Ala Ala Trp Gly Thr Glu Cys Glu
    1025                1030                1035

Glu Cys Pro Lys Pro Gly Thr Lys Glu Tyr Glu Thr Leu Cys Pro
    1040                1045                1050

Arg Gly Ala Gly Phe Ala Asn Arg Gly Asp Val Leu Thr Gly Arg
    1055                1060                1065

Pro Phe Tyr Lys Asp Ile Asn Glu Cys Lys Ala Phe Pro Gly Met
    1070                1075                1080

Cys Thr Tyr Gly Lys Cys Arg Asn Thr Ile Gly Ser Phe Lys Cys
    1085                1090                1095

Arg Cys Asn Ser Gly Phe Ala Leu Asp Met Glu Glu Arg Asn Cys
    1100                1105                1110

Thr Asp Ile Asp Glu Cys Arg Ile Ser Pro Asp Leu Cys Gly Ser
    1115                1120                1125

Gly Ile Cys Val Asn Thr Pro Gly Ser Phe Glu Cys Glu Cys Phe
    1130                1135                1140

Glu Gly Tyr Glu Ser Gly Phe Met Met Met Lys Asn Cys Met Asp
    1145                1150                1155

Ile Asp Glu Cys Glu Arg Asn Pro Leu Leu Cys Arg Gly Gly Thr
    1160                1165                1170

Cys Val Asn Thr Glu Gly Ser Phe Gln Cys Asp Cys Pro Leu Gly
    1175                1180                1185

His Glu Leu Ser Pro Ser Arg Glu Asp Cys Val Asp Ile Asn Glu
    1190                1195                1200

Cys Ser Leu Ser Asp Asn Leu Cys Arg Asn Gly Lys Cys Val Asn
    1205                1210                1215

Met Ile Gly Thr Tyr Gln Cys Ser Cys Asn Pro Gly Tyr Gln Ala
    1220                1225                1230

Thr Pro Asp Arg Gln Gly Cys Thr Asp Ile Asp Glu Cys Met Ile
    1235                1240                1245

Met Asn Gly Gly Cys Asp Thr Gln Cys Thr Asn Ser Glu Gly Ser
    1250                1255                1260

Tyr Glu Cys Ser Cys Ser Glu Gly Tyr Ala Leu Met Pro Asp Gly
    1265                1270                1275

Arg Ser Cys Ala Asp Ile Asp Glu Cys Glu Asn Asn Pro Asp Ile
    1280                1285                1290

Cys Asp Gly Gly Gln Cys Thr Asn Ile Pro Gly Glu Tyr Arg Cys
    1295                1300                1305

Leu Cys Tyr Asp Gly Phe Met Ala Ser Met Asp Met Lys Thr Cys

```
                 1310           1315           1320
Ile Asp Val Asn Glu Cys Asp Leu Asn Ser Asn Ile Cys Met Phe
     1325           1330           1335
Gly Glu Cys Glu Asn Thr Lys Gly Ser Phe Ile Cys His Cys Gln
     1340           1345           1350
Leu Gly Tyr Ser Val Lys Lys Gly Thr Thr Gly Cys Thr Asp Val
     1355           1360           1365
Asp Glu Cys Glu Ile Gly Ala His Asn Cys Asp Met His Ala Ser
     1370           1375           1380
Cys Leu Asn Ile Pro Gly Ser Phe Lys Cys Ser Cys Arg Glu Gly
     1385           1390           1395
Trp Ile Gly Asn Gly Ile Lys Cys Ile Asp Leu Asp Glu Cys Ser
     1400           1405           1410
Asn Gly Thr His Gln Cys Ser Ile Asn Ala Gln Cys Val Asn Thr
     1415           1420           1425
Pro Gly Ser Tyr Arg Cys Ala Cys Ser Glu Gly Phe Thr Gly Asp
     1430           1435           1440
Gly Phe Thr Cys Ser Asp Val Asp Glu Cys Ala Glu Asn Ile Asn
     1445           1450           1455
Leu Cys Glu Asn Gly Gln Cys Leu Asn Val Pro Gly Ala Tyr Arg
     1460           1465           1470
Cys Glu Cys Glu Met Gly Phe Thr Pro Ala Ser Asp Ser Arg Ser
     1475           1480           1485
Cys Gln Asp Ile Asp Glu Cys Ser Phe Gln Asn Ile Cys Val Phe
     1490           1495           1500
Gly Thr Cys Asn Asn Leu Pro Gly Met Phe His Cys Ile Cys Asp
     1505           1510           1515
Asp Gly Tyr Glu Leu Asp Arg Thr Gly Gly Asn Cys Thr Asp Ile
     1520           1525           1530
Asp Glu Cys Ala Asp Pro Ile Asn Cys Val Asn Gly Leu Cys Val
     1535           1540           1545
Asn Thr Pro Gly Arg Tyr Glu Cys Asn Cys Pro Pro Asp Phe Gln
     1550           1555           1560
Leu Asn Pro Thr Gly Val Gly Cys Val Asp Asn Arg Val Gly Asn
     1565           1570           1575
Cys Tyr Leu Lys Phe Gly Pro Arg Gly Asp Gly Ser Leu Ser Cys
     1580           1585           1590
Asn Thr Glu Ile Gly Val Gly Val Ser Arg Ser Ser Cys Cys Cys
     1595           1600           1605
Ser Leu Gly Lys Ala Trp Gly Asn Pro Cys Glu Thr Cys Pro Pro
     1610           1615           1620
Val Asn Ser Thr Glu Tyr Tyr Thr Leu Cys Pro Gly Gly Glu Gly
     1625           1630           1635
Phe Arg Pro Asn Pro Ile Thr Ile Ile Leu Glu Asp Ile Asp Glu
     1640           1645           1650
Cys Gln Glu Leu Pro Gly Leu Cys Gln Gly Gly Asn Cys Ile Asn
     1655           1660           1665
Thr Phe Gly Ser Phe Gln Cys Glu Cys Pro Gln Gly Tyr Tyr Leu
     1670           1675           1680
Ser Glu Asp Thr Arg Ile Cys Glu Asp Ile Asp Glu Cys Phe Ala
     1685           1690           1695
His Pro Gly Val Cys Gly Pro Gly Thr Cys Tyr Asn Thr Leu Gly
     1700           1705           1710
```

```
Asn Tyr Thr Cys Ile Cys Pro Pro Glu Tyr Met Gln Val Asn Gly
1715                1720                1725

Gly His Asn Cys Met Asp Met Arg Lys Ser Phe Cys Tyr Arg Ser
1730                1735                1740

Tyr Asn Gly Thr Thr Cys Glu Asn Glu Leu Pro Phe Asn Val Thr
1745                1750                1755

Lys Arg Met Cys Cys Cys Thr Tyr Asn Val Gly Lys Ala Trp Asn
1760                1765                1770

Lys Pro Cys Glu Pro Cys Pro Thr Pro Gly Thr Ala Asp Phe Lys
1775                1780                1785

Thr Ile Cys Gly Asn Ile Pro Gly Phe Thr Phe Asp Ile His Thr
1790                1795                1800

Gly Lys Ala Val Asp Ile Asp Glu Cys Lys Glu Ile Pro Gly Ile
1805                1810                1815

Cys Ala Asn Gly Val Cys Ile Asn Gln Ile Gly Ser Phe Arg Cys
1820                1825                1830

Glu Cys Pro Thr Gly Phe Ser Tyr Asn Asp Leu Leu Leu Val Cys
1835                1840                1845

Glu Asp Ile Asp Glu Cys Ser Asn Gly Asp Asn Leu Cys Gln Arg
1850                1855                1860

Asn Ala Asp Cys Ile Asn Ser Pro Gly Ser Tyr Arg Cys Glu Cys
1865                1870                1875

Ala Ala Gly Phe Lys Leu Ser Pro Asn Gly Ala Cys Val Asp Arg
1880                1885                1890

Asn Glu Cys Leu Glu Ile Pro Asn Val Cys Ser His Gly Leu Cys
1895                1900                1905

Val Asp Leu Gln Gly Ser Tyr Gln Cys Ile Cys His Asn Gly Phe
1910                1915                1920

Lys Ala Ser Gln Asp Gln Thr Met Cys Met Asp Val Asp Glu Cys
1925                1930                1935

Glu Arg His Pro Cys Gly Asn Gly Thr Cys Lys Asn Thr Val Gly
1940                1945                1950

Ser Tyr Asn Cys Leu Cys Tyr Pro Gly Phe Glu Leu Thr His Asn
1955                1960                1965

Asn Asp Cys Leu Asp Ile Asp Glu Cys Ser Ser Phe Phe Gly Gln
1970                1975                1980

Val Cys Arg Asn Gly Arg Cys Phe Asn Glu Ile Gly Ser Phe Lys
1985                1990                1995

Cys Leu Cys Asn Glu Gly Tyr Glu Leu Thr Pro Asp Gly Lys Asn
2000                2005                2010

Cys Ile Asp Thr Asn Glu Cys Val Ala Leu Pro Gly Ser Cys Ser
2015                2020                2025

Pro Gly Thr Cys Gln Asn Leu Glu Gly Ser Phe Arg Cys Ile Cys
2030                2035                2040

Pro Pro Gly Tyr Glu Val Lys Ser Glu Asn Cys Ile Asp Ile Asn
2045                2050                2055

Glu Cys Asp Glu Asp Pro Asn Ile Cys Leu Phe Gly Ser Cys Thr
2060                2065                2070

Asn Thr Pro Gly Gly Phe Gln Cys Leu Cys Pro Pro Gly Phe Val
2075                2080                2085

Leu Ser Asp Asn Gly Arg Arg Cys Phe Asp Thr Arg Gln Ser Phe
2090                2095                2100
```

```
Cys Phe Thr Asn Phe Glu Asn Gly Lys Cys Ser Val Pro Lys Ala
    2105                2110                2115
Phe Asn Thr Thr Lys Ala Lys Cys Cys Cys Ser Lys Met Pro Gly
    2120                2125                2130
Glu Gly Trp Gly Asp Pro Cys Glu Leu Cys Pro Lys Asp Asp Glu
    2135                2140                2145
Val Ala Phe Gln Asp Leu Cys Pro Tyr Gly His Gly Thr Val Pro
    2150                2155                2160
Ser Leu His Asp Thr Arg Glu Asp Val Asn Glu Cys Leu Glu Ser
    2165                2170                2175
Pro Gly Ile Cys Ser Asn Gly Gln Cys Ile Asn Thr Asp Gly Ser
    2180                2185                2190
Phe Arg Cys Glu Cys Pro Met Gly Tyr Asn Leu Asp Tyr Thr Gly
    2195                2200                2205
Val Arg Cys Val Asp Thr Asp Glu Cys Ser Ile Gly Asn Pro Cys
    2210                2215                2220
Gly Asn Gly Thr Cys Thr Asn Val Ile Gly Ser Phe Glu Cys Asn
    2225                2230                2235
Cys Asn Glu Gly Phe Glu Pro Gly Pro Met Met Asn Cys Glu Asp
    2240                2245                2250
Ile Asn Glu Cys Ala Gln Asn Pro Leu Leu Cys Ala Phe Arg Cys
    2255                2260                2265
Met Asn Thr Phe Gly Ser Tyr Glu Cys Thr Cys Pro Ile Gly Tyr
    2270                2275                2280
Ala Leu Arg Glu Asp Gln Lys Met Cys Lys Asp Leu Asp Glu Cys
    2285                2290                2295
Ala Glu Gly Leu His Asp Cys Glu Ser Arg Gly Met Met Cys Lys
    2300                2305                2310
Asn Leu Ile Gly Thr Phe Met Cys Ile Cys Pro Pro Gly Met Ala
    2315                2320                2325
Arg Arg Pro Asp Gly Glu Gly Cys Val Asp Glu Asn Glu Cys Arg
    2330                2335                2340
Thr Lys Pro Gly Ile Cys Glu Asn Gly Arg Cys Val Asn Ile Ile
    2345                2350                2355
Gly Ser Tyr Arg Cys Glu Cys Asn Glu Gly Phe Gln Ser Ser Ser
    2360                2365                2370
Ser Gly Thr Glu Cys Leu Asp Asn Arg Gln Gly Leu Cys Phe Ala
    2375                2380                2385
Glu Val Leu Gln Thr Ile Cys Gln Met Ala Ser Ser Ser Arg Asn
    2390                2395                2400
Leu Val Thr Lys Ser Glu Cys Cys Cys Asp Gly Gly Arg Gly Trp
    2405                2410                2415
Gly His Gln Cys Glu Leu Cys Pro Leu Pro Gly Thr Ala Gln Tyr
    2420                2425                2430
Lys Lys Ile Cys Pro His Gly Pro Gly Tyr Thr Thr Asp Gly Arg
    2435                2440                2445
Asp Ile Asp Glu Cys Lys Val Met Pro Asn Leu Cys Thr Asn Gly
    2450                2455                2460
Gln Cys Ile Asn Thr Met Gly Ser Phe Arg Cys Phe Cys Lys Val
    2465                2470                2475
Gly Tyr Thr Thr Asp Ile Ser Gly Thr Ser Cys Ile Asp Leu Asp
    2480                2485                2490
Glu Cys Ser Gln Ser Pro Lys Pro Cys Asn Tyr Ile Cys Lys Asn
```

-continued

```
             2495                2500                2505
Thr Glu Gly Ser Tyr Gln Cys Ser Cys Pro Arg Gly Tyr Val Leu
     2510                2515                2520
Gln Glu Asp Gly Lys Thr Cys Lys Asp Leu Asp Glu Cys Gln Thr
     2525                2530                2535
Lys Gln His Asn Cys Gln Phe Leu Cys Val Asn Thr Leu Gly Gly
     2540                2545                2550
Phe Thr Cys Lys Cys Pro Pro Gly Phe Thr Gln His His Thr Ala
     2555                2560                2565
Cys Ile Asp Asn Asn Glu Cys Gly Ser Gln Pro Ser Leu Cys Gly
     2570                2575                2580
Ala Lys Gly Ile Cys Gln Asn Thr Pro Gly Ser Phe Ser Cys Glu
     2585                2590                2595
Cys Gln Arg Gly Phe Ser Leu Asp Ala Thr Gly Leu Asn Cys Glu
     2600                2605                2610
Asp Val Asp Glu Cys Asp Gly Asn His Arg Cys Gln His Gly Cys
     2615                2620                2625
Gln Asn Ile Leu Gly Gly Tyr Arg Cys Gly Cys Pro Gln Gly Tyr
     2630                2635                2640
Ile Gln His Tyr Gln Trp Asn Gln Cys Val Asp Glu Asn Glu Cys
     2645                2650                2655
Ser Asn Pro Asn Ala Cys Gly Ser Ala Ser Cys Tyr Asn Thr Leu
     2660                2665                2670
Gly Ser Tyr Lys Cys Ala Cys Pro Ser Gly Phe Ser Phe Asp Gln
     2675                2680                2685
Phe Ser Ser Ala Cys His Asp Val Asn Glu Cys Ser Ser Ser Lys
     2690                2695                2700
Asn Pro Cys Asn Tyr Gly Cys Ser Asn Thr Glu Gly Gly Tyr Leu
     2705                2710                2715
Cys Gly Cys Pro Pro Gly Tyr Tyr Arg Val Gly Gln Gly His Cys
     2720                2725                2730
Val Ser Gly Met Gly Phe Asn Lys Gly Gln Tyr Leu Ser Leu Asp
     2735                2740                2745
Thr Glu Val Asp Glu Glu Asn Ala Leu Ser Pro Glu Ala Cys Tyr
     2750                2755                2760
Glu Cys Lys Ile Asn Gly Tyr Ser Lys Lys Asp Ser Arg Gln Lys
     2765                2770                2775
Arg Ser Ile His Glu Pro Asp Pro Thr Ala Val Glu Gln Ile Ser
     2780                2785                2790
Leu Glu Ser Val Asp Met Asp Ser Pro Val Asn Met Lys Phe Asn
     2795                2800                2805
Leu Ser His Leu Gly Ser Lys Glu His Ile Leu Glu Leu Arg Pro
     2810                2815                2820
Ala Ile Gln Pro Leu Asn Asn His Ile Arg Tyr Val Ile Ser Gln
     2825                2830                2835
Gly Asn Asp Asp Ser Val Phe Arg Ile His Gln Arg Asn Gly Leu
     2840                2845                2850
Ser Tyr Leu His Thr Ala Lys Lys Lys Leu Met Pro Gly Thr Tyr
     2855                2860                2865
Thr Leu Glu Ile Thr Ser Ile Pro Leu Tyr Lys Lys Lys Glu Leu
     2870                2875                2880
Lys Lys Leu Glu Glu Ser Asn Glu Asp Asp Tyr Leu Leu Gly Glu
     2885                2890                2895
```

Leu Gly Glu Ala Leu Arg Met Arg Leu Gln Ile Gln Leu Tyr
2900            2905                2910

<210> SEQ ID NO 34
<211> LENGTH: 2871
<212> TYPE: PRT
<213> ORGANISM: Homo sapiens

<400> SEQUENCE: 34

Met Arg Arg Gly Arg Leu Leu Glu Ile Ala Leu Gly Phe Thr Val Leu
1               5                   10                  15

Leu Ala Ser Tyr Thr Ser His Gly Ala Asp Ala Asn Leu Glu Ala Gly
            20                  25                  30

Asn Val Lys Glu Thr Arg Ala Ser Arg Ala Lys Arg Arg Gly Gly Gly
        35                  40                  45

Gly His Asp Ala Leu Lys Gly Pro Asn Val Cys Gly Ser Arg Tyr Asn
    50                  55                  60

Ala Tyr Cys Cys Pro Gly Trp Lys Thr Leu Pro Gly Gly Asn Gln Cys
65                  70                  75                  80

Ile Val Pro Ile Cys Arg His Ser Cys Gly Asp Gly Phe Cys Ser Arg
                85                  90                  95

Pro Asn Met Cys Thr Cys Pro Ser Gly Gln Ile Ala Pro Ser Cys Gly
            100                 105                 110

Ser Arg Ser Ile Gln His Cys Asn Ile Arg Cys Met Asn Gly Gly Ser
        115                 120                 125

Cys Ser Asp Asp His Cys Leu Cys Gln Lys Gly Tyr Ile Gly Thr His
    130                 135                 140

Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
                165                 170                 175

Cys Glu Arg Asp Tyr Arg Thr Gly Pro Cys Phe Thr Val Ile Ser Asn
            180                 185                 190

Gln Met Cys Gln Gly Gln Leu Ser Gly Ile Val Cys Thr Lys Thr Leu
        195                 200                 205

Cys Cys Ala Thr Val Gly Arg Ala Trp Gly His Pro Cys Glu Met Cys
    210                 215                 220

Pro Ala Gln Pro His Pro Cys Arg Arg Gly Phe Ile Pro Asn Ile Arg
225                 230                 235                 240

Thr Gly Ala Cys Gln Asp Val Asp Glu Cys Gln Ala Ile Pro Gly Leu
                245                 250                 255

Cys Gln Gly Gly Asn Cys Ile Asn Thr Val Gly Ser Phe Glu Cys Lys
            260                 265                 270

Cys Pro Ala Gly His Lys Leu Asn Glu Val Ser Gln Lys Cys Glu Asp
        275                 280                 285

Ile Asp Glu Cys Ser Thr Ile Pro Gly Ile Cys Glu Gly Gly Glu Cys
    290                 295                 300

Thr Asn Thr Val Ser Ser Tyr Phe Cys Lys Cys Pro Pro Gly Phe Tyr
305                 310                 315                 320

Thr Ser Pro Asp Gly Thr Arg Cys Ile Asp Val Arg Pro Gly Tyr Cys
                325                 330                 335

Tyr Thr Ala Leu Thr Asn Gly Arg Cys Ser Asn Gln Leu Pro Gln Ser
            340                 345                 350

Ile Thr Lys Met Gln Cys Cys Cys Asp Ala Gly Arg Cys Trp Ser Pro

```
            355                 360                 365
Gly Val Thr Val Ala Pro Glu Met Cys Pro Ile Arg Ala Thr Glu Asp
    370                 375                 380
Phe Asn Lys Leu Cys Ser Val Pro Met Val Ile Pro Gly Arg Pro Glu
385                 390                 395                 400
Tyr Pro Pro Pro Leu Gly Pro Ile Pro Pro Val Leu Pro Val Pro
                405                 410                 415
Pro Gly Phe Pro Pro Gly Pro Gln Ile Pro Val Pro Arg Pro Pro Val
            420                 425                 430
Glu Tyr Leu Tyr Pro Ser Arg Glu Pro Pro Arg Val Leu Pro Val Asn
        435                 440                 445
Val Thr Asp Tyr Cys Gln Leu Val Arg Tyr Leu Cys Gln Asn Gly Arg
    450                 455                 460
Cys Ile Pro Thr Pro Gly Ser Cys Arg Cys Cys Asn Lys Gly Phe
465                 470                 475                 480
Gln Leu Asp Leu Arg Gly Glu Cys Ile Asp Val Asp Glu Cys Glu Lys
                485                 490                 495
Asn Pro Cys Ala Gly Gly Glu Cys Ile Asn Asn Gln Gly Ser Tyr Thr
            500                 505                 510
Cys Gln Cys Arg Ala Gly Tyr Gln Ser Thr Leu Thr Arg Thr Glu Cys
        515                 520                 525
Arg Asp Ile Asp Glu Cys Leu Gln Asn Gly Arg Ile Cys Asn Asn Gly
    530                 535                 540
Arg Cys Ile Asn Thr Asp Gly Ser Phe His Cys Val Cys Asn Ala Gly
545                 550                 555                 560
Phe His Val Thr Arg Asp Gly Lys Asn Cys Glu Asp Met Asp Glu Cys
                565                 570                 575
Ser Ile Arg Asn Met Cys Leu Asn Gly Met Cys Ile Asn Glu Asp Gly
            580                 585                 590
Ser Phe Lys Cys Ile Cys Lys Pro Gly Phe Gln Leu Ala Ser Asp Gly
        595                 600                 605
Arg Tyr Cys Lys Asp Ile Asn Glu Cys Glu Thr Pro Gly Ile Cys Met
    610                 615                 620
Asn Gly Arg Cys Val Asn Thr Asp Gly Ser Tyr Arg Cys Glu Cys Phe
625                 630                 635                 640
Pro Gly Leu Ala Val Gly Leu Asp Gly Arg Val Cys Val Asp Thr His
                645                 650                 655
Met Arg Ser Thr Cys Tyr Gly Gly Tyr Lys Arg Gly Gln Cys Ile Lys
            660                 665                 670
Pro Leu Phe Gly Ala Val Thr Lys Ser Glu Cys Cys Cys Ala Ser Thr
        675                 680                 685
Glu Tyr Ala Phe Gly Glu Pro Cys Gln Pro Cys Pro Ala Gln Asn Ser
    690                 695                 700
Ala Glu Tyr Gln Ala Leu Cys Ser Ser Gly Pro Gly Met Thr Ser Ala
705                 710                 715                 720
Gly Ser Asp Ile Asn Glu Cys Ala Leu Asp Pro Asp Ile Cys Pro Asn
                725                 730                 735
Gly Ile Cys Glu Asn Leu Arg Gly Thr Tyr Lys Cys Ile Cys Asn Ser
            740                 745                 750
Gly Tyr Glu Val Asp Ser Thr Gly Lys Asn Cys Val Asp Ile Asn Glu
        755                 760                 765
Cys Val Leu Asn Ser Leu Leu Cys Asp Asn Gly Gln Cys Arg Asn Thr
    770                 775                 780
```

```
Pro Gly Ser Phe Val Cys Thr Cys Pro Lys Gly Phe Ile Tyr Lys Pro
785                 790                 795                 800

Asp Leu Lys Thr Cys Glu Asp Ile Asp Glu Cys Glu Ser Ser Pro Cys
                805                 810                 815

Ile Asn Gly Val Cys Lys Asn Ser Pro Gly Ser Phe Ile Cys Glu Cys
            820                 825                 830

Ser Ser Glu Ser Thr Leu Asp Pro Thr Lys Thr Ile Cys Ile Glu Thr
        835                 840                 845

Ile Lys Gly Thr Cys Trp Gln Thr Val Ile Asp Gly Arg Cys Glu Ile
850                 855                 860

Asn Ile Asn Gly Ala Thr Leu Lys Ser Gln Cys Cys Ser Ser Leu Gly
865                 870                 875                 880

Ala Ala Trp Gly Ser Pro Cys Thr Leu Cys Gln Val Asp Pro Ile Cys
                885                 890                 895

Gly Lys Gly Tyr Ser Arg Ile Lys Gly Thr Gln Cys Glu Asp Ile Asp
            900                 905                 910

Glu Cys Glu Val Phe Pro Gly Val Cys Lys Asn Gly Leu Cys Val Asn
        915                 920                 925

Thr Arg Gly Ser Phe Lys Cys Gln Cys Pro Ser Gly Met Thr Leu Asp
930                 935                 940

Ala Thr Gly Arg Ile Cys Leu Asp Ile Arg Leu Glu Thr Cys Phe Leu
945                 950                 955                 960

Arg Tyr Glu Asp Glu Glu Cys Thr Leu Pro Ile Ala Gly Arg His Arg
                965                 970                 975

Met Asp Ala Cys Cys Cys Ser Val Gly Ala Ala Trp Gly Thr Glu Glu
            980                 985                 990

Cys Glu Glu Cys Pro Met Arg Asn Thr Pro Glu Tyr Glu Glu Leu Cys
        995                 1000                1005

Pro Arg Gly Pro Gly Phe Ala Thr Lys Glu Ile Thr Asn Gly Lys
    1010                1015                1020

Pro Phe Phe Lys Asp Ile Asn Glu Cys Lys Met Ile Pro Ser Leu
    1025                1030                1035

Cys Thr His Gly Lys Cys Arg Asn Thr Ile Gly Ser Phe Lys Cys
    1040                1045                1050

Arg Cys Asp Ser Gly Phe Ala Leu Asp Ser Glu Glu Arg Asn Cys
    1055                1060                1065

Thr Asp Ile Asp Glu Cys Arg Ile Ser Pro Asp Leu Cys Gly Arg
    1070                1075                1080

Gly Gln Cys Val Asn Thr Pro Gly Asp Phe Glu Cys Lys Cys Asp
    1085                1090                1095

Glu Gly Tyr Glu Ser Gly Phe Met Met Met Lys Asn Cys Met Asp
    1100                1105                1110

Ile Asp Glu Cys Gln Arg Asp Pro Leu Leu Cys Arg Gly Gly Val
    1115                1120                1125

Cys His Asn Thr Glu Gly Ser Tyr Arg Cys Glu Cys Pro Pro Gly
    1130                1135                1140

His Gln Leu Ser Pro Asn Ile Ser Ala Cys Ile Asp Ile Asn Glu
    1145                1150                1155

Cys Glu Leu Ser Ala His Leu Cys Pro Asn Gly Arg Cys Val Asn
    1160                1165                1170

Leu Ile Gly Lys Tyr Gln Cys Ala Cys Asn Pro Gly Tyr His Ser
    1175                1180                1185
```

```
Thr Pro Asp Arg Leu Phe Cys Val Asp Ile Asp Glu Cys Ser Ile
1190            1195            1200

Met Asn Gly Gly Cys Glu Thr Phe Cys Thr Asn Ser Glu Gly Ser
1205            1210            1215

Tyr Glu Cys Ser Cys Gln Pro Gly Phe Ala Leu Met Pro Asp Gln
1220            1225            1230

Arg Ser Cys Thr Asp Ile Asp Glu Cys Glu Asp Asn Pro Asn Ile
1235            1240            1245

Cys Asp Gly Gly Gln Cys Thr Asn Ile Pro Gly Glu Tyr Arg Cys
1250            1255            1260

Leu Cys Tyr Asp Gly Phe Met Ala Ser Glu Asp Met Lys Thr Cys
1265            1270            1275

Val Asp Val Asn Glu Cys Asp Leu Asn Pro Asn Ile Cys Leu Ser
1280            1285            1290

Gly Thr Cys Glu Asn Thr Lys Gly Ser Phe Ile Cys His Cys Asp
1295            1300            1305

Met Gly Tyr Ser Gly Lys Lys Gly Lys Thr Gly Cys Thr Asp Ile
1310            1315            1320

Asn Glu Cys Glu Ile Gly Ala His Asn Cys Gly Lys His Ala Val
1325            1330            1335

Cys Thr Asn Thr Ala Gly Ser Phe Lys Cys Ser Cys Ser Pro Gly
1340            1345            1350

Trp Ile Gly Asp Gly Ile Lys Cys Thr Asp Leu Asp Glu Cys Ser
1355            1360            1365

Asn Gly Thr His Met Cys Ser Gln His Ala Asp Cys Lys Asn Thr
1370            1375            1380

Met Gly Ser Tyr Arg Cys Leu Cys Lys Glu Gly Tyr Thr Gly Asp
1385            1390            1395

Gly Phe Thr Cys Thr Asp Leu Asp Glu Cys Ser Glu Asn Leu Asn
1400            1405            1410

Leu Cys Gly Asn Gly Gln Cys Leu Asn Ala Pro Gly Gly Tyr Arg
1415            1420            1425

Cys Glu Cys Asp Met Gly Phe Val Pro Ser Ala Asp Gly Lys Ala
1430            1435            1440

Cys Glu Asp Ile Asp Glu Cys Ser Leu Pro Asn Ile Cys Val Phe
1445            1450            1455

Gly Thr Cys His Asn Leu Pro Gly Leu Phe Arg Cys Glu Cys Glu
1460            1465            1470

Ile Gly Tyr Glu Leu Asp Arg Ser Gly Gly Asn Cys Thr Asp Val
1475            1480            1485

Asn Glu Cys Leu Asp Pro Thr Thr Cys Ile Ser Gly Asn Cys Val
1490            1495            1500

Asn Thr Pro Gly Ser Tyr Ile Cys Asp Cys Pro Pro Asp Phe Glu
1505            1510            1515

Leu Asn Pro Thr Arg Val Gly Cys Val Asp Thr Arg Ser Gly Asn
1520            1525            1530

Cys Tyr Leu Asp Ile Arg Pro Arg Gly Asp Asn Gly Asp Thr Ala
1535            1540            1545

Cys Ser Asn Glu Ile Gly Val Gly Val Ser Lys Ala Ser Cys Cys
1550            1555            1560

Cys Ser Leu Gly Lys Ala Trp Gly Thr Pro Cys Glu Met Cys Pro
1565            1570            1575

Ala Val Asn Thr Ser Glu Tyr Lys Ile Leu Cys Pro Gly Gly Glu
```

```
                    1580              1585              1590
Gly Phe Arg Pro Asn Pro Ile Thr Val Ile Leu Glu Asp Ile Asp
        1595              1600              1605
Glu Cys Gln Glu Leu Pro Gly Leu Cys Gln Gly Gly Lys Cys Ile
        1610              1615              1620
Asn Thr Phe Gly Ser Phe Gln Cys Arg Cys Pro Thr Gly Tyr Tyr
        1625              1630              1635
Leu Asn Glu Asp Thr Arg Val Cys Asp Asp Val Asn Glu Cys Glu
        1640              1645              1650
Thr Pro Gly Ile Cys Gly Pro Gly Thr Cys Tyr Asn Thr Val Gly
        1655              1660              1665
Asn Tyr Thr Cys Ile Cys Pro Pro Asp Tyr Met Gln Val Asn Gly
        1670              1675              1680
Gly Asn Asn Cys Met Asp Met Arg Arg Ser Leu Cys Tyr Arg Asn
        1685              1690              1695
Tyr Tyr Ala Asp Asn Gln Thr Cys Asp Gly Glu Leu Leu Phe Asn
        1700              1705              1710
Met Thr Lys Lys Met Cys Cys Cys Ser Tyr Asn Ile Gly Arg Ala
        1715              1720              1725
Trp Asn Lys Pro Cys Glu Gln Cys Pro Ile Pro Ser Thr Asp Glu
        1730              1735              1740
Phe Ala Thr Leu Cys Gly Ser Gln Arg Pro Gly Phe Val Ile Asp
        1745              1750              1755
Ile Tyr Thr Gly Leu Pro Val Asp Ile Asp Glu Cys Arg Glu Ile
        1760              1765              1770
Pro Gly Val Cys Glu Asn Gly Val Cys Ile Asn Met Val Gly Ser
        1775              1780              1785
Phe Arg Cys Glu Cys Pro Val Gly Phe Phe Tyr Asn Asp Lys Leu
        1790              1795              1800
Leu Val Cys Glu Asp Ile Asp Glu Cys Gln Asn Gly Pro Val Cys
        1805              1810              1815
Gln Arg Asn Ala Glu Cys Ile Asn Thr Ala Gly Ser Tyr Arg Cys
        1820              1825              1830
Asp Cys Lys Pro Gly Tyr Arg Phe Thr Ser Thr Gly Gln Cys Asn
        1835              1840              1845
Asp Arg Asn Glu Cys Gln Glu Ile Pro Asn Ile Cys Ser His Gly
        1850              1855              1860
Gln Cys Ile Asp Thr Val Gly Ser Phe Tyr Cys Leu Cys His Thr
        1865              1870              1875
Gly Phe Lys Thr Asn Asp Asp Gln Thr Met Cys Leu Asp Ile Asn
        1880              1885              1890
Glu Cys Glu Arg Asp Ala Cys Gly Asn Gly Thr Cys Arg Asn Thr
        1895              1900              1905
Ile Gly Ser Phe Asn Cys Arg Cys Asn His Gly Phe Ile Leu Ser
        1910              1915              1920
His Asn Asn Asp Cys Ile Asp Val Asp Glu Cys Ala Ser Gly Asn
        1925              1930              1935
Gly Asn Leu Cys Arg Asn Gly Gln Cys Ile Asn Thr Val Gly Ser
        1940              1945              1950
Phe Gln Cys Gln Cys Asn Glu Gly Tyr Glu Val Ala Pro Asp Gly
        1955              1960              1965
Arg Thr Cys Val Asp Ile Asn Glu Cys Leu Leu Glu Pro Arg Lys
        1970              1975              1980
```

-continued

```
Cys Ala Pro Gly Thr Cys Gln Asn Leu Asp Gly Ser Tyr Arg Cys
    1985              1990              1995

Ile Cys Pro Pro Gly Tyr Ser Leu Gln Asn Glu Lys Cys Glu Asp
    2000              2005              2010

Ile Asp Glu Cys Val Glu Glu Pro Glu Ile Cys Ala Leu Gly Thr
    2015              2020              2025

Cys Ser Asn Thr Glu Gly Ser Phe Lys Cys Leu Cys Pro Glu Gly
    2030              2035              2040

Phe Ser Leu Ser Ser Gly Arg Arg Cys Gln Asp Leu Arg Met
    2045              2050              2055

Ser Tyr Cys Tyr Ala Lys Phe Glu Gly Gly Lys Cys Ser Ser Pro
    2060              2065              2070

Lys Ser Arg Asn His Ser Lys Gln Glu Cys Cys Ala Leu Lys
    2075              2080              2085

Gly Glu Gly Trp Gly Asp Pro Cys Glu Leu Cys Pro Thr Glu Pro
    2090              2095              2100

Asp Glu Ala Phe Arg Gln Ile Cys Pro Tyr Gly Ser Gly Ile Ile
    2105              2110              2115

Val Gly Pro Asp Asp Ser Ala Val Asp Met Asp Glu Cys Lys Glu
    2120              2125              2130

Pro Asp Val Cys Lys His Gly Gln Cys Ile Asn Thr Asp Gly Ser
    2135              2140              2145

Tyr Arg Cys Glu Cys Pro Phe Gly Tyr Ile Leu Ala Gly Asn Glu
    2150              2155              2160

Cys Val Asp Thr Asp Glu Cys Ser Val Gly Asn Pro Cys Gly Asn
    2165              2170              2175

Gly Thr Cys Lys Asn Val Ile Gly Gly Phe Glu Cys Thr Cys Glu
    2180              2185              2190

Glu Gly Phe Glu Pro Gly Pro Met Met Thr Cys Glu Asp Ile Asn
    2195              2200              2205

Glu Cys Ala Gln Asn Pro Leu Leu Cys Ala Phe Arg Cys Val Asn
    2210              2215              2220

Thr Tyr Gly Ser Tyr Glu Cys Lys Cys Pro Val Gly Tyr Val Leu
    2225              2230              2235

Arg Glu Asp Arg Arg Met Cys Lys Asp Glu Asp Glu Cys Glu Glu
    2240              2245              2250

Gly Lys His Asp Cys Thr Glu Lys Gln Met Glu Cys Lys Asn Leu
    2255              2260              2265

Ile Gly Thr Tyr Met Cys Ile Cys Gly Pro Gly Tyr Gln Arg Arg
    2270              2275              2280

Pro Asp Gly Glu Gly Cys Val Asp Glu Asn Glu Cys Gln Thr Lys
    2285              2290              2295

Pro Gly Ile Cys Glu Asn Gly Arg Cys Leu Asn Thr Arg Gly Ser
    2300              2305              2310

Tyr Thr Cys Glu Cys Asn Asp Gly Phe Thr Ala Ser Pro Asn Gln
    2315              2320              2325

Asp Glu Cys Leu Asp Asn Arg Glu Gly Tyr Cys Phe Thr Glu Val
    2330              2335              2340

Leu Gln Asn Met Cys Gln Ile Gly Ser Ser Asn Arg Asn Pro Val
    2345              2350              2355

Thr Lys Ser Glu Cys Cys Cys Asp Gly Gly Arg Gly Trp Gly Pro
    2360              2365              2370
```

-continued

His Cys Glu Ile Cys Pro Phe Gln Gly Thr Val Ala Phe Lys Lys
2375                     2380                 2385

Leu Cys Pro His Gly Arg Gly Phe Met Thr Asn Gly Ala Asp Ile
2390                     2395                 2400

Asp Glu Cys Lys Val Ile His Asp Val Cys Arg Asn Gly Glu Cys
2405                     2410                 2415

Val Asn Asp Arg Gly Ser Tyr His Cys Ile Cys Lys Thr Gly Tyr
2420                     2425                 2430

Thr Pro Asp Ile Thr Gly Thr Ser Cys Val Asp Leu Asn Glu Cys
2435                     2440                 2445

Asn Gln Ala Pro Lys Pro Cys Asn Phe Ile Cys Lys Asn Thr Glu
2450                     2455                 2460

Gly Ser Tyr Gln Cys Ser Cys Pro Lys Gly Tyr Ile Leu Gln Glu
2465                     2470                 2475

Asp Gly Arg Ser Cys Lys Asp Leu Asp Glu Cys Ala Thr Lys Gln
2480                     2485                 2490

His Asn Cys Gln Phe Leu Cys Val Asn Thr Ile Gly Gly Phe Thr
2495                     2500                 2505

Cys Lys Cys Pro Pro Gly Phe Thr Gln His His Thr Ser Cys Ile
2510                     2515                 2520

Asp Asn Asn Glu Cys Thr Ser Asp Ile Asn Leu Cys Gly Ser Lys
2525                     2530                 2535

Gly Ile Cys Gln Asn Thr Pro Gly Ser Phe Thr Cys Glu Cys Gln
2540                     2545                 2550

Arg Gly Phe Ser Leu Asp Gln Thr Gly Ser Ser Cys Glu Asp Val
2555                     2560                 2565

Asp Glu Cys Glu Gly Asn His Arg Cys Gln His Gly Cys Gln Asn
2570                     2575                 2580

Ile Ile Gly Gly Tyr Arg Cys Ser Cys Pro Gln Gly Tyr Leu Gln
2585                     2590                 2595

His Tyr Gln Trp Asn Gln Cys Val Asp Glu Asn Glu Cys Leu Ser
2600                     2605                 2610

Ala His Ile Cys Gly Gly Ala Ser Cys His Asn Thr Leu Gly Ser
2615                     2620                 2625

Tyr Lys Cys Met Cys Pro Ala Gly Phe Gln Tyr Glu Gln Phe Ser
2630                     2635                 2640

Gly Gly Cys Gln Asp Ile Asn Glu Cys Gly Ser Ala Gln Ala Pro
2645                     2650                 2655

Cys Ser Tyr Gly Cys Ser Asn Thr Glu Gly Gly Tyr Leu Cys Gly
2660                     2665                 2670

Cys Pro Pro Gly Tyr Phe Arg Ile Gly Gln Gly His Cys Val Ser
2675                     2680                 2685

Gly Met Gly Met Gly Arg Gly Asn Pro Glu Pro Pro Val Ser Gly
2690                     2695                 2700

Glu Met Asp Asp Asn Ser Leu Ser Pro Glu Ala Cys Tyr Glu Cys
2705                     2710                 2715

Lys Ile Asn Gly Tyr Pro Lys Arg Gly Arg Lys Arg Arg Ser Thr
2720                     2725                 2730

Asn Glu Thr Asp Ala Ser Asn Ile Glu Asp Gln Ser Glu Thr Glu
2735                     2740                 2745

Ala Asn Val Ser Leu Ala Ser Trp Asp Val Glu Lys Thr Ala Ile
2750                     2755                 2760

Phe Ala Phe Asn Ile Ser His Val Ser Asn Lys Val Arg Ile Leu

```
                   2765                2770                2775
Glu Leu Leu Pro Ala Leu Thr Thr Leu Thr Asn His Asn Arg Tyr
            2780                2785                2790
Leu Ile Glu Ser Gly Asn Glu Asp Gly Phe Phe Lys Ile Asn Gln
            2795                2800                2805
Lys Glu Gly Ile Ser Tyr Leu His Phe Thr Lys Lys Pro Val
            2810                2815                2820
Ala Gly Thr Tyr Ser Leu Gln Ile Ser Ser Thr Pro Leu Tyr Lys
            2825                2830                2835
Lys Lys Glu Leu Asn Gln Leu Glu Asp Lys Tyr Asp Lys Asp Tyr
            2840                2845                2850
Leu Ser Gly Glu Leu Gly Asp Asn Leu Lys Met Lys Ile Gln Val
            2855                2860                2865
Leu Leu His
        2870

<210> SEQ ID NO 35
<211> LENGTH: 2809
<212> TYPE: PRT
<213> ORGANISM: Homo sapiens

<400> SEQUENCE: 35

Met Thr Leu Glu Gly Leu Tyr Leu Ala Arg Gly Pro Leu Ala Arg Leu
1               5                   10                  15
Leu Leu Ala Trp Ser Ala Leu Leu Cys Met Ala Gly Gly Gln Gly Arg
            20                  25                  30
Trp Asp Gly Ala Leu Glu Ala Ala Gly Pro Gly Arg Val Arg Arg Arg
        35                  40                  45
Gly Ser Pro Gly Ile Leu Gln Gly Pro Asn Val Cys Gly Ser Arg Phe
    50                  55                  60
His Ala Tyr Cys Cys Pro Gly Trp Arg Thr Phe Pro Gly Arg Ser Gln
65                  70                  75                  80
Cys Val Val Pro Ile Cys Arg Arg Ala Cys Gly Glu Gly Phe Cys Ser
                85                  90                  95
Gln Pro Asn Leu Cys Thr Cys Ala Asp Gly Thr Leu Ala Pro Ser Cys
            100                 105                 110
Gly Val Ser Arg Gly Ser Gly Cys Ser Val Ser Cys Met Asn Gly Gly
        115                 120                 125
Thr Cys Arg Gly Ala Ser Cys Leu Cys Gln Lys Gly Tyr Thr Gly Thr
    130                 135                 140
Val Cys Gly Gln Pro Ile Cys Asp Arg Gly Cys His Asn Gly Gly Arg
145                 150                 155                 160
Cys Ile Gly Pro Asn Arg Cys Ala Cys Val Tyr Gly Phe Met Gly Pro
                165                 170                 175
Gln Cys Glu Arg Asp Tyr Arg Thr Gly Pro Cys Phe Gly Gln Val Gly
            180                 185                 190
Pro Glu Gly Cys Gln His Gln Leu Thr Gly Leu Val Cys Thr Lys Ala
        195                 200                 205
Leu Cys Cys Ala Thr Val Gly Arg Ala Trp Gly Leu Pro Cys Glu Leu
    210                 215                 220
Cys Pro Ala Gln Pro His Pro Cys Arg Arg Gly Phe Ile Pro Asn Ile
225                 230                 235                 240
His Thr Gly Ala Cys Gln Asp Val Asp Glu Cys Gln Ala Val Pro Gly
                245                 250                 255
```

```
Leu Cys Gln Gly Gly Ser Cys Val Asn Met Val Gly Ser Phe His Cys
            260                 265                 270

Arg Cys Pro Val Gly His Arg Leu Ser Asp Ser Ser Ala Ala Cys Glu
            275                 280                 285

Asp Tyr Arg Ala Gly Ala Cys Phe Ser Val Leu Phe Gly Gly Arg Cys
290                 295                 300

Ala Gly Asp Leu Ala Gly His Tyr Thr Arg Arg Gln Cys Cys Cys Asp
305                 310                 315                 320

Arg Gly Arg Cys Trp Ala Ala Gly Pro Val Pro Glu Leu Cys Pro Pro
                325                 330                 335

Arg Gly Ser Asn Glu Phe Gln Gln Leu Cys Ala Gln Arg Leu Pro Leu
            340                 345                 350

Leu Pro Gly His Pro Gly Leu Phe Pro Gly Leu Leu Gly Phe Gly Ser
            355                 360                 365

Asn Gly Met Gly Pro Pro Leu Gly Pro Ala Arg Leu Asn Pro His Gly
            370                 375                 380

Ser Asp Ala Arg Gly Ile Pro Ser Leu Gly Pro Gly Asn Ser Asn Ile
385                 390                 395                 400

Gly Thr Ala Thr Leu Asn Gln Thr Ile Asp Ile Cys Arg His Phe Thr
                405                 410                 415

Asn Leu Cys Leu Asn Gly Arg Cys Leu Pro Thr Pro Ser Ser Tyr Arg
            420                 425                 430

Cys Glu Cys Asn Val Gly Tyr Thr Gln Asp Val Arg Gly Glu Cys Ile
            435                 440                 445

Asp Val Asp Glu Cys Thr Ser Ser Pro Cys His His Gly Asp Cys Val
450                 455                 460

Asn Ile Pro Gly Thr Tyr His Cys Arg Cys Tyr Pro Gly Phe Gln Ala
465                 470                 475                 480

Thr Pro Thr Arg Gln Ala Cys Val Asp Val Asp Glu Cys Ile Val Ser
                485                 490                 495

Gly Gly Leu Cys His Leu Gly Arg Cys Val Asn Thr Glu Gly Ser Phe
            500                 505                 510

Gln Cys Val Cys Asn Ala Gly Phe Glu Leu Ser Pro Asp Gly Lys Asn
            515                 520                 525

Cys Val Asp His Asn Glu Cys Ala Thr Ser Thr Met Cys Val Asn Gly
            530                 535                 540

Val Cys Leu Asn Glu Asp Gly Ser Phe Ser Cys Leu Cys Lys Pro Gly
545                 550                 555                 560

Phe Leu Leu Ala Pro Gly Gly His Tyr Cys Met Asp Ile Asp Glu Cys
                565                 570                 575

Gln Thr Pro Gly Ile Cys Val Asn Gly His Cys Thr Asn Thr Glu Gly
            580                 585                 590

Ser Phe Arg Cys Gln Cys Leu Gly Gly Leu Ala Val Gly Thr Asp Gly
            595                 600                 605

Arg Val Cys Val Asp Thr His Val Arg Ser Thr Cys Tyr Gly Ala Ile
            610                 615                 620

Glu Lys Gly Ser Cys Ala Arg Pro Phe Pro Gly Thr Val Thr Lys Ser
625                 630                 635                 640

Glu Cys Cys Cys Ala Asn Pro Asp His Gly Phe Gly Glu Pro Cys Gln
                645                 650                 655

Leu Cys Pro Ala Lys Asp Ser Ala Glu Phe Gln Ala Leu Cys Ser Ser
            660                 665                 670

Gly Leu Gly Ile Thr Thr Asp Gly Arg Asp Ile Asn Glu Cys Ala Leu
```

-continued

```
              675                 680                 685
Asp Pro Glu Val Cys Ala Asn Gly Val Cys Glu Asn Leu Arg Gly Ser
690                 695                 700

Tyr Arg Cys Val Cys Asn Leu Gly Tyr Glu Ala Gly Ala Ser Gly Lys
705                 710                 715                 720

Asp Cys Thr Asp Val Asp Glu Cys Ala Leu Asn Ser Leu Leu Cys Asp
                725                 730                 735

Asn Gly Trp Cys Gln Asn Ser Pro Gly Ser Tyr Ser Cys Ser Cys Pro
            740                 745                 750

Pro Gly Phe His Phe Trp Gln Asp Thr Glu Ile Cys Lys Asp Val Asp
                755                 760                 765

Glu Cys Leu Ser Ser Pro Cys Val Ser Gly Val Cys Arg Asn Leu Ala
            770                 775                 780

Gly Ser Tyr Thr Cys Lys Cys Gly Pro Gly Ser Arg Leu Asp Pro Ser
785                 790                 795                 800

Gly Thr Phe Cys Leu Asp Ser Thr Lys Gly Thr Cys Trp Leu Lys Ile
                805                 810                 815

Gln Glu Ser Arg Cys Glu Val Asn Leu Gln Gly Ala Ser Leu Arg Ser
            820                 825                 830

Glu Cys Cys Ala Thr Leu Gly Ala Ala Trp Gly Ser Pro Cys Glu Arg
            835                 840                 845

Cys Glu Ile Asp Pro Ala Cys Ala Arg Gly Phe Ala Arg Met Thr Gly
850                 855                 860

Val Thr Cys Asp Val Asn Glu Cys Glu Ser Phe Pro Gly Val Cys
865                 870                 875                 880

Pro Asn Gly Arg Cys Val Asn Thr Ala Gly Ser Phe Arg Cys Glu Cys
            885                 890                 895

Pro Glu Gly Leu Met Leu Asp Ala Ser Gly Arg Leu Cys Val Asp Val
            900                 905                 910

Arg Leu Glu Pro Cys Phe Leu Arg Trp Asp Glu Asp Glu Cys Gly Val
            915                 920                 925

Thr Leu Pro Gly Lys Tyr Arg Met Asp Val Cys Cys Cys Ser Ile Gly
            930                 935                 940

Ala Val Trp Gly Val Glu Cys Glu Ala Cys Pro Asp Pro Glu Ser Leu
945                 950                 955                 960

Glu Phe Ala Ser Leu Cys Pro Arg Gly Leu Gly Phe Ala Ser Arg Asp
                965                 970                 975

Phe Leu Ser Gly Arg Pro Phe Tyr Lys Asp Val Asn Glu Cys Lys Val
                980                 985                 990

Phe Pro Gly Leu Cys Thr His Gly Thr Cys Arg Asn Thr Val Gly Ser
                995                 1000                1005

Phe His Cys Ala Cys Ala Gly Gly Phe Ala Leu Asp Ala Gln Glu
            1010                1015                1020

Arg Asn Cys Thr Asp Ile Asp Glu Cys Arg Ile Ser Pro Asp Leu
            1025                1030                1035

Cys Gly Gln Gly Thr Cys Val Asn Thr Pro Gly Ser Phe Glu Cys
            1040                1045                1050

Glu Cys Phe Pro Gly Tyr Glu Ser Gly Phe Met Leu Met Lys Asn
            1055                1060                1065

Cys Met Asp Val Asp Glu Cys Ala Arg Asp Pro Leu Leu Cys Arg
            1070                1075                1080

Gly Gly Thr Cys Thr Asn Thr Asp Gly Ser Tyr Lys Cys Gln Cys
            1085                1090                1095
```

-continued

Pro Pro Gly His Glu Leu Thr Ala Lys Gly Thr Ala Cys Glu Asp
1100                1105                1110

Ile Asp Glu Cys Ser Leu Ser Asp Gly Leu Cys Pro His Gly Gln
1115                1120                1125

Cys Val Asn Val Ile Gly Ala Phe Gln Cys Ser Cys His Ala Gly
1130                1135                1140

Phe Gln Ser Thr Pro Asp Arg Gln Gly Cys Val Asp Ile Asn Glu
1145                1150                1155

Cys Arg Val Gln Asn Gly Gly Cys Asp Val His Cys Ile Asn Thr
1160                1165                1170

Glu Gly Ser Tyr Arg Cys Ser Cys Gly Gln Gly Tyr Ser Leu Met
1175                1180                1185

Pro Asp Gly Arg Ala Cys Ala Asp Val Asp Glu Cys Glu Glu Asn
1190                1195                1200

Pro Arg Val Cys Asp Gln Gly His Cys Thr Asn Met Pro Gly Gly
1205                1210                1215

His Arg Cys Leu Cys Tyr Asp Gly Phe Met Ala Thr Pro Asp Met
1220                1225                1230

Arg Thr Cys Val Asp Val Asp Glu Cys Asp Leu Asn Pro His Ile
1235                1240                1245

Cys Leu His Gly Asp Cys Glu Asn Thr Lys Gly Ser Phe Val Cys
1250                1255                1260

His Cys Gln Leu Gly Tyr Met Val Arg Lys Gly Ala Thr Gly Cys
1265                1270                1275

Ser Asp Val Asp Glu Cys Glu Val Gly His Asn Cys Asp Ser
1280                1285                1290

His Ala Ser Cys Leu Asn Ile Pro Gly Ser Phe Ser Cys Arg Cys
1295                1300                1305

Leu Pro Gly Trp Val Gly Asp Gly Phe Glu Cys His Asp Leu Asp
1310                1315                1320

Glu Cys Val Ser Gln Glu His Arg Cys Ser Pro Arg Gly Asp Cys
1325                1330                1335

Leu Asn Val Pro Gly Ser Tyr Arg Cys Thr Cys Arg Gln Gly Phe
1340                1345                1350

Ala Gly Asp Gly Phe Phe Cys Glu Asp Arg Asp Glu Cys Ala Glu
1355                1360                1365

Asn Val Asp Leu Cys Asp Asn Gly Gln Cys Leu Asn Ala Pro Gly
1370                1375                1380

Gly Tyr Arg Cys Glu Cys Glu Met Gly Phe Asp Pro Thr Glu Asp
1385                1390                1395

His Arg Ala Cys Gln Asp Val Asp Glu Cys Ala Gln Gly Asn Leu
1400                1405                1410

Cys Ala Phe Gly Ser Cys Glu Asn Leu Pro Gly Met Phe Arg Cys
1415                1420                1425

Ile Cys Asn Gly Gly Tyr Glu Leu Asp Arg Gly Gly Asn Cys
1430                1435                1440

Thr Asp Ile Asn Glu Cys Ala Asp Pro Val Asn Cys Ile Asn Gly
1445                1450                1455

Val Cys Ile Asn Thr Pro Gly Ser Tyr Leu Cys Ser Cys Pro Gln
1460                1465                1470

Asp Phe Glu Leu Asn Pro Ser Gly Val Gly Cys Val Asp Thr Arg
1475                1480                1485

```
Ala Gly Asn Cys Phe Leu Glu Thr His Asp Arg Gly Asp Ser Gly
    1490                1495                1500

Ile Ser Cys Ser Ala Glu Ile Gly Val Gly Val Thr Arg Ala Ser
1505                1510                1515

Cys Cys Cys Ser Leu Gly Arg Ala Trp Gly Asn Pro Cys Glu Leu
    1520                1525                1530

Cys Pro Met Ala Asn Thr Thr Glu Tyr Arg Thr Leu Cys Pro Gly
    1535                1540                1545

Gly Glu Gly Phe Gln Pro Asn Arg Ile Thr Val Ile Leu Glu Asp
    1550                1555                1560

Ile Asp Glu Cys Gln Glu Leu Pro Gly Leu Cys Gln Gly Gly Asp
    1565                1570                1575

Cys Val Asn Thr Phe Gly Ser Phe Gln Cys Glu Cys Pro Pro Gly
    1580                1585                1590

Tyr His Leu Ser Glu His Thr Arg Ile Cys Glu Asp Ile Asp Glu
    1595                1600                1605

Cys Ser Thr His Ser Gly Ile Cys Gly Pro Gly Thr Cys Tyr Asn
    1610                1615                1620

Thr Leu Gly Asn Tyr Thr Cys Val Cys Pro Ala Glu Tyr Leu Gln
    1625                1630                1635

Val Asn Gly Gly Asn Asn Cys Met Asp Met Arg Lys Ser Val Cys
    1640                1645                1650

Phe Arg His Tyr Asn Gly Thr Cys Gln Asn Glu Leu Ala Phe Asn
    1655                1660                1665

Val Thr Arg Lys Met Cys Cys Cys Ser Tyr Asn Ile Gly Gln Ala
    1670                1675                1680

Trp Asn Arg Pro Cys Glu Ala Cys Pro Thr Pro Ile Ser Pro Asp
    1685                1690                1695

Tyr Gln Ile Leu Cys Gly Asn Gln Ala Pro Gly Phe Leu Thr Asp
    1700                1705                1710

Ile His Thr Gly Lys Pro Leu Asp Ile Asp Glu Cys Gly Glu Ile
    1715                1720                1725

Pro Ala Ile Cys Ala Asn Gly Ile Cys Ile Asn Gln Ile Gly Ser
    1730                1735                1740

Phe Arg Cys Glu Cys Pro Ala Gly Phe Asn Tyr Asn Ser Ile Leu
    1745                1750                1755

Leu Ala Cys Glu Asp Val Asp Glu Cys Gly Ser Arg Glu Ser Pro
    1760                1765                1770

Cys Gln Gln Asn Ala Asp Cys Ile Asn Ile Pro Gly Ser Tyr Arg
    1775                1780                1785

Cys Lys Cys Thr Arg Gly Tyr Lys Leu Ser Pro Gly Gly Ala Cys
    1790                1795                1800

Val Gly Arg Asn Glu Cys Arg Glu Ile Pro Asn Val Cys Ser His
    1805                1810                1815

Gly Asp Cys Met Asp Thr Glu Gly Ser Tyr Met Cys Leu Cys His
    1820                1825                1830

Arg Gly Phe Gln Ala Ser Ala Asp Gln Thr Leu Cys Met Asp Ile
    1835                1840                1845

Asp Glu Cys Asp Arg Gln Pro Cys Gly Asn Gly Thr Cys Lys Asn
    1850                1855                1860

Ile Ile Gly Ser Tyr Asn Cys Leu Cys Phe Pro Gly Phe Val Val
    1865                1870                1875

Thr His Asn Gly Asp Cys Val Asp Phe Asp Glu Cys Thr Thr Leu
```

-continued

```
            1880              1885              1890
Val Gly Gln Val Cys Arg Phe Gly His Cys Leu Asn Thr Ala Gly
    1895              1900              1905

Ser Phe His Cys Leu Cys Gln Asp Gly Phe Glu Leu Thr Ala Asp
    1910              1915              1920

Gly Lys Asn Cys Val Asp Thr Asn Glu Cys Leu Ser Leu Ala Gly
    1925              1930              1935

Thr Cys Leu Pro Gly Thr Cys Gln Asn Leu Glu Gly Ser Phe Arg
    1940              1945              1950

Cys Ile Cys Pro Pro Gly Phe Gln Val Gln Ser Asp His Cys Ile
    1955              1960              1965

Asp Ile Asp Glu Cys Ser Glu Glu Pro Asn Leu Cys Leu Phe Gly
    1970              1975              1980

Thr Cys Thr Asn Ser Pro Gly Ser Phe Gln Cys Leu Cys Pro Pro
    1985              1990              1995

Gly Phe Val Leu Ser Asp Asn Gly His Arg Cys Phe Asp Thr Arg
    2000              2005              2010

Gln Ser Phe Cys Phe Thr Arg Phe Glu Ala Gly Lys Cys Ser Val
    2015              2020              2025

Pro Lys Ala Phe Asn Thr Thr Lys Thr Arg Cys Cys Cys Ser Lys
    2030              2035              2040

Arg Pro Gly Glu Gly Trp Gly Asp Pro Cys Glu Leu Cys Pro Gln
    2045              2050              2055

Glu Gly Ser Ala Ala Phe Gln Glu Leu Cys Pro Phe Gly His Gly
    2060              2065              2070

Ala Val Pro Gly Pro Asp Asp Ser Arg Glu Asp Val Asn Glu Cys
    2075              2080              2085

Ala Glu Asn Pro Gly Val Cys Thr Asn Gly Val Cys Val Asn Thr
    2090              2095              2100

Asp Gly Ser Phe Arg Cys Glu Cys Pro Phe Gly Tyr Ser Leu Asp
    2105              2110              2115

Phe Thr Gly Ile Asn Cys Val Asp Thr Asp Glu Cys Ser Val Gly
    2120              2125              2130

His Pro Cys Gly Gln Gly Thr Cys Thr Asn Val Ile Gly Gly Phe
    2135              2140              2145

Glu Cys Ala Cys Ala Asp Gly Phe Glu Pro Gly Leu Met Met Thr
    2150              2155              2160

Cys Glu Asp Ile Asp Glu Cys Ser Leu Asn Pro Leu Leu Cys Ala
    2165              2170              2175

Phe Arg Cys His Asn Thr Glu Gly Ser Tyr Leu Cys Thr Cys Pro
    2180              2185              2190

Ala Gly Tyr Thr Leu Arg Glu Asp Gly Ala Met Cys Arg Asp Val
    2195              2200              2205

Asp Glu Cys Ala Asp Gly Gln Gln Asp Cys His Ala Arg Gly Met
    2210              2215              2220

Glu Cys Lys Asn Leu Ile Gly Thr Phe Ala Cys Val Cys Pro Pro
    2225              2230              2235

Gly Met Arg Pro Leu Pro Gly Ser Gly Glu Gly Cys Thr Asp Asp
    2240              2245              2250

Asn Glu Cys His Ala Gln Pro Asp Leu Cys Val Asn Gly Arg Cys
    2255              2260              2265

Val Asn Thr Ala Gly Ser Phe Arg Cys Asp Cys Asp Glu Gly Phe
    2270              2275              2280
```

```
Gln Pro Ser Pro Thr Leu Thr Glu Cys His Asp Ile Arg Gln Gly
2285                2290                2295

Pro Cys Phe Ala Glu Val Leu Gln Thr Met Cys Arg Ser Leu Ser
    2300                2305                2310

Ser Ser Ser Glu Ala Val Thr Arg Ala Glu Cys Cys Gly Gly
    2315                2320                2325

Gly Arg Gly Trp Gly Pro Arg Cys Glu Leu Cys Pro Leu Pro Gly
    2330                2335                2340

Thr Ser Ala Tyr Arg Lys Leu Cys Pro His Gly Ser Gly Tyr Thr
    2345                2350                2355

Ala Glu Gly Arg Asp Val Asp Glu Cys Arg Met Leu Ala His Leu
    2360                2365                2370

Cys Ala His Gly Glu Cys Ile Asn Ser Leu Gly Ser Phe Arg Cys
    2375                2380                2385

His Cys Gln Ala Gly Tyr Thr Pro Asp Ala Thr Ala Thr Thr Cys
    2390                2395                2400

Leu Asp Met Asp Glu Cys Ser Gln Val Pro Lys Pro Cys Thr Phe
    2405                2410                2415

Leu Cys Lys Asn Thr Lys Gly Ser Phe Leu Cys Ser Cys Pro Arg
    2420                2425                2430

Gly Tyr Leu Leu Glu Glu Asp Gly Arg Thr Cys Lys Asp Leu Asp
    2435                2440                2445

Glu Cys Thr Ser Arg Gln His Asn Cys Gln Phe Leu Cys Val Asn
    2450                2455                2460

Thr Val Gly Ala Phe Thr Cys Arg Cys Pro Pro Gly Phe Thr Gln
    2465                2470                2475

His His Gln Ala Cys Phe Asp Asn Asp Glu Cys Ser Ala Gln Pro
    2480                2485                2490

Gly Pro Cys Gly Ala His Gly His Cys His Asn Thr Pro Gly Ser
    2495                2500                2505

Phe Arg Cys Glu Cys His Gln Gly Phe Thr Leu Val Ser Ser Gly
    2510                2515                2520

His Gly Cys Glu Asp Val Asn Glu Cys Asp Gly Pro His Arg Cys
    2525                2530                2535

Gln His Gly Cys Gln Asn Gln Leu Gly Gly Tyr Arg Cys Ser Cys
    2540                2545                2550

Pro Gln Gly Phe Thr Gln His Ser Gln Trp Ala Gln Cys Val Asp
    2555                2560                2565

Glu Asn Glu Cys Ala Leu Ser Pro Pro Thr Cys Gly Ser Ala Ser
    2570                2575                2580

Cys Arg Asn Thr Leu Gly Gly Phe Arg Cys Val Cys Pro Ser Gly
    2585                2590                2595

Phe Asp Phe Asp Gln Ala Leu Gly Gly Cys Gln Glu Val Asp Glu
    2600                2605                2610

Cys Ala Gly Arg Arg Gly Pro Cys Ser Tyr Ser Cys Ala Asn Thr
    2615                2620                2625

Pro Gly Gly Phe Leu Cys Gly Cys Pro Gln Gly Tyr Phe Arg Ala
    2630                2635                2640

Gly Gln Gly His Cys Val Ser Gly Leu Gly Phe Ser Pro Gly Pro
    2645                2650                2655

Gln Asp Thr Pro Asp Lys Glu Glu Leu Leu Ser Ser Glu Ala Cys
    2660                2665                2670
```

```
Tyr Glu Cys Lys Ile Asn Gly Leu Ser Pro Arg Asp Arg Pro Arg
    2675                2680                2685

Arg Ser Ala His Arg Asp His Gln Val Asn Leu Ala Thr Leu Asp
    2690                2695                2700

Ser Glu Ala Leu Leu Thr Leu Gly Leu Asn Leu Ser His Leu Gly
    2705                2710                2715

Arg Ala Glu Arg Ile Leu Glu Leu Arg Pro Ala Leu Glu Gly Leu
    2720                2725                2730

Glu Gly Arg Ile Arg Tyr Val Ile Val Arg Gly Asn Glu Gln Gly
    2735                2740                2745

Phe Phe Arg Met His His Leu Arg Gly Val Ser Ser Leu Gln Leu
    2750                2755                2760

Gly Arg Arg Arg Pro Gly Pro Gly Thr Tyr Arg Leu Glu Val Val
    2765                2770                2775

Ser His Met Ala Gly Pro Trp Gly Val Gln Pro Glu Gly Gln Pro
    2780                2785                2790

Gly Pro Trp Gly Gln Ala Leu Arg Leu Lys Val Gln Leu Gln Leu
    2795                2800                2805

Leu

<210> SEQ ID NO 36
<211> LENGTH: 1256
<212> TYPE: PRT
<213> ORGANISM: Homo sapiens

<400> SEQUENCE: 36

Met Pro Gly Pro Arg Gly Ala Ala Gly Gly Leu Ala Pro Glu Met Arg
1               5                   10                  15

Gly Ala Gly Ala Ala Gly Leu Leu Ala Leu Leu Leu Leu Leu Leu Leu
                20                  25                  30

Leu Leu Leu Gly Leu Gly Gly Arg Val Glu Gly Gly Pro Ala Gly Glu
            35                  40                  45

Arg Gly Ala Gly Gly Gly Ala Leu Ala Arg Glu Arg Phe Lys Val
        50                  55                  60

Val Phe Ala Pro Val Ile Cys Lys Arg Thr Cys Leu Lys Gly Gln Cys
65                  70                  75                  80

Arg Asp Ser Cys Gln Gln Gly Ser Asn Met Thr Leu Ile Gly Glu Asn
                85                  90                  95

Gly His Ser Thr Asp Thr Leu Thr Gly Ser Gly Phe Arg Val Val Val
            100                 105                 110

Cys Pro Leu Pro Cys Met Asn Gly Gly Gln Cys Ser Ser Arg Asn Gln
        115                 120                 125

Cys Leu Cys Pro Pro Asp Phe Thr Gly Arg Phe Cys Gln Val Pro Ala
    130                 135                 140

Gly Gly Ala Gly Gly Gly Thr Gly Gly Ser Gly Pro Gly Leu Ser Arg
145                 150                 155                 160

Thr Gly Ala Leu Ser Thr Gly Ala Leu Pro Leu Ala Pro Glu Gly
                165                 170                 175

Asp Ser Val Ala Ser Lys His Ala Ile Tyr Ala Val Gln Val Ile Ala
            180                 185                 190

Asp Pro Pro Gly Pro Gly Glu Gly Pro Pro Ala Gln His Ala Ala Phe
        195                 200                 205

Leu Val Pro Leu Gly Pro Gly Gln Ile Ser Ala Glu Val Gln Ala Pro
    210                 215                 220
```

```
Pro Pro Val Val Asn Val Arg Val His His Pro Glu Ala Ser Val
225                 230                 235                 240

Gln Val His Arg Ile Glu Ser Ser Asn Ala Glu Ser Ala Ala Pro Ser
            245                 250                 255

Gln His Leu Leu Pro His Pro Lys Pro Ser His Pro Arg Pro Pro Thr
                260                 265                 270

Gln Lys Pro Leu Gly Arg Cys Phe Gln Asp Thr Leu Pro Lys Gln Pro
            275                 280                 285

Cys Gly Ser Asn Pro Leu Pro Gly Leu Thr Lys Gln Glu Asp Cys Cys
        290                 295                 300

Gly Ser Ile Gly Thr Ala Trp Gly Gln Ser Lys Cys His Lys Cys Pro
305                 310                 315                 320

Gln Leu Gln Tyr Thr Gly Val Gln Lys Pro Gly Pro Val Arg Gly Glu
                325                 330                 335

Val Gly Ala Asp Cys Pro Gln Gly Tyr Lys Arg Leu Asn Ser Thr His
                340                 345                 350

Cys Gln Asp Ile Asn Glu Cys Ala Met Pro Gly Val Cys Arg His Gly
        355                 360                 365

Asp Cys Leu Asn Asn Pro Gly Ser Tyr Arg Cys Val Cys Pro Pro Gly
370                 375                 380

His Ser Leu Gly Pro Ser Arg Thr Gln Cys Ile Ala Asp Lys Pro Glu
385                 390                 395                 400

Glu Lys Ser Leu Cys Phe Arg Leu Val Ser Pro Glu His Gln Cys Gln
                405                 410                 415

His Pro Leu Thr Thr Arg Leu Thr Arg Gln Leu Cys Cys Cys Ser Val
                420                 425                 430

Gly Lys Ala Trp Gly Ala Arg Cys Gln Arg Cys Pro Thr Asp Gly Thr
            435                 440                 445

Ala Ala Phe Lys Glu Ile Cys Pro Ala Gly Lys Gly Tyr His Ile Leu
        450                 455                 460

Thr Ser His Gln Thr Leu Thr Ile Gln Gly Glu Ser Asp Phe Ser Leu
465                 470                 475                 480

Phe Leu His Pro Asp Gly Pro Pro Lys Pro Gln Gln Leu Pro Glu Ser
                485                 490                 495

Pro Ser Gln Ala Pro Pro Pro Glu Asp Thr Glu Glu Glu Arg Gly Val
            500                 505                 510

Thr Thr Asp Ser Pro Val Ser Glu Glu Arg Ser Val Gln Gln Ser His
            515                 520                 525

Pro Thr Ala Thr Thr Thr Pro Ala Arg Pro Tyr Pro Glu Leu Ile Ser
            530                 535                 540

Arg Pro Ser Pro Pro Thr Met Arg Trp Phe Leu Pro Asp Leu Pro Pro
545                 550                 555                 560

Ser Arg Ser Ala Val Glu Ile Ala Pro Thr Gln Val Thr Glu Thr Asp
                565                 570                 575

Glu Cys Arg Leu Asn Gln Asn Ile Cys Gly His Gly Glu Cys Val Pro
            580                 585                 590

Gly Pro Pro Asp Tyr Ser Cys His Cys Asn Pro Gly Tyr Arg Ser His
                595                 600                 605

Pro Gln His Arg Tyr Cys Val Asp Val Asn Glu Cys Glu Ala Glu Pro
            610                 615                 620

Cys Gly Pro Gly Arg Gly Ile Cys Met Asn Thr Gly Gly Ser Tyr Asn
625                 630                 635                 640

Cys His Cys Asn Arg Gly Tyr Arg Leu His Val Gly Ala Gly Gly Arg
```

```
            645                 650                 655
Ser Cys Val Asp Leu Asn Glu Cys Ala Lys Pro His Leu Cys Gly Asp
            660                 665                 670

Gly Gly Phe Cys Ile Asn Phe Pro Gly His Tyr Lys Cys Asn Cys Tyr
            675                 680                 685

Pro Gly Tyr Arg Leu Lys Ala Ser Arg Pro Val Cys Glu Asp Ile
            690                 695                 700

Asp Glu Cys Arg Asp Pro Ser Ser Cys Pro Asp Gly Lys Cys Glu Asn
705                 710                 715                 720

Lys Pro Gly Ser Phe Lys Cys Ile Ala Cys Gln Pro Gly Tyr Arg Ser
                    725                 730                 735

Gln Gly Gly Gly Ala Cys Arg Asp Val Asn Glu Cys Ala Glu Gly Ser
                    740                 745                 750

Pro Cys Ser Pro Gly Trp Cys Glu Asn Leu Pro Gly Ser Phe Arg Cys
                    755                 760                 765

Thr Cys Ala Gln Gly Tyr Ala Pro Ala Pro Asp Gly Arg Ser Cys Leu
            770                 775                 780

Asp Val Asp Glu Cys Glu Ala Gly Asp Val Cys Asp Asn Gly Ile Cys
785                 790                 795                 800

Ser Asn Thr Pro Gly Ser Phe Gln Cys Gln Cys Leu Ser Gly Tyr His
                    805                 810                 815

Leu Ser Arg Asp Arg Ser His Cys Glu Asp Ile Asp Glu Cys Asp Phe
            820                 825                 830

Pro Ala Ala Cys Ile Gly Gly Asp Cys Ile Asn Thr Asn Gly Ser Tyr
            835                 840                 845

Arg Cys Leu Cys Pro Gln Gly His Arg Leu Val Gly Gly Arg Lys Cys
            850                 855                 860

Gln Asp Ile Asp Glu Cys Ser Gln Asp Pro Ser Leu Cys Leu Pro His
865                 870                 875                 880

Gly Ala Cys Lys Asn Leu Gln Gly Ser Tyr Val Cys Val Cys Asp Glu
                    885                 890                 895

Gly Phe Thr Pro Thr Gln Asp Gln His Gly Cys Glu Glu Val Glu Gln
            900                 905                 910

Pro His His Lys Lys Glu Cys Tyr Leu Asn Phe Asp Asp Thr Val Phe
            915                 920                 925

Cys Asp Ser Val Leu Ala Thr Asn Val Thr Gln Gln Glu Cys Cys Cys
930                 935                 940

Ser Leu Gly Ala Gly Trp Gly Asp His Cys Glu Ile Tyr Pro Cys Pro
945                 950                 955                 960

Val Tyr Ser Ser Ala Glu Phe His Ser Leu Cys Pro Asp Gly Lys Gly
                    965                 970                 975

Tyr Thr Gln Asp Asn Asn Ile Val Asn Tyr Gly Ile Pro Ala His Arg
            980                 985                 990

Asp Ile Asp Glu Cys Met Leu Phe Gly Ser Glu Ile Cys Lys Glu Gly
            995                 1000                1005

Lys Cys Val Asn Thr Gln Pro Gly Tyr Glu Cys Tyr Cys Lys Gln
    1010                1015                1020

Gly Phe Tyr Tyr Asp Gly Asn Leu Leu Glu Cys Val Asp Val Asp
    1025                1030                1035

Glu Cys Leu Asp Glu Ser Asn Cys Arg Asn Gly Val Cys Glu Asn
    1040                1045                1050

Thr Arg Gly Gly Tyr Arg Cys Ala Cys Thr Pro Pro Ala Glu Tyr
    1055                1060                1065
```

Ser Pro Ala Gln Arg Gln Cys Leu Ser Pro Glu Glu Met Glu Arg
    1070                1075                1080

Ala Pro Glu Arg Arg Asp Val Cys Trp Ser Gln Arg Gly Glu Asp
    1085                1090                1095

Gly Met Cys Ala Gly Pro Leu Ala Gly Pro Ala Leu Thr Phe Asp
    1100                1105                1110

Asp Cys Cys Cys Arg Gln Gly Arg Gly Trp Gly Ala Gln Cys Arg
    1115                1120                1125

Pro Cys Pro Pro Arg Gly Ala Gly Ser His Cys Pro Thr Ser Gln
    1130                1135                1140

Ser Glu Ser Asn Ser Phe Trp Asp Thr Ser Pro Leu Leu Leu Gly
    1145                1150                1155

Lys Pro Pro Arg Asp Glu Asp Ser Ser Glu Glu Asp Ser Asp Glu
    1160                1165                1170

Cys Arg Cys Val Ser Gly Arg Cys Val Pro Arg Pro Gly Gly Ala
    1175                1180                1185

Val Cys Glu Cys Pro Gly Gly Phe Gln Leu Asp Ala Ser Arg Ala
    1190                1195                1200

Arg Cys Val Asp Ile Asp Glu Cys Arg Glu Leu Asn Gln Arg Gly
    1205                1210                1215

Leu Leu Cys Lys Ser Glu Arg Cys Val Asn Thr Ser Gly Ser Phe
    1220                1225                1230

Arg Cys Val Cys Lys Ala Gly Phe Ala Arg Ser Arg Pro His Gly
    1235                1240                1245

Ala Cys Val Pro Gln Arg Arg Arg
    1250                1255

<210> SEQ ID NO 37
<211> LENGTH: 1823
<212> TYPE: PRT
<213> ORGANISM: Homo sapiens

<400> SEQUENCE: 37

Met Ala Leu Ser Ser Ala Trp Arg Ser Val Leu Pro Leu Trp Leu Leu
1               5                   10                  15

Trp Ser Ala Ala Cys Ser Arg Ala Ala Ser Gly Asp Asp Asn Ala Phe
                20                  25                  30

Pro Phe Asp Ile Glu Gly Ser Ser Ala Val Gly Arg Gln Asp Pro Pro
            35                  40                  45

Glu Thr Ser Glu Pro Arg Val Ala Leu Gly Arg Leu Pro Pro Ala Ala
        50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn

```
                165                 170                 175
Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
225                 230                 235                 240

Cys Asn Cys Gly Gly Pro Cys Asp Ser Val Thr Gly Glu Cys Leu
            245                 250                 255

Glu Glu Gly Phe Glu Pro Pro Thr Gly Met Asp Cys Pro Thr Ile Ser
            260                 265                 270

Cys Asp Lys Cys Val Trp Asp Leu Thr Asp Ala Leu Arg Leu Ala Ala
        275                 280                 285

Leu Ser Ile Glu Glu Gly Lys Ser Gly Val Leu Ser Val Ser Ser Gly
    290                 295                 300

Ala Ala Ala His Arg His Val Asn Glu Ile Asn Ala Thr Ile Tyr Leu
305                 310                 315                 320

Leu Lys Thr Lys Leu Ser Glu Arg Glu Asn Gln Tyr Ala Leu Arg Lys
            325                 330                 335

Ile Gln Ile Asn Asn Ala Glu Asn Thr Met Lys Ser Leu Leu Ser Asp
            340                 345                 350

Val Glu Glu Leu Val Glu Lys Glu Asn Gln Ala Ser Arg Lys Gly Gln
        355                 360                 365

Leu Val Gln Lys Glu Ser Met Asp Thr Ile Asn His Ala Ser Gln Leu
    370                 375                 380

Val Glu Gln Ala His Asp Met Arg Asp Lys Ile Gln Glu Ile Asn Asn
385                 390                 395                 400

Lys Met Leu Tyr Tyr Gly Glu Glu His Glu Leu Ser Pro Lys Glu Ile
            405                 410                 415

Ser Glu Lys Leu Val Leu Ala Gln Lys Met Leu Glu Glu Ile Arg Ser
            420                 425                 430

Arg Gln Pro Phe Phe Thr Gln Arg Glu Leu Val Asp Glu Glu Ala Asp
        435                 440                 445

Glu Ala Tyr Glu Leu Leu Ser Gln Ala Glu Ser Trp Gln Arg Leu His
    450                 455                 460

Asn Glu Thr Arg Thr Leu Phe Pro Val Val Leu Glu Gln Leu Asp Asp
465                 470                 475                 480

Tyr Asn Ala Lys Leu Ser Asp Leu Gln Glu Ala Leu Asp Gln Ala Leu
            485                 490                 495

Asn Tyr Val Arg Asp Ala Glu Asp Met Asn Arg Ala Thr Ala Ala Arg
            500                 505                 510

Gln Arg Asp His Glu Lys Gln Gln Glu Arg Val Arg Glu Gln Met Glu
        515                 520                 525

Val Val Asn Met Ser Leu Ser Thr Ser Ala Asp Ser Leu Thr Thr Pro
    530                 535                 540

Arg Leu Thr Leu Ser Glu Leu Asp Asp Ile Ile Lys Asn Ala Ser Gly
545                 550                 555                 560

Ile Tyr Ala Glu Ile Asp Gly Ala Lys Ser Glu Leu Gln Val Lys Leu
            565                 570                 575

Ser Asn Leu Ser Asn Leu Ser His Asp Leu Val Gln Glu Ala Ile Asp
            580                 585                 590
```

```
His Ala Gln Asp Leu Gln Gln Glu Ala Asn Glu Leu Ser Arg Lys Leu
            595                 600                 605

His Ser Ser Asp Met Asn Gly Leu Val Gln Lys Ala Leu Asp Ala Ser
            610                 615                 620

Asn Val Tyr Glu Asn Ile Val Asn Tyr Val Ser Glu Ala Asn Glu Thr
625                 630                 635                 640

Ala Glu Phe Ala Leu Asn Thr Thr Asp Arg Ile Tyr Asp Ala Val Ser
                645                 650                 655

Gly Ile Asp Thr Gln Ile Ile Tyr His Lys Asp Ser Glu Asn Leu
            660                 665                 670

Leu Asn Gln Ala Arg Glu Leu Gln Ala Lys Ala Glu Ser Ser Ser Asp
                675                 680                 685

Glu Ala Val Ala Asp Thr Ser Arg Arg Val Gly Gly Ala Leu Ala Arg
690                 695                 700

Lys Ser Ala Leu Lys Thr Arg Leu Ser Asp Ala Val Lys Gln Leu Gln
705                 710                 715                 720

Ala Ala Glu Arg Gly Asp Ala Gln Gln Arg Leu Gly Gln Ser Arg Leu
                725                 730                 735

Ile Thr Glu Glu Ala Asn Arg Thr Thr Met Glu Val Gln Ala Thr
            740                 745                 750

Ala Pro Met Ala Asn Asn Leu Thr Asn Trp Ser Gln Asn Leu Gln His
                755                 760                 765

Phe Asp Ser Ser Ala Tyr Asn Thr Ala Val Asn Ser Ala Arg Asp Ala
770                 775                 780

Val Arg Asn Leu Thr Glu Val Val Pro Gln Leu Leu Asp Gln Leu Arg
785                 790                 795                 800

Thr Val Glu Gln Lys Arg Pro Ala Ser Asn Val Ser Ala Ser Ile Gln
                805                 810                 815

Arg Ile Arg Glu Leu Ile Ala Gln Thr Arg Ser Val Ala Ser Lys Ile
            820                 825                 830

Gln Val Ser Met Met Phe Asp Gly Gln Ser Ala Val Glu Val His Ser
            835                 840                 845

Arg Thr Ser Met Asp Asp Leu Lys Ala Phe Thr Ser Leu Ser Leu Tyr
            850                 855                 860

Met Lys Pro Pro Val Lys Arg Pro Glu Leu Thr Glu Thr Ala Asp Gln
865                 870                 875                 880

Phe Ile Leu Tyr Leu Gly Ser Lys Asn Ala Lys Lys Glu Tyr Met Gly
                885                 890                 895

Leu Ala Ile Lys Asn Asp Asn Leu Val Tyr Val Tyr Asn Leu Gly Thr
                900                 905                 910

Lys Asp Val Glu Ile Pro Leu Asp Ser Lys Pro Val Ser Ser Trp Pro
            915                 920                 925

Ala Tyr Phe Ser Ile Val Lys Ile Glu Arg Val Gly Lys His Gly Lys
            930                 935                 940

Val Phe Leu Thr Val Pro Ser Leu Ser Ser Thr Ala Glu Glu Lys Phe
945                 950                 955                 960

Ile Lys Lys Gly Glu Phe Ser Gly Asp Asp Ser Leu Leu Asp Leu Asp
                965                 970                 975

Pro Glu Asp Thr Val Phe Tyr Val Gly Gly Val Pro Ser Asn Phe Lys
            980                 985                 990

Leu Pro Thr Ser Leu Asn Leu Pro  Gly Phe Val Gly Cys  Leu Glu Leu
            995                 1000                1005
```

```
Ala Thr Leu Asn Asn Asp Val Ile Ser Leu Tyr Asn Phe Lys His
1010                1015                1020

Ile Tyr Asn Met Asp Pro Ser Thr Ser Val Pro Cys Ala Arg Asp
1025                1030                1035

Lys Leu Ala Phe Thr Gln Ser Arg Ala Ala Ser Tyr Phe Phe Asp
1040                1045                1050

Gly Ser Gly Tyr Ala Val Val Arg Asp Ile Thr Arg Arg Gly Lys
1055                1060                1065

Phe Gly Gln Val Thr Arg Phe Asp Ile Glu Val Arg Thr Pro Ala
1070                1075                1080

Asp Asn Gly Leu Ile Leu Leu Met Val Asn Gly Ser Met Phe Phe
1085                1090                1095

Arg Leu Glu Met Arg Asn Gly Tyr Leu His Val Phe Tyr Asp Phe
1100                1105                1110

Gly Phe Ser Gly Gly Pro Val His Leu Glu Asp Thr Leu Lys Lys
1115                1120                1125

Ala Gln Ile Asn Asp Ala Lys Tyr His Glu Ile Ser Ile Ile Tyr
1130                1135                1140

His Asn Asp Lys Lys Met Ile Leu Val Val Asp Arg Arg His Val
1145                1150                1155

Lys Ser Met Asp Asn Glu Lys Met Lys Ile Pro Phe Thr Asp Ile
1160                1165                1170

Tyr Ile Gly Gly Ala Pro Pro Glu Ile Leu Gln Ser Arg Ala Leu
1175                1180                1185

Arg Ala His Leu Pro Leu Asp Ile Asn Phe Arg Gly Cys Met Lys
1190                1195                1200

Gly Phe Gln Phe Gln Lys Lys Asp Phe Asn Leu Leu Glu Gln Thr
1205                1210                1215

Glu Thr Leu Gly Val Gly Tyr Gly Cys Pro Glu Asp Ser Leu Ile
1220                1225                1230

Ser Arg Arg Ala Tyr Phe Asn Gly Gln Ser Phe Ile Ala Ser Ile
1235                1240                1245

Gln Lys Ile Ser Phe Phe Asp Gly Phe Glu Gly Gly Phe Asn Phe
1250                1255                1260

Arg Thr Leu Gln Pro Asn Gly Leu Leu Phe Tyr Tyr Ala Ser Gly
1265                1270                1275

Ser Asp Val Phe Ser Ile Ser Leu Asp Asn Gly Thr Val Ile Met
1280                1285                1290

Asp Val Lys Gly Ile Lys Val Gln Ser Val Asp Lys Gln Tyr Asn
1295                1300                1305

Asp Gly Leu Ser His Phe Val Ile Ser Ser Val Ser Pro Thr Arg
1310                1315                1320

Tyr Glu Leu Ile Val Asp Lys Ser Arg Val Gly Ser Lys Asn Pro
1325                1330                1335

Thr Lys Gly Lys Ile Glu Gln Thr Gln Ala Ser Glu Lys Lys Phe
1340                1345                1350

Tyr Phe Gly Gly Ser Pro Ile Ser Ala Gln Tyr Ala Asn Phe Thr
1355                1360                1365

Gly Cys Ile Ser Asn Ala Tyr Phe Thr Arg Val Asp Arg Asp Val
1370                1375                1380

Glu Val Glu Asp Phe Gln Arg Tyr Thr Glu Lys Val His Thr Ser
1385                1390                1395

Leu Tyr Glu Cys Pro Ile Glu Ser Ser Pro Leu Phe Leu Leu His
```

-continued

```
            1400                1405                1410

Lys Lys Gly Lys Asn Leu Ser Lys Pro Lys Ala Ser Gln Asn Lys
    1415                1420                1425

Lys Gly Gly Lys Ser Lys Asp Ala Pro Ser Trp Asp Pro Val Ala
    1430                1435                1440

Leu Lys Leu Pro Glu Arg Asn Thr Pro Arg Asn Ser His Cys His
    1445                1450                1455

Leu Ser Asn Ser Pro Arg Ala Ile Glu His Ala Tyr Gln Tyr Gly
    1460                1465                1470

Gly Thr Ala Asn Ser Arg Gln Glu Phe Glu His Leu Lys Gly Asp
    1475                1480                1485

Phe Gly Ala Lys Ser Gln Phe Ser Ile Arg Leu Arg Thr Arg Ser
    1490                1495                1500

Ser His Gly Met Ile Phe Tyr Val Ser Asp Gln Glu Glu Asn Asp
    1505                1510                1515

Phe Met Thr Leu Phe Leu Ala His Gly Arg Leu Val Tyr Met Phe
    1520                1525                1530

Asn Val Gly His Lys Lys Leu Lys Ile Arg Ser Gln Glu Lys Tyr
    1535                1540                1545

Asn Asp Gly Leu Trp His Asp Val Ile Phe Ile Arg Glu Arg Ser
    1550                1555                1560

Ser Gly Arg Leu Val Ile Asp Gly Leu Arg Val Leu Glu Glu Ser
    1565                1570                1575

Leu Pro Pro Thr Glu Ala Thr Trp Lys Ile Lys Gly Pro Ile Tyr
    1580                1585                1590

Leu Gly Gly Val Ala Pro Gly Lys Ala Val Lys Asn Val Gln Ile
    1595                1600                1605

Asn Ser Ile Tyr Ser Phe Ser Gly Cys Leu Ser Asn Leu Gln Leu
    1610                1615                1620

Asn Gly Ala Ser Ile Thr Ser Ala Ser Gln Thr Phe Ser Val Thr
    1625                1630                1635

Pro Cys Phe Glu Gly Pro Met Glu Thr Gly Thr Tyr Phe Ser Thr
    1640                1645                1650

Glu Gly Gly Tyr Val Val Leu Asp Glu Ser Phe Asn Ile Gly Leu
    1655                1660                1665

Lys Phe Glu Ile Ala Phe Glu Val Arg Pro Arg Ser Ser Ser Gly
    1670                1675                1680

Thr Leu Val His Gly His Ser Val Asn Gly Glu Tyr Leu Asn Val
    1685                1690                1695

His Met Lys Asn Gly Gln Val Ile Val Lys Val Asn Asn Gly Ile
    1700                1705                1710

Arg Asp Phe Ser Thr Ser Val Thr Pro Lys Gln Ser Leu Cys Asp
    1715                1720                1725

Gly Arg Trp His Arg Ile Thr Val Ile Arg Asp Ser Asn Val Val
    1730                1735                1740

Gln Leu Asp Val Asp Ser Glu Val Asn His Val Val Gly Pro Leu
    1745                1750                1755

Asn Pro Lys Pro Ile Asp His Arg Glu Pro Val Phe Val Gly Gly
    1760                1765                1770

Val Pro Glu Ser Leu Leu Thr Pro Arg Leu Ala Pro Ser Lys Pro
    1775                1780                1785

Phe Thr Gly Cys Ile Arg His Phe Val Ile Asp Gly His Pro Val
    1790                1795                1800
```

```
Ser Phe Ser Lys Ala Ala Leu Val Ser Gly Ala Val Ser Ile Asn
        1805                1810                1815

Ser Cys Pro Ala Ala
        1820

<210> SEQ ID NO 38
<211> LENGTH: 2551
<212> TYPE: PRT
<213> ORGANISM: Homo sapiens

<400> SEQUENCE: 38

Met Met Leu Gln His Leu Val Ile Phe Cys Leu Gly Leu Val Val Gln
1               5                   10                  15

Asn Phe Cys Ser Pro Ala Glu Thr Thr Gly Gln Ala Arg Arg Cys Asp
            20                  25                  30

Arg Lys Ser Leu Leu Thr Ile Arg Thr Glu Cys Arg Ser Cys Ala Leu
        35                  40                  45

Asn Leu Gly Val Lys Cys Pro Asp Gly Tyr Thr Met Ile Thr Ser Gly
    50                  55                  60

Ser Val Gly Val Arg Asp Cys Arg Tyr Thr Phe Glu Val Arg Thr Tyr
65                  70                  75                  80

Ser Leu Ser Leu Pro Gly Cys Arg His Ile Cys Arg Lys Asp Tyr Leu
                85                  90                  95

Gln Pro Arg Cys Cys Pro Gly Arg Trp Gly Pro Asp Cys Ile Glu Cys
            100                 105                 110

Pro Gly Gly Ala Gly Ser Pro Cys Asn Gly Arg Gly Ser Cys Ala Glu
        115                 120                 125

Gly Met Glu Gly Asn Gly Thr Cys Ser Cys Gln Glu Gly Phe Gly Gly
    130                 135                 140

Thr Ala Cys Glu Thr Cys Ala Asp Asp Asn Leu Phe Gly Pro Ser Cys
145                 150                 155                 160

Ser Ser Val Cys Asn Cys Val His Gly Val Cys Asn Ser Gly Leu Asp
                165                 170                 175

Gly Asp Gly Thr Cys Glu Cys Tyr Ser Ala Tyr Thr Gly Pro Lys Cys
            180                 185                 190

Asp Lys Pro Ile Pro Glu Cys Ala Ala Leu Leu Cys Pro Glu Asn Ser
        195                 200                 205

Arg Cys Ser Pro Ser Thr Glu Asp Glu Asn Lys Leu Glu Cys Lys Cys
    210                 215                 220

Leu Pro Asn Tyr Arg Gly Asp Gly Lys Tyr Cys Asp Pro Ile Asn Pro
225                 230                 235                 240

Cys Leu Arg Lys Ile Cys His Pro His Ala His Cys Thr Tyr Leu Gly
                245                 250                 255

Pro Asn Arg His Ser Cys Thr Cys Gln Glu Gly Tyr Arg Gly Asp Gly
            260                 265                 270

Gln Val Cys Leu Pro Val Asp Pro Cys Gln Ile Asn Phe Gly Asn Cys
        275                 280                 285

Pro Thr Lys Ser Thr Val Cys Lys Tyr Asp Gly Pro Gly Gln Ser His
    290                 295                 300

Cys Glu Cys Lys Glu His Tyr Gln Asn Phe Val Pro Gly Val Gly Cys
305                 310                 315                 320

Ser Met Thr Asp Ile Cys Lys Ser Asp Asn Pro Cys His Arg Asn Ala
                325                 330                 335

Asn Cys Thr Thr Val Ala Pro Gly Arg Thr Glu Cys Ile Cys Gln Lys
```

-continued

```
                340                 345                 350
Gly Tyr Val Gly Asp Gly Leu Thr Cys Tyr Gly Asn Ile Met Glu Arg
            355                 360                 365
Leu Arg Glu Leu Asn Thr Glu Pro Arg Gly Lys Trp Gln Gly Arg Leu
        370                 375                 380
Thr Ser Phe Ile Ser Leu Leu Asp Lys Ala Tyr Ala Trp Pro Leu Ser
385                 390                 395                 400
Lys Leu Gly Pro Phe Thr Val Leu Pro Thr Asp Lys Gly Leu Lys
                405                 410                 415
Gly Phe Asn Val Asn Glu Leu Leu Val Asp Asn Lys Ala Ala Gln Tyr
            420                 425                 430
Phe Val Lys Leu His Ile Ile Ala Gly Gln Met Asn Ile Glu Tyr Met
        435                 440                 445
Asn Asn Thr Asp Met Phe Tyr Thr Leu Thr Gly Lys Ser Gly Glu Ile
    450                 455                 460
Phe Asn Ser Asp Lys Asp Asn Gln Ile Lys Leu Lys Leu His Gly Gly
465                 470                 475                 480
Lys Lys Lys Val Lys Ile Ile Gln Gly Asp Ile Ile Ala Ser Asn Gly
                485                 490                 495
Leu Leu His Ile Leu Asp Arg Ala Met Asp Lys Leu Glu Pro Thr Phe
            500                 505                 510
Glu Ser Asn Asn Glu Gln Thr Ile Met Thr Met Leu Gln Pro Arg Tyr
        515                 520                 525
Ser Lys Phe Arg Ser Leu Leu Glu Glu Thr Asn Leu Gly His Ala Leu
    530                 535                 540
Asp Glu Asp Gly Val Gly Gly Pro Tyr Thr Ile Phe Val Pro Asn Asn
545                 550                 555                 560
Glu Ala Leu Asn Asn Met Lys Asp Gly Thr Leu Asp Tyr Leu Leu Ser
                565                 570                 575
Pro Glu Gly Ser Arg Lys Leu Leu Glu Leu Val Arg Tyr His Ile Val
            580                 585                 590
Pro Phe Thr Gln Leu Glu Val Ala Thr Leu Ile Ser Thr Pro His Ile
        595                 600                 605
Arg Ser Met Ala Asn Gln Leu Ile Gln Phe Asn Thr Thr Asp Asn Gly
    610                 615                 620
Gln Ile Leu Ala Asn Asp Val Ala Met Glu Glu Ile Glu Ile Thr Ala
625                 630                 635                 640
Lys Asn Gly Arg Ile Tyr Thr Leu Thr Gly Val Leu Ile Pro Pro Ser
                645                 650                 655
Ile Val Pro Ile Leu Pro His Arg Cys Asp Glu Thr Lys Arg Glu Met
            660                 665                 670
Lys Leu Gly Thr Cys Val Ser Cys Ser Leu Val Tyr Trp Ser Arg Cys
        675                 680                 685
Pro Ala Asn Ser Glu Pro Thr Ala Leu Phe Thr His Arg Cys Val Tyr
    690                 695                 700
Ser Gly Arg Phe Gly Ser Leu Lys Ser Gly Cys Ala Arg Tyr Cys Asn
705                 710                 715                 720
Ala Thr Val Lys Ile Pro Lys Cys Cys Lys Gly Phe Tyr Gly Pro Asp
                725                 730                 735
Cys Asn Gln Cys Pro Gly Gly Phe Ser Asn Pro Cys Ser Gly Asn Gly
            740                 745                 750
Gln Cys Ala Asp Ser Leu Gly Gly Asn Gly Thr Cys Ile Cys Glu Glu
        755                 760                 765
```

```
Gly Phe Gln Gly Ser Gln Cys Gln Phe Cys Ser Asp Pro Asn Lys Tyr
    770                 775                 780

Gly Pro Arg Cys Asn Lys Cys Leu Cys Val His Gly Thr Cys Asn
785                 790                 795                 800

Asn Arg Ile Asp Ser Asp Gly Ala Cys Leu Thr Gly Thr Cys Arg Asp
            805                 810                 815

Gly Ser Ala Gly Arg Leu Cys Asp Lys Gln Thr Ser Ala Cys Gly Pro
                820                 825                 830

Tyr Val Gln Phe Cys His Ile His Ala Thr Cys Glu Tyr Ser Asn Gly
        835                 840                 845

Thr Ala Ser Cys Ile Cys Lys Ala Gly Tyr Glu Gly Asp Gly Thr Leu
    850                 855                 860

Cys Ser Glu Met Asp Pro Cys Thr Gly Leu Thr Pro Gly Gly Cys Ser
865                 870                 875                 880

Arg Asn Ala Glu Cys Ile Lys Thr Gly Thr Gly Thr His Thr Cys Val
                885                 890                 895

Cys Gln Gln Gly Trp Thr Gly Asn Gly Arg Asp Cys Ser Glu Ile Asn
            900                 905                 910

Asn Cys Leu Leu Pro Ser Ala Gly Gly Cys His Asp Asn Ala Ser Cys
        915                 920                 925

Leu Tyr Val Gly Pro Gly Gln Asn Glu Cys Cys Lys Lys Gly Phe
    930                 935                 940

Arg Gly Asn Gly Ile Asp Cys Glu Pro Ile Thr Ser Cys Leu Glu Gln
945                 950                 955                 960

Thr Gly Lys Cys His Pro Leu Ala Ser Cys Gln Ser Thr Ser Ser Gly
                965                 970                 975

Val Trp Ser Cys Val Cys Gln Glu Gly Tyr Glu Gly Asp Gly Phe Leu
            980                 985                 990

Cys Tyr Gly Asn Ala Ala Val Glu Leu Ser Phe Leu Ser Glu Ala Ala
        995                 1000                1005

Ile Phe Asn Arg Trp Ile Asn Asn Ala Ser Leu Gln Pro Thr Leu
    1010                1015                1020

Ser Ala Thr Ser Asn Leu Thr Val Leu Val Pro Ser Gln Gln Ala
    1025                1030                1035

Thr Glu Asp Met Asp Gln Asp Glu Lys Ser Phe Trp Leu Ser Gln
    1040                1045                1050

Ser Asn Ile Pro Ala Leu Ile Lys Tyr His Met Leu Leu Gly Thr
    1055                1060                1065

Tyr Arg Val Ala Asp Leu Gln Thr Leu Ser Ser Ser Asp Met Leu
    1070                1075                1080

Ala Thr Ser Leu Gln Gly Asn Phe Leu His Leu Ala Lys Val Asp
    1085                1090                1095

Gly Asn Ile Thr Ile Glu Gly Ala Ser Ile Val Asp Gly Asp Asn
    1100                1105                1110

Ala Ala Thr Asn Gly Val Ile His Ile Asn Lys Val Leu Val
    1115                1120                1125

Pro Gln Arg Arg Leu Thr Gly Ser Leu Pro Asn Leu Leu Met Arg
    1130                1135                1140

Leu Glu Gln Met Pro Asp Tyr Ser Ile Phe Arg Gly Tyr Ile Ile
    1145                1150                1155

Gln Tyr Asn Leu Ala Asn Ala Ile Glu Ala Ala Asp Ala Tyr Thr
    1160                1165                1170
```

```
Val Phe Ala Pro Asn Asn Asn Ala Ile Glu Asn Tyr Ile Arg Glu
1175                1180                1185

Lys Lys Val Leu Ser Leu Glu Glu Asp Val Leu Arg Tyr His Val
    1190                1195                1200

Val Leu Glu Glu Lys Leu Leu Lys Asn Asp Leu His Asn Gly Met
    1205                1210                1215

His Arg Glu Thr Met Leu Gly Phe Ser Tyr Phe Leu Ser Phe Phe
    1220                1225                1230

Leu His Asn Asp Gln Leu Tyr Val Asn Glu Ala Pro Ile Asn Tyr
    1235                1240                1245

Thr Asn Val Ala Thr Asp Lys Gly Val Ile His Gly Leu Gly Lys
    1250                1255                1260

Val Leu Glu Ile Gln Lys Asn Arg Cys Asp Asn Asn Asp Thr Thr
    1265                1270                1275

Ile Ile Arg Gly Arg Cys Arg Thr Cys Ser Ser Glu Leu Thr Cys
    1280                1285                1290

Pro Phe Gly Thr Lys Ser Leu Gly Asn Glu Lys Arg Arg Cys Ile
    1295                1300                1305

Tyr Thr Ser Tyr Phe Met Gly Arg Arg Thr Leu Phe Ile Gly Cys
    1310                1315                1320

Gln Pro Lys Cys Val Arg Thr Val Ile Thr Arg Glu Cys Cys Ala
    1325                1330                1335

Gly Phe Phe Gly Pro Gln Cys Gln Pro Cys Pro Gly Asn Ala Gln
    1340                1345                1350

Asn Val Cys Phe Gly Asn Gly Ile Cys Leu Asp Gly Val Asn Gly
    1355                1360                1365

Thr Gly Val Cys Glu Cys Gly Gly Phe Ser Gly Thr Ala Cys
    1370                1375                1380

Glu Thr Cys Thr Glu Gly Lys Tyr Gly Ile His Cys Asp Gln Ala
1385                1390                1395

Cys Ser Cys Val His Gly Arg Cys Asn Gln Gly Pro Leu Gly Asp
    1400                1405                1410

Gly Ser Cys Asp Cys Asp Val Gly Trp Arg Gly Val His Cys Asp
    1415                1420                1425

Asn Ala Thr Thr Glu Asp Asn Cys Asn Gly Thr Cys His Thr Ser
    1430                1435                1440

Ala Asn Cys Leu Thr Asn Ser Asp Gly Thr Ala Ser Cys Lys Cys
    1445                1450                1455

Ala Ala Gly Phe Gln Gly Asn Gly Thr Ile Cys Thr Ala Ile Asn
    1460                1465                1470

Ala Cys Glu Ile Ser Asn Gly Gly Cys Ser Ala Lys Ala Asp Cys
    1475                1480                1485

Lys Arg Thr Thr Pro Gly Arg Arg Val Cys Thr Cys Lys Ala Gly
    1490                1495                1500

Tyr Thr Gly Asp Gly Ile Val Cys Leu Glu Ile Asn Pro Cys Leu
    1505                1510                1515

Glu Asn His Gly Gly Cys Asp Lys Asn Ala Glu Cys Thr Gln Thr
    1520                1525                1530

Gly Pro Asn Gln Ala Ala Cys Asn Cys Leu Pro Ala Tyr Thr Gly
    1535                1540                1545

Asp Gly Lys Val Cys Thr Leu Ile Asn Val Cys Leu Thr Lys Asn
    1550                1555                1560

Gly Gly Cys Ser Glu Phe Ala Ile Cys Asn His Thr Gly Gln Val
```

```
              1565                1570                1575

Glu Arg Thr Cys Thr Cys Lys Pro Asn Tyr Ile Gly Asp Gly Phe
    1580                1585                1590

Thr Cys Arg Gly Ser Ile Tyr Gln Glu Leu Pro Lys Asn Pro Lys
    1595                1600                1605

Thr Ser Gln Tyr Phe Phe Gln Leu Gln Glu His Phe Val Lys Asp
    1610                1615                1620

Leu Val Gly Pro Gly Pro Phe Thr Val Phe Ala Pro Leu Ser Ala
    1625                1630                1635

Ala Phe Asp Glu Glu Ala Arg Val Lys Asp Trp Asp Lys Tyr Gly
    1640                1645                1650

Leu Met Pro Gln Val Leu Arg Tyr His Val Val Ala Cys His Gln
    1655                1660                1665

Leu Leu Leu Glu Asn Leu Lys Leu Ile Ser Asn Ala Thr Ser Leu
    1670                1675                1680

Gln Gly Glu Pro Ile Val Ile Ser Val Ser Gln Ser Thr Val Tyr
    1685                1690                1695

Ile Asn Asn Lys Ala Lys Ile Ile Ser Ser Asp Ile Ile Ser Thr
    1700                1705                1710

Asn Gly Ile Val His Ile Ile Asp Lys Leu Leu Ser Pro Lys Asn
    1715                1720                1725

Leu Leu Ile Thr Pro Lys Asp Asn Ser Gly Arg Ile Leu Gln Asn
    1730                1735                1740

Leu Thr Thr Leu Ala Thr Asn Asn Gly Tyr Ile Lys Phe Ser Asn
    1745                1750                1755

Leu Ile Gln Asp Ser Gly Leu Leu Ser Val Ile Thr Asp Pro Ile
    1760                1765                1770

His Thr Pro Val Thr Leu Phe Trp Pro Thr Asp Gln Ala Leu His
    1775                1780                1785

Ala Leu Pro Ala Glu Gln Gln Asp Phe Leu Phe Asn Gln Asp Asn
    1790                1795                1800

Lys Asp Lys Leu Lys Glu Tyr Leu Lys Phe His Val Ile Arg Asp
    1805                1810                1815

Ala Lys Val Leu Ala Val Asp Leu Pro Thr Ser Thr Ala Trp Lys
    1820                1825                1830

Thr Leu Gln Gly Ser Glu Leu Ser Val Lys Cys Gly Ala Gly Arg
    1835                1840                1845

Asp Ile Gly Asp Leu Phe Leu Asn Gly Gln Thr Cys Arg Ile Val
    1850                1855                1860

Gln Arg Glu Leu Leu Phe Asp Leu Gly Val Ala Tyr Gly Ile Asp
    1865                1870                1875

Cys Leu Leu Ile Asp Pro Thr Leu Gly Gly Arg Cys Asp Thr Phe
    1880                1885                1890

Thr Thr Phe Asp Ala Ser Gly Glu Cys Gly Ser Cys Val Asn Thr
    1895                1900                1905

Pro Ser Cys Pro Arg Trp Ser Lys Pro Lys Gly Val Lys Gln Lys
    1910                1915                1920

Cys Leu Tyr Asn Leu Pro Phe Lys Arg Asn Leu Glu Gly Cys Arg
    1925                1930                1935

Glu Arg Cys Ser Leu Val Ile Gln Ile Pro Arg Cys Cys Lys Gly
    1940                1945                1950

Tyr Phe Gly Arg Asp Cys Gln Ala Cys Pro Gly Gly Pro Asp Ala
    1955                1960                1965
```

```
Pro Cys Asn Asn Arg Gly Val Cys Leu Asp Gln Tyr Ser Ala Thr
    1970            1975            1980

Gly Glu Cys Lys Cys Asn Thr Gly Phe Asn Gly Thr Ala Cys Glu
    1985            1990            1995

Met Cys Trp Pro Gly Arg Phe Gly Pro Asp Cys Leu Pro Cys Gly
    2000            2005            2010

Cys Ser Asp His Gly Gln Cys Asp Asp Gly Ile Thr Gly Ser Gly
    2015            2020            2025

Gln Cys Leu Cys Glu Thr Gly Trp Thr Gly Pro Ser Cys Asp Thr
    2030            2035            2040

Gln Ala Val Leu Pro Ala Val Cys Thr Pro Pro Cys Ser Ala His
    2045            2050            2055

Ala Thr Cys Lys Glu Asn Asn Thr Cys Glu Cys Asn Leu Asp Tyr
    2060            2065            2070

Glu Gly Asp Gly Ile Thr Cys Thr Val Val Asp Phe Cys Lys Gln
    2075            2080            2085

Asp Asn Gly Gly Cys Ala Lys Val Ala Arg Cys Ser Gln Lys Gly
    2090            2095            2100

Thr Lys Val Ser Cys Ser Cys Gln Lys Gly Tyr Lys Gly Asp Gly
    2105            2110            2115

His Ser Cys Thr Glu Ile Asp Pro Cys Ala Asp Gly Leu Asn Gly
    2120            2125            2130

Gly Cys His Glu His Ala Thr Cys Lys Met Thr Gly Pro Gly Lys
    2135            2140            2145

His Lys Cys Glu Cys Lys Ser His Tyr Val Gly Asp Gly Leu Asn
    2150            2155            2160

Cys Glu Pro Glu Gln Leu Pro Ile Asp Arg Cys Leu Gln Asp Asn
    2165            2170            2175

Gly Gln Cys His Ala Asp Ala Lys Cys Val Asp Leu His Phe Gln
    2180            2185            2190

Asp Thr Thr Val Gly Val Phe His Leu Arg Ser Pro Leu Gly Gln
    2195            2200            2205

Tyr Lys Leu Thr Phe Asp Lys Ala Arg Glu Ala Cys Ala Asn Glu
    2210            2215            2220

Ala Ala Thr Met Ala Thr Tyr Asn Gln Leu Ser Tyr Ala Gln Lys
    2225            2230            2235

Ala Lys Tyr His Leu Cys Ser Ala Gly Trp Leu Glu Thr Gly Arg
    2240            2245            2250

Val Ala Tyr Pro Thr Ala Phe Ala Ser Gln Asn Cys Gly Ser Gly
    2255            2260            2265

Val Val Gly Ile Val Asp Tyr Gly Pro Arg Pro Asn Lys Ser Glu
    2270            2275            2280

Met Trp Asp Val Phe Cys Tyr Arg Met Lys Asp Val Asn Cys Thr
    2285            2290            2295

Cys Lys Val Gly Tyr Val Gly Asp Gly Phe Ser Cys Ser Gly Asn
    2300            2305            2310

Leu Leu Gln Val Leu Met Ser Phe Pro Ser Leu Thr Asn Phe Leu
    2315            2320            2325

Thr Glu Val Leu Ala Tyr Ser Asn Ser Ser Ala Arg Gly Arg Ala
    2330            2335            2340

Phe Leu Glu His Leu Thr Asp Leu Ser Ile Arg Gly Thr Leu Phe
    2345            2350            2355
```

-continued

Val Pro Gln Asn Ser Gly Leu Gly Glu Asn Glu Thr Leu Ser Gly
    2360                2365                2370

Arg Asp Ile Glu His His Leu Ala Asn Val Ser Met Phe Phe Tyr
    2375                2380                2385

Asn Asp Leu Val Asn Gly Thr Thr Leu Gln Thr Arg Leu Gly Ser
    2390                2395                2400

Lys Leu Leu Ile Thr Ala Ser Gln Asp Pro Leu Gln Pro Thr Glu
    2405                2410                2415

Thr Arg Phe Val Asp Gly Arg Ala Ile Leu Gln Trp Asp Ile Phe
    2420                2425                2430

Ala Ser Asn Gly Ile Ile His Val Ile Ser Arg Pro Leu Lys Ala
    2435                2440                2445

Pro Pro Ala Pro Val Thr Leu Thr His Thr Gly Leu Gly Ala Gly
    2450                2455                2460

Ile Phe Phe Ala Ile Ile Leu Val Thr Gly Ala Val Ala Leu Ala
    2465                2470                2475

Ala Tyr Ser Tyr Phe Arg Ile Asn Arg Arg Thr Ile Gly Phe Gln
    2480                2485                2490

His Phe Glu Ser Glu Glu Asp Ile Asn Val Ala Ala Leu Gly Lys
    2495                2500                2505

Gln Gln Pro Glu Asn Ile Ser Asn Pro Leu Tyr Glu Ser Thr Thr
    2510                2515                2520

Ser Ala Pro Pro Glu Pro Ser Tyr Asp Pro Phe Thr Asp Ser Glu
    2525                2530                2535

Glu Arg Gln Leu Glu Gly Asn Asp Pro Leu Arg Thr Leu
    2540                2545                2550

<210> SEQ ID NO 39
<211> LENGTH: 2471
<212> TYPE: PRT
<213> ORGANISM: Homo sapiens

<400> SEQUENCE: 39

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
                20                  25                  30

Glu Pro Cys Val Asn Glu Gly Met Cys Val Thr Tyr His Asn Gly Thr
                35                  40                  45

Gly Tyr Cys Lys Cys Pro Glu Gly Phe Leu Gly Glu Tyr Cys Gln His
            50                  55                  60

Arg Asp Pro Cys Glu Lys Asn Arg Cys Gln Asn Gly Gly Thr Cys Val
65              70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
                100                 105                 110

Arg Pro Cys Leu Asn Gly Gly Thr Cys His Met Leu Ser Arg Asp Thr
            115                 120                 125

Tyr Glu Cys Thr Cys Gln Val Gly Phe Thr Gly Lys Glu Cys Gln Trp
        130                 135                 140

Thr Asp Ala Cys Leu Ser His Pro Cys Ala Asn Gly Ser Thr Cys Thr
145             150                 155                 160

Thr Val Ala Asn Gln Phe Ser Cys Lys Cys Leu Thr Gly Phe Thr Gly
                165                 170                 175

-continued

```
Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
            195                 200                 205

Cys Pro Gln Gly Phe Thr Gly Gln Tyr Cys Asp Ser Leu Tyr Val Pro
210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
            275                 280                 285

Gln Trp Thr Gly Gln Phe Cys Thr Glu Asp Val Asp Glu Cys Leu Leu
            290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
            355                 360                 365

Ala Gly Leu Leu Cys His Leu Asp Asp Ala Cys Ile Ser Asn Pro Cys
            370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
            435                 440                 445

Ala Gly Pro Arg Cys Glu Met Asp Ile Asn Glu Cys His Ser Asp Pro
450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
            515                 520                 525

Cys Gln Ile Asp Ile Asp Asp Cys Ser Ser Thr Pro Cys Leu Asn Gly
530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590
```

```
Cys Ile Cys Asn Pro Gly Tyr Met Gly Ala Ile Cys Ser Asp Gln Ile
            595                 600                 605

Asp Glu Cys Tyr Ser Ser Pro Cys Leu Asn Asp Gly Arg Cys Ile Asp
        610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
        835                 840                 845

Lys Glu Ser Pro Asn Phe Glu Ser Tyr Thr Cys Leu Cys Ala Pro Gly
    850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
        915                 920                 925

Gly Val Asn Thr Phe Ser Cys Leu Cys Leu Pro Gly Phe Thr Gly Asp
    930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
            980                 985                 990

Glu Ser Ser Cys Phe Asn Gly Gly Thr Cys Val Asp Gly Ile Asn Ser
        995                 1000                1005

Phe Ser  Cys Leu Cys Pro Val  Gly Phe Thr Gly Ser  Phe Cys Leu
```

-continued

```
                1010                1015                1020

His Glu Ile Asn Glu Cys Ser Ser His Pro Cys Leu Asn Glu Gly
                1025                1030                1035

Thr Cys Val Asp Gly Leu Gly Thr Tyr Arg Cys Ser Cys Pro Leu
                1040                1045                1050

Gly Tyr Thr Gly Lys Asn Cys Gln Thr Leu Val Asn Leu Cys Ser
                1055                1060                1065

Arg Ser Pro Cys Lys Asn Lys Gly Thr Cys Val Gln Lys Lys Ala
                1070                1075                1080

Glu Ser Gln Cys Leu Cys Pro Ser Gly Trp Ala Gly Ala Tyr Cys
                1085                1090                1095

Asp Val Pro Asn Val Ser Cys Asp Ile Ala Ala Ser Arg Arg Gly
                1100                1105                1110

Val Leu Val Glu His Leu Cys Gln His Ser Gly Val Cys Ile Asn
                1115                1120                1125

Ala Gly Asn Thr His Tyr Cys Gln Cys Pro Leu Gly Tyr Thr Gly
                1130                1135                1140

Ser Tyr Cys Glu Glu Gln Leu Asp Glu Cys Ala Ser Asn Pro Cys
                1145                1150                1155

Gln His Gly Ala Thr Cys Ser Asp Phe Ile Gly Gly Tyr Arg Cys
                1160                1165                1170

Glu Cys Val Pro Gly Tyr Gln Gly Val Asn Cys Glu Tyr Glu Val
                1175                1180                1185

Asp Glu Cys Gln Asn Gln Pro Cys Gln Asn Gly Gly Thr Cys Ile
                1190                1195                1200

Asp Leu Val Asn His Phe Lys Cys Ser Cys Pro Pro Gly Thr Arg
                1205                1210                1215

Gly Leu Leu Cys Glu Glu Asn Ile Asp Asp Cys Ala Arg Gly Pro
                1220                1225                1230

His Cys Leu Asn Gly Gly Gln Cys Met Asp Arg Ile Gly Gly Tyr
                1235                1240                1245

Ser Cys Arg Cys Leu Pro Gly Phe Ala Gly Glu Arg Cys Glu Gly
                1250                1255                1260

Asp Ile Asn Glu Cys Leu Ser Asn Pro Cys Ser Ser Glu Gly Ser
                1265                1270                1275

Leu Asp Cys Ile Gln Leu Thr Asn Asp Tyr Leu Cys Val Cys Arg
                1280                1285                1290

Ser Ala Phe Thr Gly Arg His Cys Glu Thr Phe Val Asp Val Cys
                1295                1300                1305

Pro Gln Met Pro Cys Leu Asn Gly Gly Thr Cys Ala Val Ala Ser
                1310                1315                1320

Asn Met Pro Asp Gly Phe Ile Cys Arg Cys Pro Pro Gly Phe Ser
                1325                1330                1335

Gly Ala Arg Cys Gln Ser Ser Cys Gly Gln Val Lys Cys Arg Lys
                1340                1345                1350

Gly Glu Gln Cys Val His Thr Ala Ser Gly Pro Arg Cys Phe Cys
                1355                1360                1365

Pro Ser Pro Arg Asp Cys Glu Ser Gly Cys Ala Ser Ser Pro Cys
                1370                1375                1380

Gln His Gly Gly Ser Cys His Pro Gln Arg Gln Pro Pro Tyr Tyr
                1385                1390                1395

Ser Cys Gln Cys Ala Pro Pro Phe Ser Gly Ser Arg Cys Glu Leu
                1400                1405                1410
```

```
Tyr Thr Ala Pro Pro Ser Thr Pro Pro Ala Thr Cys Leu Ser Gln
1415                 1420                 1425

Tyr Cys Ala Asp Lys Ala Arg Asp Gly Val Cys Asp Glu Ala Cys
1430                 1435                 1440

Asn Ser His Ala Cys Gln Trp Asp Gly Gly Asp Cys Ser Leu Thr
1445                 1450                 1455

Met Glu Asn Pro Trp Ala Asn Cys Ser Ser Pro Leu Pro Cys Trp
1460                 1465                 1470

Asp Tyr Ile Asn Asn Gln Cys Asp Glu Leu Cys Asn Thr Val Glu
1475                 1480                 1485

Cys Leu Phe Asp Asn Phe Glu Cys Gln Gly Asn Ser Lys Thr Cys
1490                 1495                 1500

Lys Tyr Asp Lys Tyr Cys Ala Asp His Phe Lys Asp Asn His Cys
1505                 1510                 1515

Asp Gln Gly Cys Asn Ser Glu Glu Cys Gly Trp Asp Gly Leu Asp
1520                 1525                 1530

Cys Ala Ala Asp Gln Pro Glu Asn Leu Ala Glu Gly Thr Leu Val
1535                 1540                 1545

Ile Val Val Leu Met Pro Pro Glu Gln Leu Leu Gln Asp Ala Arg
1550                 1555                 1560

Ser Phe Leu Arg Ala Leu Gly Thr Leu Leu His Thr Asn Leu Arg
1565                 1570                 1575

Ile Lys Arg Asp Ser Gln Gly Glu Leu Met Val Tyr Pro Tyr Tyr
1580                 1585                 1590

Gly Glu Lys Ser Ala Ala Met Lys Lys Gln Arg Met Thr Arg Arg
1595                 1600                 1605

Ser Leu Pro Gly Glu Gln Glu Gln Glu Val Ala Gly Ser Lys Val
1610                 1615                 1620

Phe Leu Glu Ile Asp Asn Arg Gln Cys Val Gln Asp Ser Asp His
1625                 1630                 1635

Cys Phe Lys Asn Thr Asp Ala Ala Ala Ala Leu Leu Ala Ser His
1640                 1645                 1650

Ala Ile Gln Gly Thr Leu Ser Tyr Pro Leu Val Ser Val Val Ser
1655                 1660                 1665

Glu Ser Leu Thr Pro Glu Arg Thr Gln Leu Leu Tyr Leu Leu Ala
1670                 1675                 1680

Val Ala Val Val Ile Ile Leu Phe Ile Ile Leu Leu Gly Val Ile
1685                 1690                 1695

Met Ala Lys Arg Lys Arg Lys His Gly Ser Leu Trp Leu Pro Glu
1700                 1705                 1710

Gly Phe Thr Leu Arg Arg Asp Ala Ser Asn His Lys Arg Arg Glu
1715                 1720                 1725

Pro Val Gly Gln Asp Ala Val Gly Leu Lys Asn Leu Ser Val Gln
1730                 1735                 1740

Val Ser Glu Ala Asn Leu Ile Gly Thr Gly Thr Ser Glu His Trp
1745                 1750                 1755

Val Asp Asp Glu Gly Pro Gln Pro Lys Lys Val Lys Ala Glu Asp
1760                 1765                 1770

Glu Ala Leu Leu Ser Glu Glu Asp Asp Pro Ile Asp Arg Arg Pro
1775                 1780                 1785

Trp Thr Gln Gln His Leu Glu Ala Ala Asp Ile Arg Arg Thr Pro
1790                 1795                 1800
```

```
Ser Leu Ala Leu Thr Pro Pro Gln Ala Glu Gln Glu Val Asp Val
    1805                1810                1815

Leu Asp Val Asn Val Arg Gly Pro Asp Gly Cys Thr Pro Leu Met
    1820                1825                1830

Leu Ala Ser Leu Arg Gly Gly Ser Ser Asp Leu Ser Asp Glu Asp
    1835                1840                1845

Glu Asp Ala Glu Asp Ser Ser Ala Asn Ile Ile Thr Asp Leu Val
    1850                1855                1860

Tyr Gln Gly Ala Ser Leu Gln Ala Gln Thr Asp Arg Thr Gly Glu
    1865                1870                1875

Met Ala Leu His Leu Ala Ala Arg Tyr Ser Arg Ala Asp Ala Ala
    1880                1885                1890

Lys Arg Leu Leu Asp Ala Gly Ala Asp Ala Asn Ala Gln Asp Asn
    1895                1900                1905

Met Gly Arg Cys Pro Leu His Ala Ala Val Ala Ala Asp Ala Gln
    1910                1915                1920

Gly Val Phe Gln Ile Leu Ile Arg Asn Arg Val Thr Asp Leu Asp
    1925                1930                1935

Ala Arg Met Asn Asp Gly Thr Thr Pro Leu Ile Leu Ala Ala Arg
    1940                1945                1950

Leu Ala Val Glu Gly Met Val Ala Glu Leu Ile Asn Cys Gln Ala
    1955                1960                1965

Asp Val Asn Ala Val Asp Asp His Gly Lys Ser Ala Leu His Trp
    1970                1975                1980

Ala Ala Ala Val Asn Asn Val Glu Ala Thr Leu Leu Leu Leu Lys
    1985                1990                1995

Asn Gly Ala Asn Arg Asp Met Gln Asp Asn Lys Glu Glu Thr Pro
    2000                2005                2010

Leu Phe Leu Ala Ala Arg Glu Gly Ser Tyr Glu Ala Ala Lys Ile
    2015                2020                2025

Leu Leu Asp His Phe Ala Asn Arg Asp Ile Thr Asp His Met Asp
    2030                2035                2040

Arg Leu Pro Arg Asp Val Ala Arg Asp Arg Met His His Asp Ile
    2045                2050                2055

Val Arg Leu Leu Asp Glu Tyr Asn Val Thr Pro Ser Pro Pro Gly
    2060                2065                2070

Thr Val Leu Thr Ser Ala Leu Ser Pro Val Ile Cys Gly Pro Asn
    2075                2080                2085

Arg Ser Phe Leu Ser Leu Lys His Thr Pro Met Gly Lys Lys Ser
    2090                2095                2100

Arg Arg Pro Ser Ala Lys Ser Thr Met Pro Thr Ser Leu Pro Asn
    2105                2110                2115

Leu Ala Lys Glu Ala Lys Asp Ala Lys Gly Ser Arg Arg Lys Lys
    2120                2125                2130

Ser Leu Ser Glu Lys Val Gln Leu Ser Glu Ser Ser Val Thr Leu
    2135                2140                2145

Ser Pro Val Asp Ser Leu Glu Ser Pro His Thr Tyr Val Ser Asp
    2150                2155                2160

Thr Thr Ser Ser Pro Met Ile Thr Ser Pro Gly Ile Leu Gln Ala
    2165                2170                2175

Ser Pro Asn Pro Met Leu Ala Thr Ala Ala Pro Pro Ala Pro Val
    2180                2185                2190

His Ala Gln His Ala Leu Ser Phe Ser Asn Leu His Glu Met Gln
```

-continued

```
                2195                2200                2205

Pro Leu Ala His Gly Ala Ser Thr Val Leu Pro Ser Val Ser Gln
    2210                2215                2220

Leu Leu Ser His His His Ile Val Ser Pro Gly Ser Gly Ser Ala
    2225                2230                2235

Gly Ser Leu Ser Arg Leu His Pro Val Pro Val Pro Ala Asp Trp
    2240                2245                2250

Met Asn Arg Met Glu Val Asn Glu Thr Gln Tyr Asn Glu Met Phe
    2255                2260                2265

Gly Met Val Leu Ala Pro Ala Glu Gly Thr His Pro Gly Ile Ala
    2270                2275                2280

Pro Gln Ser Arg Pro Pro Glu Gly Lys His Ile Thr Thr Pro Arg
    2285                2290                2295

Glu Pro Leu Pro Pro Ile Val Thr Phe Gln Leu Ile Pro Lys Gly
    2300                2305                2310

Ser Ile Ala Gln Pro Ala Gly Ala Pro Gln Pro Gln Ser Thr Cys
    2315                2320                2325

Pro Pro Ala Val Ala Gly Pro Leu Pro Thr Met Tyr Gln Ile Pro
    2330                2335                2340

Glu Met Ala Arg Leu Pro Ser Val Ala Phe Pro Thr Ala Met Met
    2345                2350                2355

Pro Gln Gln Asp Gly Gln Val Ala Gln Thr Ile Leu Pro Ala Tyr
    2360                2365                2370

His Pro Phe Pro Ala Ser Val Gly Lys Tyr Pro Thr Pro Pro Ser
    2375                2380                2385

Gln His Ser Tyr Ala Ser Ser Asn Ala Ala Glu Arg Thr Pro Ser
    2390                2395                2400

His Ser Gly His Leu Gln Gly Glu His Pro Tyr Leu Thr Pro Ser
    2405                2410                2415

Pro Glu Ser Pro Asp Gln Trp Ser Ser Ser Ser Pro His Ser Ala
    2420                2425                2430

Ser Asp Trp Ser Asp Val Thr Thr Ser Pro Thr Pro Gly Gly Ala
    2435                2440                2445

Gly Gly Gly Gln Arg Gly Pro Gly Thr His Met Ser Glu Pro Pro
    2450                2455                2460

His Asn Asn Met Gln Val Tyr Ala
    2465                2470

<210> SEQ ID NO 40
<211> LENGTH: 3623
<212> TYPE: PRT
<213> ORGANISM: Homo sapiens

<400> SEQUENCE: 40

Met Met Asn Met Ser Leu Pro Phe Leu Trp Ser Leu Leu Thr Leu Leu
1               5                   10                  15

Ile Phe Ala Glu Val Asn Gly Glu Ala Gly Glu Leu Glu Leu Gln Arg
                20                  25                  30

Gln Lys Arg Ser Ile Asn Leu Gln Gln Pro Arg Met Ala Thr Glu Arg
        35                  40                  45

Gly Asn Leu Val Phe Leu Thr Gly Ser Ala Gln Asn Ile Glu Phe Arg
    50                  55                  60

Thr Gly Ser Leu Gly Lys Ile Lys Leu Asn Asp Glu Asp Leu Ser Glu
65                  70                  75                  80
```

-continued

```
Cys Leu His Gln Ile Gln Lys Asn Lys Glu Asp Ile Ile Glu Leu Lys
             85                  90                  95
Gly Ser Ala Ile Gly Leu Pro Gln Asn Ile Ser Ser Gln Ile Tyr Gln
        100                 105                 110
Leu Asn Ser Lys Leu Val Asp Leu Glu Arg Lys Phe Gln Gly Leu Gln
    115                 120                 125
Gln Thr Val Asp Lys Lys Val Cys Ser Ser Asn Pro Cys Gln Asn Gly
130                 135                 140
Gly Thr Cys Leu Asn Leu His Asp Ser Phe Phe Cys Ile Cys Pro Pro
145                 150                 155                 160
Gln Trp Lys Gly Pro Leu Cys Ser Ala Asp Val Asn Glu Cys Glu Ile
                165                 170                 175
Tyr Ser Gly Thr Pro Leu Ser Cys Gln Asn Gly Gly Thr Cys Val Asn
            180                 185                 190
Thr Met Gly Ser Tyr Ser Cys His Cys Pro Pro Glu Thr Tyr Gly Pro
        195                 200                 205
Gln Cys Ala Ser Lys Tyr Asp Asp Cys Glu Gly Gly Ser Val Ala Arg
    210                 215                 220
Cys Val His Gly Ile Cys Glu Asp Leu Met Arg Glu Gln Ala Gly Glu
225                 230                 235                 240
Pro Lys Tyr Ser Cys Val Cys Asp Ala Gly Trp Met Phe Ser Pro Asn
                245                 250                 255
Ser Pro Ala Cys Thr Leu Asp Arg Asp Glu Cys Ser Phe Gln Pro Gly
            260                 265                 270
Pro Cys Ser Thr Leu Val Gln Cys Phe Asn Thr Gln Gly Ser Phe Tyr
        275                 280                 285
Cys Gly Ala Cys Pro Thr Gly Trp Gln Gly Asn Gly Tyr Ile Cys Glu
    290                 295                 300
Asp Ile Asn Glu Cys Glu Ile Asn Asn Gly Gly Cys Ser Val Ala Pro
305                 310                 315                 320
Pro Val Glu Cys Val Asn Thr Pro Gly Ser Ser His Cys Gln Ala Cys
                325                 330                 335
Pro Pro Gly Tyr Gln Gly Asp Gly Arg Val Cys Thr Leu Thr Asp Ile
            340                 345                 350
Cys Ser Val Ser Asn Gly Gly Cys His Pro Asp Ala Ser Cys Ser Ser
        355                 360                 365
Thr Leu Gly Ser Leu Pro Leu Cys Thr Cys Leu Pro Gly Tyr Thr Gly
    370                 375                 380
Asn Gly Tyr Gly Pro Asn Gly Cys Val Gln Leu Ser Asn Ile Cys Leu
385                 390                 395                 400
Ser His Pro Cys Leu Asn Gly Gln Cys Ile Asp Thr Val Ser Gly Tyr
                405                 410                 415
Phe Cys Lys Cys Asp Ser Gly Trp Thr Gly Val Asn Cys Thr Glu Asn
            420                 425                 430
Ile Asn Glu Cys Leu Ser Asn Pro Cys Leu Asn Gly Gly Thr Cys Val
        435                 440                 445
Asp Gly Val Asp Ser Phe Ser Cys Glu Cys Thr Arg Leu Trp Thr Gly
    450                 455                 460
Ala Leu Cys Gln Val Pro Gln Val Cys Gly Glu Ser Leu Ser Gly
465                 470                 475                 480
Ile Asn Gly Ser Phe Ser Tyr Arg Ser Pro Asp Val Gly Tyr Val His
                485                 490                 495
Asp Val Asn Cys Phe Trp Val Ile Lys Thr Glu Met Gly Lys Val Leu
```

```
                500             505             510
Arg Ile Thr Phe Thr Phe Phe Arg Leu Glu Ser Met Asp Asn Cys Pro
            515             520             525
His Glu Phe Leu Gln Val Tyr Asp Gly Asp Ser Ser Ala Phe Gln
        530             535             540
Leu Gly Arg Phe Cys Gly Ser Ser Leu Pro His Glu Leu Leu Ser Ser
545             550             555             560
Asp Asn Ala Leu Tyr Phe His Leu Tyr Ser Glu His Leu Arg Asn Gly
                565             570             575
Arg Gly Phe Thr Val Arg Trp Glu Thr Gln Pro Glu Cys Gly Gly
            580             585             590
Ile Leu Thr Gly Pro Tyr Gly Ser Ile Lys Ser Pro Gly Tyr Pro Gly
            595             600             605
Asn Tyr Pro Pro Gly Arg Asp Cys Val Trp Ile Val Thr Ser Pro
        610             615             620
Asp Leu Leu Val Thr Phe Thr Phe Gly Thr Leu Ser Leu Glu His His
625             630             635             640
Asp Asp Cys Asn Lys Asp Tyr Leu Glu Ile Arg Asp Gly Pro Leu Tyr
                645             650             655
Gln Asp Pro Leu Leu Gly Lys Phe Cys Thr Thr Phe Ser Val Pro Pro
            660             665             670
Leu Gln Thr Thr Gly Pro Phe Ala Arg Ile His Phe His Ser Asp Ser
        675             680             685
Gln Ile Ser Asp Gln Gly Phe His Ile Thr Tyr Leu Thr Ser Pro Ser
    690             695             700
Asp Leu Arg Cys Gly Gly Asn Tyr Thr Asp Pro Glu Gly Glu Leu Phe
705             710             715             720
Leu Pro Glu Leu Ser Gly Pro Phe Thr His Thr Arg Gln Cys Val Tyr
            725             730             735
Met Met Lys Gln Pro Gln Gly Glu Gln Ile Gln Ile Asn Phe Thr His
        740             745             750
Val Glu Leu Gln Cys Gln Ser Asp Ser Ser Gln Asn Tyr Ile Glu Val
            755             760             765
Arg Asp Gly Glu Thr Leu Leu Gly Lys Val Cys Gly Asn Gly Thr Ile
770             775             780
Ser His Ile Lys Ser Ile Thr Asn Ser Val Trp Ile Arg Phe Lys Ile
785             790             795             800
Asp Ala Ser Val Glu Lys Ala Ser Phe Arg Ala Val Tyr Gln Val Ala
                805             810             815
Cys Gly Asp Glu Leu Thr Gly Glu Gly Val Ile Arg Ser Pro Phe Phe
            820             825             830
Pro Asn Val Tyr Pro Gly Glu Arg Thr Cys Arg Trp Thr Ile His Gln
            835             840             845
Pro Gln Ser Gln Val Ile Leu Leu Asn Phe Thr Val Phe Glu Ile Gly
        850             855             860
Ser Ser Ala His Cys Glu Thr Asp Tyr Val Glu Ile Gly Ser Ser Ser
865             870             875             880
Ile Leu Gly Ser Pro Glu Asn Lys Lys Tyr Cys Gly Thr Asp Ile Pro
                885             890             895
Ser Phe Ile Thr Ser Val Tyr Asn Phe Leu Tyr Val Thr Phe Val Lys
            900             905             910
Ser Ser Ser Thr Glu Asn His Gly Phe Met Ala Lys Phe Ser Ala Glu
            915             920             925
```

```
Asp Leu Ala Cys Gly Glu Ile Leu Thr Glu Ser Thr Gly Thr Ile Gln
        930                 935                 940

Ser Pro Gly His Pro Asn Val Tyr Pro His Gly Ile Asn Cys Thr Trp
945                 950                 955                 960

His Ile Leu Val Gln Pro Asn His Leu Ile His Leu Met Phe Glu Thr
            965                 970                 975

Phe His Leu Glu Phe His Tyr Asn Cys Thr Asn Asp Tyr Leu Glu Val
            980                 985                 990

Tyr Asp Thr Asp Ser Glu Thr Ser  Leu Gly Arg Tyr Cys  Gly Lys Ser
            995                 1000                1005

Ile Pro  Pro Ser Leu Thr Ser  Ser Gly Asn Ser Leu  Met Leu Val
    1010                 1015                 1020

Phe Val  Thr Asp Ser Asp Leu  Ala Tyr Glu Gly Phe  Leu Ile Asn
    1025                 1030                 1035

Tyr Glu  Ala Ile Ser Ala Ala  Thr Ala Cys Leu Gln  Asp Tyr Thr
    1040                 1045                 1050

Asp Asp  Leu Gly Thr Phe Thr  Ser Pro Asn Phe Pro  Asn Asn Tyr
    1055                 1060                 1065

Pro Asn  Asn Trp Glu Cys Ile  Tyr Arg Ile Thr Val  Arg Thr Gly
    1070                 1075                 1080

Gln Leu  Ile Ala Val His Phe  Thr Asn Phe Ser Leu  Glu Glu Ala
    1085                 1090                 1095

Ile Gly  Asn Tyr Tyr Thr Asp  Phe Leu Glu Ile Arg  Asp Gly Gly
    1100                 1105                 1110

Tyr Glu  Lys Ser Pro Leu Leu  Gly Ile Phe Tyr Gly  Ser Asn Leu
    1115                 1120                 1125

Pro Pro  Thr Ile Ile Ser His  Ser Asn Lys Leu Trp  Leu Lys Phe
    1130                 1135                 1140

Lys Ser  Asp Gln Ile Asp Thr  Arg Ser Gly Phe Ser  Ala Tyr Trp
    1145                 1150                 1155

Asp Gly  Ser Ser Thr Gly Cys  Gly Gly Asn Leu Thr  Thr Ser Ser
    1160                 1165                 1170

Gly Thr  Phe Ile Ser Pro Asn  Tyr Pro Met Pro Tyr  Tyr His Ser
    1175                 1180                 1185

Ser Glu  Cys Tyr Trp Trp Leu  Lys Ser Ser His Gly  Ser Ala Phe
    1190                 1195                 1200

Glu Leu  Glu Phe Lys Asp Phe  His Leu Glu His His  Pro Asn Cys
    1205                 1210                 1215

Thr Leu  Asp Tyr Leu Ala Val  Tyr Asp Gly Pro Ser  Ser Asn Ser
    1220                 1225                 1230

His Leu  Leu Thr Gln Leu Cys  Gly Asp Glu Lys Pro  Pro Leu Ile
    1235                 1240                 1245

Arg Ser  Ser Gly Asp Ser Met  Phe Ile Lys Leu Arg  Thr Asp Glu
    1250                 1255                 1260

Gly Gln  Gln Gly Arg Gly Phe  Lys Ala Glu Tyr Arg  Gln Thr Cys
    1265                 1270                 1275

Glu Asn  Val Val Ile Val Asn  Gln Thr Tyr Gly Ile  Leu Glu Ser
    1280                 1285                 1290

Ile Gly  Tyr Pro Asn Pro Tyr  Ser Glu Asn Gln His  Cys Asn Trp
    1295                 1300                 1305

Thr Ile  Arg Ala Thr Thr Gly  Asn Thr Val Asn Tyr  Thr Phe Leu
    1310                 1315                 1320
```

```
Ala Phe Asp Leu Glu His His Ile Asn Cys Ser Thr Asp Tyr Leu
1325                1330                    1335

Glu Leu Tyr Asp Gly Pro Arg Gln Met Gly Arg Tyr Cys Gly Val
    1340                1345                    1350

Asp Leu Pro Pro Pro Gly Ser Thr Thr Ser Ser Lys Leu Gln Val
    1355                1360                    1365

Leu Leu Leu Thr Asp Gly Val Gly Arg Arg Glu Lys Gly Phe Gln
    1370                1375                    1380

Met Gln Trp Phe Val Tyr Gly Cys Gly Gly Glu Leu Ser Gly Ala
    1385                1390                    1395

Thr Gly Ser Phe Ser Ser Pro Gly Phe Pro Asn Arg Tyr Pro Pro
    1400                1405                    1410

Asn Lys Glu Cys Ile Trp Tyr Ile Arg Thr Asp Pro Gly Ser Ser
    1415                1420                    1425

Ile Gln Leu Thr Ile His Asp Phe Asp Val Glu Tyr His Ser Arg
    1430                1435                    1440

Cys Asn Phe Asp Val Leu Glu Ile Tyr Gly Gly Pro Asp Phe His
    1445                1450                    1455

Ser Pro Arg Ile Ala Gln Leu Cys Thr Gln Arg Ser Pro Glu Asn
    1460                1465                    1470

Pro Met Gln Val Ser Ser Thr Gly Asn Glu Leu Ala Ile Arg Phe
    1475                1480                    1485

Lys Thr Asp Leu Ser Ile Asn Gly Arg Gly Phe Asn Ala Ser Trp
    1490                1495                    1500

Gln Ala Val Thr Gly Gly Cys Gly Gly Ile Phe Gln Ala Pro Ser
    1505                1510                    1515

Gly Glu Ile His Ser Pro Asn Tyr Pro Ser Pro Tyr Arg Ser Asn
    1520                1525                    1530

Thr Asp Cys Ser Trp Val Ile Arg Val Asp Arg Asn His Arg Val
    1535                1540                    1545

Leu Leu Asn Phe Thr Asp Phe Asp Leu Glu Pro Gln Asp Ser Cys
    1550                1555                    1560

Ile Met Ala Tyr Asp Gly Leu Ser Ser Thr Met Ser Arg Leu Ala
    1565                1570                    1575

Arg Thr Cys Gly Arg Glu Gln Leu Ala Asn Pro Ile Val Ser Ser
    1580                1585                    1590

Gly Asn Ser Leu Phe Leu Arg Phe Gln Ser Gly Pro Ser Arg Gln
    1595                1600                    1605

Asn Arg Gly Phe Arg Ala Gln Phe Arg Gln Ala Cys Gly Gly His
    1610                1615                    1620

Ile Leu Thr Ser Ser Phe Asp Thr Val Ser Ser Pro Arg Phe Pro
    1625                1630                    1635

Ala Asn Tyr Pro Asn Asn Gln Asn Cys Ser Trp Ile Ile Gln Ala
    1640                1645                    1650

Gln Pro Pro Leu Asn His Ile Thr Leu Ser Phe Thr His Phe Glu
    1655                1660                    1665

Leu Glu Arg Ser Thr Thr Cys Ala Arg Asp Phe Val Glu Ile Leu
    1670                1675                    1680

Asp Gly Gly His Glu Asp Ala Pro Leu Arg Gly Arg Tyr Cys Gly
    1685                1690                    1695

Thr Asp Met Pro His Pro Ile Thr Ser Phe Ser Ser Ala Leu Thr
    1700                1705                    1710

Leu Arg Phe Val Ser Asp Ser Ser Ile Ser Ala Gly Gly Phe His
```

```
            1715                1720                1725

Thr Thr Val Thr Ala Ser Val Ser Ala Cys Gly Gly Thr Phe Tyr
    1730                1735                1740

Met Ala Glu Gly Ile Phe Asn Ser Pro Gly Tyr Pro Asp Ile Tyr
    1745                1750                1755

Pro Pro Asn Val Glu Cys Val Trp Asn Ile Val Ser Ser Pro Gly
    1760                1765                1770

Asn Arg Leu Gln Leu Ser Phe Ile Ser Phe Gln Leu Glu Asp Ser
    1775                1780                1785

Gln Asp Cys Ser Arg Asp Phe Val Glu Ile Arg Glu Gly Asn Ala
    1790                1795                1800

Thr Gly His Leu Val Gly Arg Tyr Cys Gly Asn Ser Phe Pro Leu
    1805                1810                1815

Asn Tyr Ser Ser Ile Val Gly His Thr Leu Trp Val Arg Phe Ile
    1820                1825                1830

Ser Asp Gly Ser Gly Ser Gly Thr Gly Phe Gln Ala Thr Phe Met
    1835                1840                1845

Lys Ile Phe Gly Asn Asp Asn Ile Val Gly Thr His Gly Lys Val
    1850                1855                1860

Ala Ser Pro Phe Trp Pro Glu Asn Tyr Pro His Asn Ser Asn Tyr
    1865                1870                1875

Gln Trp Thr Val Asn Val Asn Ala Ser His Val Val His Gly Arg
    1880                1885                1890

Ile Leu Glu Met Asp Ile Glu Glu Ile Gln Asn Cys Tyr Tyr Asp
    1895                1900                1905

Lys Leu Arg Ile Tyr Asp Gly Pro Ser Ile His Ala Arg Leu Ile
    1910                1915                1920

Gly Ala Tyr Cys Gly Thr Gln Thr Glu Ser Phe Ser Ser Thr Gly
    1925                1930                1935

Asn Ser Leu Thr Phe His Phe Tyr Ser Asp Ser Ser Ile Ser Gly
    1940                1945                1950

Lys Gly Phe Leu Leu Glu Trp Phe Ala Val Asp Ala Pro Asp Gly
    1955                1960                1965

Val Leu Pro Thr Ile Ala Pro Gly Ala Cys Gly Gly Phe Leu Arg
    1970                1975                1980

Thr Gly Asp Ala Pro Val Phe Leu Phe Ser Pro Gly Trp Pro Asp
    1985                1990                1995

Ser Tyr Ser Asn Arg Val Asp Cys Thr Trp Leu Ile Gln Ala Pro
    2000                2005                2010

Asp Ser Thr Val Glu Leu Asn Ile Leu Ser Leu Asp Ile Glu Ser
    2015                2020                2025

His Arg Thr Cys Ala Tyr Asp Ser Leu Val Ile Arg Asp Gly Asp
    2030                2035                2040

Asn Asn Leu Ala Gln Gln Leu Ala Val Leu Cys Gly Arg Glu Ile
    2045                2050                2055

Pro Gly Pro Ile Arg Ser Thr Gly Glu Tyr Met Phe Ile Arg Phe
    2060                2065                2070

Thr Ser Asp Ser Ser Val Thr Arg Ala Gly Phe Asn Ala Ser Phe
    2075                2080                2085

His Lys Ser Cys Gly Gly Tyr Leu His Ala Asp Arg Gly Ile Ile
    2090                2095                2100

Thr Ser Pro Lys Tyr Pro Glu Thr Tyr Pro Ser Asn Leu Asn Cys
    2105                2110                2115
```

-continued

| | | | | | | | | | | |
|---|---|---|---|---|---|---|---|---|---|---|
|Ser|Trp|His|Val|Leu|Val|Gln|Ser|Gly|Leu|Thr|Ile|Ala|Val|His|
|2120| | | | |2125| | | |2130| |

Phe Glu Gln Pro Phe Gln Ile Pro Asn Gly Asp Ser Ser Cys Asn
2135                    2140                    2145

Gln Gly Asp Tyr Leu Val Leu Arg Asn Gly Pro Asp Ile Cys Ser
2150                    2155                    2160

Pro Pro Leu Gly Pro Pro Gly Gly Asn Gly His Phe Cys Gly Ser
2165                    2170                    2175

His Ala Ser Ser Thr Leu Phe Thr Ser Asp Asn Gln Met Phe Val
2180                    2185                    2190

Gln Phe Ile Ser Asp His Ser Asn Glu Gly Gln Gly Phe Lys Ile
2195                    2200                    2205

Lys Tyr Glu Ala Lys Ser Leu Ala Cys Gly Gly Asn Val Tyr Ile
2210                    2215                    2220

His Asp Ala Asp Ser Ala Gly Tyr Val Thr Ser Pro Asn His Pro
2225                    2230                    2235

His Asn Tyr Pro Pro His Ala Asp Cys Ile Trp Ile Leu Ala Ala
2240                    2245                    2250

Pro Pro Glu Thr Arg Ile Gln Leu Gln Phe Glu Asp Arg Phe Asp
2255                    2260                    2265

Ile Glu Val Thr Pro Asn Cys Thr Ser Asn Tyr Leu Glu Leu Arg
2270                    2275                    2280

Asp Gly Val Asp Ser Asp Ala Pro Ile Leu Ser Lys Phe Cys Gly
2285                    2290                    2295

Thr Ser Leu Pro Ser Ser Gln Trp Ser Ser Gly Glu Val Met Tyr
2300                    2305                    2310

Leu Arg Phe Arg Ser Asp Asn Ser Pro Thr His Val Gly Phe Lys
2315                    2320                    2325

Ala Lys Tyr Ser Ile Ala Gln Cys Gly Gly Arg Val Pro Gly Gln
2330                    2335                    2340

Ser Gly Val Val Glu Ser Ile Gly His Pro Thr Leu Pro Tyr Arg
2345                    2350                    2355

Asp Asn Leu Phe Cys Glu Trp His Leu Gln Gly Leu Ser Gly His
2360                    2365                    2370

Tyr Leu Thr Ile Ser Phe Glu Asp Phe Asn Leu Gln Asn Ser Ser
2375                    2380                    2385

Gly Cys Glu Lys Asp Phe Val Glu Ile Trp Asp Asn His Thr Ser
2390                    2395                    2400

Gly Asn Ile Leu Gly Arg Tyr Cys Gly Asn Thr Ile Pro Asp Ser
2405                    2410                    2415

Ile Asp Thr Ser Ser Asn Thr Ala Val Val Arg Phe Val Thr Asp
2420                    2425                    2430

Gly Ser Val Thr Ala Ser Gly Phe Arg Leu Arg Phe Glu Ser Ser
2435                    2440                    2445

Met Glu Glu Cys Gly Gly Asp Leu Gln Gly Ser Ile Gly Thr Phe
2450                    2455                    2460

Thr Ser Pro Asn Tyr Pro Asn Pro His Gly Arg Ile Cys
2465                    2470                    2475

Glu Trp Arg Ile Thr Ala Pro Glu Gly Arg Arg Ile Thr Leu Met
2480                    2485                    2490

Phe Asn Asn Leu Arg Leu Ala Thr His Pro Ser Cys Asn Asn Glu
2495                    2500                    2505

```
His Val Ile Val Phe Asn Gly Ile Arg Ser Asn Ser Pro Gln Leu
2510                2515                2520

Glu Lys Leu Cys Ser Ser Val Asn Val Ser Asn Glu Ile Lys Ser
2525                2530                2535

Ser Gly Asn Thr Met Lys Val Ile Phe Phe Thr Asp Gly Ser Arg
2540                2545                2550

Pro Tyr Gly Gly Phe Thr Ala Ser Tyr Thr Ser Ser Glu Asp Ala
2555                2560                2565

Val Cys Gly Gly Ser Leu Pro Asn Thr Pro Glu Gly Asn Phe Thr
2570                2575                2580

Ser Pro Gly Tyr Asp Gly Val Arg Asn Tyr Ser Arg Asn Leu Asn
2585                2590                2595

Cys Glu Trp Thr Leu Ser Asn Pro Asn Gln Gly Asn Ser Ser Ile
2600                2605                2610

Ser Ile His Phe Glu Asp Phe Tyr Leu Glu Ser His Gln Asp Cys
2615                2620                2625

Gln Phe Asp Val Leu Glu Phe Arg Val Gly Asp Ala Asp Gly Pro
2630                2635                2640

Leu Met Trp Arg Leu Cys Gly Pro Ser Lys Pro Thr Leu Pro Leu
2645                2650                2655

Val Ile Pro Tyr Ser Gln Val Trp Ile His Phe Val Thr Asn Glu
2660                2665                2670

Arg Val Glu His Ile Gly Phe His Ala Lys Tyr Ser Phe Thr Asp
2675                2680                2685

Cys Gly Gly Ile Gln Ile Gly Asp Ser Gly Val Ile Thr Ser Pro
2690                2695                2700

Asn Tyr Pro Asn Ala Tyr Asp Ser Leu Thr His Cys Ser Ser Leu
2705                2710                2715

Leu Glu Ala Pro Gln Gly His Thr Ile Thr Leu Thr Phe Ser Asp
2720                2725                2730

Phe Asp Ile Glu Pro His Thr Thr Cys Ala Trp Asp Ser Val Thr
2735                2740                2745

Val Arg Asn Gly Gly Ser Pro Glu Ser Pro Ile Ile Gly Gln Tyr
2750                2755                2760

Cys Gly Asn Ser Asn Pro Arg Thr Ile Gln Ser Gly Ser Asn Gln
2765                2770                2775

Leu Val Val Thr Phe Asn Ser Asp His Ser Leu Gln Gly Gly Gly
2780                2785                2790

Phe Tyr Ala Thr Trp Asn Thr Gln Thr Leu Gly Cys Gly Gly Ile
2795                2800                2805

Phe His Ser Asp Asn Gly Thr Ile Arg Ser Pro His Trp Pro Gln
2810                2815                2820

Asn Phe Pro Glu Asn Ser Arg Cys Ser Trp Thr Ala Ile Thr His
2825                2830                2835

Lys Ser Lys His Leu Glu Ile Ser Phe Asp Asn Phe Leu Ile
2840                2845                2850

Pro Ser Gly Asp Gly Gln Cys Gln Asn Ser Phe Val Lys Val Trp
2855                2860                2865

Ala Gly Thr Glu Glu Val Asp Lys Ala Leu Leu Ala Thr Gly Cys
2870                2875                2880

Gly Asn Val Ala Pro Gly Pro Val Ile Thr Pro Ser Asn Thr Phe
2885                2890                2895

Thr Ala Val Phe Gln Ser Gln Glu Ala Pro Ala Gln Gly Phe Ser
```

```
            2900                2905                2910
Ala Ser Phe Val Ser Arg Cys Gly Ser Asn Phe Thr Gly Pro Ser
            2915                2920                2925

Gly Tyr Ile Ile Ser Pro Asn Tyr Pro Lys Gln Tyr Asp Asn Asn
            2930                2935                2940

Met Asn Cys Thr Tyr Val Ile Glu Ala Asn Pro Leu Ser Val Val
            2945                2950                2955

Leu Leu Thr Phe Val Ser Phe His Leu Glu Ala Arg Ser Ala Val
            2960                2965                2970

Thr Gly Ser Cys Val Asn Asp Gly Val His Ile Ile Arg Gly Tyr
            2975                2980                2985

Ser Val Met Ser Thr Pro Phe Ala Thr Val Cys Gly Asp Glu Met
            2990                2995                3000

Pro Ala Pro Leu Thr Ile Ala Gly Pro Val Leu Leu Asn Phe Tyr
            3005                3010                3015

Ser Asn Glu Gln Ile Thr Asp Phe Gly Phe Lys Phe Ser Tyr Arg
            3020                3025                3030

Ile Ile Ser Cys Gly Gly Val Phe Asn Phe Ser Ser Gly Ile Ile
            3035                3040                3045

Thr Ser Pro Ala Tyr Ser Tyr Ala Asp Tyr Pro Asn Asp Met His
            3050                3055                3060

Cys Leu Tyr Thr Ile Thr Val Ser Asp Asp Lys Val Ile Glu Leu
            3065                3070                3075

Lys Phe Ser Asp Phe Asp Val Val Pro Ser Thr Ser Cys Ser His
            3080                3085                3090

Asp Tyr Leu Ala Ile Tyr Asp Gly Ala Asn Thr Ser Asp Pro Leu
            3095                3100                3105

Leu Gly Lys Phe Cys Gly Ser Lys Arg Pro Pro Asn Val Lys Ser
            3110                3115                3120

Ser Asn Asn Ser Met Leu Leu Val Phe Lys Thr Asp Ser Phe Gln
            3125                3130                3135

Thr Ala Lys Gly Trp Lys Met Ser Phe Arg Gln Thr Leu Gly Pro
            3140                3145                3150

Gln Gln Gly Cys Gly Gly Tyr Leu Thr Gly Ser Asn Asn Thr Phe
            3155                3160                3165

Ala Ser Pro Asp Ser Asp Ser Asn Gly Met Tyr Asp Lys Asn Leu
            3170                3175                3180

Asn Cys Val Trp Ile Ile Ile Ala Pro Val Asn Lys Val Ile His
            3185                3190                3195

Leu Thr Phe Asn Thr Phe Ala Leu Glu Ala Ala Ser Thr Arg Gln
            3200                3205                3210

Arg Cys Leu Tyr Asp Tyr Val Lys Leu Tyr Asp Gly Asp Ser Glu
            3215                3220                3225

Asn Ala Asn Leu Ala Gly Thr Phe Cys Gly Ser Thr Val Pro Ala
            3230                3235                3240

Pro Phe Ile Ser Ser Gly Asn Phe Leu Thr Val Gln Phe Ile Ser
            3245                3250                3255

Asp Leu Thr Leu Glu Arg Glu Gly Phe Asn Ala Thr Tyr Thr Ile
            3260                3265                3270

Met Asp Met Pro Cys Gly Gly Thr Tyr Asn Ala Thr Trp Thr Pro
            3275                3280                3285

Gln Asn Ile Ser Ser Pro Asn Ser Ser Asp Pro Asp Val Pro Phe
            3290                3295                3300
```

Ser Ile Cys Thr Trp Val Ile Asp Ser Pro His Gln Gln Val
3305                3310                3315

Lys Ile Thr Val Trp Ala Leu Gln Leu Thr Ser Gln Asp Cys Thr
3320                3325                3330

Gln Asn Tyr Leu Gln Leu Gln Asp Ser Pro Gln Gly His Gly Asn
3335                3340                3345

Ser Arg Phe Gln Phe Cys Gly Arg Asn Ala Ser Ala Val Pro Val
3350                3355                3360

Phe Tyr Ser Ser Met Ser Thr Ala Met Val Ile Phe Lys Ser Gly
3365                3370                3375

Val Val Asn Arg Asn Ser Arg Met Ser Phe Thr Tyr Gln Ile Ala
3380                3385                3390

Asp Cys Asn Arg Asp Tyr His Lys Ala Phe Gly Asn Leu Arg Ser
3395                3400                3405

Pro Gly Trp Pro Asp Asn Tyr Asp Asn Asp Lys Asp Cys Thr Val
3410                3415                3420

Thr Leu Thr Ala Pro Gln Asn His Thr Ile Ser Leu Phe Phe His
3425                3430                3435

Ser Leu Gly Ile Glu Asn Ser Val Glu Cys Arg Asn Asp Phe Leu
3440                3445                3450

Glu Val Arg Asn Gly Ser Asn Ser Asn Ser Pro Leu Leu Gly Lys
3455                3460                3465

Tyr Cys Gly Thr Leu Leu Pro Asn Pro Val Phe Ser Gln Asn Asn
3470                3475                3480

Glu Leu Tyr Leu Arg Phe Lys Ser Asp Ser Val Thr Ser Asp Arg
3485                3490                3495

Gly Tyr Glu Ile Ile Trp Thr Ser Ser Pro Ser Gly Cys Gly Gly
3500                3505                3510

Thr Leu Tyr Gly Asp Arg Gly Ser Phe Thr Ser Pro Gly Tyr Pro
3515                3520                3525

Gly Thr Tyr Pro Asn Asn Thr Tyr Cys Glu Trp Val Leu Val Ala
3530                3535                3540

Pro Ala Gly Arg Leu Val Thr Ile Asn Phe Tyr Phe Ile Ser Ile
3545                3550                3555

Asp Asp Pro Gly Asp Cys Val Gln Asn Tyr Leu Thr Leu Tyr Asp
3560                3565                3570

Gly Pro Asn Ala Ser Ser Pro Ser Ser Gly Pro Tyr Cys Gly Gly
3575                3580                3585

Asp Thr Ser Ile Ala Pro Phe Val Ala Ser Ser Asn Gln Val Phe
3590                3595                3600

Ile Lys Phe His Ala Asp Tyr Ala Arg Arg Pro Ser Ala Phe Arg
3605                3610                3615

Leu Thr Trp Asp Ser
3620

<210> SEQ ID NO 41
<211> LENGTH: 737
<212> TYPE: PRT
<213> ORGANISM: Homo sapiens

<400> SEQUENCE: 41

Met Gln Pro Arg Arg Ala Gln Ala Pro Gly Ala Gln Leu Leu Pro Ala
1               5                   10                  15

Leu Ala Leu Leu Leu Leu Leu Leu Gly Ala Gly Pro Arg Gly Ser Ser

```
                  20                  25                  30
Leu Ala Asn Pro Val Pro Ala Ala Pro Leu Ser Ala Pro Gly Pro Cys
            35                  40                  45
Ala Ala Gln Pro Cys Arg Asn Gly Gly Val Cys Thr Ser Arg Pro Glu
 50                  55                  60
Pro Asp Pro Gln His Pro Ala Pro Ala Gly Glu Pro Gly Tyr Ser Cys
 65                  70                  75                  80
Thr Cys Pro Ala Gly Ile Ser Gly Ala Asn Cys Gln Leu Val Ala Asp
            85                  90                  95
Pro Cys Ala Ser Asn Pro Cys His His Gly Asn Cys Ser Ser Ser Ser
            100                 105                 110
Ser Ser Ser Ser Asp Gly Tyr Leu Cys Ile Cys Asn Glu Gly Tyr Glu
            115                 120                 125
Gly Pro Asn Cys Glu Gln Ala Leu Pro Ser Leu Pro Ala Thr Gly Trp
            130                 135                 140
Thr Glu Ser Met Ala Pro Arg Gln Leu Gln Pro Val Pro Ala Thr Gln
145                 150                 155                 160
Glu Pro Asp Lys Ile Leu Pro Arg Ser Gln Ala Thr Val Thr Leu Pro
                165                 170                 175
Thr Trp Gln Pro Lys Thr Gly Gln Lys Val Val Glu Met Lys Trp Asp
            180                 185                 190
Gln Val Glu Val Ile Pro Asp Ile Ala Cys Gly Asn Ala Ser Ser Asn
            195                 200                 205
Ser Ser Ala Gly Gly Arg Leu Val Ser Phe Glu Val Pro Gln Asn Thr
            210                 215                 220
Ser Val Lys Ile Arg Gln Asp Ala Thr Ala Ser Leu Ile Leu Leu Trp
225                 230                 235                 240
Lys Val Thr Ala Thr Gly Phe Gln Gln Cys Ser Leu Ile Asp Gly Arg
                245                 250                 255
Ser Val Thr Pro Leu Gln Ala Ser Gly Gly Leu Val Leu Leu Glu Glu
            260                 265                 270
Met Leu Ala Leu Gly Asn Asn His Phe Ile Gly Phe Val Asn Asp Ser
            275                 280                 285
Val Thr Lys Ser Ile Val Ala Leu Arg Leu Thr Leu Val Val Lys Val
            290                 295                 300
Ser Thr Cys Val Pro Gly Glu Ser His Ala Asn Asp Leu Glu Cys Ser
305                 310                 315                 320
Gly Lys Gly Lys Cys Thr Thr Lys Pro Ser Glu Ala Thr Phe Ser Cys
                325                 330                 335
Thr Cys Glu Glu Gln Tyr Val Gly Thr Phe Cys Glu Glu Tyr Asp Ala
            340                 345                 350
Cys Gln Arg Lys Pro Cys Gln Asn Asn Ala Ser Cys Ile Asp Ala Asn
            355                 360                 365
Glu Lys Gln Asp Gly Ser Asn Phe Thr Cys Val Cys Leu Pro Gly Tyr
            370                 375                 380
Thr Gly Glu Leu Cys Gln Ser Lys Ile Asp Tyr Cys Ile Leu Asp Pro
385                 390                 395                 400
Cys Arg Asn Gly Ala Thr Cys Ile Ser Ser Leu Ser Gly Phe Thr Cys
                405                 410                 415
Gln Cys Pro Glu Gly Tyr Phe Gly Ser Ala Cys Glu Glu Lys Val Asp
            420                 425                 430
Pro Cys Ala Ser Ser Pro Cys Gln Asn Asn Gly Thr Cys Tyr Val Asp
            435                 440                 445
```

-continued

```
Gly Val His Phe Thr Cys Asn Cys Ser Pro Gly Phe Thr Gly Pro Thr
    450                 455                 460
Cys Ala Gln Leu Ile Asp Phe Cys Ala Leu Ser Pro Cys Ala His Gly
465                 470                 475                 480
Thr Cys Arg Ser Val Gly Thr Ser Tyr Lys Cys Leu Cys Asp Pro Gly
                485                 490                 495
Tyr His Gly Leu Tyr Cys Glu Glu Tyr Asn Glu Cys Leu Ser Ala
            500                 505                 510
Pro Cys Leu Asn Ala Ala Thr Cys Arg Asp Leu Val Asn Gly Tyr Glu
            515                 520                 525
Cys Val Cys Leu Ala Glu Tyr Lys Gly Thr His Cys Glu Leu Tyr Lys
    530                 535                 540
Asp Pro Cys Ala Asn Val Ser Cys Leu Asn Gly Ala Thr Cys Asp Ser
545                 550                 555                 560
Asp Gly Leu Asn Gly Thr Cys Ile Cys Ala Pro Gly Phe Thr Gly Glu
                565                 570                 575
Glu Cys Asp Ile Asp Ile Asn Glu Cys Asp Ser Asn Pro Cys His His
            580                 585                 590
Gly Gly Ser Cys Leu Asp Gln Pro Asn Gly Tyr Asn Cys His Cys Pro
    595                 600                 605
His Gly Trp Val Gly Ala Asn Cys Glu Ile His Leu Gln Trp Lys Ser
610                 615                 620
Gly His Met Ala Glu Ser Leu Thr Asn Met Pro Arg His Ser Leu Tyr
625                 630                 635                 640
Ile Ile Ile Gly Ala Leu Cys Val Ala Phe Ile Leu Met Leu Ile Ile
                645                 650                 655
Leu Ile Val Gly Ile Cys Arg Ile Ser Arg Ile Glu Tyr Gln Gly Ser
            660                 665                 670
Ser Arg Pro Ala Tyr Glu Glu Phe Tyr Asn Cys Arg Ser Ile Asp Ser
    675                 680                 685
Glu Phe Ser Asn Ala Ile Ala Ser Ile Arg His Ala Arg Phe Gly Lys
690                 695                 700
Lys Ser Arg Pro Ala Met Tyr Asp Val Ser Pro Ile Ala Tyr Glu Asp
705                 710                 715                 720
Tyr Ser Pro Asp Asp Lys Pro Leu Val Thr Leu Ile Lys Thr Lys Asp
                725                 730                 735
Leu

<210> SEQ ID NO 42
<211> LENGTH: 1218
<212> TYPE: PRT
<213> ORGANISM: Homo sapiens

<400> SEQUENCE: 42

Met Arg Ser Pro Arg Thr Arg Gly Arg Ser Gly Arg Pro Leu Ser Leu
1               5                   10                  15
Leu Leu Ala Leu Leu Cys Ala Leu Arg Ala Lys Val Cys Gly Ala Ser
            20                  25                  30
Gly Gln Phe Glu Leu Glu Ile Leu Ser Met Gln Asn Val Asn Gly Glu
        35                  40                  45
Leu Gln Asn Gly Asn Cys Cys Gly Gly Ala Arg Asn Pro Gly Asp Arg
    50                  55                  60
Lys Cys Thr Arg Asp Glu Cys Asp Thr Tyr Phe Lys Val Cys Leu Lys
65                  70                  75                  80
```

```
Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495
```

-continued

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
        530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
            595                 600                 605

Ser Gly Gly Lys Phe Thr Cys Asp Cys Asn Lys Gly Phe Thr Gly Thr
        610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
        690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
        850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His

```
            915                 920                 925
Pro Cys Thr Gly Val Gly Glu Cys Arg Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
        995                 1000                1005

Asn Asn Glu Ile His Val Ala Ile Ser Ala Glu Asp Ile Arg Asp
    1010                1015                1020

Asp Gly Asn Pro Ile Lys Glu Ile Thr Asp Lys Ile Ile Asp Leu
    1025                1030                1035

Val Ser Lys Arg Asp Gly Asn Ser Ser Leu Ile Ala Ala Val Ala
    1040                1045                1050

Glu Val Arg Val Gln Arg Arg Pro Leu Lys Asn Arg Thr Asp Phe
    1055                1060                1065

Leu Val Pro Leu Leu Ser Ser Val Leu Thr Val Ala Trp Ile Cys
    1070                1075                1080

Cys Leu Val Thr Ala Phe Tyr Trp Cys Leu Arg Lys Arg Arg Lys
    1085                1090                1095

Pro Gly Ser His Thr His Ser Ala Ser Glu Asp Asn Thr Thr Asn
    1100                1105                1110

Asn Val Arg Glu Gln Leu Asn Gln Ile Lys Asn Pro Ile Glu Lys
    1115                1120                1125

His Gly Ala Asn Thr Val Pro Ile Lys Asp Tyr Glu Asn Lys Asn
    1130                1135                1140

Ser Lys Met Ser Lys Ile Arg Thr His Asn Ser Glu Val Glu Glu
    1145                1150                1155

Asp Asp Met Asp Lys His Gln Gln Lys Ala Arg Phe Ala Lys Gln
    1160                1165                1170

Pro Ala Tyr Thr Leu Val Asp Arg Glu Glu Lys Pro Pro Asn Gly
    1175                1180                1185

Thr Pro Thr Lys His Pro Asn Trp Thr Asn Lys Gln Asp Asn Arg
    1190                1195                1200

Asp Leu Glu Ser Ala Gln Ser Leu Asn Arg Met Glu Tyr Ile Val
    1205                1210                1215

<210> SEQ ID NO 43
<211> LENGTH: 950
<212> TYPE: PRT
<213> ORGANISM: Homo sapiens

<400> SEQUENCE: 43

Met Gly Val Pro Ala Phe Phe Arg Trp Leu Ser Arg Lys Tyr Pro Ser
1               5                   10                  15

Ile Ile Val Asn Cys Val Glu Glu Lys Pro Lys Glu Cys Asn Gly Val
            20                  25                  30

Lys Ile Pro Val Asp Ala Ser Lys Pro Asn Pro Asn Asp Val Glu Phe
        35                  40                  45

Asp Asn Leu Tyr Leu Asp Met Asn Gly Ile Ile His Pro Cys Thr His
    50                  55                  60
```

-continued

```
Pro Glu Asp Lys Pro Ala Pro Lys Asn Glu Asp Met Met Val Ala
 65                  70                  75                  80

Ile Phe Glu Tyr Ile Asp Arg Leu Phe Ser Ile Val Arg Pro Arg Arg
                 85                  90                  95

Leu Leu Tyr Met Ala Ile Asp Gly Val Ala Pro Arg Ala Lys Met Asn
                100                 105                 110

Gln Gln Arg Ser Arg Arg Phe Arg Ala Ser Lys Glu Gly Met Glu Ala
            115                 120                 125

Ala Val Glu Lys Gln Arg Val Arg Glu Glu Ile Leu Ala Lys Gly Gly
        130                 135                 140

Phe Leu Pro Pro Glu Glu Ile Lys Glu Arg Phe Asp Ser Asn Cys Ile
145                 150                 155                 160

Thr Pro Gly Thr Glu Phe Met Asp Asn Leu Ala Lys Cys Leu Arg Tyr
                165                 170                 175

Tyr Ile Ala Asp Arg Leu Asn Asn Asp Pro Gly Trp Lys Asn Leu Thr
                180                 185                 190

Val Ile Leu Ser Asp Ala Ser Ala Pro Gly Glu Gly Glu His Lys Ile
            195                 200                 205

Met Asp Tyr Ile Arg Arg Gln Arg Ala Gln Pro Asn His Asp Pro Asn
        210                 215                 220

Thr His His Cys Leu Cys Gly Ala Asp Ala Asp Leu Ile Met Leu Gly
225                 230                 235                 240

Leu Ala Thr His Glu Pro Asn Phe Thr Ile Ile Arg Glu Glu Phe Lys
                245                 250                 255

Pro Asn Lys Pro Lys Pro Cys Gly Leu Cys Asn Gln Phe Gly His Glu
                260                 265                 270

Val Lys Asp Cys Glu Gly Leu Pro Arg Glu Lys Lys Gly Lys His Asp
            275                 280                 285

Glu Leu Ala Asp Ser Leu Pro Cys Ala Glu Gly Glu Phe Ile Phe Leu
        290                 295                 300

Arg Leu Asn Val Leu Arg Glu Tyr Leu Glu Arg Glu Leu Thr Met Ala
305                 310                 315                 320

Ser Leu Pro Phe Thr Phe Asp Val Glu Arg Ser Ile Asp Asp Trp Val
                325                 330                 335

Phe Met Cys Phe Phe Val Gly Asn Asp Phe Leu Pro His Leu Pro Ser
                340                 345                 350

Leu Glu Ile Arg Glu Asn Ala Ile Asp Arg Leu Val Asn Ile Tyr Lys
            355                 360                 365

Asn Val Val His Lys Thr Gly Gly Tyr Leu Thr Glu Ser Gly Tyr Val
        370                 375                 380

Asn Leu Gln Arg Val Gln Met Ile Met Leu Ala Val Gly Glu Val Glu
385                 390                 395                 400

Asp Ser Ile Phe Lys Lys Arg Lys Asp Asp Glu Asp Ser Phe Arg Arg
                405                 410                 415

Arg Gln Lys Glu Lys Arg Lys Arg Met Lys Arg Asp Gln Pro Ala Phe
                420                 425                 430

Thr Pro Ser Gly Ile Leu Thr Pro His Ala Leu Gly Ser Arg Asn Ser
            435                 440                 445

Pro Gly Ser Gln Val Ala Ser Asn Pro Arg Gln Ala Ala Tyr Glu Met
        450                 455                 460

Arg Met Gln Asn Asn Ser Ser Pro Ser Ile Ser Pro Asn Thr Ser Phe
465                 470                 475                 480

Thr Ser Asp Gly Ser Pro Ser Pro Leu Gly Gly Ile Lys Arg Lys Ala
```

```
            485                 490                 495
Glu Asp Ser Asp Ser Glu Pro Glu Pro Glu Asp Asn Val Arg Leu Trp
            500                 505                 510

Glu Ala Gly Trp Lys Gln Arg Tyr Tyr Lys Asn Lys Phe Asp Val Asp
            515                 520                 525

Ala Ala Asp Glu Lys Phe Arg Arg Lys Val Val Gln Ser Tyr Val Glu
            530                 535                 540

Gly Leu Cys Trp Val Leu Arg Tyr Tyr Gln Gly Cys Ala Ser Trp
545                 550                 555                 560

Lys Trp Tyr Tyr Pro Phe His Tyr Ala Pro Phe Ala Ser Asp Phe Glu
                    565                 570                 575

Gly Ile Ala Asp Met Pro Ser Asp Phe Glu Lys Gly Thr Lys Pro Phe
            580                 585                 590

Lys Pro Leu Glu Gln Leu Met Gly Val Phe Pro Ala Ala Ser Gly Asn
            595                 600                 605

Phe Leu Pro Pro Ser Trp Arg Lys Leu Met Ser Asp Pro Asp Ser Ser
            610                 615                 620

Ile Ile Asp Phe Tyr Pro Glu Asp Phe Ala Ile Asp Leu Asn Gly Lys
625                 630                 635                 640

Lys Tyr Ala Trp Gln Gly Val Ala Leu Leu Pro Phe Val Asp Glu Arg
                    645                 650                 655

Arg Leu Arg Ala Ala Leu Glu Glu Val Tyr Pro Asp Leu Thr Pro Glu
            660                 665                 670

Glu Thr Arg Arg Asn Ser Leu Gly Gly Asp Val Leu Phe Val Gly Lys
            675                 680                 685

His His Pro Leu His Asp Phe Ile Leu Glu Leu Tyr Gln Thr Gly Ser
            690                 695                 700

Thr Glu Pro Val Glu Val Pro Pro Glu Leu Cys His Gly Ile Gln Gly
705                 710                 715                 720

Lys Phe Ser Leu Asp Glu Glu Ala Ile Leu Pro Asp Gln Ile Val Cys
                    725                 730                 735

Ser Pro Val Pro Met Leu Arg Asp Leu Thr Gln Asn Thr Val Val Ser
            740                 745                 750

Ile Asn Phe Lys Asp Pro Gln Phe Ala Glu Asp Tyr Ile Phe Lys Ala
            755                 760                 765

Val Met Leu Pro Gly Ala Arg Lys Pro Ala Ala Val Leu Lys Pro Ser
            770                 775                 780

Asp Trp Glu Lys Ser Ser Asn Gly Arg Gln Trp Lys Pro Gln Leu Gly
785                 790                 795                 800

Phe Asn Arg Asp Arg Arg Pro Val His Leu Asp Gln Ala Ala Phe Arg
                    805                 810                 815

Thr Leu Gly His Val Met Pro Arg Gly Ser Gly Thr Gly Ile Tyr Ser
            820                 825                 830

Asn Ala Ala Pro Pro Pro Val Thr Tyr Gln Gly Asn Leu Tyr Arg Pro
            835                 840                 845

Leu Leu Arg Gly Gln Ala Gln Ile Pro Lys Leu Met Ser Asn Met Arg
            850                 855                 860

Pro Gln Asp Ser Trp Arg Gly Pro Pro Leu Phe Gln Gln Arg
865                 870                 875                 880

Phe Asp Arg Gly Val Gly Ala Glu Pro Leu Leu Pro Trp Asn Arg Met
                    885                 890                 895

Leu Gln Thr Gln Asn Ala Ala Phe Gln Pro Asn Gln Tyr Gln Met Leu
            900                 905                 910
```

```
Ala Gly Pro Gly Gly Tyr Pro Pro Arg Arg Asp Asp Arg Gly Gly Arg
        915                 920                 925

Gln Gly Tyr Pro Arg Glu Gly Arg Lys Tyr Pro Leu Pro Pro Pro Ser
        930                 935                 940

Gly Arg Tyr Asn Trp Asn
945             950

<210> SEQ ID NO 44
<211> LENGTH: 686
<212> TYPE: PRT
<213> ORGANISM: Homo sapiens

<400> SEQUENCE: 44

Met Thr Glu Ser Gln Gly Thr Val Thr Phe Lys Asp Val Ala Ile Asp
1               5                   10                  15

Phe Thr Gln Glu Glu Trp Lys Arg Leu Asp Pro Ala Gln Arg Lys Leu
            20                  25                  30

Tyr Arg Asn Val Met Leu Glu Asn Tyr Asn Asn Leu Ile Thr Val Gly
        35                  40                  45

Tyr Pro Phe Thr Lys Pro Asp Val Ile Phe Lys Leu Glu Gln Glu Glu
    50                  55                  60

Glu Pro Trp Val Met Glu Glu Val Leu Arg Arg His Trp Gln Gly
65                  70                  75                  80

Glu Ile Trp Gly Val Asp His Gln Lys Asn Gln Asp Arg Leu Leu
                85                  90                  95

Arg Gln Val Glu Val Lys Phe Gln Lys Thr Leu Thr Glu Glu Lys Gly
            100                 105                 110

Asn Glu Cys Gln Lys Lys Phe Ala Asn Val Phe Pro Leu Asn Ser Asp
        115                 120                 125

Phe Phe Pro Ser Arg His Asn Leu Tyr Glu Tyr Asp Leu Phe Gly Lys
    130                 135                 140

Cys Leu Glu His Asn Phe Asp Cys His Asn Asn Val Lys Cys Leu Met
145                 150                 155                 160

Arg Lys Glu His Cys Glu Tyr Asn Glu Pro Val Lys Ser Tyr Gly Asn
                165                 170                 175

Ser Ser Ser His Phe Val Ile Thr Pro Phe Lys Cys Asn His Cys Gly
            180                 185                 190

Lys Gly Phe Asn Gln Thr Leu Asp Leu Ile Arg His Leu Arg Ile His
        195                 200                 205

Thr Gly Glu Lys Pro Tyr Glu Cys Ser Asn Cys Arg Lys Ala Phe Ser
    210                 215                 220

His Lys Glu Lys Leu Ile Lys His Tyr Lys Ile His Ser Arg Glu Gln
225                 230                 235                 240

Ser Tyr Lys Cys Asn Glu Cys Gly Lys Ala Phe Ile Lys Met Ser Asn
                245                 250                 255

Leu Ile Arg His Gln Arg Ile His Thr Gly Glu Lys Pro Tyr Ala Cys
            260                 265                 270

Lys Glu Cys Glu Lys Ser Phe Ser Gln Lys Ser Asn Leu Ile Asp His
        275                 280                 285

Glu Lys Ile His Thr Gly Glu Lys Pro Tyr Glu Cys Asn Glu Cys Gly
    290                 295                 300

Lys Ala Phe Ser Gln Lys Gln Ser Leu Ile Ala His Gln Lys Val His
305                 310                 315                 320

Thr Gly Glu Lys Pro Tyr Ala Cys Asn Glu Cys Gly Lys Ala Phe Pro
```

```
                325                 330                 335
Arg Ile Ala Ser Leu Ala Leu His Met Arg Ser His Thr Gly Glu Lys
            340                 345                 350
Pro Tyr Lys Cys Asp Lys Cys Gly Lys Ala Phe Ser Gln Phe Ser Met
            355                 360                 365
Leu Ile Ile His Val Arg Ile His Thr Gly Glu Lys Pro Tyr Glu Cys
            370                 375                 380
Asn Glu Cys Gly Lys Ala Phe Ser Gln Ser Ser Ala Leu Thr Val His
385                 390                 395                 400
Met Arg Ser His Thr Gly Glu Lys Pro Tyr Glu Cys Lys Glu Cys Arg
            405                 410                 415
Lys Ala Phe Ser His Lys Lys Asn Phe Ile Thr His Gln Lys Ile His
            420                 425                 430
Thr Arg Glu Lys Pro Tyr Glu Cys Asn Glu Cys Gly Lys Ala Phe Ile
            435                 440                 445
Gln Met Ser Asn Leu Val Arg His Gln Arg Ile His Thr Gly Glu Lys
            450                 455                 460
Pro Tyr Ile Cys Lys Glu Cys Gly Lys Ala Phe Ser Gln Lys Ser Asn
465                 470                 475                 480
Leu Ile Ala His Glu Lys Ile His Ser Gly Glu Lys Pro Tyr Glu Cys
            485                 490                 495
Asn Glu Cys Gly Lys Ala Phe Ser Gln Lys Gln Asn Phe Ile Thr His
            500                 505                 510
Gln Lys Val His Thr Gly Glu Lys Pro Tyr Asp Cys Asn Glu Cys Gly
            515                 520                 525
Lys Ala Phe Ser Gln Ile Ala Ser Leu Thr Leu His Leu Arg Ser His
530                 535                 540
Thr Gly Glu Lys Pro Tyr Glu Cys Asp Lys Cys Gly Lys Ala Phe Ser
545                 550                 555                 560
Gln Cys Ser Leu Leu Asn Leu His Met Arg Ser His Thr Gly Glu Lys
            565                 570                 575
Pro Tyr Val Cys Asn Glu Cys Gly Lys Ala Phe Ser Gln Arg Thr Ser
            580                 585                 590
Leu Ile Val His Met Arg Gly His Thr Gly Glu Lys Pro Tyr Glu Cys
            595                 600                 605
Asn Lys Cys Gly Lys Ala Phe Ser Gln Ser Ser Leu Thr Ile His
            610                 615                 620
Ile Arg Gly His Thr Gly Glu Lys Pro Phe Asp Cys Ser Lys Cys Gly
625                 630                 635                 640
Lys Ala Phe Ser Gln Ile Ser Ser Leu Thr Leu His Met Arg Lys His
            645                 650                 655
Thr Gly Glu Lys Pro Tyr His Cys Ile Glu Cys Gly Lys Ala Phe Ser
            660                 665                 670
Gln Lys Ser His Leu Val Arg His Gln Arg Ile His Thr His
            675                 680                 685

<210> SEQ ID NO 45
<211> LENGTH: 1721
<212> TYPE: PRT
<213> ORGANISM: Homo sapiens

<400> SEQUENCE: 45

Val Pro Pro Gly Gly Ser Ser Val Cys Thr Ala Val Gly Ser Cys Glu
1               5                   10                  15
```

Leu Val Gln Arg Gly Pro Ser Gly Pro Ala Pro Gly His Met Arg Arg
                20                  25                  30

Pro Pro Pro Leu Gly Pro Thr Thr Ala Ser Gly Pro Glu Gly Asn Val
            35                  40                  45

Arg Asn Leu Gln Lys Arg Gln Ala Pro Gly Pro Gly Ala Ala Gly Gly
        50                  55                  60

Cys Gly Pro Glu Ala Gly Gly Cys Arg Glu Asn Lys Gln Lys Arg Arg
65                  70                  75                  80

Met Val Ala Arg Ala Thr Pro Gly Arg Gly Glu Val Glu Ser Asp Lys
                85                  90                  95

Ser Val Ala Ala Ser Gly Ala Gly Lys Ala Ala Arg Arg Gln Val Glu
            100                 105                 110

Gly Arg Arg Gly Pro Val Ser Pro Ser Asp Ser Asp Pro Arg Gly
        115                 120                 125

Leu Glu Ala Ala Lys Glu Ala Glu Leu Pro Leu Gln Thr Glu Arg His
        130                 135                 140

Thr Lys Glu Lys Arg Lys Val Thr Glu Ala Ser Ser Asp Asp Pro Gln
145                 150                 155                 160

Pro Gly Leu Asp Leu Val Arg Lys Glu Ser Leu Thr Ser Ser Glu Ser
                165                 170                 175

Phe Gln Thr Val Glu Cys Leu Gln Ser Leu Gly Lys Glu Ser Ile Ile
            180                 185                 190

Glu Gly Ile Lys Arg Arg Ile Arg Asn Lys Lys Leu Lys Ser Leu Glu
        195                 200                 205

Asn Pro Pro Leu Lys Ile Thr Glu Asn Glu Ala Thr Gln Asn Ile Lys
210                 215                 220

Val Glu Phe Gln Asp Glu Leu Tyr Lys Asn Thr Pro Lys Tyr Ser Cys
225                 230                 235                 240

Asn Ile Leu Ser Pro Glu Val Glu Asn Asn Ser Val Leu Lys Leu Arg
                245                 250                 255

Asp Cys Asn Cys Phe Pro His Ser Lys Gly Cys Asn Asp Glu Asn Asn
            260                 265                 270

Leu Pro Tyr Lys Pro Asp Gly Gly Cys Met His Val Ala Glu Asn Phe
        275                 280                 285

Ser Lys Lys Glu Asn Leu Arg Ser Leu Ala Glu Lys Ser Asp Thr Asn
290                 295                 300

Ser Ile Pro Gln Leu Leu Gln Thr Glu Glu Asn Val Met Gly Val Asn
305                 310                 315                 320

Lys Leu Leu Pro Glu Glu Ser Asp Leu Tyr Gln Ser Lys Thr Asn Gly
                325                 330                 335

Leu Leu Ser Cys Leu Gln His Glu Lys Asn Lys Tyr Ser Ile Glu Glu
            340                 345                 350

Ser Ser Val Gly Arg Lys Pro Arg Lys Arg Met Lys Leu Ser Glu Lys
        355                 360                 365

Ala Asp Glu Thr Val Thr Glu Met Asn Phe Ser Asn Gly Tyr Asn Lys
370                 375                 380

Ser Glu Leu Met Leu Gln Glu Asn Gln Met Ile Ala Asp Gly Lys Glu
385                 390                 395                 400

Ala Glu Thr Lys Ser Pro Leu Asn Val Leu Arg Lys Val Ser His Asn
                405                 410                 415

Thr Val Ser Leu Met Asp His Leu Leu Ser Val Pro Glu Thr Val Glu
            420                 425                 430

Lys Glu Thr Ser Ser Glu His His Val Asn Ala Val Phe Gln Lys Thr

```
                435                 440                 445
Ile Glu Pro Leu Leu Lys Glu Glu Thr Glu Asn Ala Ser Glu Pro Leu
450                 455                 460
Gly Tyr Glu Ser Met Ala Ser Lys Glu Asp Phe Lys Ser Met Lys Ser
465                 470                 475                 480
Phe Ile Gly Lys Ser Pro Asn Glu Tyr His Ile Glu Arg Arg Ser Ser
                485                 490                 495
Arg Glu Asp Leu Arg Ser Ala Ser Glu Glu Leu Lys Leu Ser Cys Gln
                500                 505                 510
Arg Thr Ile Pro Met Thr Gly Lys Arg Thr Trp Pro Tyr Tyr Ser Cys
                515                 520                 525
Ala Arg Ile Ser Ala Trp Cys Trp Lys Lys Ala Ser Leu Pro Glu Ser
                530                 535                 540
Ser Tyr Phe Leu Arg Gly Ser Gln Glu Ser Cys Arg Gln Val Asp Val
545                 550                 555                 560
Pro Lys His Gln Thr Asn Gln Thr His Leu Thr Asp Ser Lys Leu Leu
                565                 570                 575
Leu Gln Ser Ser Leu Thr Glu Thr Asn Thr Glu Ser Ser Ser Lys Glu
                580                 585                 590
Lys Leu Asp Ser Asn Ser Asn Cys Leu Ser Ser Val Ser Ala Val Glu
                595                 600                 605
Pro Thr Leu Met Val Ile Lys Glu Pro Ile Ile Lys Asp Asp Lys Lys
                610                 615                 620
Ile Lys Ser Glu Glu Leu Ser Arg Arg Gly Ser Glu Val Ile Ser Asn
625                 630                 635                 640
Thr Thr Glu Asp Thr Gln Leu Thr Ser Glu Thr Gln Ser Leu Thr Gly
                645                 650                 655
Asn Lys Lys Lys Ala Arg Gly Asn Leu Thr Lys Leu Asn Leu Thr Ala
                660                 665                 670
Thr Ser Lys Asp Gly Gln Glu Ala Asn Asn Ser Ala Gly Lys Thr Ile
                675                 680                 685
His Arg Lys Ala Cys Ile Ala Gln Gln Thr Phe Ile Val Pro Asp Leu
                690                 695                 700
Val Lys Ile Leu Asn Thr Gly Arg Leu Thr Asn Phe Lys Ile Pro Leu
705                 710                 715                 720
Leu Lys Asn Lys Ser Glu Lys Arg Lys Glu Val Asn Ala Lys Ser Ser
                725                 730                 735
Glu Arg Glu Ala Tyr Ser Pro Leu Glu Leu Leu Asp Asn Leu Ser Gly
                740                 745                 750
Ala Asp Val Arg Gln Asn Arg Ser Lys Glu Asn Val Ser Met Met Met
                755                 760                 765
Leu Gly Pro Gln Thr Leu Ser Ile Arg Asn Ser Val Thr Pro Val Gln
                770                 775                 780
Ala Ser Ser Asp Ser Phe Tyr Asn Lys Lys Ser Tyr Ser Ile Ser Pro
785                 790                 795                 800
Ser Phe Thr Lys Gln Gly Asn Asn Ser Lys Pro Ser Asn His Val Ser
                805                 810                 815
Glu Pro Gly Asn Ile Val Ser Asn Lys Glu Val Ala Ser Leu Thr Val
                820                 825                 830
Glu Asn Asn Ala Phe Ser Cys Asp Pro Gly Tyr Val Glu Lys Ser Pro
                835                 840                 845
Ser Phe Cys Cys Asn Glu Gln Glu Thr Phe Arg Pro Val Ser Ser Glu
                850                 855                 860
```

```
Val Arg Gly Arg Lys Ile Thr Lys Asn Phe Ser Glu Val Gly Phe Pro
865                 870                 875                 880

Asp Ile Leu Lys Ala Tyr Glu Asp Val Leu Leu Ile Asp Val Ile
            885                 890                 895

Gln Asp Asp Pro Asp Leu Phe Gly Val Ser Asn Glu Gly Glu Leu Ser
                900                 905                 910

Phe Thr Ser Glu Val Pro Lys Ile Ser Gln Glu Pro Asn Val Ala Gly
            915                 920                 925

Glu His Gln Ser Thr Asp Ser Lys Tyr Met Glu Thr Pro Val Lys Lys
930                 935                 940

Glu Pro Ser Asp Asp Leu Arg Glu Leu Pro Val Leu Asp Cys Gly Trp
945                 950                 955                 960

Ile Lys Pro Asp Ile Cys Ala Ser Asn Ser Ala Glu Ser Glu Ile Lys
                965                 970                 975

Arg Asp Pro Lys Asp Val Asn Thr Ser Leu Gly Glu Val Ala Asn Glu
            980                 985                 990

Thr Ser Glu Asn Glu Thr Leu Gly Asp Phe Ser Glu Gln Ile Lys Gly
        995                 1000                1005

Ser Asp Leu Asp Glu Lys His Arg Phe Thr Asp Lys Val Ile Thr
1010                1015                1020

Lys Glu Glu Lys Glu Asn Ile Tyr Glu Val Cys Lys Ser Lys Asp
1025                1030                1035

Ser Arg Asn Ala Asp Phe Met Val Gly Glu Cys Gln Phe Ala Val
1040                1045                1050

Pro Val Pro Lys Pro Leu Cys Leu Leu Val Pro Pro Leu Asn Leu
1055                1060                1065

Ser Gly Arg Gln Glu Asp Thr Ile Leu Asn Thr Trp Met Asn Asp
1070                1075                1080

Phe Arg Phe Leu Gly Lys His Ser Val Leu Lys Leu Gln Asn Pro
1085                1090                1095

Glu Thr Cys Glu Ile Phe Lys Arg Glu Lys Asn Val Gly Val Phe
1100                1105                1110

Gln Lys Ser Leu Gly Leu Met Ile Pro Tyr Lys Tyr Cys Lys Phe
1115                1120                1125

His Phe Asn Thr Leu Arg Gly Cys Glu Arg Pro Leu Cys Lys Phe
1130                1135                1140

Ala His Val Pro Glu Gln Gly Asp Glu Lys Val Cys Met Asp Val
1145                1150                1155

Phe Lys Lys Tyr Ile Asn Ile Asn Glu Leu Cys Leu Leu Gln Arg
1160                1165                1170

Ala Val Asn Ile Phe Met Glu Tyr Tyr Arg Lys Phe Pro Pro Gly
1175                1180                1185

Val Tyr Phe Asp Leu Gln Val Leu Asn Asp Leu Leu Asn Ser Leu
1190                1195                1200

Leu Lys His Cys Leu Leu Lys Glu Val Phe Gln Ile Val Asn Leu
1205                1210                1215

Ser Ile Met Val Lys Met Leu Pro Ser Leu Lys Ile Leu Leu Asn
1220                1225                1230

Ile Phe Glu Tyr Val Ala Thr Met Lys Leu Arg Asn Ala Val Pro
1235                1240                1245

Ala Leu Ile Asp Ile Phe Cys Lys Leu Val Glu Ala Gly Met Val
1250                1255                1260
```

-continued

```
Leu Asp Pro Glu His Phe Asn Tyr Ile Val Lys Leu Leu Tyr Gln
1265                1270                1275

Val Gln Ala Ser Lys Gln Glu Ile Thr Ala Val Leu Glu Met Lys
1280                1285                1290

Ser Arg Leu Gln Met Arg Arg Phe Lys Lys Asn Trp Lys Cys Asp
1295                1300                1305

Leu Asp Ser Ala Leu Asn Lys Leu Glu His Cys Lys Glu Lys Gly
1310                1315                1320

Asp Trp Thr Lys Leu Gly Lys Leu Tyr Ile Asn Val Lys Met Gly
1325                1330                1335

Cys Glu Lys Phe Ala Asp Phe Gln Thr Phe Cys Ala Cys Ile Ala
1340                1345                1350

Glu Thr Leu Thr Lys Asn Tyr Glu Asp Glu Arg Pro Asp Ile Pro
1355                1360                1365

Phe Cys Glu Phe Ala Glu Thr Val Ser Lys Asp Pro Gln Asn Ser
1370                1375                1380

Lys Val Asp Lys Gly Val Leu Gly Arg Ile Gly Ile Ser Ala Met
1385                1390                1395

Tyr Phe Tyr His Lys Leu Leu Gln Trp Ser Lys Gly Arg Lys Val
1400                1405                1410

Leu Glu Lys Leu Tyr Glu Leu Lys Ile His Phe Thr Ser Leu Lys
1415                1420                1425

Gly Leu Ile Gly Pro Glu Lys Leu Ala Ser Arg Cys Gln Ile Val
1430                1435                1440

Asn Val Ala Ala Glu Ile Phe Leu Lys Ser Gly Ser Leu Asp Gly
1445                1450                1455

Ala Ile Trp Val Met Arg Glu Ser Glu Trp Ile Ile Asn Thr Pro
1460                1465                1470

Leu Trp Pro Cys Asp Arg Leu Asp Val Leu Asn Arg His Asn Leu
1475                1480                1485

Leu Cys Thr Ile Ala His Glu Ile Leu Ala Lys Ser Leu Tyr Arg
1490                1495                1500

Gln Thr Phe Glu Val Leu Gln Asn Leu Pro Gly Phe Gln Asn Ser
1505                1510                1515

Gln Glu Thr Val Glu Val Ser Gln Tyr Ser Leu Leu Phe Asn Lys
1520                1525                1530

Leu Leu Gly Ser Cys Ile Glu Ser Ser Ser Leu Gly Met Ser Ser
1535                1540                1545

Ser Val Ala Glu Phe Met Ile Ser Lys Ser Ile Pro Ile Asp Phe
1550                1555                1560

Ser Phe Leu Arg Arg Leu Ile Thr Ser Leu Gly Arg Ser Arg Leu
1565                1570                1575

Trp Leu Lys Ala Arg Ala His Tyr Lys Ser Ala Leu Ser Leu Gly
1580                1585                1590

Cys Tyr Pro Pro Leu Glu Gly Asn Leu Tyr Arg Lys Leu Leu Leu
1595                1600                1605

Ile Pro Ser Tyr Leu Ser Glu Ile Glu Met Leu Leu Ala Ile Glu
1610                1615                1620

Ile Phe Met Val Ser Asn Ala Ser Ser Ile Gln Ser Pro Gly Thr
1625                1630                1635

Ser Thr Gln Ile Leu Gln Ile Val Leu Lys Arg Cys Glu Asp Asn
1640                1645                1650

Gln Ser Arg Ser Asn Asp Asp Tyr Gln Ala Ala Val Glu Arg Leu
```

```
            1655                1660                1665
Ile Met Ala Ala Arg Ile Ser Asp Pro Lys Leu Phe Val Lys His
        1670                1675                1680

Met Thr Val Asn Val Asn Lys Glu Gln Val Tyr Ser Leu Glu His
        1685                1690                1695

Cys Ser Ala Leu Lys Trp Leu Lys Glu Asn Met Lys Trp Ala Gly
        1700                1705                1710

Lys Val Trp Leu Phe Ser Asn His
        1715                1720

<210> SEQ ID NO 46
<211> LENGTH: 700
<212> TYPE: PRT
<213> ORGANISM: Homo sapiens

<400> SEQUENCE: 46

Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
    290                 295                 300
```

```
Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
        340                 345                 350

Thr Asn Phe Gly Arg Cys Val Asp Leu Phe Ala Pro Gly Glu Asp Ile
    355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln Asp Tyr Lys Asp Asp Asp Lys
690                 695                 700
```

METHOD OF REDUCING TOTAL CHOLESTEROL LEVEL BY ADMINISTERING MATRILIN-2 POLYPEPTIDE

This application claims the benefit of U.S. provisional application No. 61/055,266; filed May 22, 2008, which is herein incorporated by reference in its entirety.

FIELD OF THE INVENTION

The present invention relates to methods for treating various lipid disorders with matrilin-2 polypeptides.

BACKGROUND OF THE INVENTION

Atherosclerotic coronary heart disease (CHD) represents the major cause for death and cardiovascular morbidity in the western world. Risk factors for atherosclerotic coronary heart disease include hypertension, diabetes mellitus, family history, male gender, cigarette smoke, high serum cholesterol, high low density lipoprotein (LDL) cholesterol levels and low high density lipoprotein (HDL) cholesterol levels. In general, a total cholesterol level in excess of about 225-250 mg/dl is associated with significant elevation of risk of CHD.

A variety of clinical studies have demonstrated that elevated levels of total cholesterol or LDL cholesterol promote human atherosclerosis. Epidemiologic investigations have established that cardiovascular morbidity and mortality vary directly with the level of total cholesterol and LDL cholesterol.

One method for lowering LDL cholesterol levels is by administration of HMG-CoA reductase inhibiting drugs. These drugs antagonize HMG-CoA reductase and cholesterol synthesis in the liver and increase the number of hepatic LDL receptors on the cell-surface to enhance uptake and catabolism of LDL. A drawback of such an approach is that these drugs commonly suffer from a disadvantageous side-effect profile, including, for example, liver toxicity. An alternate approach is to modulate the LDL receptor pathway directly.

PCSK9 (proprotein convertase subtilisin/kexin type 9) is a serine protease family member that binds to and regulates LDL receptor expression on the surface of cells. Inhibition of the LDL receptor-PCSK9 interaction is an attractive approach to the treatment of cholesterol disorders. Inhibition of interactions between large proteins (i.e., protein-protein interactions or PPI) by the use of antibodies or small molecule inhibitors is, however, generally regarded as being particularly difficult and challenging. Large proteins such as PCSK9, with a molecular weight of about 74 KDa, and LDLR, with a molecular weight of about 160 KDa (glycosylated on cell surface; 115 KDa in immature form), are likely to exhibit extensive intermolecular contacts over a large area. The existence of extensive contacts makes it unlikely that a given antibody or small molecule inhibitor will successfully block their binding. Nevertheless, new agents that inhibit the activity of PCSK9 would be useful and the development of such agents would be the product of considerable efforts to overcome technical challenges.

Extracellular matrix proteins, such as matrilins, would appear to be an unlikely place in which to find such an inhibitor. Matrilins are a family of extracellular matrix proteins that, generally, show a similar structure including one or two von Willebrand factor A (vWFA) domains, a varying number of epidermal growth factor (EGF)-like repeats, and a C-terminal coiled-coil domain.

The functions of matrilins have been, heretofore, poorly defined. Matrilins have been thought to play a role in stabilizing the extracellular matrix structure, since they can self-associate into supramolecular structures, resulting in the formation of filamentous networks. It has been shown that at least in the case of matrilin-1 and matrilin-3, these networks can either be associated with collagen fibrils or be collagen-independent. Members of the matrilin family are found in a wide variety of extracellular matrices. Matrilin-1, formerly called cartilage matrix protein, and matrilin-3 are abundant in cartilage, while matrilin-2 and matrilin-4 show a broader tissue distribution.

SUMMARY OF THE INVENTION

The present invention addresses the need in the art for PCSK9 inhibitors by providing matrilin-2 and active fragments thereof.

The present invention provides a method for reducing total cholesterol level, low density lipoprotein cholesterol level, apolipoprotein B level, total cholesterol/high density lipoprotein ratio or low density lipoprotein/high density lipoprotein ratio, in a subject, comprising administering, to said subject, a therapeutically effective amount of a matrilin-2 polypeptide or an active fragment thereof or a polypeptide comprising an EGF-A domain from a polypeptide selected from the group consisting of APOER2, VLDLR, SCUBE2, OIT3, SCUBE1, LRP1, LRP2, LRP4/LRP10, SCUBE3, LRP5, MEGF6/EGFL3, LRP6, LRP1B, PROS1, GAS6, TLL1, NID1, TLL2, EGF, fibrilin 1, fibrilin 2, fibrilin 3, LTBP3, laminin apha 4, stabilin 2, NOTCH2NL, cubilin, DNER, jagged 1, 5'-3' exoribonuclease 2, ZNF569 and FLJ36157; optionally in association with a further chemotherapeutic agent (e.g., simvastatin and/or ezetimibe). In an embodiment of the invention, the polypeptide or active fragment thereof binds specifically to a PCSK9 catalytic domain or to a domain of PCSK9 which interacts with an LDL receptor EGF-A domain. In an embodiment of the invention, the matrilin-2 polypeptide or active fragment thereof comprises the EGF-A domain of matrilin-2 (e.g., wherein the EGF-A domain comprises the amino acid sequence set forth in SEQ ID NO: 1). In an embodiment of the invention, the matrilin-2 polypeptide or active fragment thereof comprises the mature fragment of matrilin-2 (e.g., wherein the mature fragment comprises amino acid 24-956 of SEQ ID NO: 2). In an embodiment of the invention, the polypeptide or fragment is fused to an immunoglobulin, for example, wherein the immunoglobulin is a γ1 or γ4 or a monomeric variant thereof (e.g., wherein the immunoglobulin comprises an amino acid sequence selected from the group consisting of SEQ ID NOs: 5-9).

The scope of the present invention also includes a method for treating or preventing hypercholesterolemia, hyperlipidemia, hypertriglyceridaemia, sitosterolemia, atherosclerosis, arteriosclerosis, coronary heart disease, vascular inflammation or xanthoma, in an subject, comprising administering, to said subject, a therapeutically effective amount of a matrilin-2 polypeptide or an active fragment thereof or a polypeptide comprising an EGF-A domain from a polypeptide selected from the group consisting of APOER2, VLDLR, SCUBE2, OIT3, SCUBE1, LRP1, LRP2, LRP4/LRP10, SCUBE3, LRP5, MEGF6/EGFL3, LRP6, LRP1B, PROS1, GAS6, TLL1, NID1, TLL2, EGF, fibrilin 1, fibrilin 2, fibrilin 3, LTBP3, laminin apha 4, stabilin 2, NOTCH2NL, cubilin, DNER, jagged 1, 5'-3' exoribonuclease 2, ZNF569 and FLJ36157; optionally in association with a further chemotherapeutic agent (e.g., simvastatin and/or ezetimibe). In an embodiment of the invention, the polypeptide or fragment binds specifically to a PCSK9 catalytic domain or to a domain of PCSK9 which interacts with an LDL receptor EGF-A domain. In an embodiment of the invention, the matrilin-2 polypeptide or active fragment thereof comprises the EGF-A domain of matrilin-2 (e.g., wherein the EGF-A domain comprises the amino acid sequence set forth in SEQ ID NO: 1). In an embodiment of the invention, the matrilin-2 polypeptide or active fragment thereof comprises the mature fragment of matrilin-2 (e.g., wherein the mature fragment comprises amino acid 24-956 of SEQ ID NO: 2). In an embodiment of the invention, the polypeptide or fragment is fused to an immunoglobulin, for example; wherein the immunoglobulin is a γ1 or γ4 or a monomeric variant thereof (e.g., wherein the immunoglobulin comprises an amino acid sequence selected from the group consisting of SEQ ID NOs: 5-9).

The present invention further provides a screening method for identifying a polypeptide which binds to PCSK9 comprising: (i) identifying a polypeptide comprising Cys-Leu and Asn-Asn and Asp-Leu motifs; then (ii) identifying a polypeptide selected from those identified in step (i) which comprises the motif: Asn-$X_1$-Cys-Leu-$X_2$-Asn-Asn-$X_3$-His-$X_4$-Cys-$X_5$-Asp-Leu; wherein $X_1$, $X_2$, $X_3$, $X_4$ and $X_5$ are independently zero or more amino acids; and then (iii) identifying a polypeptide selected from those identified in step (ii) which comprises at least 80% sequence similarity, over the length of said polypeptide identified in step (ii), to a low density lipoprotein receptor EGF-A domain amino acid sequence; wherein said polypeptide identified in step (iii) binds PCSK9. In an embodiment of the invention, independently, $X_1$ is one amino acid, $X_2$ is one amino acid, $X_3$ is 4 amino acids, $X_4$ is one amino acid and $X_5$ is one amino acid. In an embodiment of the invention, wherein said $X_1$, $X_2$, $X_3$, $X_4$ and $X_5$ are independently zero to 10 amino acids. In an embodiment of the invention, wherein the motif is NECLDNNGGCSH-VCNDL (SEQ ID NO: 14). In an embodiment of the invention, the screening method further comprises contacting PCSK9 and said polypeptide and determining if said PCSK9 and said polypeptide bind, for example using an amplified luminescent proximity homogeneous assay.

The present invention also provides, a method for reducing total cholesterol level, low density lipoprotein cholesterol level, apolipoprotein B level, total cholesterol/high density lipoprotein ratio or low density lipoprotein/high density lipoprotein ratio, in a subject, comprising administering, to said subject, a therapeutically effective amount of a polypeptide identified by any of the screening methods discusses herein. Moreover, the present invention also provides a method for treating or preventing hypercholesterolemia, hyperlipidemia, hypertriglyceridaemia, sitosterolemia, atherosclerosis, arteriosclerosis, coronary heart disease, vascular inflammation or xanthoma, in a subject, comprising administering, to said subject, a therapeutically effective amount of a polypeptide identified by any of the screening methods disclosed herein.

The present invention also provides a pharmaceutical composition comprising a matrilin-2 polypeptide or active fragment thereof or a multimer comprising said polypeptide or fragment or a polypeptide comprising an EGF-A domain from a polypeptide selected from the group consisting of APOER2, VLDLR, SCUBE2, OIT3, SCUBE1, LRP1, LRP2, LRP4/LRP10, SCUBE3, LRP5, MEGF6/EGFL3, LRP6, LRP1B, PROS1, GAS6, TLL1, NID1, TLL2, EGF, fibrilin 1, fibrilin 2, fibrilin 3, LTBP3, laminin apha 4, stabilin 2, NOTCH2NL, cubilin, DNER, jagged 1, 5'-3' exoribonuclease 2, ZNF569 and FLJ36157; which polypeptide or fragment inhibits binding between PCSK9 and LDL receptor; and a pharmaceutically acceptable carrier. Said pharmaceutical composition is optionally in association with a further chemotherapeutic agent e.g., simvastatin and/or ezetimibe. In an embodiment of the invention, wherein the matrilin-2 polypeptide or active fragment thereof in the pharmaceutical composition binds specifically to a PCSK9 catalytic domain or to a domain of PCSK9 which interacts with an LDL receptor EGF-A domain. In an embodiment of the invention, the matrilin-2 polypeptide or active fragment thereof comprises the amino acid sequence set forth in SEQ ID NO: 2. In an embodiment of the invention, the matrilin-2 polypeptide or active fragment thereof comprises the EGF-A domain of matrilin-2, e.g., wherein the EGF-A domain comprises the amino acid sequence set forth in SEQ ID NO: 1. In an embodiment of the invention, the matrilin-2 polypeptide or active fragment thereof comprises the mature fragment of matrilin-2, e.g., wherein the mature fragment comprises amino acid 24-956 of SEQ ID NO: 2. In an embodiment of the invention, the matrilin-2 polypeptide or active fragment thereof in the pharmaceutical composition is fused to an immunoglobulin, for example, a γ1 or γ4 or a monomeric variant thereof, e.g., selected from the group consisting of SEQ ID NOs: 5-9.

Additionally, the present invention provides a complex comprising PCSK9 bound to matrilin-2 or an active fragment thereof or a polypeptide comprising an EGF-A domain from a polypeptide selected from the group consisting of APOER2, VLDLR, SCUBE2, OIT3, SCUBE1, LRP1, LRP2, LRP4/LRP10, SCUBE3, LRP5, MEGF6/EGFL3, LRP6, LRP1B, PROS1, GAS6, TLL1, NID1, TLL2, EGF, fibrilin 1, fibrilin 2, fibrilin 3, LTBP3, laminin apha 4, stabilin 2, NOTCH2NL, cubilin, DNER, jagged 1, 5'-3' exoribonuclease 2, ZNF569 and FLJ36157.

The present invention also provides an isolated fusion polypeptide comprising a matrilin-2 polypeptide or an active-fragment thereof or a polypeptide comprising an EGF-A domain from a polypeptide selected from the group consisting of APOER2, VLDLR, SCUBE2, OIT3, SCUBE1, LRP1, LRP2, LRP4/LRP10, SCUBE3, LRP5, MEGF6/EGFL3, LRP6, LRP1B, PROS1, GAS6, TLL1, NID1, TLL2, EGF, fibrilin 1, fibrilin 2, fibrilin 3, LTBP3, laminin apha 4, stabilin 2, NOTCH2NL, cubilin, DNER, jagged 1, 5'-3' exoribonuclease 2, ZNF569 and FLJ36157; fused to an immunoglobulin (e.g., γ1 or γ4 or a monomeric variant thereof) wherein there is optionally a peptide linker between said polypeptide or fragment and said immunoglobulin. In an embodiment of the invention, the matrilin-2 polypeptide or active fragment thereof comprises the EGF-A domain of matrilin-2, e.g., wherein the EGF-A domain comprises the amino acid sequence set forth in SEQ ID NO: 1. In an embodiment of the invention, the matrilin-2 polypeptide or active fragment thereof comprises the mature fragment of matrilin-2, e.g., wherein the mature fragment comprises amino acid 24-956 of SEQ ID NO: 2. In an embodiment of the invention, the immunoglobulin comprises an amino acid sequence selected from the group consisting of SEQ ID NOs: 5-9.

| | |
|---|---|
| 1. Agarose gel control | 2. LDLR (Bait flow through) |
| 3. PCSK9 (Prey flow through) | 4. LDLR-PCSK9 (Bait-Prey) |
| 5. PCSK9 control | |

Figure 2:
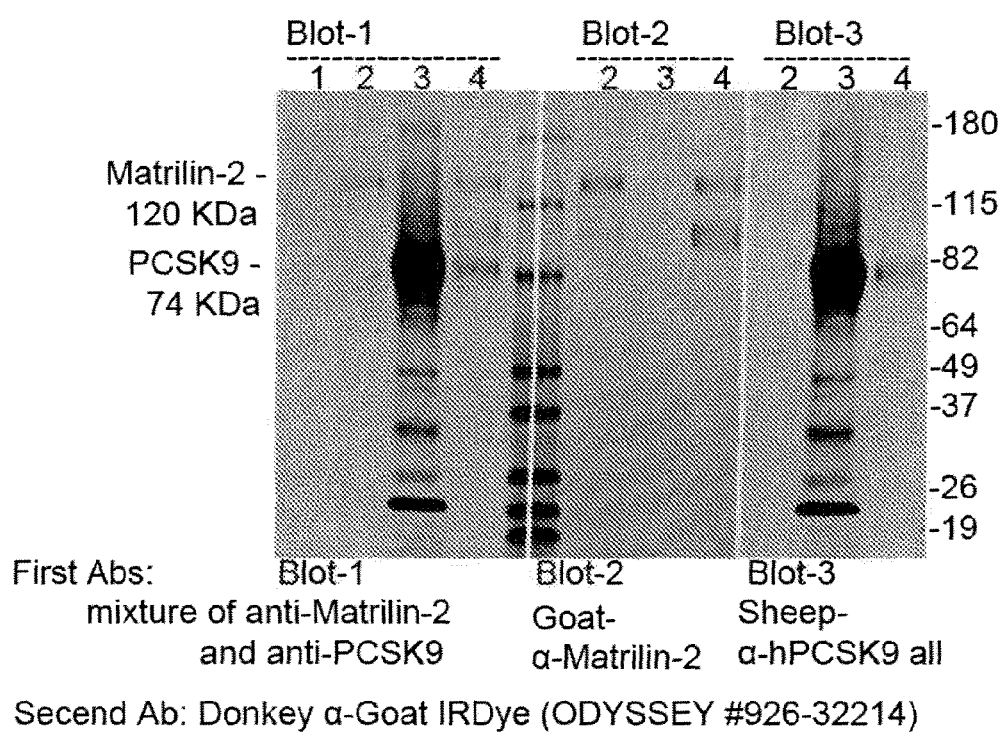

FIG. 2. Pull-Down PolyHis hMatrilin-2/hPCSK9 interaction Western Blot Samples. Samples in each numbered lane are summarized below.

| 1. Agarose gel control | 2. hMatrilin-2 (Bait flow through) |
|---|---|
| 3. hPCSK9 (Prey flow through) | 4. Matrilin-2-PCSK9 (Bait-Prey) |

DETAILED DESCRIPTION OF THE INVENTION

The present invention addresses the need in the art for PCSK9 inhibitors by providing matrilin-2 and active fragments thereof. A particularly surprising and unexpected result of the present application is definition of a previously unknown function of matrilin-2. Specifically, matrilin-2 polypeptide has been demonstrated to have the ability to associate with and inhibit PCSK9.

Inhibitors of PCSK9 binding to LDL receptor include any of the following polypeptides: matrilin-2, APOER2, VLDLR, SCUBE2, OIT3, SCUBE1, LRP1, LRP2, LRP4/LRP10, SCUBE3, LRP5, MEGF6/EGFL3, LRP6, LRP1B, PROS1, GAS6, TLL1, NID1, TLL2, EGF, fibrilin 1, fibrilin 2, fibrilin 3, LTBP3, laminin apha 4, stabilin 2, NOTCH2NL, cubilin, DNER, jagged 1, 5'-3' exoribonuclease 2, ZNF569 or FLJ36157 as well as active-fragments thereof or EGF-A domains contained in any of the foregoing. Such inhibitors also include any polypeptide comprising at least about 8, 10, 11, 12, 13, 14, 15, 16, 17, 18, 19, 20, 25, 50 or 100 contiguous amino acids from any of the foregoing polypeptides.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook, et al., 1989"); *DNA Cloning: A Practical Approach*, Volumes I and II (D. N. Glover ed. 1985); *Oligonucleotide Synthesis* (M. J. Gait ed. 1984); Nucleic Acid Hybridization (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" includes DNA and RNA, including single-stranded molecules, double-stranded molecules and others.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" includes a DNA that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

As used herein, the term "oligonucleotide" refers to a nucleic acid, generally of no more than about 100 nucleotides (e.g., 30, 40, 50, 60, 70, 80, or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, e.g., on a nucleic acid synthesizer.

A "protein sequence", "peptide sequence" or "polypeptide sequence" or "amino acid sequence" includes a series of two or more amino acids in a protein, peptide or polypeptide.

The terms "isolated polynucleotide" or "isolated polypeptide" include a polynucleotide (e.g., RNA or DNA molecule, or a mixed polymer) or a polypeptide, respectively, which are partially or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

"Amplification" of DNA as used herein includes the use of polymerase chain reaction (PCR) to increase the concentration of a particular DNA sequence within a mixture of DNA sequences. For a description of PCR see Saiki, et al., Science (1988) 239:487.

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein. Host cells include Chinese hamster ovary (CHO) cells, murine macrophage J774 cells or any other macrophage cell line and human intestinal epithelial Caco2 cells. For example, the BL21 *E. coli* host cell comprises the T7 expression system and includes the Ion and ompT proteases (see e.g., Studier, F. W. and Moffatt, B. A. (1986) J. Mol. Biol. 189, 113; Rosenberg, A. H., Lade, B. N., Chui, D., Lin, S., Dunn, J. J. and Studier, F. W. (1987) Gene 56, 125; Studier, F. W., Rosenberg, A. H., Dunn, J. J. and Dubendorff, J. W. (1990) Meth. Enzymol. 185, 60-89; Studier, F. W. (1991) J. Mol. Biol. 219, 37-44; Zhang, X. and Studier, F. W. (1997) J. Mol Biol. 269, 10-27; Derman, A. I., Prinz, W. A., Belin, D., and Beckwith, J. (1993) Science 262, 1744-1747; Wood, W. B. (1966) J. Mol. Biol. 16, 118-133; Leahy, D. J., Hendrickson, W. A., Aukhil, I., and Erickson, H. P. (1992) Science 258, 987-991; Phillips, T. A., Van Bogelen, R. A., and Neidhardt, F. C. (1984) J. Bacteriol. 159, 283-287; Prinz, W. A., Aslund, F., Holmgren, A., and Beckwith, J. (1997) J. Biol. Chem. 272, 15661-15667; Stewart, E. J., Aslund, F. and Beckwith, J. (1998) EMBO J. 17, 5543-5550; Bessette, P. H., Aslund, F., Beckwith, J. and Georgiou, G. (1999) Proc. Natl. Acad. Sci. 96, 13703-13708; Kane, J. F (1995) Curr. Opin. Biotechnol. 6, 494-500; Kurland, C. and Gallant, J. (1996) 7: 489-493; Brinkmann, U., Mattes, R. E. and Buckel, P. (1989) Gene 85, 109-114; Seidel, H. M., Pompliano, D. L. and Knowes, J. R. (1992) Biochemistry 31, 2598-2608; Rosenberg, A. H., Goldman, E., Dunn, J. J., Studier F. W. and Zubay, G. (1993) J. Bacteriol. 175, 716-722; or Del Tito, B. J., Ward, J. M.; Hodgson, J. (1995) J. Bacteriol. 177, 7086-7091; U.S. Pat. Nos. 4,952,496, 5,693,489 and 5,869,320; Davanloo, P., et al., (1984) Proc. Natl. Acad. Sci. USA 81: 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259.). BL21 (DE3) lacks the Ion and ompT proteases. BL21(DE3)pLysS lacks the Ion and ompT proteases and is resistant to 34 µg/ml chloramphenicol.

The nucleotide sequence of a nucleic acid may be determined by any method known in the art (e.g., chemical sequencing or enzymatic sequencing). "Chemical sequencing" of DNA includes methods such as that of Maxam and Gilbert (1977) (Proc. Natl. Acad. Sci. USA 74:560), in which DNA is randomly cleaved using individual base-specific reactions. "Enzymatic sequencing" of DNA includes methods such as that of Sanger (Sanger, et al., (1977) Proc. Natl. Acad. Sci. USA 74:5463).

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences when the sequences direct RNA polymerase mediated transcription of the coding sequence into RNA, e.g., mRNA, which then may be RNA spliced (if it contains introns) and, optionally, translated into a protein encoded by the coding sequence.

The terms "express" and "expression" include allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species.

The term "vector" includes a vehicle (e.g., a plasmid) by which a DNA or RNA sequence can be introduced into a host cell, so as to transform the host and, optionally, promote expression and/or replication of the introduced sequence. Plasmids are the most commonly used form of vector but all other forms of vectors which serve a similar function and which are, or become, known in the art are suitable for use herein. See, e.g., Pouwels, et al., *Cloning Vectors: A Laboratory Manual,* 1985 and Supplements, Elsevier, N. Y., and Rodriguez et al. (eds.), *Vectors: A Survey of Molecular Cloning Vectors and Their Uses,* 1988, Buttersworth, Boston, Mass.

The term "expression system" includes a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors. An example of an expression system is the T7 polymerase-based expression system discussed above regarding the BL21 host cells.

Expression of nucleic acids encoding the polypeptides of this invention can be carried out by conventional methods in either prokaryotic or eukaryotic cells. Although *E. coli* host cells are employed most frequently in prokaryotic systems, many other bacteria, such as various strains of *Pseudomonas* and *Bacillus*, are known in the art and can be used as well. Suitable host cells for expressing nucleic acids encoding the polypeptides include prokaryotes and higher eukaryotes. Prokaryotes include both gram-negative and gram-positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. A representative vector for amplifying DNA is pBR322 or many of its derivatives (e.g., pUC18 or 19). Vectors that can be used to express the polypeptides include, but are not limited to, those containing the lac promoter (pUC-series); trp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) *Vectors: A Survey of Molecular Cloning Vectors and Their Uses,* 1988, Buttersworth, Boston, pp. 205-236. Many polypeptides can be expressed, at high levels, in an *E. coli*/T7 expression system.

Higher eukaryotic tissue culture cells may also be used for the recombinant production of the polypeptides of the invention. Transformation or transfection and propagation of such cells have become a routine procedure. Examples of useful cell lines include HeLa cells, Chinese hamster ovary (CHO) cell lines, J774 cells, Caco2 cells, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also, usually, contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Examples of expression vectors include pET-based vectors, pDEST14, pCR®3.1, pCDNA1, pCD (Okayama, et al., (1985) Mol. Cell Biol. 5:1136), pMC1neo Poly-A (Thomas, et al., (1987) Cell 59:503), pREP8, pSVSPORT and derivatives thereof, and baculovirus vectors such as pAC373 or pAC610.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as *E. coli*. Accordingly, when glycosylation is desired, a polypeptide can be expressed in a glycosylating host, generally a eukaryotic cell. Insect cells often carry out post-translational glycosylations which are similar to those of mammalian cells. For this reason, insect cell expression systems have been developed to express, efficiently, mammalian proteins having native patterns of glycosylation. An insect cell which may be used in this invention is any cell derived from an organism of the class Insecta. Preferably, the insect is *Spodoptera fruigiperda* (Sf9 or Sf21) or *Trichoplusia ni* (High 5). Examples of insect expression systems that can be used with the present invention, for example to produce PCSK9 polypeptide, include Bac-To-Bac (Invitrogen Corporation, Carlsbad, Calif.) or Gateway (Invitrogen Corporation, Carlsbad, Calif.). If desired, deglycosylation enzymes can be used to remove carbohydrates attached during production in eukaryotic expression systems.

The present invention contemplates use of superficial or slight modifications to the amino acid or nucleotide sequences which correspond to the polypeptides of the invention.

In particular, the present invention contemplates sequence conservative variants of the nucleic acids which encode the polypeptides of the invention. "Sequence-conservative variants" of a polynucleotide sequence are those in which a change of one or more nucleotides in a given codon results in no alteration in the amino acid encoded at that position. Function-conservative variants of the polypeptides of the invention are also contemplated by the present invention. "Function-conservative variants" are those in which one or more amino acid residues in a protein or enzyme have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes use of polynucleotides encoding matrilin-2 and active fragments thereof as well as nucleic acids which hybridize to the polynucleotides. In an embodiment of the invention, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Stringency of southern blotting conditions can be altered by altering the conditions under which the blot is washed following hybridization. For example, for low stringency, wash the filter twice in 0.2× SSC, 0.1% SDS solution for 10 minutes each at about 25° C.; for moderate stringency, also wash the filter twice in pre-warmed (42° C.) 0.2× SSC, 0.1% SDS solution for 15 minutes each at 42° C.; for high stringency, in addition to the low and moderate stringency washes, also wash the filter twice in pre-warmed (68° C.) 0.1× SSC, 0.1% SDS solution for 15 minutes each at 68° C. for high-stringent wash. In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra).

Also included in the present invention are polypeptides comprising amino acid sequences which are at least about 70% identical or similar, preferably at least about 80% identical or similar, more preferably at least about 90% identical or similar and most preferably at least about 95% identical or similar (e.g., 95%, 96%, 97%, 98%, 99%, 100%) to the reference matrilin-2 nucleotide and amino acid sequences (e.g., any set forth herein) when the comparison is performed by a BLAST algorithm wherein the parameters of the algorithm are selected to give the largest match between the respective sequences over the entire length of the respective reference sequences. In addition to the sequence identities discussed herein, the polypeptides of the present invention may also be characterized in that they, for example, bind to PCSK9, inhibit PCSK9 binding to LDL receptor, and/or treat or ameliorate of any of the diseases or disorders discussed herein (e.g., hypercholesterolemia, hyperlipidemia, hypertriglyceridaemia, sitosterolemia, atherosclerosis, arteriosclerosis, coronary heart disease, vascular inflammation and xanthoma).

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M., et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, N.Y.

Matrilin-2

The present invention includes compositions and methods comprising matrilin-2 and active fragments thereof from any species, for example, human. For example, in an embodiment of the invention, the active fragment of matrilin is the EGF-A domain of matrilin-2. In an embodiment of the invention, matrilin-2 EGF-A domain comprises the amino acid sequence:

```
NYCALNKPGCEHECVNMEESYYC        (SEQ ID NO: 1)
```

In an embodiment of the invention, human matrilin-2 precursor (isoform a) comprises the amino acid sequence set forth below wherein amino acids 24-956 comprise a mature human matrilin-2 fragment:

```
MEKMLAGCFLLILGQIVLLPAEARERSRGRSISRGRHARTHPQTALLES

SCENKRADLVFIIDSSRSVNTHDYAKVKEFIVDILQFLDIGPDVTRVGL

LQYGSTVKNEFSLKTFKRKSEVERAVKRMRHLSTGTMTGLAIQYALNIA

FSEAEGARPLRENVPRVIMIVTDGRPQDSVAEVAAKARDTGILIFAIGV

GQVDFNTLKSIGSEPHEDHVFLVANFSQIETLTSVFQKKLCTAHMCSTL

EHNCAHFCINIPGSYVCRCKQGYILNSDQTTCRIQDLCAMEDHNCEQLC

VNVPGSFVCQCYSGYALAEDGKRCVAVDYCASENHGCEHECVNADGSYL

CQCHEGFALNPDKKTCTKIDYCASSNHGCQHECVNTDDSYSCHCLKGFT

LNPDKKTCRRINYCALNKPGCEHECVNMEESYYCRCHRGYTLDPNGKTC

SRVDHCAQQDHGCEQLCLNTEDSFVCQCSEGFLINEDLKTCSRVDYCLL

SDHGCEYSCVNMDRSFACQCPEGHVLRSDGKTCAKLDSCALGDHGCEHS

CVSSEDSFVCQCFEGYILREDGKTCRRKDVCQAIDHGCEHICVNSDDSY

TCECLEGFRLAEDGKRCRRKDVCKSTHHGCEHICVNNGNSYICKCSEGF

VLAEDGRRCKKCTEGPIDLVEVIDGSKSLGEENFEVVKQFVTGIIDSLT

ISPKAARVGLLQYSTQVHTEFTLRNFNSAKDMKKAVAHMKYMGKGSMTG

LALKHMFERSFTQGEGARPLSTRVPRAAIVETDGRAQDDVSEWASKAKA

NGITMYAVGVGKAIEEELQEIASEPTNKHLFYAEDESTMDEISEKLKKG

ICEALEDSDGRQDSPAGELPKTVQQPTESEPVTINIQDLLSCSNFAVQH

RYLFEEDNLLRSTQKLSHSTKPSGSPLEEKHDQCKCENLIMFQNLANEE

VRKLTQRLEEMTQRMEALENRLRYR
(SEQ ID NO: 2; human matrilin-2 EGF-A domain
underscored; signal peptide italicized).
See also Genbank accession no. NP_002371.
```

In an embodiment of the invention, human matrilin-2 precursor (isoform b) comprises the amino acid sequence set forth below wherein amino acids 24-956 comprise a mature human matrilin-2 fragment:

```
MEKNILAGCFLLILGQIVLLPAEARERSRGRSISRGRHARTHPQTALLE

SSCENKRADLVFIIDSSRSVNTHDYAKVKEFIVDILQFLDIGPDVTRVG

LLQYGSTVKNEFSLKTFKRKSEVERAVKRMRHLSTGTMTGLAIQYALNI

AFSEAEGARPLRENVPRVIMIVTDGRPQDSVAEVAAKARDTGILIFAIG

VGQVDENTLKSIGSEPHEDHVELVANFSQIETLTSVFQKKLCTAHMCST

LEHNCAHFCINIPGSYVCRCKQGYILNSDQTTCRIQDLCAMEDHNCEQL

CVNVPGSFVCQCYSGYALAEDGKRCVAVDYCASENHGCEHECVNADGSY

LCQCHEGFALNPDKKTCTKIDYCASSNHGCQHECVNTDDSYSCHCLKGF

TLNPDKKTCRRINYCALNKPGCEHECVNMEESYYCRCHRGYTLDPNGKT

CSRVDHCAQQDHGCEQLCLNTEDSFVCQCSEGFLINEDLKTCSRVDYCL

LSDHGCEYSCVNMDRSFACQCPEGHVLRSDGKTCAKLDSCALGDHGCEH

SCVSSEDSFVCQCFEGYILREDGKTCRRKDVCQAIDHGCEHICVNSDDS

YTCECLEGFRLAEDGKRCRRKDVCKSTHHGCEHICVNNGNSYICKCSEG

FVLAEDGRRCKKCTEGPIDLVFVIDGSKSLGEENFEVVKQFVTGIIDSL

TISPKAARVGLLQYSTQVHTEFTLRNFNSAKDMKKAVAHMKYMGKGSMT

GLALKHMFERSFTQGEGARPLSTRVPRAAIVFTDGRAQDDVSEWASKAK

ANGITMYAVGVGKAIEEELQEIASEPTNKHLFYAEDFSTMDEISEKLKK

GICEALEDSDGRQDSPAGELPKTVQQPTVQHRYLFEEDNLLRSTQKLSH

STKPSGSPLEEKHDQCKCENLIMFQNLANEEVRKLTQRLEEMTQRMEAL

ENRLRYR
(SEQ ID NO: 15; human matrilin-2 EGF-A domain
underscored; signal peptide italicized)
See also Genbank accession nos. NP_002371.3
(isoform a) and NP_085072.2 (isoform b)
```

In an embodiment of the invention, mouse matrilin-2 precursor comprises the following amino acid sequence:

```
MEKMLVGCLL MLGQLFLVLP VDGRERPQAR FPSRGRHVRM

YPQTALLESS CENKRADLVF IIDSSRSVNT YDYAKVKEFI

LDILQFLDIG PDVTRVGLLQ YGSTVKNEFS LKTFKRKSEV

ERAVKRMRHL STGTMTGLAI QYALNIAFSE AEGARPLREN

VPRIIMIVTD GRPQDSVAEV AAKARNTGIL IFAIGVGQVD

LNTLKAIGSE PHKDHVFLVA NFSQIESLTS VFQNKLCTVH

MCSVLEHNCA HFCLNTPGSY ICKCKQGYIL STDQKTCRIQ

DLCATEDHGC EQLCVNMLGS FVCQCYSGYT LAEDGKRCTA

VDYCASENHG CEHECVNAES SYLCRCHEGF ALNSDKKTCS

KIDYCASSNH GCQHECVNAQ TSALCRCLKG FMLNPDRKTC

RRINYCALNK PGCEHECVNT EEGHYCRCRQ GYNLDPNGKT

CSRVDHCAQQ DHGCEQLCLN TEESFVCQCS EGFLINDDLK

TCSRADYCLL SNHGCEYSCV NTDKSFACQC PEGHVLRSDG

KTCAKLDSCA LGDHGCEHSC VSSEDSFVCQ CFEGYILRDD

GKTCRRKDVC QDVNHGCEHL CVNSGESYVC KCLEGFRLAE

DGKRCRRKNV CKSTQHGCEH MCVNNGNSYL CRCSEGFVLA

EDGKHCKRCT EGPIDLVFVI DGSKSLGEEN FETVKHFVTG

IIDSLAVSPK AARVGLLQYS TQVRTEFTLR GFSSAKEMKK

AVTHMKYMGK GSMTGLALKH MFERSFTQVE GARPPSTQVP

RVAIVFTDGR AQDDVSEWAS KAKANGITMY AVGVGKAIEE

ELQEIASEPI DKHLFYAEDF STMGEISEKL KEGICEALED

SGGRQDSAAW DLPQQAHQPT VQHRFLFEED NLSRSTQKLF

HSTKSSGNPL EESQDQCKCE NLILFQNVAN EEVRKLTQRL

EEMTQRMEAL ENRLKYR
(SEQ ID NO: 3; mouse matrilin-2 EGF-A
domain underscored). See also Genbank
accession no. AAH92298.1 and AAM11539.1
and AAC53163 and AAH05429.1 and EDL08853.1.
```

In an embodiment of the invention, mouse matrilin-2 EGF-A domain comprises the amino acid sequence: NYCALNKPGCEHECVNTEEGHYC (SEQ ID NO: 4) The present invention includes pharmaceutical compositions including matrilin-2 polypeptide in a multimer, for example, matrilin-2 homodimers, as well as heterodimers and heterotrimers including other matrilin polypeptides, for example, matrilin-2/matrilin-1/matrilin-2; matrilin-1/matrilin-2/matrilin-1; matrilin-1/matrilin-2/matrilin-4; matrilin-2/matrilin-4/matrilin-2; or matrilin-4/matrilin-2/matrilin-4.

The matrilin-2 polypeptides and active-fragments thereof of the invention are, in an embodiment of the invention, conjugated to a chemical moiety. The chemical moiety may be, inter alia, a polymer. In an embodiment of the invention, the chemical moiety is a polymer which increases the half-life of the polypeptide or fragment in the body of a subject to whom it is administered. Polymers include, but are not limited to, polyethylene glycol (PEG) (e.g., PEG with a molecular weight of 2 kDa, 5 kDa, 10 kDa, 12kDa, 20 kDa, 30 kDa or 40 kDa), dextran and monomethoxypolyethylene glycol (mPEG).

The present invention also includes fusions comprising a matrilin-2 polypeptide or active fragment thereof. For example, embodiments of the invention include those wherein the polypeptide or fragment is fused to another N-terminal and/or C-terminal matrilin-2 precursor residue (e.g., 1, 2, 3, 4, 5, 6, 7, 8, 9 or 10 residues). The present invention also includes those wherein the matrilin-2 polypeptide or fragment is fused to a heterologous polypeptide which is not identical to that of the native matrilin-2 precursor. For example, such heterologous polypeptides include GST (glutathione-S-transferase), His$_6$, myc, haemagglutinin (YPYDVPDYA; SEQ ID NO: 49) or cellulose binding protein (CBP).

The present invention further comprises any matrilin-2 polypeptide or active-fragment thereof fused to an immunoglobulin (Ig) such as IgG1, IgG2, IgG3 or IgG4 or a fragment or mutant thereof. In an embodiment of the invention, the matrilin-2 polypeptide is tethered to the Ig by a linker of any reasonable size, such as 2, 3, 4, 5, 6, 7, 8, 9, or 10 residues. For example, in an embodiment of the invention, the linker is Gly-Ser. In an embodiment of the invention, a mature polypeptide sequence of mouse immunoglobulin heavy chain constant region (hinge to CH3 only), isotype γ1 comprises the amino acid sequence:

```
                                       (SEQ ID NO: 5)
VPRDCGCKPCICTVPEVSSVFIFPPKPKDVLTITLTPKVTCVVVDISK

DDPEVQFSWFVDDVEVHTAQTKPREEQFNSTFRSVSELPIMHQDWLNG

KEFKCRVNSAAFPAPIEKTISKTKGRPKAPQVYTIPPPKEQMAKDKVS

LTCMITDFFPEDITVEWQWNGQPAENYKNTQPIMDTDGSYFVYSKLNV

QKSNWEAGNTFTCSVLHEGLHNHHTEKSLSHSPGK
```

In an embodiment of the invention, a mature polypeptide sequence of human immunoglobulin heavy chain constant region (hinge to CH3 only), isotype γ4 comprises the amino acid sequence:

```
                                       (SEQ ID NO: 6)
ESKYGPPCPSCPAPEFLGGPSVFLFPPKPKDTLMISRTPEVTCVVVDV

SQEDPEVQFNWYVDGVEVHNAKTKPREEQFNSTYRVVSVLTVLHQDWL

NGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRL

TVDKSRWQEGNVFSCSVMHEALHNHYTQKSLSLSLGK
```

In an embodiment of the invention, a mature polypeptide sequence of human immunoglobulin heavy chain constant region (hinge to CH3 only), isotype γ4 monomeric variant (C to S mutations in the hinge underscored) comprises the amino acid sequence:

```
                                       (SEQ ID NO: 7)
ESKYGPPSPSSPAPEFLGGPSVELFPPKPKDTLMISRTPEVTCVVVDV

SQEDPEVQFNWYVDGVEVHNAKTKPREEQFNSTYRVVSVLTVLHQDWL

NGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRL

TVDKSRWQEGNVFSCSVMHEALHNHYTQKSLSLSLGK
```

In an embodiment of the invention, a mature polypeptide sequence of human immunoglobulin heavy chain constant region (hinge to CH3 only), isotype γ1 comprises the amino acid sequence:

```
                                              (SEQ ID NO: 8)
VEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFL

YSKLTVDKSRWQQGNVFSCSVMHEALHNHYTQKSLSLSPGK
```

In an embodiment of the invention, a mature polypeptide sequence of human immunoglobulin heavy chain constant region (hinge to CH3 only), isotype γ1 monomeric variant (C to S mutations in the hinge underscored)

```
                                              (SEQ ID NO: 9)
VEPKSSDKTHTSPPSPAPELLGGPSVFLFPPKPKDTLMISRTPEVTCV

VVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFL

YSKLTVDKSRWQQGNVFSCSVMHEALHNHYTQKSLSLSPGK
```

The term "active fragment" of a matrilin-2 polypeptide includes, e.g., any fragment of matrilin which maintains an activity of matrilin-2 to any detectable degree (e.g., 1%, 10%, 20%, 50%, 75%, 80%, 90%, 95%, 99%), for example, binding to PCSK9, inhibition of PCSK9 binding to LDL receptor, and/or treatment or amelioration of any of the diseases or disorders discussed herein (e.g., hypercholesterolemia, hyperlipidemia, hypertriglyceridaemia, sitosterolemia, atherosclerosis, arteriosclerosis, coronary heart disease, vascular inflammation and xanthoma).

PCSK9

The present invention includes compositions and methods comprising matrilin-2 and active fragments thereof which bind specifically to PCSK9, for example, human PCSK9. PCSK9 includes human PCSK9 and homologues thereof, e.g.,

```
HUMAN gi|31317307|ref|NP_777596.2|
proprotein convertase subtilisin/kexin type 9
preproprotein [Homo sapiens]
                                             (SEQ ID NO: 10)
MGTVSSERSWWPLPLLLLLLLLGPAGARAQEDEDGDYEELVLALRSE

EDGLAEAPEHGTTATEHRCAKDPWRLPGTYVVVLKEETHLSQSERTAR

RLQAQAARRGYLTKILHVFHGLLPGFLVKMSGDLLELALKLPHVDYIE

EDSSVFAQSIPWNLERITPPRYRADEYQPPDGGSLVEVYLLDTSIQSD

HREIEGRVMVTDFENVPEEDGTRFHRQASKCDSHGTHLAGVVSGRDAG

VAKGASMRSLRVLNCQGKGTVSGTLIGLEFIRKSQLVQPVGPLVVLLP

LAGGYSRVLNAACQRLARAGVVLVTAAGNFRDDACLYSPASAPEVITV

GATNAQDQPVTLGTLGTNFGRCVDLFAPGEDIIGASSDCSTCFVSQSG

TSQAAAHVAGIAAMMLSAEPELTLAELRQRLIHFSAKDVINEAWFPED

QRVLTPNLVAALPPSTHGAGWQLFCRTVWSAHSGPTRMATAVARCAPD

EELLSCSSFSRSGKRRGERMEAQGGKLVCRAHNAFGGEGVYAIARCCL

LPQANCSVHTAPPAEASMGTRVHCHQQGHVLTGCSSHWEVEDLGTHKP

PVLRPRGQPNQCVGHREASIHASCCHAPGLECKVKEHGIPAPQEQVTV

ACEEGWTLTGCSALPGTSHVLGAYAVDNTCVVRSRDVSTTGSTSEGAV

TAVAICCRSRHLAQASQELQ

CHIMP gi|114556790|ref|XP_001154126.1|
proprotein convertase subtilisin/kexin
type 9 [Pan troglodytes]
                                             (SEQ ID NO: 11)
MGTVSSRRSWWPLPLLLLLLLLLGPAGARAQEDEDGLAEAPEHGTTAT

FHRCAKDPWRLPGTYVVVLKEETHLSQSERTARRLQAQAARRGYLTKI

LHVFHGLLPGFLVKMSGDLLELALKLPHVDYIEEDSSVFAQSIPWNLE

RITPPRYRADEYQPPDGGSLVEVYLLDTSIQSDHREIEGRVMVTDFEN

VPEEDGTRFHRQASKCDSHGTHLAGVVSGRDAGVAKGASMRSLRVLNC

QGKGTVSGTLIGLEFIRKSQLVQPVGPLVVLLPLAGGYSRVLNAACQR

LARAGVVLVTAAGNFRDDACLYSPASAPEVITVGATNAQDQPVTLGTL

GTNFGRCVDLFAPGEDIIGASSDCSTCFVSQSGTSQAAAHVAGIAAMM

LSAEPELTLAELRQRLIHFSAKDVINEAWFPEDQRVLTPNLVAALPPS

THGAGWQLFCRTVWSAHSGPTRMATAVARCAPDEELLSCSSFSRSGKR

RGERMEAQGGKLVCRAHNAFGGEGVYAIARCCLLPQANCSIHTAPPAE

AGMGTRVHCHQQGHVLTGCSSHWEVEDLGTHKPPMLRPRGQPNQCVGH

REASIHASCCRAPGLECKVKEHGIPAPQEQVTVACEEGWTLTGCSALP

GTSHVLGAYAVDNTCVVRSRDVSTAGSTSEEAVAAVAICCRSRHLAQA

SQELQ

MOUSE gi|23956352|ref|NP_705793.1| proprotein
convertase subtilisin/kexin type 9
[Mus musculus]
                                             (SEQ ID NO: 12)
MGTHCSAWLRWPLLPLLPPLLLLLLLLCPTGAGAQDEDGDYEELMLAL

PSQEDGLADEAAHVATATFRRCSKEAWRLPGTYIVVLMEETQRLQIEQ

TAHRLQTRAARRGYVIKVLHIFYDLFPGFLVKMSSDLLGLALKLPHVE

YIEEDSFVFAQSIPWNLERIIPAWHQTEEDRSPDGSSQVEVYLLDTSI

QGAHREIEGRVTITDFNSVPEEDGTRFHRQASKCDSHGTHLAGVVSGR

DAGVAKGTSLHSLRVLNCQGKGTVSGTLIGLEFIRKSQLIQPSGPLVV

LLPLAGGYSRILNAACRHLARTGVVLVAAAGNFRDDACLYSPASAPEV

ITVGATNAQDQPVTLGTLGTNFGRCVDLFAPGKDIIGASSDCSTCFMS

QSGTSQAAAHVAGIVARMLSREPTLTLAELRQRLIHFSTKDVINMAWF

PEDQQVLTPNLVATLPPSTHETGGQLLCRTVWSAHSGPTRTATATARC

APEEELLSCSSFSRSGRRRGDWIEAIGGQQVCKALNAFGGEGVYAVAR

CCLVPRANCSIHNTPAARAGLETHVHCHQKDHVLTGCSFHWEVEDLSV

RRQPALRSRRQPGQCVGHQAASVYASCCHAPGLECKIKEHGISGPSEQ

VTVACEAGWTLTGCNVLPGASLTLGAYSVDNLCVARVHDTARADRTSG

EATVAAAICCRSRPSAKASWVQ

RAT gi|77020250|ref|NP_954862.2|proprotein
convertase subtilisin/kexin type 9
[Rattus norvegicus]
                                             (SEQ ID NO: 13)
MGIRCSTWLRWPLSPQLLLLLLLLCPTGSRAQDEDGDYEELMLALPSQE

DSLVDEASHVATATFRRCSKEAWRLPGTYVVVLMEETQRLQVEQTAHR
```

-continued

LQTWAARRGYVIKVLHVFYDLFPGFLVKMSSDLLGLALKLPHVEYIEE

DSLVFAQSIPWNLERIIPAWQQTEEDSSPDGSSQVEVYLLDTSIQSGH

REIEGRVTITDFNSVPEEDGTRFHRQASKCDSHGTHLAGVVSGRDAGV

AKGTSLHSLRVLNCQGKGTVSGTLIGLEFIRKSQLIQPSGPLVVLLPL

AGGYSRILNTACQRLARTGVVLVAAAGNFRDDACLYSPASAPEVITVG

ATNAQDQPVTLGTLGTNFGRCVDLEAPGKDIIGASSDCSTCYMSQSGT

SQAAAHVAGIVAMMLNRDPALTLAELRQRLILFSTKDVINMAWFPEDQ

RVLTPNRVATLPPSTQETGGQLLCRTVWSAHSGPTRTATATARCAPEE

ELLSCSSFSRSGRRRGDRIEAIGGQQVCKALNAFGGEGVYAVARCCLL

PRVNCSIHNTPAARAGPQTPVHCHQKDHVLTGCSFHWEVENLRAQQQP

LLRSRHQPGQCVGHQEASVHASCCHAPGLECKIKEHGIAGPAEQVTVA

CEAGWTLTGCNVLPGASLPLGAYSVDNVCVARIRDAGRADRTSEEATV

AAAICCRSRPSAKASWVHQ

The present invention also includes embodiments comprising PCSK9 (e.g., isolated PCSK9) or an active-fragment thereof (e.g., that retains some biological activity of PCSK9 such as LDLR binding or matrilin-2 binding) bound to matrilin-2 or an active fragment thereof (e.g., isolated matrilin-2). The present invention includes, e.g., isolated PCSK9 bound to isolated matrilin-2 or isolated matrilin-2 or an active-fragment thereof bound to PCSK9 in vivo, e.g., in the body of a patient. Such complexes may be generated, for example, by contacting said PCSK9 and said matrilin-2.

Therapeutic Methods, Administration and Pharmaceutical Formulations

The present invention provides methods and compositions for treating or preventing disorders of cholesterol or lipid homeostasis and disorders associated therewith, e.g., hypercholesterolemia, hyperlipidemia, hypertriglyceridaemia, sitosterolemia, atherosclerosis, arteriosclerosis, coronary heart disease, vascular inflammation and xanthoma by administering a therapeutically effective amount of a matrilin-2 polypeptide or active-fragment thereof. The term hypercholesterolemia includes, e.g., familial and non-familial hypercholesterolemia. Familial hypercholesterolemia (FHC) is an autosomal dominant disorder characterized by elevation of serum cholesterol bound to low density lipoprotein (LDL). Familial hypercholesterolemia includes both heterozygous FHC and homozygous FHC.

Hyperlipidemia is an elevation of lipids in the bloodstream. These lipids include cholesterol, cholesterol esters, phospholipids and triglycerides. Hyperlipidemia includes for example, type I, IIa, IIb, III, IV and V.

Sitosterolemia is a rare inherited plant sterol storage disease. In general, the metabolic defect in the affected patient causes hyperabsorption of sitosterol from the gastrointestinal tract, decreased hepatic secretion of sitosterol with subsequent decreased elimination, and altered cholesterol synthesis.

Atherosclerosis includes hardening of arteries associated with deposition of fatty substances, cholesterol, cellular waste products, calcium and fibrin in the inner lining of an artery. The buildup that results is called plaque.

Arteriosclerosis includes the diffuse build-up and deposition of calcium in artery walls which leads to hardening.

The present invention also provides methods for improving blood cholesterol markers associated with increased risk of heart disease. These markers include high total cholesterol, high LDL, high total cholesterol to HDL ratio and high LDL to HDL ratio.

In general, a total cholesterol of less than 200 mg/dL is considered desirable, 200-239 mg/dL is considered borderline high and 240 mg/dL and above is considered high.

In general, a blood LDL level of less than 100 mg/dL is considered optimal; 100-129 mg/dL is considered near optimal/above optimal, 130-159 mg/dL is considered borderline high, 160-189 mg/dL is considered high and 190 mg/dL and above is considered very high.

In general, HDL levels considered normal are at least 35-40 mg/dL.

Another indicator of heart disease risk is the ratio of total cholesterol to HDL. In general, a very low risk of heart disease correlates with a ratio of <3.4 (men) or <3.3 (women); a low risk is associated with a ratio of 4.0 (men) or 3.8 (women), an average risk is associated with a ratio of 5.0 (men) or 4.5 (women), a moderate risk is associated with a ratio of 9.5 (men) or 7.0 (women) and a high risk is associated with a ratio of >23 (men) or >11 (women).

A further indicator of heart disease risk is the ratio of LDL to HDL. In general, a very low risk is associated with a ratio of 1 (men) or 1.5 (women), an average risk is associated with a ratio of 3.6 (men) or 3.2 (women), a moderate risk is associated with a ratio of 6.3 (men) or 5.0 (women) and a high risk is associated with a ratio of 8 (men) or 6.1 (women).

In an embodiment of the invention, matrilin-2 polypeptides and active-fragments thereof are formulated into a pharmaceutical formulation which comprises a pharmaceutically acceptable carrier. Such pharmaceutical compositions are within the scope of the present invention. For general information concerning formulations, see, e.g., Gilman, et al., (eds.) (1990), *The Pharmacological Bases of Therapeutics*, 8th Ed., Pergamon Press; A. Gennaro (ed.), *Remington's Pharmaceutical Sciences*, 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York, Kenneth A. Walters (ed.) (2002) *Dermatological and Transdermal Formulations* (*Drugs and the Pharmaceutical Sciences*), Vol 119, Marcel Dekker.

The matrilin-2 polypeptides and active-fragments thereof of the present invention can be formulated according to known methods to prepare pharmaceutically useful compositions, whereby the polypeptide or fragment is combined in admixture with a pharmaceutically acceptable carrier. Carriers, excipients or stabilizers are nontoxic to recipients at the dosages and concentrations employed, and include buffers such as phosphate, citrate and other organic acids; antioxidants including ascorbic acid; low molecular weight polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or PEG. The formulations to be used for in vivo administration, in general, must be sterile. This is readily accomplished by filtration through sterile filtration membranes, e.g., prior to or following lyophilization and reconstitution. Therapeutic or pharmaceutical compositions or formulations herein generally are placed into a container having a sterile access port, for example, an intravenous solution bag or vial having a stopper pierceable by a hypodermic injection needle.

The route of administration of the polypeptides and fragments of the invention are, in an embodiment of the invention, by a parenteral route (e.g., intravenous, subcutaneous, intraarterial, intratumoral, intramuscular, intraperitoneal).

Dosages and desired concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42 96.

When used to treat a disorder in a subject (e.g., as discussed herein), a therapeutically effective dosage or amount of matrilin-2 polypeptides and active-fragments thereof is administered to the subject. In an embodiment of the invention, a therapeutically effective dosage is a dosage sufficient to decrease total serum cholesterol, decrease blood LDL levels or increase blood HDL levels to any degree whatsoever. In an embodiment of the invention, a therapeutically effective dosage for treatment of hypercholesterolemia, hyperlipidemia, hypertriglyceridaemia, sitosterolemia, atherosclerosis, arteriosclerosis, coronary heart disease, vascular inflammation or xanthoma or for treatment of any blood marker of heart disease risk (e.g., as discussed herein) is about 0.1 mpk (mg per kilogram of body weight) to about 10 mpk (e.g., 0.25, 0.5, 0.75 1, 2, 3, 4, 5, 6, 7, 8, 9, 10 mpk) once a day, every 2 days, every 4 days or every 5 days or once a week.

When possible, administration and dosage of an agent (e.g., further therapeutic agents discussed herein) is done according to the schedule listed in the product information sheet of the agents, in the Physicians' Desk Reference 2003 (Physicians' Desk Reference, 57th Ed); Medical Economics Company; ISBN: 1563634457; 57th edition (November 2002), as well as therapeutic protocols well known in the art.

A physician or clinician may monitor critical blood markers such as cholesterol, HDL or LDL levels in a subject being treated or about to be treated with matrilin-2 polypeptides and active-fragments and make adjustments to the subject's treatment regimen as needed to reach a positive medical outcome.

The term "subject" or "patient" or the like refers to mammals (e.g., mice, rats, primates, monkeys, cats, dogs, rabbits), for example, humans.

Further Chemotherapeutic Agents

The present invention provides compositions including matrilin-2 or an active fragment thereof in association with any additional chemotherapeutic agent. In an embodiment of the invention, the further chemotherapeutic agent is another PCSK9 inhibitor, a cardiovascular agent, an adrenergic blocker, an antihypertensive agent, an angiotensin system inhibitor, an angiotensin-converting enzyme (ACE) inhibitor, a coronary vasodilator, a diuretic or an adrenergic stimulant. In an embodiment of the invention, the further therapeutic agent is a cholesterol lowering medication such as an HMG-CoA reductase inhibitor. Compositions comprising such matrilin-2 polypeptides and active-fragments thereof in association with a further chemotherapeutic agent are within the scope of the present invention as are methods of use of such compositions, e.g., as discussed herein.

PCSK9 inhibitors include for example, antibodies that bind specifically to PCSK9 and inhibit binding and or destruction of LDL receptors. Other PCSK9 inhibitors include, for example, an EGF-A domain of the LDL receptor that binds to PCSK9 and inhibits binding and/or destruction of LDL receptors.

Cardiovascular agents which form part of the present invention include those for treatment or prevention of lipid and/or cholesterol disorders or hypertension and other cardiovascular disorders and diseases. Disorders of lipid or cholesterol metabolism may be caused or aggravated by hypertension. Hypertension is defined as persistently high blood pressure. Generally, adults are classified as being hypertensive when systolic blood pressure is persistently above 140 mmHg or when diastolic blood pressure is above 90 mmHg. Long-term risks for cardiovascular mortality increase in a direct relationship with persistent blood pressure. Examples of antihypertensive agents which may be used in the present invention include e.g., calcium channel blockers, angiotensin-converting enzyme (ACE) inhibitors, angiotensin-II receptor antagonists, diuretics, adrenergic blockers including beta-adrenergic receptor blockers and alpha-adrenergic receptor blockers, diuretics, Other cardiac drugs that may be provided in association with a polypeptide or fragment of the present invention includes anti-anginal agents, such as adrenergic stimulants or coronary vasodilators and HMG-CoA reductase inhibitors.

HMG-CoA reductase inhibitors inhibit the HMG-CoA reductase enzyme and, thus, reduce production of cholesterol in the body of a subject. HMG-CoA reductase inhibitors include, e.g., lovastatin, atorvastatin, pravastatin, rosuvastatin, fluvastatin, rivastatin and simvastatin.

Adrenergic blockers include those compounds which are β-receptor inhibitors and/or α-receptor inhibitors. Adrenergic blockers which are β-receptor inhibitors include a class of drugs that antagonize the cardiovascular effects of catecholamines in hypertension, angina pectoris, and cardiac arrhythmias. β-adrenergic receptor blockers include, but are not limited to, bunolol hydrochloride (1(2H)-Naphthalenone, 5-[3-(1,1-dimethylethyl)amino]-2-hydroxypropoxy]-3,4-dihydro-, hydrochloride, CAS RN 31969-05-8 which can be obtained from Parke-Davis); acebutolol (±N-[3-Acetyl-4-[2-hydroxy-3-[(1 methylethyl)amino]propoxy]phenyl]-butanamide, or (±)-3'-Acetyl-4'-[2-hydroxy-3-(isopropylamino) propoxy]butyranilide); acebutolol hydrochloride (such as N-[3-acetyl-4-[2-hydroxy-3-[1-methyl-ethyle)amino]propoxy]phenyl]-, monohydrocochloride, (±)-3'-Acetyl-4'-[2-hydroxy-3-(isopropylamino)propoxy]butyranilide monohydrochloride, for example, SECTRAL® Capsules available from Wyeth-Ayerst); alprenolol hydrochloride (2-Propanol, 1-[(1-methylethyl)amino]-3-[2-(2-propenyl)phenoxy]-, hydrochloride, CAS RN 13707-88-5 see Netherlands Patent Application No. 6,605,692); atenolol (such as benzeneacetamide 4-[2'-hydroxy-3'-[(1-methylethyl)amino]propoxy]-, for example, TENORMIN® I.V. Injection available from AstraZeneca); carteolol hydrochloride (such as 5-[3-[(1,1-dimethylethyl)amino]-2-hydroxypropoxy]-3,4-dihydro-2(1H)-quinolinone monohydrochloride, for example, Cartrol® Filmtab® Tablets available from Abbott); Celiprolol hydrochloride (3-[3-Acetyl-4-[3-(tert-butylamino)-2-hydroxypropoxyl]phenyl]-1,1-diethylurea monohydrochloride, CAS RN 57470-78-7, also see in U.S. Pat. No. 4,034,009); cetamolol hydrochloride (Acetamide, 2-[2-[3-[(1,1-dimethylethyl) amino]-2-hydroxypropoxy]-phenoxy]-N-methyl-, monohydrochloride, CAS RN 77590-95-5, see also U.S. Pat. No. 4,059,622); labetalol hydrochloride (such as 5-[1-hydroxy-2-[(1-methyl-3-phenylpropyl) amino]ethyl]salicylamide monohydrochloride, for example, NORMODYNE® Tablets available from Schering; esmolol hydrochloride ((±)-Methyl p-[2-hydroxy-3-(isopropylamino) propoxy]hydrocinnamate hydrochloride, for example, BREVIBLOC® Injection available from Baxter); levobetaxolol hydrochloride (such as (S)-1-[p-[2-(cyclopropylmethoxy)ethyl]phenoxy]-3-(isopropylamino)-2-propanol hydrochloride, for example, BETAXON™ Ophthalmic Suspension available from Alcon); levobunolol hydrochloride (such as (−)-5-[3-(tert-Butylamino)-2-hydroxypropoxy]-3,4-dihydro-1(2H)-naphthalenone hydrochloride, for example, BETAGAN® Liquifilm® with C CAP® Compliance Cap available from Allergan); nadolol (such as 1-(tert-butylamino)-3-[(5,6,7,8-tetrahydro-cis-6,7-dihydroxy-1-naphthyl)oxy]-2-propanol, for example, Nadolol Tablets available from Mylan); practolol (Acetamide, N-[4-[2-hydroxy-3-[1-methylethyl) amino]-propoxy]phenyl]-, CAS RN 6673-35-4, see also U.S. Pat. No. 3,408,387); propranolol hydrochloride (1-(Isopropylamino)-3-(1-naphthyloxy)-2-propanol hydrochloride CAS RN 318-98-9); sotalol hydrochloride (such as d,l-N-[4-[1-hydroxy-2-[(1-methylethyl)amino]ethyl]-phenyl]methane-sulfonamide monohydrochloride, for example, BETA-PACE AF™ Tablets available from Berlex); timolol (2-Propanol, 1-[(1,1-dimethylethyl)amino]-3-[[4-4(4-morpholinyl)-1,2,5-thiadiazol-3-yl]oxy]-,hemihydrate, (S)—, CAS RN 91524-16-2); timolol maleate (S)-1-[(1,1-dimethylethyl) amino]-3-[[4-(4-morpholinyl)-1,2,5-thiadiazol-3-yl]oxy]-2-propanol (Z)-2-butenedioate (1:1) salt, CAS RN 26921-17-5); bisoprolol (2-Propanol, 1-[4-[[2-(1-methylethoxy)ethoxy]-methyl]phenoxyl]-3-[(1-methylethyl) amino]-, (±), CAS RN 66722-44-9); bisoprolol fumarate (such as (±)-1-[4-[[2-(1-Methylethoxy) ethoxy]methyl]phenoxy]-3-[(1-methylethyl)amino]-2-propanol (E)-2-butenedioate (2:1) (salt), for example, ZEBETA™ Tablets available from Lederle Consumer); nebivalol (2H-1-Benzopyran-2-methanol, αα'-[iminobis(methylene)]bis[6-fluoro-3,4-dihydro-, CAS RN 99200-09-6 see also U.S. Pat. No. 4,654,362); cicloprolol hydrochloride, such 2-Propanol, 1-[4-[2-(cyclopropylmethoxy)ethoxy]phenoxy]-3-[1-methylethyl) amino]-, hydrochloride, A.A.S. RN 63686-79-3); and dexpropranolol hydrochloride (2-Propanol, 1-[1-methylethyl)amino]-3-(1-naphthalenyloxy)-hydrochloride (CAS RN 13071-11-9); diacetolol hydrochloride (Acetamide, N-[3-acetyl-4-[2-hydroxy-3-[(1-methyl-ethyl)amino]propoxy][phenyl]-, monohydrochloride CAS RN 69796-04-9); dilevalol hydrochloride (Benzamide, 2-hydroxy-5-[1-hydroxy-2-[1-methyl-3-phenylpropyl)amino]ethyl]-, monohydrochloride, CAS RN 75659-08-4); exaprolol hydrochloride (2-Propanol, 1-(2-cyclohexylphenoxy)-3-[(1-methylethyl)amino]-, hydrochloride CAS RN 59333-90-3); flestolol sulfate (Benzoic acid, 2-fluro-, 3-[[2-[aminocarbonyl) amino]-1-dimethylethyl]amino]-2-hydroxypropyl ester, (±)-sulfate (1:1) (salt), CAS RN 88844-73-9; metalol hydrochloride (Methanesulfonamide, N-[4-[1-hydroxy-2-(methylamino)propyl]phenyl]-, monohydrochloride CAS RN 7701-65-7); metoprolol 2-Propanol, 1-[4-(2-methoxyethyl)phenoxy]-3-[1-methylethyl)amino]-; CAS RN 37350-58-6); metoprolol tartrate (such as 2-Propanol, 1-[4-(2-methoxyethyl)phenoxy]-3-[(1-methylethypamino]-, for example, LOPRESSOR® available from Novartis); pamatolol sulfate (Carbamic acid, [2-[4-[2-hydroxy-3-[(1-methylethyl)amino] propoxyl]phenyl]-ethyl]-, methyl ester, (±) sulfate (salt) (2:1), CAS RN 59954-01-7); penbutolol sulfate (2-Propanol, 1-(2-cyclopentylphenoxy)-3-[1,1-dimethylethyl)amino]1, (S)—, sulfate (2:1) (salt), CAS RN 38363-32-5); practolol (Acetamide, N-[4-[2-hydroxy-3-[(1-methylethyl)amino]-propoxy]phenyl]-, CAS RN 6673-35-4;) tiprenolol hydrochloride (Propanol, 1-[(1-methylethyl)amino]-3-[2-(methylthio)-phenoxy]-, hydrochloride, (±), CAS RN 39832-43-4); tolamolol (Benzamide, 4-[2-[[2-hydroxy-3-(2-methylphenoxy)-propyl]amino]ethoxyl]-, CAS RN 38103-61-6).

Adrenergic receptors which are a-receptor inhibitors act to block vasoconstriction induced by endogenous catecholamines. The resulting fall in peripheral resistance leads to a fall in mean blood pressure. The magnitude of this effect is dependent upon the degree of sympathetic tone at the time the antagonist is administered.

Suitable adrenergic receptors which are a-receptor inhibitors include, but are not limited to, fenspiride hydrochloride (which may be prepared as disclosed in U.S. Pat. No. 3,399,192 herein incorporated by reference); proroxan (CAS RN 33743-96-3); alfuzosin hydrochloride (CAS RN: 81403-68-1); and labetalol hydrochloride as described above or combinations thereof.

Adrenergic blockers with α and β receptor inhibitor activity which may be used with the present invention include, but are not limited to, bretylium tosylate (CAS RN: 61-75-6); dihydroergtamine mesylate (such as ergotaman-3',6',18-trione,9,-10-dihydro-12'-hydroxy-2'-methyl-5'-(phenylmethyl)-, (5'(alpha))-, monomethanesulfonate, for example, DHE 45® Injection available from Novartis); carvedilol (such as (±)-1-(Carbazol-4-yloxy)-3-[[2-(o-methoxyphenoxy)ethyl]amino]-2-propanol, for example, COREG® Tablets available from SmithKline Beecham); labetalol (such as 5-[1-hydroxy-2-[(1-methyl-3-phenylpropyl) amino]ethyl] salicylamide monohydrochloride, for example, NORMO-DYNE® Tablets available from Schering); bretylium tosylate (Benzenemethanaminium, 2-bromo-N-ethyl-N,N-dimethyl-, salt with 4-methylbenzenesulfonic acid (1:1) CAS RN 61-75-6); phentolamine mesylate (Phenol, 3-[[(4,5-dihydro-1H-imidazol-2-yl)methyl](4-methylphenyl)amino]-, monomethanesulfonate (salt) CAS RN 65-28-1); solypertine tartrate (5H-1,3-Dioxolo[4,5-f]indole, 7-[2-[4-(2-methoxyphenyl)-1-piperazinyl]ethyl]-, (2R,3R)-2,3-dihydroxybutanedioate (1:1) CAS RN 5591-43-5); zolertine hydrochloride (Piperazine, 1-phenyl-4-[2-(1H-tetrazol-5-yl)ethyl]-, monohydrochloride (8Cl, 9Cl) CAS RN 7241-94-3)

An angiotensin system inhibitor is an agent that interferes with the function, synthesis or catabolism of angiotensin II. These agents which may be used in the present invention include but are not limited to angiotensin-converting enzyme (ACE) inhibitors, angiotensin II antagonists, angiotensin II receptor antagonists, agents that activate the catabolism of angiotensin Hand agents that prevent the synthesis of angiotensin I from which angiotensin II is ultimately derived. The renin-angiotensin system is involved in the regulation of hemodynamics and water and electrolyte balance. Factors that lower blood volume, renal profusion, or the concentration of Na+ in plasma tend to activate the system, while factors that increase these parameters tend to suppress its function. Angiotensin I and angiotensin are synthesized by the enzymatic renin-angiotensin pathway. The synthetic process is initiated when the enzyme renin acts on angiotensinogen, a pseudoglobulin in blood plasma, to produce the cecapeptide angiotensin I. Angiotensin I is converted by angiotensin-converting enzyme (ACE) to angiotensin II. The latter is an active pressor substance which has been implicated as a causative agent in several forms of hypertension in various mammalian species.

Angiotensin II receptor antagonists are compounds which interfere with the activity of angiotensin II by binding to angiotensin II receptors and interfering with its activity. Angiotensin II receptor antagonists which may be used in the present invention are well known and include peptide compounds and non-peptide compounds. Non-limiting examples of angiotensin II receptor antagonists include: candesartan cilexetil (1H-Benzimidazole-7-carboxylic acid, 2-ethoxy-1-[[2'-(1H-tetrazol-5-yl) [1,1'-biphenyl]-4-yl]methyl]-, 1-[[(cyclohexyloxy)carbonyl]oxy]ethyl ester) CAS RN 145040-37-5); telmisartan([1,1'-Biphenyl]-2-carboxylic acid, 4'-[(1,4'-dimethyl-2'-propyl[2,6'-bi-1H-benzimidazol]-1'-yl)methyl]-CAS RN 144701-48-4); candesartan (1H-Benzimidazole-7-carboxylic acid, 2-ethoxy-1-[[2'-(1H-tetrazol-5-yl)[1,1'-biphenyl]-4-yl]methyl]-CAS RN 139481-59-7); losartan potassium (1H-Imidazole-5-methanol, 2-butyl-4-chloro-1-[[2'-(1H-tetrazol-5-yl)[1,1-biphenyl]-4-yl]methyl]-, monopotassium Irbesartan1,3-Diazaspiro[4.4]non-1-en-4-one, 2-butyl-3-[[2'-(1H-tetrazol-5-yl)[1,1'-biphenyl]-4-yl]methyl]-CAS RN 138402-11-6).

Angiotensin-converting enzyme (ACE), is an enzyme which catalyzes the conversion of angiotensin I to angiotensin II. ACE inhibitors which may be used in the present invention include amino acids and derivatives thereof, peptides, including di and tri peptides and antibodies to ACE which intervene renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Suitable ACE inhibitors include, but are not limited to, benazepril hydrochloride (such as 3-[[1-(ethoxycarbonyl)-3-phenyl-(1S)-propyl]amino]-2,3,4,5-tetrahydro-2-oxo-1H-1-(3S)-benzazepine-1-acetic acid monohydrochloride, for example, LOTREL® Capsules available from Novartis); captopril (such as 1-[(2S)-3-mercapto-2-methylpropionyl]-L-proline, for example, CAPTOPRIL Tablets available from Mylan); fosinopril (such as L-proline, 4-cyclohexyl-1-[[[2-methyl-1-(1-oxopropoxy)propoxy](4-phenylbutyl) phosphinyl]acetyl]-, sodium salt, trans-., for example, MONOPRIL® Tablets available from Bristol-Myers Squibb); moexipril hydrochloride (such as [3S-[2[R*(R*)], 3R*]]-2-[2-[[1-(Ethoxycarbonyl)-3-phenylpropyl]amino]-1-oxopropyl]-1,2,3,4-tetrahydro-6,7-dimethoxy-3-isoquinolinecarboxylic acid, monohydrochloride, for example, UNIRETIC® Tablets available from Schwarz); perindopril erbumine (such as 2S,3aS,7aS)-1-[(S)—N—[(S)— 1-Carboxybutyl]alanyl]hexahydro-2-indolinecarboxylic acid, 1-ethyl ester, compound with tert-butylamine (1:1), for example, ACEON® Tablets available from Solvay); quinapril (such as [3S-[2[R*(R*)], 3R*]]-2-[2-[[1-(ethoxycarbonyl)-3-phenylpropyl]amino]-1-oxopropyl]-1,2,3,4-tetrahydro-3-isoquinolinecarboxylic acid, monohydrochloride, for example, ACCURETIC® Tablets available from Parke-Davis); ramipril (such as 2-aza-bicyclo[3.3.0]-octane-3-carboxylic acid derivative, for example, ALTACE® Capsules available from Monarch); enalapril maleate (such as (S)-1-[N-[1-(ethoxycarbonyl)-3-phenylpropyl]-L-alanyl]-L-proline, (Z)-2-butenedioate salt (1:1)., for example, VASOTEC® Tablets available from Merck); lisinopril (such as (S)-1-[N 2-(1-carboxy-3-phenylpropyl)-L-lysyl]-L-proline dihydrate, for example, PRINZIDE® Tablets available from Merck); delapril (which may be prepared as disclosed in U.S. Pat. No. 4,385,051); and spirapril (which may be prepared as disclosed in U.S. Pat. No. 4,470,972); benazeprilat (1H-1-Benzazepine-1-acetic acid, 3-[[(1S)-1-carboxy-3-phenylpropyl]amino]-2,3,4,5-tetrahydro-2-oxo-, (3S)-CAS RN 86541-78-8); delapril hydrochloride (Glycine, N-[(1S)-1-(ethoxycarbonyl)-3-phenylpropyl]-1-alanyl-N-(2,3-dihydro-1H-inden-2-yl)-, monohydrochloride CAS RN 83435-67-0); fosinopril sodium (L-Proline, 4-cyclohexyl-1-[[(R)-[(1S)-2-methyl-1-(1-oxopropoxy)propoxy](4-phenylbutyl)phosphinyl]acetyl]-, sodium salt, (4S)-CAS RN 88889-14-9); libenzapril (1H-1-Benzazepine-1-acetic acid, 3-[[(1S)-5-amino-1-carboxypentyl]amino]-2,3,4,5-tetrahydro-2-oxo-, (3S)-CAS RN 109214-55-3); pentopril (1H-Indole-1-pentanoic acid, 2-carboxy-2,3-dihydro-.alpha.,.gamma.-dimethyl-.delta.-oxo-, .alpha.-ethyl ester, (.alpha.R,.gamma.R,2S)-CAS RN 82924-03-6); perindopril 1H-Indole-2-carboxylic acid, 1-[(2S)-2-[[(1S)-1-(ethoxycarbonyl)butyl]amino]-1-oxopropyl]octahydro-, (2S,3aS,7aS)-CAS RN 82834-16-0); quinapril hydrochloride (3-Isoquinolinecarboxylic acid, 2-[(2S)-2-[[(1S)-1-(ethoxycarbonyl)-3-phenylpropyl]amino]-1-oxopropyl]-1,2,3,4-tetrahydro-, monohydrochloride, (3S)-CAS RN 82586-55-); quinaprilat (3-Isoquinolinecarboxylic acid, 2-[(2S)-2-[[(1S)-1-carboxy-3-phenylpropyl]amino]-1-oxopropyl]-1,2,3,4-tetrahydro-, (3S)-CAS RN 82768-85-2); spirapril hydrochloride (1,4-Dithia-7-azaspiro[4.4]nonane-8-carboxylic acid, 7-[(2S)-2-[[(1S)-1-(ethoxycarbonyl)-3-phenylpropyl]amino]-1-oxopropyl]-, monohydrochloride, (8S)-CAS RN 94841-17-5); spiraprilat 1(4-Dithia-7-azaspiro[4.4]nonane-8-carboxylic acid, 7-[(2S)-2-[[(1S)-1-carboxy-3-phenylpropyl]amino]-1-oxopropyl]-, (8S)-CAS RN 83602-05-5); teprotide (Bradykinin potentiator BPP9a CAS RN 35115-60-7); lisinopril (L-Proline, N2-[(1S)-1-carboxy-3-phenylpropyl]-L-lysyl-CAS RN 76547-98-3); zofenopril (L-Proline, 1-[(2S)-3-(benzoylthio)-2-methyl-1-oxopropyl]-4-(phenylthio)-, calcium salt (2:1), (4S)-CAS RN 81938-43-4).

"Calcium channel blockers" are a chemically diverse class of compounds having important therapeutic value in the control of a variety of diseases including several cardiovascular disorders such as hypertension, angina, and cardiac arrhythmias (Fleckenstein, *Cir. Res. V.* 52 (suppl. 1), p. 13-16 (1983); Fleckenstein, *Experimental Facts and Therapeutic Prospects*, John Wiley, New York (1983); McCall, D., *Curr. Pract Cardiol.*, v. 10, p. 1-11 (1985)). Calcium channel blockers are a heterogeneous group of drugs that prevent or slow the entry of calcium into cells by regulating cellular calcium channels (Remington, *The Science and Practice of Pharmacy*, Nineteenth Edition, Mack Publishing Company, Eaton, Pa., p. 963 (1995)). Calcium channel blockers useful in the present invention include but are not limited to, the besylate salt of amlodipine (such as 3-ethyl-5-methyl-2-(2-aminoethoxymethyl)-4-(2-chlorophenyl)-1,4-dihydro-6-methyl-3,5-pyridinedicarboxylate benzenesulphonate, for example, NORVASC® available from Pfizer); clentiazem maleate (1,5-Benzothiazepin-4(5H)-one, 3-(acetyloxy)-8-chloro-5-[2-(dimethylamino)ethyl]-2,3-dihydro-2-(4-methoxyphenyl)-(2S-cis)-, (Z)-2-butenedioate (1:1), see also U.S. Pat. No. 4,567,195); isradipine (3,5-Pyridinedicarboxylic acid, 4-(4-benzofurazanyl)-1,4-dihydro-2,6-dimethyl-, methyl 1-methylethyl ester, (±)-4(4-benzofurazanyl)-1,4-dihydro-2,6-dimethyl-3,5-pyridinedicarboxylate, see also U.S. Pat. No. 4,466,972); nimodipine (such as is isopropyl (2-methoxyethyl) 1,4-dihydro-2,6-dimethyl-4-(3-nitrophenyl)-3,5-pyridine—dicarboxylate, for example, NIMOTOP® available from Bayer); felodipine (such as ethyl methyl 4-(2,3-dichlorophenyl)-1,4-dihydro-2,6-dimethyl-3,5-pyridinedicarboxylate, for example, PLENDIL® Extended-Release Tablets available from AstraZeneca LP); nilvadipine (3,5-Pyridinedicarboxylic acid, 2-cyano-1,4-dihydro-6-methyl-4-(3-nitrophenyl)-, 3-methyl 5-(1-methylethyl) ester, also see U.S. Pat. No. 3,799,934); nifedipine (such as 3,5-pyridinedicarboxylic acid, 1,4-dihydro-2,6-dimethyl-4-(2-nitrophenyl)-, dimethyl ester, for example, PROCARDIA XL® Extended Release Tablets available from Pfizer); diltiazem hydrochloride (such as 1,5-Benzothiazepin-4(5H)-one, 3-(acetyloxy)-5[2-(dimethylamino)ethyl]-2,-3-dihydro-2(4-methoxyphenyl)-, monohydrochloride, (+)-cis., for example, TIAZAC® Capsules available from Forest); verapamil hydrochloride (such as benzeneacetonitrile, (alpha)-[[3-[[2-(3,4-dimethoxyphenyl) ethyl]methylamino]propyl]-3,4-dimethoxy-(alpha)-(1-methylethyl) hydrochloride, for example, ISOPTIN® SR Tablets available from Knoll Labs); teludipine hydrochloride (3,5-Pyridinedicarboxylic acid, 2-[(dimethylamino)methyl]-4-[2-[2-[(1E)-3-(1,1-dimethylethoxy)-3-oxo-1-propenyl] phenyl]-1,4-dihydro-6-methyl-, diethyl ester, monohydrochloride) CAS RN 108700-03-4); belfosdil (Phosphonic acid, [2-(2-phenoxyethyl)-1,3-propanediyl]bis-, tetrabutyl ester CAS RN 103486-79-9); fostedil (Phosphonic acid, [[4-(2-benzothiazolyl)phenyl]methyl]-, diethyl ester CAS RN 75889-62-2).

Cardiovascular agents of the present invention which also act as "anti-anginal agents" are useful in the present invention. Angina includes those symptoms that occur when myocardial oxygen availability is insufficient to meet myocardial oxygen demand. Non-limiting examples of these agents include: ranolazine (hydrochloride1-Piperazineacetamide, N-(2,6-dimethylphenyl)-4-[2-hydroxy-3-(2-methoxyphenoxy)propyl]-, dihydrochloride CAS RN 95635-56-6); betaxolol hydrochloride (2-Propanol, 1-[4-[2 (cyclopropylmethoxy)ethyl]phenoxy]-3-[(1-methylethyl)amino]-,hydrochloride CAS RN 63659-19-8); butoprozine hydrochloride (Methanone, [4-[3(dibutylamino)propoxy]phenyl](2-ethyl-3-indolizinyl)-, monohydrochloride CAS RN 62134-34-3); cinepazet maleate1-Piperazineacetic acid, 4-[1-oxo-3-(3,4,5-trimethoxyphenyl)-2-propenyl]-, ethyl ester, (2Z)-2-butenedioate (1:1) CAS RN 50679-07-7); tosifen (Benzenesulfonamide, 4-methyl-N-[[[(1S)-1-methyl-2-phenylethyl]amino] carbonyl]-CAS RN 32295-18-4); verapamilhydrochloride (Benzeneacetonitrile, .alpha.-[3-[[2-(3,4-dimethoxyphenyl) ethyl]methylamino]propyl]-3,4-dimethoxy-.alpha.-(1-methylethyl)-, monohydrochloride CAS RN 152-11-4); molsidomine (1,2,3-Oxadiazolium, 5-[(ethoxycarbonyl)amino]-3-(4-morpholinyl)-, inner salt CAS RN 25717-80-0); ranolazine hydrochloride (1-Piperazineacetamide, N-(2,6-dimethylphenyl)-4-[2-hydroxy-3-(2-methoxyphenoxy)propyl]-, dihydrochloride CAS RN 95635-56-6); tosifen (Benzenesulfonamide, 4-methyl-N-[[[(1S)-1-methyl-2-phenylethyl]amino]carbonyl]-CAS RN 32295-18-4).

"Coronary vasodilators" may act to reduce angina systems by increasing the oxygen supply to the heart. Coronary vasodilators useful in the present invention include, but are not limited to, diltiazem hydrochloride (such as 1,5-Benzothiazepin-4(5H)-one, 3-(acetyloxy)-5[2-(dimethylamino) ethyl]-2,-3-dihydro-2(4-methoxyphenyl)-, monohydrochloride, (+)-cis, for example, TIAZAC® Capsules available from Forest); isosorbide dinitrate (such as 1,4:3,6-dianhydro-D-glucitol 2,5-dinitrate, for example, ISORDIL® TITRA-DOSE® Tablets available from Wyeth-Ayerst); sosorbide mononitrate (such as 1,4:3,6-dianhydro-D-glucitol, 5-nitrate, an organic nitrate, for example, Ismo® Tablets available from Wyeth-Ayerst); nitroglycerin (such as 2,3 propanetriol trinitrate, for example, NITROSTAT® Tablets available from Parke-Davis); verapamil hydrochloride (such as benzeneacetonitrile, (±)-(alpha)[3[[2-(3,4 dimethoxyphenyl)ethyl]methylamino]propyl]-3,4-dimethoxy-(alpha)-(1-methylethyl) hydrochloride, for example, COVERA HS® Extended-Release Tablets available from Searle); chromonar (which may be prepared as disclosed in U.S. Pat. No. 3,282,938); clonitate (Annalen 1870 155); droprenilamine (which may be prepared as disclosed in German Patent No. 2,521,113); lidoflazine (which may be prepared as disclosed in U.S. Pat. No. 3,267,104); prenylamine (which may be prepared as disclosed in U.S. Pat. No. 3,152,173); propatyl nitrate (which may be prepared as disclosed in French Patent No. 1,103,113); mioflazine hydrochloride (1-Piperazineacetamide, 3-(aminocarbonyl)-4-[4,4-bis(4-fluorophenyl)butyl]-N-(2,6-dichlorophenyl)-, dihydrochloride CAS RN 83898-67-3); mixidine (Benzeneethanamine, 3,4-dimethoxy-N-(1-methyl-2-pyrrolidinylidene)-Pyrrolidine, 2-[(3,4-dimethoxyphenethyl)imino]-1-methyl-1-Methyl-2-[(3,4-dimethoxyphenethyl)imino]pyrrolidine CAS RN 27737-38-8); molsidomine (1,2,3-Oxadiazolium, 5-[(ethoxycarbonyl) amino]-3-(4-morpholinyl)-, inner salt CAS RN 25717-80-0); isosorbide mononitrate (D-Glucitol, 1,4:3,6-dianhydro-, 5-nitrate CAS RN 16051-77-7); erythrityl tetranitrate (1,2,3, 4-Butanetetrol, tetranitrate, (2R,3S)-rel-CAS RN 7297-25-8); clonitrate(1,2-Propanediol, 3-chloro-, dinitrate (7Cl, 8Cl, 9Cl) CAS RN 2612-33-1); dipyridamole Ethanol, 2,2',2",2'''-[(4,8-di-1-piperidinylpyrimido[5,4-d]pyrimidine-2,6-diyl) dinitrilo]tetrakis-CAS RN 58-32-2); nicorandil (CAS RN 65141-46-03-); pyridinecarboxamide (N[2-(nitrooxy)ethyl]-Nisoldipine3,5-Pyridinedicarboxylic acid, 1,4-dihydro-2,6-dimethyl-4-(2-nitrophenyl)-, methyl 2-methylpropyl ester CAS RN 63675-72-9); nifedipine3,5-Pyridinedicarboxylic acid, 1,4-dihydro-2,6-dimethyl-4-(2-nitrophenyl)-, dimethyl ester CAS RN 21829-25-4); perhexiline maleate (Piperidine, 2-(2,2-dicyclohexylethyl)-, (2Z)-2-butenedioate (1:1) CAS RN 6724-53-4); oxprenolol hydrochloride2-Propanol, 1-[(1-methylethyl)amino]-3-[2-(2-propenyloxy)phenoxy]-, hydrochloride CAS RN 6452-73-9); pentrinitrol (1,3-Propanediol, 2,2-bis[(nitrooxy)methyl]-, mononitrate (ester) CAS RN 1607-17-6); verapamil (Benzeneacetonitrile, .alpha.-[3-[[2-(3,4-dimethoxyphenyl)ethyl]methylamino]propyl]-3,4-dimethoxy-.alpha.-(1-methylethyl)-CAS RN 52-53-9).

The term "diuretic" includes compounds that increase the excretion of solutes (mainly NaCl) and water. In general, the primary goal of diuretic therapy is to reduce extracellular fluid volume in order to lower blood pressure or rid the body of excess interstitial fluid (edema). Non-limiting examples of diuretics which may be used within the scope of this invention include althiazide (which may be prepared as disclosed in British Patent No. 902,658); benzthiazide (which may be prepared as disclosed in U.S. Pat. No. 3,108,097); buthiazide (which may be prepared as disclosed in British Patent Nos. 861,367); chlorothiazide (which may be prepared as disclosed in U.S. Pat. No. 2,809,194); spironolactone (CAS Number 52-01-7); and triamterene (CAS Number 396-01-0).

"Adrenergic stimulants" useful as cardiovascular agents in the present invention include, but are not limited to, guanfacine hydrochloride (such as N-amidino-2-(2,6-dichlorophenyl) acetamide hydrochloride, for example, TENEX® Tablets available from Robins); methyldopa-hydrochlorothiazide (such as levo-3-(3,4-dihydroxyphenyl)-2-methylalanine) combined with Hydrochlorothiazide (such as 6-chloro-3,4-dihydro-2H-1,2,4-benzothiadiazine-7-sulfonamide 1,1-dioxide, for example, the combination as, for example, ALDORIL® Tablets available from Merck); methyldopa-chlorothiazide (such as 6-chloro-2H-.1,2,4-benzothiadiazine-7-sulfonamide 1,1-dioxide and methyldopa as described above, for example, ALDOCLORr® Tablets available from Merck); clonidine hydrochloride (such as 2-(2,6-dichlorophenylamino)-2-imidazoline hydrochloride and chlorthalidone (such as 2-chloro-5-(1-hydroxy-3-oxo-1-isoindolinyl) benzenesulfonamide), for example, COMBI-PRES® Tablets available from Boehringer Ingelheim); clonidine hydrochloride (such as 2-(2,6-dichlorophenylamino)-2- imidazoline hydrochloride, for example, CATAPRES® Tablets available from Boehringer Ingelheim); clonidine (1H-Imidazol-2-amine, N-(2,6-dichlorophenyl)-4,5-dihydro-CAS RN 4205-90-7).

The present inventin also includes a matrilin-2 polypeptide or active-fragment thereof in association with any azetidinone which inhibits intestinal cholesterol absorption. Such azetidinones include ezetimibe.

Further chemotherapeutic agents that may be provided in association with a matrilin-2 polypeptide or active-fragment thereof include fish oil, eicosaepenanoic acid, docosahexanoic acid, linoleic acid, niacin, fibrates such as fenofibrate, gemfibrozil and bile acid sequestrants such as cholestyramine, colestipol and colesevelam.

Other chemotherapeutic agents include althiazide (2H-1,2,4-Benzothiadiazine-7-sulfonamide, 6-chloro-3,4-dihydro-3-[(2-propenylthio)methyl]-, 1,1-dioxide CAS RN 5588-16-9); benzthiazide (2H-1,2,4-Benzothiadiazine-7-sulfonamide, 6-chloro-3-[[(phenylmethyl)thio]methyl]-, 1,1-dioxide CAS RN 91-33-8); captopril (L-Proline, 1-[(2S)-3-mercapto-2-methyl-1-oxopropyl]-CAS RN 62571-86-2); carvedilol (2-Propanol, 1-(9H-carbazol-4-yloxy)-3-[[2-(2-methoxyphenoxy)ethyl]amino]-CAS RN 72956-09-3), chlorothiazide (sodium 2-Propanol, 1-(9H-carbazol-4-yloxy)-3-[[2-(2-methoxyphenoxy)ethyl]amino]-CAS RN 72956-09-3); clonidine hydrochloride (1H-Imidazol-2-amine, N-(2,6-dichlorophenyl)-4,5-dihydro-, monohydrochloride CAS RN 4205-91-8); cyclothiazide (2H-1,2,4-Benzothiadiazine-7-sulfonamide, 3-bicyclo[2.2.1]hept-5-en-2-yl-6-chloro-3,4-dihydro-, 1,1-dioxide CAS RN 2259-96-3); delapril hydrochloride (2H-1,2,4-Benzothiadiazine-7-sulfonamide, 3-bicyclo[2.2.1]hept-5-en-2-yl-6-chloro-3,4-dihydro-, 1,1-dioxide CAS RN 2259-96-3); dilevalol hydrochloride (2H-1,2,4-Benzothiadiazine-7-sulfonamide, 3-bicyclo[2.2.1]hept-5-en-2-yl-6-chloro-3,4-dihydro-, 1,1-dioxide CAS RN 2259-96-3); delapril hydrochloride (Glycine, N-[(1S)-1-(ethoxycarbonyl)-3-phenylpropyl]-L-alanyl-N-(2,3-dihydro-1H-inden-2-yl)-, monohydrochloride CAS RN 83435-67-0); doxazosin mesylate (Piperazine, 1-(4-amino-6,7-dimethoxy-2-quinazolinyl)-4-[(2,3-dihydro-1,4-benzodioxin-2-yl)carbonyl]-, monomethanesulfonate CAS RN 77883-43-3); fosinopril sodium (L-Proline, 4-cyclohexyl-1-[[(R)-[(1S)-2-methyl-1-(1-oxopropoxy)propox); moexipril hydrochloride (3-Isoquinolinecarboxylic acid, 2-[(2S)-2-[[(1S)-1-(ethoxycarbonyl)-3-phenylpropyl]amino]-1-oxopropyl]-1,2,3,4-tetrahydro-6,7-dimethoxy-, monohydrochloride, (3S)-CAS RN 82586-52-5); monatepil maleate (1-Piperazinebutanamide, N-(6,11-dihydrodibenzo(b,e)thiepin-11-yl)-4-(4-fluorophenyl)-, (±)-, (Z)-2-butenedioate (1:1) (±)-N-(6,11-Dihydrodibenzo(b,e)thiepin-11-yl)-4-(p-fluorophenyl)-1-piperazinebutyramide maleate (1:1) CAS RN 132046-06-1), Metoprolol succinate (Butanedioic acid, compd. with 1-[4-(2-methoxyethyl)phenoxy]-3-[(1-methylethyl)amino]-2-propanol (1:2) CAS RN 98418-47-4); guanfacine hydrochloride (Benzeneacetamide, N-(aminoiminomethyl)-2,6-dichloro-, monohydrochloride CAS RN 29110-48-3; methyldopa (L-Tyrosine, 3-hydroxy-.alpha.-methyl-CAS RN 555-30-6); quinaprilat (3-Isoquinolinecarboxylic acid, 2-[(2S)-2-[[(1S)-1-carboxy-3-phenylpropyl]amino]-1-oxopropyl]-1,2,3,4-tetrahydro-, (3S)-CAS RN 82768-85-2); quinapril hydrochloride (3-Isoquinolinecarboxylic acid, 2-[(2S)-2-[[(1S)-1-(ethoxycarbonyl)-3-phenylpropyl]amino]-1-oxopropyl]-1,2,3,4-tetrahydro-, monohydrochloride, (3S)-CAS RN 82586-55-8); Primidolol (2,4(1H,3H)-Pyrimidinedione, 1-[2-[[2-hydroxy-3-(2-methylphenoxy)propyl]amino]ethyl]-5-methyl-CAS RN 67227-55-8); prazosin hydrochloride (Piperazine, 1-(4-amino-6,7-dimethoxy-2-quinazolinyl)-4-(2-furanylcarbonyl)-, monohydrochloride CAS RN 19237-84-4); pelanserin hydrochloride 2,4(1H,3H)-Quinazolinedione, 3-[3-(4-phenyl-1-piperazinyl)propyl]-, monohydrochloride CAS RN 42877-18-9); phenoxybenzamine hydrochloride (Benzenemethanamine, N-(2-chloroethyl)-N-(1-methyl-2-phenoxyethyl)-, hydrochloride CAS RN 63-92-3); candesartan cilexetil (1H-Benzimidazole-7-carboxylic acid, 2-ethoxy-1-[[2'-(1H-tetrazol-5-yl)[1,1'-biphenyl]-4-yl]methyl]-, 1-[[(cyclohexyloxy)carbonyl]oxy]ethyl ester CAS RN 145040-37-5); telmisartan (1,1'-Biphenyl]-2-carboxylic acid, 4'-[(1,4'-dimethyl-2'-propy)[2,6'-bi-1H-benzimidazol]-1'-yl)methyl]-CAS RN 144701-48-4); candesartan1H-Benzimidazole-7-carboxylic acid, 2-ethoxy-1-[[2'-(1H-tetrazol-5-yl)[1,1'-biphenyl]-4-yl]methyl]-CAS RN 139481-59-7); amlodipine besylate3,5-Pyridinedicarboxylic acid, 2-[(2-aminoethoxy)methyl]-4-(2-chlorophenyl)-1,4-dihydro-6-methyl-, 3-ethyl 5-methyl ester, monobenzenesulfonate CAS RN 111470-99-6 Amlodipine maleate 3,5-Pyridinedicarboxylic acid, 24(2-aminoethoxy)methyl]-4-(2-chlorophenyl)-1,4-dihydro-6-methyl-, 3-ethyl 5-methyl ester, (2Z)-2-butenedioate (1:1) CAS RN 88150-47-4); terazosin hydrochloride (Piperazine, 1-(4-amino-6,7-dimethoxy-2-quinazolinyl)-4-[(tetrahydro-2-furanyl)carbonyl]-, monohydrochloride CAS RN 63074-08-8); bevantolol hydrochloride (2-Propanol, 1-[[2-(3,4-dimethoxyphenyl)ethyl]amino]-3-(3-methylphenoxy)-, hydrochloride CAS RN 42864-78-8); ramipril (Cyclopenta[b]pyrrole-2-carboxylic acid, 1-[(2S)-2-[[(1S)-1-(ethoxycarbonyl)-3-phenylpropyl]amino]-1-oxopropyl]octahydro-, (2S,3aS,6aS)-CAS RN 87333-19-5).

The term "in association with" indicates that the components of a composition of the invention can be formulated into a single composition for simultaneous delivery or formulated separately into two or more compositions (e.g., a kit). Furthermore, each component can be administered to a subject at a different time than when the other component is administered; for example, each administration may be given non-simultaneously (e.g., separately or sequentially) at several intervals over a given period of time. Moreover, the separate components may be administered to a subject by the same or by a different route.

Antibodies

The present invention includes compositions, e.g., pharmaceutical compositions comprising anti-matrilin-2 antibodies and antigen-binding fragments thereof as well as methods of using such antibodies. The term anti-matrilin-2 antibody or the like includes any antibody that binds specifically to matrilin-2. The anti-matrilin-2 antibodies and antigen-binding fragments thereof used in the present invention include antibodies and fragments which were raised against or bind to the whole matrilin-2 protein as well as antibodies raised against or bind to particular short epitopes within matrilin-2, e.g., the EGF-A domain of matrilin-2 or a portion thereof.

Compositions including the anti-matrilin-2 antibodies or antigen-binding fragments thereof can include, for example, a buffer or a carrier or any of the components discussed herein in connection with pharmaceutically acceptable carriers.

Thus, the invention includes monoclonal antibodies, camelized single domain antibodies, polyclonal antibodies, bispecific antibodies, chimeric antibodies, recombinant antibodies, anti-idiotypic antibodies, humanized antibodies, bispecific antibodies, diabodies, single chain antibodies, disulfide Fvs (dsfv), Fvs, Fabs, Fab's, F(ab')$_2$s and domain antibodies. Thus, the term antibody covers, but is not limited to, monoclonal antibodies, polyclonal antibodies, multispecific antibodies (e.g., bispecific antibodies). The term antigen-binding fragment of an antibody encompasses a fragment or a derivative of an antibody, typically including at least a portion of the antigen-binding or variable regions (e.g., one or more CDRs) of the parental antibody that retains at least some of the binding specificity of the parental antibody. Examples of antibody antigen-binding fragments include, but are not limited to, Fab, Fab', F(ab')$_2$, and Fv fragments; dsFv; (dsFv)$_2$, ds diabodies; dsFv-dsFv'; single-chain antibody molecules, e.g., sc-Fv, sc-Fv dimers (bivalent diabodies); bispecific diabodies; and multispecific antibodies formed from antibody fragments.

The present invention includes anti-matrilin-2 antibodies and antigen-binding fragments thereof which binds specifically to matrilin-2, for example, human matrilin-2. In an embodiment of the invention an antibody or fragment that binds specifically to human matrilin-2 binds preferentially to human matrilin-2 as compared to that of, for example, mouse matrilin-2. Preferential binding to human matrilin-2 means binding with an affinity which is greater than that of mouse matrilin-2 binding to any degree (e.g., 1%, 10%, 50%, 100%, or 10× higher affinity). Specific anti-matrilin-2 binding refers to binding of the antibody to matrilin-2 or an antigenic fragment thereof with a $K_D$ at least about 100-fold higher than that of any other protein that might be bound and/or a $K_D$ of about 500 nM or a lower number or about 1 nM or a lower number.

Any suitable method for generating antibodies may be used. For example, a recipient may be immunized with matrilin-2 or an immunogenic fragment thereof. Any suitable method of immunization can be used. Such methods can include adjuvants, other immunostimulants, repeated booster immunizations, and the use of one or more immunization routes. Any suitable source of matrilin-2 can be used as the immunogen for the generation of the antibodies and fragments of the compositions and methods disclosed herein. Such forms include, but are not limited whole protein, peptide(s), and epitopes generated through recombinant, synthetic, chemical or enzymatic degradation means known in the art.

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein fragment.

Monoclonal antibodies (mAbs) may be prepared from various mammalian hosts, such as mice, rats, other rodents, humans, other primates, etc. Description of techniques for preparing such monoclonal antibodies may be found in, e.g., Stites et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or an antigen binding fragment thereof by screening a DNA library from human B cells according, e.g., to the general protocol outlined by Huse et al. (1989) Science 246:1275-1281.

Other suitable techniques involve selection of libraries of antibodies in phage or similar vectors. See, e.g., Huse et al. supra; and Ward et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance that provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemilluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. Nos. 4,816,567 and 6,331,415; and Queen et al. (1989) Proc. Nat'l Acad. Sci. USA 86:10029-10033; or made in transgenic mice, see Mendez et al. (1997) Nature Genetics 15:146-156.

Mice which produce human immunoglobulins when immunized with a given antigen are also available in the art. See e.g., Lonberg, N., et al., (1994) Nature 368(6474): 856-859; Lonberg, N. (1994) Handbook of Experimental Pharmacology 113:49-101; Lonberg, N., et al., (1995) Intern. Rev. Immunol. 13:65-93, and Harding, F., et al., (1995) Ann. N.Y Acad. Sci 764:536-546); Taylor, L., et al., (1992) Nucleic Acids Research 20:6287-6295; Chen, J., et al., (1993) International Immunology 5: 647-656; Tuaillon, et al., (1993) Proc. Natl. Acad. Sci USA 90:3720-3724; Choi, et al., (1993) Nature Genetics 4:117-123; Chen, J., et al., (1993) EMBO J. 12: 821-830; Tuaillon, et al., (1994) J Immunol. 152:2912-2920; Lonberg, et al., (1994) Nature 368(6474): 856-859; Lonberg, N. (1994) Handbook of Experimental Pharmacology 113:49-101; Taylor, L., et al., (1994) International Immunology 6: 579-591; Lonberg, N., et al., (1995) Intern. Rev. Immunol. Vol. 13: 65-93; Harding, F., et al., (1995) Ann. N.Y Acad. Sci 764:536-546; Fishwild, D., et at, (1996) Nature Biotechnology 14: 845-851 and Harding, et al., (1995) Annals NY Acad. Sci. 764:536-546. See further, U.S. Pat. Nos. 5,545,806; 5,569,825; 5,625,126; 5,633,425; 5,789,650; 5,877,397; 5,661,016; 5,814,318; 5,874, 299; 5,770,429 and 5,545,807; and International Patent Application Publication Nos. WO 98/24884; WO 94/25585; WO 93/12227; WO 92/22645 and WO 92/03918.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

"Disulfide stabilized Fv fragments" and "dsFv" include molecules having a variable heavy chain ($V_H$) and/or a variable light chain ($V_L$) which are linked by a disulfide bridge.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the $V_H$ and $V_L$ chains to pair and form a binding site (e.g., 5-12 residues long). For a review of scFv, see Pluckthun (1994) THE PHARMACOLOGY OF MONOCLONAL ANTIBODIES, VOL 113, Rosenburg and Moore eds. Springer-Verlag, New York, pp. 269-315. See also, International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen-binding sites. In some instances, the two binding sites have the same antigen specificities. However, bivalent antibodies may be bispecific. For example, the present invention comprises scfv dimers and dsfv dimers, each of which scfv and dsfv moieties may have a common or different antigen binding specificity.

In an embodiment of the invention, a (dsfv)$_2$ comprises three peptide chains: two $V_H$ moieties linked by a peptide linker and bound by disulfide bridges to two $V_L$ moieties.

In an embodiment of the invention, a bispecific ds diabody comprises a $VH_1$-$VL_2$ (tethered by a peptide linker) linked, by a disulfide bridge between the $VH_1$ and $VL_1$, to a $VL_1$-$VH_2$ moiety (also tethered by a peptide linker). In an embodiment of the invention, a bispecific dsfv-dsfv' also comprises three peptide chains: a $VH_1$-$VH_2$ moiety wherein the heavy chains are linked by a peptide linker (e.g., a long flexible linker) and are bound to $VL_1$ and $VL_2$ moieties, respectively, by disulfide bridges; wherein each disulfide paired heavy and light chain has a different antigen specificity. In an embodiment of the invention, an scfv dimer (a bivalent diabody) comprises a $V_H$-$V_L$ moiety wherein the heavy and light chains are bound to by a peptide linker and dimerized with another such moiety such that $V_H$s of one chain coordinate with the $V_L$s of another chain and form two identical binding sites. In an embodiment of the invention a bispecific diabody comprises $VH_1$-$VL_2$ moiety (linked by a peptide linker) associated with a $VL_1$-$VH_2$ (linked by a peptide linker), wherein the $VH_1$ and $VL_1$ coordinate and the $VH_2$ and $VL_2$ coordinate and each coordinated set has diverse antigen specificities.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made recombinantly or by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

Monoclonal antibodies include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., (1984) Proc. Natl. Acad. Sci. USA 81: 6851-6855). For example, variable domains are obtained from an antibody from an experimental animal (the "parental antibody"), such as a mouse, and the constant domain sequences are obtained from human antibodies, so that the resulting chimeric antibody will be less likely to elicit an adverse immune response in a human subject than the parental mouse antibody.

A recombinant antibody or antigen-binding fragment thereof of the invention is, in an embodiment of the invention, an antibody which is produced recombinantly, e.g., expressed from a polynucleotide which has been introduced into an organism (e.g., a plasmid containing a polynucleotide encoding the antibody or fragment transformed into a bacterial cell (e.g., E. coli) or a mammalian cell (e.g., CHO cell)), followed by isolation of the antibody or fragment from the organism.

The present invention also includes camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079, which are hereby incorporated by reference in their entireties). Camelidae (camels, dromedaries and llamas) comprise IgG antibodies in which are devoid of light chains and therefore called 'heavy-chain' IgGs or HCAb (for heavy-chain antibody). HCAbs typically have a molecular weight of ~95 kDa since they consist only of the heavy-chain variable domains. Although the HCAbs are devoid of light chains, they have an authentic antigen-binding repertoire (Hamers-Casterman et al., Nature (1993) 363:446-448; Nguyen et al., Adv. lmmunol. (2001) 79:261-296; Nguyen et al., Immunogenetics. (2002) 54:39-47). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

Anti-matrilin-2 antibodies and antigen-binding fragments thereof have several uses including, for example detection and purification of matrilin-2 or PCSK9. For example, an anti-matrilin-2 antibody can be used to purify matrilin-2 in an affinity-based purification scheme. In such a purification scheme, an anti-matrilin-2 antibody can be immobilized to a matrix, such a sepharose or agarose beads, and bound to matrilin-2 which, in turn can be used to purify PCSK9 from a substance put in contact with the immobilized antibody complex. Alternatively, such an immobilized anti-matrilin-2 antibody can be used to purify matrilin-2 directly. Alternatively, the antibody can be used as a primary antibody in a western blot for the detection of matrilin-2.

Screening Methods

The present invention further provides a method for identification of proteins which interact with PCSK9. The method comprises the first step: (i) identifying polypeptide comprising Cys-Leu and Asn-Asn and Asp-Leu motifs. Identification of proteins with such motifs can be done using various method known in the art. For example, identification can be done by computer assisted means. In an embodiment of the invention, Perl computer language scripts may be generated to search proteins for such databases. Such searches may include the analysis of databases including sequences, for example, public databases such as GenBank, TrEMBL, IPI, SWISS-PROT, PFAM or ProDom.

The Perl script was as follows:

```
#!/usr/local/bin/perl -w
use strict;
my $usage = "pattern_search aa_fasta\n";
die $usage if (!defined $ARGV[0]);
$/ = "\n>";
open (DAT, $ARGV[0]) || die "cannot open $ARGV[0]!\n";
open (OUT, ">hits.pep.fasta") || die "cannot open output!\n";
open (OUT1, ">hits") || die "cannot open output1!\n";
open (OUT2, ">hits.allaa.fasta") || die "cannot open output2!\n";
my $processed = 0;
while (<DAT>) {
    chomp;
    s/^\>//;
```

-continued

```
    my ($def, $seq) = split (/\n/, $_, 2);
    $seq =~ s/\s+//g;
    $seq =~ tr/a-z/A-Z/;
    my $hit = match($seq);
    if (defined $hit && length($hit) > 0) {
        print OUT ">$def\n$hit\n";
        print OUT2 ">$_\n";
        print OUT1 "$def\t$hit\n";
    }
    $processed++;
}
close DAT;
close OUT;
close OUT1;
close OUT2;
print STDERR "processed $processed seqs\n";
###################SUBS############
sub match {
    my $seq = shift;
    if ($seq =~ /CL/ && $seq =~ /NN/ && $seq =~ /DL/) {
        if ($seq =~ /(N\w*CL\w*NN\w*H\w*C\w*DL)/) {    ###loose
        #if ($seq =~ /(N\wCL\wNN\w{4}H\wC\wDL)/) {    ###tight
        #if ($seq =~
/(N\w{0,10}CL\w{0,10}NN\w{0,40}H\w{0,10}C\w{0,10}DL
)/) {        ###medium, increase by 10, increase by 5 still same as tight
        #if ($seq =~
/(N\w{0,20}CL\w{0,20}NN\w{0,80}H\w{0,20}C\w{0,20}DL
)/) {        ###medium, increase by 20, increase by 5 still same as tight
            return $1;
        }
    }
}
```

The second step is: (ii) identifying polypeptides which were identified in step (i) comprising the motif:

Asn-$X_1$-Cys-Leu-$X_2$-Asn-Asn-$X_3$-His-$X_4$-Cys-$X_5$-Asp-Leu; wherein $X_1$, $X_2$, $X_3$, $X_4$ and $X_5$ are independently zero or more amino acids; or wherein, independently, $X_1$ is one amino acid, $X_2$ is one amino acid, $X_3$ is 4 amino acids, $X_4$ is one amino acid and $X_5$ is one amino acid; or wherein said $X_1$, $X_2$, $X_3$, $X_4$ and $X_5$ are independently zero to 10 amino acids; or wherein the motif is NECLDNNGGCSHVCNDL (SEQ ID NO: 14). This search may also be performed with e.g., a perl script.

The third step is: (iii) identifying the polypeptide identified in step (ii) which yields an E value of 10 or lower, when the comparison is performed using BLASTP algorithm with default parameters except that the filter for low complexity was deactivated, over the length of said polypeptide identified in step (ii), to a low density lipoprotein receptor EGF-A domain amino acid sequence (e.g., NECLDNNGGCSH-VCNDL (SEQ ID NO: 14)). Such a search may be performed, for example, using perl script or other search algorithms such as BLAST (e.g., BLASTP), BLITZ (MPsrch) (Sturrock, S. S. and Collins, J. F. (1993) MPsrch, Version 1.5, Biocomputing Research Unit. University of Edinburgh), FASTA (Pearson, W. R. and Lipman, D. J. (1988) Proc. Natl Acad. Sci. USA, 85, 2444-2448), Scanps (Barton, G. J. (1993) Science, 257, 1609).

E value is the expectation value, which is the number of different alignents with scores equivalent to or better than S that are expected to occur in a database search by chance. The lower the E value, the more significant the score. S is the bit score which is derived from the raw alignment score S in which the statistical properties of the scoring system used have been taken into account. Because bit scores have been normalized with respect to the scoring system, they can be used to compare alignment scores from different searches.

BLASTP default parameters include:
Reward for match: 1
Penalty for mismatch: −2
Open gap: 5; Extension gap: 2 penalties
Gap x_dropoff: 50 expect 10.0 wordsize 11

Low complexity filtering, also known as masking, is the process of hiding regions of sequence having characteristics that frequently lead to spurious high scores. SEG filtering is used for BLASTP comparisons.

In an embodiment of the invention, any protein identified using such a search method may be confirmed to bind to PCSK9 directly, in vitro or in vivo. In an embodiment of the invention, binding is confirmed using an Amplified Luminescent Proximity Homogeneous Assay (ALPHASCREEN) e.g., as set forth below. In an embodiment of the invention, binding is confirmed by immunoprecipitation, 2-hybrid assay or gel retardation assay.

ALPHASCREEN relies on the use of donor and acceptor beads that are coated with a layer of hydrogel providing functional groups for bioconjugation. When a biological interaction between molecules brings the beads into proximity, a cascade of chemical reactions is initiated to produce a greatly amplified signal. Upon laser excitation, a photosensitizer in the Donor bead converts ambient oxygen to a more excited singlet state. The singlet state oxygen molecules diffuse across to react with a chemilluminescer in the acceptor bead that further activates fluorophores contained within the same bead. The fluorophores subsequently emit light at 520-620 nm. In the absence of a specific biological interaction, the singlet state oxygen molecules produced by the donor bead go undetected without the close proximity of the acceptor bead (see e.g., Kordal et al., R J, Usmani A M, Law, W T. AlphaScreen: A Highly Sensitive Nonradioactive and Homogeneous Assay Platform for Drug Discovery High Throughput Screening, Genomics, and Life Science Research Applications in Miniaturized Format. Microfabricated Sensors: Application of Optical Technology for DNA Analysis, *Amer Chemical Society* Published 2002/04-ISBN 0841237638. pp. 45-47; Bosse et al., *Drug Discovery Today.* 2000 1(1): 42-7; Seethala et al., Homogeneous Assays: AlphaScreen. Handbook of Drug Screening. Marcel Dekker Pub., 2001. pp. 106-110)

EXAMPLES

Example 1

Identification and Characterization of PCSK9/Matrilin-2 Interaction

In this example, matrilin-2 was initially identified in a sequence-based search for PCSK9 interacting proteins and this binding was confirmed in vitro in a direct binding assay.

To search for PCSK9 substrates, we generated an LDL receptor-EGF-A motif pattern involved in PCSK9 binding through Solvent Accessible Surface Area Calculation for PCSK9-LDLR EGF-A interface. The sequence NeCLDNNggcsHVCNDL (SEQ ID NO: 14) (297-313) in LDLR was determined as critical. (Capital letters indicate buried side chain atoms in the complex)

A BLASTP search was performed against human amino acid database sequences. It was noticed that, for known PCSK9 substrates, APOER2 and VLDLR, some of the "capital" letters (underlined in the alignment shown below), in the motif, were not conserved. Hence the motif was modified to NeCLdNNggcsHvCnDL (SEQ ID NO: 14).

```
APOER2:
Query:  1    NECLDNNGGCSHVCNDLKIGYEC     23
             NECL NNGGCSH+C DLKIG+EC
Sbjct: 209   NECLHNNGGCSHICTDLKIGFEC    231

VLDLR:
Query:  1    NECLDNNGGCSHVCNDLKIGYEC     23
             NECL NNGGCSH+C DL IGYEC
Sbjct: 358   NECLVNNGGCSHICKDLVIGYEC    380
```

Algorithm: The following algorithm was developed to identify polypeptides that bind to PCSK9. A Perl script was written to perform motif searches. The program first checked for the presence of 2 consecutive residues CL, NN and DL. This greatly reduced the search space and shortened search time. Then, the program performed a tiered search in tight, medium or loose stringencies, allowing different numbers of spacing residues between the "capital" residues. The motifs searched in the tiered search were as follows:

Tight: N\wCL\wNN\w{4}H\wC\wDL
Medium 10: N\w{0,10}CL\w{0,10}NN\w{0,40}H\w{0,10}C\w{0,10}DL
Loose: N\w*CL\w*NN\w*H\w*C\w*DL The "Tight" stringency search strictly required LDLR, VLDLR and APOER2 residue spacings, while the "Medium 10" allowed up to 10 residue spacing between the critical residues that were indicated; and "Loose" allowed any residue spacing between the critical residues.

The "Loose" stringency search generated hundreds of hits; so, a BLASTP search was performed to obtain only those with BLASTP alignments which yielded an E value of 10 or lower, when the comparison was performed using BLASTP algorithm with default parameters except that the filter for low complexity was deactivated, over the length of said polypeptides identified, wherein the identified proteins were compared to a low density lipoprotein receptor EGF-A domain amino acid sequence. Compared to the initial BLASTP performed against all known human protein sequences, this last round of BLASTP against the "Loose" hits only were performed with a much smaller search database space, which resulted in a greater sensitivity that picked up alignments unidentified in the initial round of BLASTP. Matrilin-2 was found in this last round of BLASTP.

Searches against >=40 aa Start2Stop 6-frame translations of database sequences were also performed and resulted in one additional hit.

TABLE 1

PCSK9-interacting genes identified by sequence analysis

| Entrez gene ID | Name | desc | Alignment | | | found_by | peptide |
|---|---|---|---|---|---|---|---|
| 3949 | LDLR | LDLR/FUT1 | | | | self | IGYECL |
| 7804 | LRPS | ApoER | Query: 1 | NECLDNNGGCSHVCNDLKIGYEC | 23 | blast, | NECLHNNGGCSHICTDLK |
| | | | | NECL NNGGCSH+C DLKIG+EC | | tight | IGFEC |
| | | | Sbjct: 209 | NECLHNNGGCSHICTDLKIGFEC | 231 | | |

TABLE 1-continued

PCSK9-interacting genes identified by sequence analysis

| Entrez gene ID | Name | desc | Alignment | | | found_by | peptide |
|---|---|---|---|---|---|---|---|
| 7436 | VLDLR | VLDLR | Query: | 1 | NECLDNNGGCSHVCNDLKIGYEC 23<br>NECL NNGGCSH+C DL IGYEC | blast,<br>tight | NECLVNNGGCSHICKDLV<br>IGYEC |
| | | | Sbjct: | 358 | NECLVNNGGCSHICKDLVIGYEC 380 | | |
| 57758 | SCUBE2 | signal peptide,<br>CUB domain, EGF-<br>like 2 (SCUBE2) | Query: | 1 | NECLDNNGGCSHVCNDLKIGYEC 23<br>+ECL+NNGGC H C ++   YEC | blast,<br>loose | DECLENNGGCQHTCVNVM<br>GSYEC |
| | | | Sbjct: | 130 | DECLENNGGCQHTCVNVMGSYEC 152 | | |
| 170392 | OIT3 | oncoprotein<br>induced transcript<br>3 (OIT3) | Query: | 1 | NECLDNNGGCSHVCNDLKIGYEC 23<br>NEC NNGGCS +C +LK Y C | blast | NECEQNNGGCSEICVNLK<br>NSYRC |
| | | | Sbjct: | 184 | NECEGNNGGCSEICVNLKNSYRC 206 | | |
| 80274 | SCUBE1 | signal peptide,<br>CUB domain, EGF-<br>like 1 (SCUBE1) | Query: | 1 | NECLDNNGGCSHVCNDLKIGYEC 23<br>NECL NNGGC H C +    +EC | blast,<br>loose | NECLVNNGGCDHFCRNTV<br>GSFEC |
| | | | Sbjct: | 284 | NECLVNNGGCDHFCRNTVGSFEC 306 | | |
| 4035 | LRP1 | low density lipo-<br>protein-related<br>protein 1 (alpha-<br>2-macroglobulin<br>receptor)(LRP1) | Query: | 1 | NECLDNN-GGCSHVCNDLKIGYEC 23<br>NECL    GCS  C DLKIG++C | blast,<br>loose | NECLSRKLSGCSQDCEDL<br>KIGFKC |
| | | | Sbjct: | 2942 | NECLSRKLSGCSQDCEDLKIGFKC 2965 | | |
| 4036 | LRP2 | Lipoprotein<br>receptor-related<br>protein-2 (LRP2),<br>also called glyco-<br>protein 330 or<br>megalin (Farquhar,<br>1995), is part of<br>the Heymann<br>nephritis anti-<br>genic complex with<br>RAP (LRPAP1; MIM<br>104225) | Query: | 1 | NECLDNNGGCSHVC 14<br>N CL+NNGGCSH+C | blast,<br>loose | NPCLENNGGCSHLC or<br>NSCSDFNGGCTHECVQEP<br>FGAKCL |
| | | | Sbjct: | 2344 | NPCLENNGGCSHLC 2357 | | |
| | | | Query: | 1 | NECLDNNGGCSHVCNDLKIGYECL 24<br>N C D NGGC+H C    G +CL | | |
| | | | Sbjct: | 1351 | NSCSDFNGGCTHECVQEPFGAKCL 1374 | | |
| 4038 | LRP4 | LRP4/LRP10 | Query: | 1 | NECLDNNGGCSHVCNDLKIGYEC 23<br>N C DNNGGC+H+C LPSGQNYTC | blast,<br>loose | NRCGDNNGGCTHLCLPSG<br>QNYTC |
| | | | Sbjct: | 700 | NRCGDNNGGCTHLCLPSGQNYTC 722 | | |
| 222663 | SCUBE3 | signal peptide CUB<br>domain, EGF-like 3<br>(SCUBE3) | Query: | 1 | NECLDNNGGCSHVCNDLKIGYEC 23<br>+EC NNGGC H+C +    +EC | blast,<br>loose | DECRLNNGGCDHICRNTV<br>GSFEC |
| | | | Sbjct: | 279 | DECRLNNGGCDHICRNTVGSFEC 301 | | |
| 4041 | LRP5 | LRP5 | Query: | 1 | NECLDNNGGCSHVC 14<br>N C D NGGCSH+C | blast,<br>loose | NPCADRNGGCSHLC or<br>NDCMHNNGQCGQLCLAIP<br>GGHRC |
| | | | Sbjct: | 603 | NPCADRNGGCSHLC 616 | | |
| | | | Query: | 1 | NECLDNNGGCSHVCNDLKIGYEC 23<br>N+C+ NNG C  +C    G+ C | | |
| | | | Sbjct: | 904 | NDCMHNNGQCGQLCLAIPGGHRC 926 | | |
| 1953 | MEGF6 | MEGF6/EGFL3 | Query: | 1 | NECLDNNGGCSHVCNDLKIGYEC 23<br>N C NNGGCSH C+    G  C | blast,<br>loose | NSCEANNGGCSHGCSHTS<br>AGPLC |
| | | | Sbjct: | 228 | NSCEANNGGCSHGCSHTSAGPLC 250 | | |
| 4040 | LRP6 | LRP6 | Query: | 1 | NECLDNNGGCSHVCNDLKIGYEC 23<br>N C + NGGCSH+C    G   C | blast,<br>loose | NPCAEENGGCSHLCLYRP<br>QGLRC |
| | | | Sbjct: | 590 | NPCAEENGGCSHLCLYRPQGLRC 612 | | |
| 53353 | LRP1B | LRP1B | Query: | 3 | CLDNNGGCSHVC 14<br>C+ NNGGCSH+C | blast,<br>loose | CMINNGGCSHLC or<br>NMCRVNNGGCSTLCLAIP<br>GGRVC |
| | | | Sbjct: | 3277 | CMINNGGCSHLC 3288 | | |
| | | | Query: | 1 | NECLDNNGGCSHVCNDLKIGYEC 23<br>N C NNGGCS +C + G C | | |
| | | | Sbjct: | 796 | NMCRVNNGGCSTLCLAIPGGRVC 818 | | |
| 5627 | PROS1 | protein S (alpha)<br>(PROS1) | Query: | 1 | NECLDN---NGGCSHVCNDLKIGYEC 23<br>NEC D    NGGCS +C++   Y C | blast,<br>loose | NECKDPSNINGGCSQICD<br>NTPGSYHC |
| | | | Sbjct: | 159 | NECKDPSNINGGCSQICDNTPGSYHC 184 | | |
| 2621 | GAS6 | growth arrest-<br>specific 6<br>(GAS6) | Query: | 1 | NECLDNNGGCSHVCNDLKIGYEC 23<br>NEC   NGGC +C++    + C | blast,<br>loose | NECSQENGGCLQICHNKP<br>GSFHC |
| | | | Sbjct: | 158 | NECSQENGGCLQICHNKPGSFHC 180 | | |
| 7092 | TLL1 | tolloid-like 1<br>(TLL1) | Query: | 1 | NECLDNNGGCSHVCNDLKIGYEC 23<br>+EC +NGGC H C +    Y C | blast,<br>loose | DECSKDNGGCQHECVNTM<br>GSYMC |
| | | | Sbjct: | 732 | DECSKDNGGCQHECVNTMGSYMC 754 | | |
| 4811 | NID1 | nidogen 1 (NID1) | Query: | 1 | NECLDNNGGCSHVC 14<br>N C NNGGC+H+C | blast,<br>loose | NYCSVNNGGCTHLC |
| | | | Sbjct: | 1077 | NYCSVNNGGCTHLC 1090 | | |
| 7093 | TLL2 | tolloid-like 2<br>(TLL2) | Query: | 1 | NECLDNNGGCSHVCNDLKIGYEC 23<br>+EC +NGGC H C +    Y C | blast | DECAKDNGGCQHECVNTF<br>GSYLC |
| | | | Sbjct: | 734 | DECAKDNGGCQHECVNTFGSYLC 756 | | |
| 1950 | EGF | EGF | Query: | 3 | CLDNNGGCSHVC 14<br>CL NGGC H+C | blast | CLYQNGGCEHIC |
| | | | Sbjct: | 745 | CLYQNGGCEHIC 756 | | |
| 2201 | FBN2 | fibrillin 2 | Query: | 1 | NECLDNNGGCSHVCNDLKIGYEC 23<br>+EC+ NGGC  C + + YEC | blast,<br>loose | DECMIMNGGCDTQCTNSE<br>GSYEC |
| | | | Sbjct: | 1243 | DECMIMNGGCDTQCTNSEGSYEC 1265 | | |

TABLE 1-continued

PCSK9-interacting genes identified by sequence analysis

| Entrez gene ID | Name | desc | Alignment | | | found_by | peptide |
|---|---|---|---|---|---|---|---|
| 2200 | FBN1 | fibrillin 1 | Query: | 1 | NECLDNNGGCSHVCNDLKIGYEC 23<br>+EC  NGGC  C + +  YEC | blast, loose | DECSIMNGGCETFCTNSE GSYEC |
|  |  |  | Sbjct: | 1199 | DECSIMNGGCETFCTNSEGSYEC 1221 |  |  |
| 84467 | FBN3 | fibrillin 3 | Query: | 1 | NECLDNNGGCSHVCNDLKIGYEC 23<br>NEC  NGGC  C + +  Y C | blast, loose | NECRVQNGGCDVHCINTE GSYRC |
|  |  |  | Sbjct: | 1157 | NECRVQNGGCDVHCINTEGSYRC 1179 |  |  |
| 4054 | LTBP3 | latent transform-ing growth factor beta binding protein 3 (LTBP3) | Query: | 1 | NECLDNNGGCSHVCNDLKIGYEC 23<br>+ECLD +   + VC + + GY C | loose | DECLDESNCRNGVCENTR GGYRC |
|  |  |  | Sbjct: | 1037 | DECLDESNCRNGVCENTRGGYRC 1059 |  |  |
| 3910 | LAMA4 | laminin alpha 4 | Query: | 1 | NECLDNNGGCSHVCNDLKIGYEC 23<br>NECLD +G C H C    G  C | loose | NECLDGSYCVHCQRNTT GEHC |
|  |  |  | Sbjct: | 89 | NECLDGSYCVH-CQRNTTGEHC 110 |  |  |
| 4147 | MATN2 | matrilin 2 | Query: | 1 | NECLDNNGGCSHVCNDLKIGYEC 23<br>N C  N  GC H C +++  Y C | loose | NYCALNKPGCEHECVNME ESYYC |
|  |  |  | Sbjct: | 404 | NYCALNKPGCEHECVNMEESYYC 426 |  |  |
| 55576 | STAB2 | stabilin 2 | Query: | 1 | NECLDNNGGCSH--VCN 15<br>N CL  NGGCS   +CN | loose | NVCLTKNGGCSEFAICN |
|  |  |  | Sbjct: | 1557 | NVCLTKNGGCSEFAICN 1573 |  |  |
| 4853 | NOTCH2 | Notch 2 | Query: | 1 | NECLDN---NGGCSHVCNDLKIGYEC 23<br>NECL N   NGG  C++L  GY C | loose | NECLSNPCQNGGTCDNLV NGYRC |
|  |  |  | Sbjct: | 759 | NECLSNPCQNGG---TCDNLVNGYRC 781 |  |  |
| 8029 | CUBN | cubilin (a receptor for intrinsic factor-vitamin B12 complexes) | Query: | 1 | NECLDNNGGCS 11<br>NEC  NNGGCS | loose | NECEINNGGCS |
|  |  |  | Sbjct: | 307 | NECEINNGGCS 317 |  |  |
| 92737 | DNER | delta-notch-like EGF repeat-containing trans-membrane (DNER) | Query: | 1 | NECLDNNGGCSHVCNDLKIGYECL 24<br>NECL    + C DL GYEC+ | loose | NECLSAPCLNAATCRDLV NGYECV |
|  |  |  | Sbjct: | 507 | NECLSAPCLNAATCRDLVNGYECV 530 |  |  |

The sequences of the polypeptide set forth in table 1 are known. In an embodiment of the invention, the amino acid sequences of said proteins are as set forth below, wherein the respective EGF domains are underscored:

SCUBE2:
>gi|10190748|ref|NP_066025.1| CEGP1 protein
[Homo sapiens]
(SEQ ID NO: 16)
MGVAGRNRPGAAWAVLLLLLLLPPLLLLAGAVPPGRGRAAGPQEDVDE

CAQGLDDCHADALCQNTPTSYKCSCKPGYQGEGRQCEDIDECGNELNG

GCVHDCLNIPGNYRCTCFDGFMLAHDGHNCLDVDECLENNGGCQHTCV

NVMGSYECCCKEGFFLSDNQHTCIHRSEEGLSCMNKDHGCSHICKEAP

RGSVACECRPGFELAKNQRDCILTCNHGNGGCQHSCDDTADGPECSCH

PQYKMHTDGRSCLEREDTVLEVTESNTTSVVDGDKRVKRRLLMETCAV

NNGGCDRTCKDTSTGVHCSCPVGFTLQLDGKTCKDIDECQTRNGGCDH

FCKNIVGSFDCGCKKGFKLLTDEKSCQDVDECSLDRTCDHSCINHPGT

FACACNRGYTLYGFTHCGDTNECSINNGGCQQVCVNTVGSYECQCHPG

YKLHWNKKDCVEVKGLLPTSVSPRVSLHCGKSGGGDGCFLRCHSGIHL

SSDVTTIRTSVTFKLNEGKCSLKNAELFPEGLRPALPEKHSSVKESFR

YVNLTCSSGKQVPGAPGRPSTPKEMFITVEFELETNQKEVTASCDLSC

IVKRTEKRLRKAIRTLRKAVHREQFHLQLSGMNLDVAKKPPRTSERQA

ESCGVGQGHAENQCVSCRAGTYYDGARERCILCPNGTFQNEEGQMTCE

PCPRPGNSGALKTPEAWNMSECGGLCQPGEYSADGFAPCQLCALGTFQ

PEAGRTSCFPCGGGLATKHQGATSFQDCETRVQCSPGHEYNTTTHRCI

RCPVGTYQPEFGKNNCVSCPGNTTTDEDGSTNITQCKNRRCGGELGDF

TGYIESPNYPGNYPANTECTWTINPPPKRRILIVVPEIFLPIEDDCGD

YLVMRKTSSSNSVTTYETCQTYERPIAFTSRSKKLWIQFKSNEGNSAR

GFQVPYVTYDEDYQELIEDIVRDGRLYASENHQEILKDKKLIKALFDV

LAHPQNYFKYTAQESREMFPRSFIRLLRSKVSRFLRPYK

OIT3:
>gi|22749297|ref|NP_689848.1| oncoprotein-induced transcript 3 [Homo sapiens]
(SEQ ID NO: 17)
MPPFLLLTCLFITGTSVSPVALDPCSAYISLNEPWRNTDHQLDESQGP

PLCDNHVNGEWYHFTGMAGDAMPTFCIPENHCGTHAPVWLNGSHPLEG

DGIVQRQACASFNGNCCLWNTTVEVKACPGGYYVYRLTKPSVCFHVYC

GHFYDICDEDCHGSCSDTSECTCAPGTVLGPDRQTCFDENECEQNNGG

CSEICVNLKNSYRCECGVGRVLRSDGKTCEDVEGCHNNNGGCSHSCLG

SEKGYQCECPRGLVLSEDNHTCQVPVLCKSNAIEVNIPRELVGGLELF

LTNTSCRGVSNGTHVNILFSLKTCGTVVDVVNDKIVASNLVTGLPKQT

PGSSGDFIIRTSKLLIPVTCEFPRLYTISEGYVPNLRNSPLEIMSRNH

GIFPPFTLEIFKDNEFEEPYREALPTLKLRDSLYFGIEPVVHVSGLESL

VESCFATPTSKIDEVLKYYLIRDGCVSDDSVKQYTSRDHLAKHFQVPV

```
-continued
FKFVGKDHKEVFLHCRVLVCGVLDERSRCAQGCHRRMRRGAGGEDSAG

LQGQTLTGGPIRIDWED

SCUBE1:
>gi|120587029|ref|NP_766638.2| signal peptide,
CUB domain, EGF-like 1 [Homo sapiens]
                                    (SEQ ID NO: 18)
MGAAAVRWHLCVLLALGTRGRLAGGSGLPGSVDVDECSEGTDDCHIDA

ICQNTPKSYKCLCKPGYKGEGKQCEDIDECENDYYNGGCVHECINIPG

NYRCTCFDGFMLAHDGHNCLDVDECQDNNGGCQQICVNAMGSYECQCH

SGFFLSDNQHTCIHRSNEGMNCMNKDHGCAHICRETPKGGVACDCRPG

FDLAQNQKDCTLTCNYGNGGCQHSCEDTDTGPTCGCHQKYALHSDGRT

CIETCAVNNGGCDRTCKDTATGVRCSCPVGFTLQPDGKTCKDINECLV

NNGGCDHFCRNTVGSFECGCRKGYKLLTDERTCQDIDECSFERTCDHI

CINSPGSFQCLCHRGYILYGTTHCGDVDECSMSNGSCDQGCVNTKGSY

ECVCPPGRRLHWNGKDCVETGKCLSRAKTSPRAQLSCSKAGGVESCFL

SCPAHTLFVPDSENSYVLSCGVPGPQGKALQKRNGTSSGLGPSCSDAP

TTPIKQKARFKIRDAKCHLRPHSQARAKETARQPLLDHCHVTFVTLKC

DSSKKRRGRKSPSKEVSHITAEFEIETKMEEASDTCEADCLRKRAEQ

SLQAAIKTLRKSIGRQQFYVQVSGTEYEVAQRPAKALEGQGACGAGQV

LQDSKCVACGPGTHFGGELGQCVSCMPGTYQDMEGQLSCTPCPSSDGL

GLPGARNVSECGGQCSPGFFSADGFKPCQACPVGTYQPEPGRTGCFPC

GGGLLTKHEGTTSFQDCEAKVHCSPGHHYNTTTHRCIRCPVGTYQPEF

GQNHCITCPGNTSTDFDGSTNVTHCKNQHCGGELGDYTGYIESPNYPG

DYPANAECVWHIAPPPKRRILIVVPEIFLPIEDECGDVLVMRKSASPT

SITTYETCQTYERPIAFTSRSRKLWIQFKSNEGNSGKGFQVPYVTYDE

DYQQLIEDIVRDGRLYASENHQEILKDKKLIKALFDVLAHPQNYFKYT

AQESKEMFPRSFIKLLRSKVSRFLRPYK

LRP1:
>gi|126012562|ref|NP_002323.2| low density
lipoprotein-related protein 1 [Homo sapiens]
                                    (SEQ ID NO: 19)
MLTPPLLLLLPLLSALVAAAIDAPKTCSPKQFACRDQITCISKGWRCD

GERDCPDGSDEAPEICPQSKAQRCQPNEHNCLGTELCVPMSRLCNGVQ

DCMDGSDEGPHCRELQGNCSRLGCQHHCVPTLDGPTCYCNSSFQLQAD

GKTCKDFDECSVYGTCSQLCTNTDGSFICGCVEGYLLQPDNRSCKAKN

EPVDRPPVLLIANSQNILATYLSGAQVSTITPTSTRQTTAMDFSYANE

TVCWVHVGDSAAQTQLKCARMPGLKGFVDEHTINTSLSLHHVEQMAID

WLTGNFYFVDDIDDRIFVCNRNGDTCVTLLDLELYNPKGIALDPAMGK

VFFTDYGQIPKVERCDMDGQNRTKLVDSKIVFPHGITLDVLVSRLVYWA

DAYLDYIEVVDYEGKGRQTIIQGILIEHLYGLTVFENYLYATNSDNAN

AQQKTSVIRVNRFNSTEYQVVTRVDKGGALHIYHQRRQPRVRSHACEN

DQYGKPGGCSDICLLANSHKARTCRCRSGFSLGSDGKSCKKPEHELFL

VYGKGRPGIIRGMDMGAKVPDEHMIPIENLMNPRALDFHAETGFIYFA

DTTSYLIGRQKIDGTERETILKDGIHNVEGVAVDWMGDNLYWTDDGPK

KTISVARLEKAAQTRKTLIEGKMTHPRAIVVDPLNGWMYWTDWEEDPK

-continued
DSRRGRLERAWMDGSHRDIFVTSKTVLWPNGLSLDIPAGRLYWVDAFY

DRIETILLNGTDRKIVYEGPELNHAFGLCHHGNYLFWTEYRSGSVYRL

ERGVGGAPPTVTLLRSERPPIFEIRMYDAQQQQVGTNKCRVNNGGCSS

LCLATPGSRQCACAEDQVLDADGVTCLANPSYVPPPQCQPGEFACANS

RCIQERWKCDGDNDCLDNSDEAPALCHQHTCPSDRFKCENNRCIPNRW

LCDGDNDCGNSEDESNATCSARTCPPNQFSCASGRCIPISWTCDLDDD

CGDRSDESASCAYPTCFPLTQFTCNNGRCININWRCDNDNDCGDNSDE

AGCSHSCSSTQFKCNSGRCIPEHWTCDGDNDCGDYSDETHANCTNQAT

RPPGGCHTDEFQCRLDGLCIPLRWRCDGDTDCMDSSDEKSCEGVTHVC

DPSVKFGCKDSARCISKAWVCDGDNDCEDNSDEENCESLACRPPSHPC

ANNTSVCLPPDKLCDGNDDCGDGSDEGELCDQCSLNNGGCSHNCSVAP

GEGIVCSCPLGMELGPDNHTCQIQSYCAKHLKCSQKCDQNKFSVKCSC

YEGWVLEPDGESCRSLDPFKPFIIFSNRHEIRRIDLHKGDYSVLVPGL

RNTIALDFHLSQSALYWTDVVEDKIYRGKLLDNGALTSFEVVIQYGLA

TPEGLAVDWIAGNIYWVESNLDQIEVAKLDGTLRTTLLAGDIEHPRAI

ALDPRDGILFWTDWDASLPRIEAASMSGAGRRTVHRETGSGGWPNGLT

VDYLEKRILWIDARSDAIYSARYDGSGHMEVLRGHEFLSHPFAVTLYG

GEVYWTDWRTNTLAKANKWTGHNVTVVQRTNTQPFDLQVYHPSRQPMA

PNPCEANGGQGPCSHLCLINYNRTVSCACPHLMKLHKDNTTCYEFKKF

LLYARQMEIRGVDLDAPYYNYIISFTVPDIDNVTVLDYDAREQRVYWS

DVRTQAIKRAFINGTGVETVVSADLPNAHGLAVDWVSRNLFWTSYDTN

KKQINVARLDGSFKNAVVQGLEQPHGLVVHPLRGKLYWTDGDNISMAN

MDGSNRTLLFSGQKGPVGLAIDFPESKLYWISSGNHTINRCNLDGSGL

EVIDAMRSQLGKATALAIMGDKLWWADQVSEKMGTCSKADGSGSVVLR

NSTTLVMHMKVYDESIQLDHKGTNPCSVNNGDCSQLCLPTSETTRSCM

CTAGYSLRSGQQACEGVGSFLLYSVHEGIRGIPLDPNDKSDALVPVSG

TSLAVGIDFHAENDTIYWVDMGLSTISRAKRDQTWREDVVTNGIGRVE

GIAVDWIAGNIYWTDQGFDVIEVARLNGSFRYVVISQGLDKPRAITVH

PEKGYLFWTEWGQYPRIERSRLDGTERVVLVNVSISWPNGISVDYQDG

KLYWCDARTDKIERIDLETGENREVVLSSNNMDMFSVSVFEDFIYWSD

RTHANGSIKRGSKDNATDSVPLRTGIGVQLKDIKVFNRDRQKGTNVCA

VANGGCQQLCLYRGRGQRACACAHGMLAEDGASCREYAGYLLYSERTI

LKSIHLSDERNLNAPVQPFEDPEHMKNVIALAFDYRAGTSPGTPNRIF

FSDIHEGNIQQINDDGSRRITIVENVGSVEGLAYHRGWDTLYWTSYTT

STITRHTVDQTRPGAFERETVITMSGDDHPRAFVLDECQNLMFWTNWN

EQHPSIMRAALSGANVLTLIEKDIRTPNGLAIDHRAEKLYFSDATLDK

IERCEYDGSHRYVILKSEPVHPFGLAVYGEHIEWTDWVRRAVQRANKH

VGSNMKLLRVDIPQQPMGIIAVANDTNSCELSPCRINNGGCQDLCLLT

HQGHVNCSCRGGRILQDDLTCRAVNSSCRAQDEFECANGECINFSLTC

DGVPHCKDKSDEKPSYCNSRRCKKTFRQCSNGRCVSNMLWCNGADDCG
```

-continued

```
DGSDEIPCNKTACGVGEFRCRDGTCIGNSSRCNQFVDCEDASDEMNCS
ATDCSSYFRLGVKGVLFQPCERTSLCYAPSWVCDGANDCGDYSDERDC
PGVKRPRCPLNYFACPSGRCIPMSWTCDKEDDCEHGEDETHCNKFCSE
AQFECQNHRCISKQWLCDGSDDCGDGSDEAAHCEGKTCGPSSFSCPGT
HVCVPERWLCDGDKDCADGADESIAAGCLYNSTCDDREFMCQNRQCIP
KHFVCDHDRDCADGSDESPECEYPTCGPSEFRCANGRCLSSRQWECDG
ENDCHDQSDEAPKNPHCTSQEHKCNASSQFLCSSGRCVAEALLCNGQD
DCGDSSDERGCHINECLSRKLSGCSQDCEDLKIGFKCRCRPGFRLKDD
GRTCADVDECSTTFPCSQRCINTHGSYKCLCVEGYAPRGGDPHSCKAV
TDEEPFLIFANRYYLRKLNLDGSNYTLLKQGLNNAVALDFDYREQMIY
WTDVTTQGSMIRRMHLNGSNVQVLHRTGLSNPDGLAVDWVGGNLYWCD
KGRDTIEVSKLNGAYRTVLVSSGLREPRALVVDVQNGYLYWTDWGDHS
LIGRIGMDGSSRSVIVDTKITWPNGLTLDYVTERIYWADAREDYIEFA
SLDGSNRHVVLSQDIPHIFALTLFEDYVYWTDWETKSINRAHKTTGTN
KTLLISTLHRPMDLHVFHALRQPDVPNHPCKVNNGGCSNLCLLSPGGG
HKCACPTNFYLGSDGRTCVSNCTASQFVCKNDKCIPFWWKCDTEDDCG
DHSDEPPDCPEFKCRPGQFQCSTGICTNPAFICDGDNDCQDNSDEANC
DIHVCLPSQFKCTNTNRCIPGIFRCNGQDNCGDGEDERDCPEVTCAPN
QFQCSITKRCIPRVWVCDRDNDCVDGSDEPANCTQMTCGVDEFRCKDS
GRCIPARWKCDGEDDCGDGSDEPKEECDERTCEPYQFRCKNNRCVPGR
WQCDYDNDCGDNSDEESCTPRPCSESEFSCANGRCIAGRWKCDGDHDC
ADGSDEKDCTPRCDMDQFQCKSGHCIPLRWRCDADADCMDGSDEEACG
TGVRTCPLDEFQCNNTLCKPLAWKCDGEDDCGDNSDENPEECARFVCP
PNRPFRCKNDRVCLWIGRQCDGTDNCGDGTDEEDCEPPTAHTTHCKDK
KEFLCRNQRCLSSSLRCNMFDDCGDGSDEEDCSIDPKLTSCATNASIC
GDEARCVRTEKAAYCACRSGEHTVPGQPGCQDINECLRFGTCSQLCNN
TKGGHLCSCARNFMKTHNTCKAEGSEYQVLYIADDNEIRSLFPGHPHS
AYEQAFQGDESVRIDAMDVHVKAGRVYWTNWHTGTISYRSLPPAAPPT
TSNRHRRQIDRGVTHLNISGLKMPRGIAIDWVAGNVYWTDSGRDVIEV
AQMKGENRKTLISGMIDEPHAIVVDPLRGTMYWSDWGNHPKIETAAMD
GTLRETLVQDNIQWPTGLAVDYHNERLYWADAKLSVIGSIRLNGTDPI
VAADSKRGLSHPFSIDVFEDYIYGVTYINNRVFKIHKFGHSPLVNLTG
GLSHASDVVLYHQHKQPEVTNPCDRKKCEWLCLLSPSGPVCTCPNGKR
LDNGTCVPVPSPTPPPDAPRPGTCNLQCFNGGSCFLNARRQPKCRCQP
RYTGDKCELDQCWEHCRNGGTCAASPSGMPTCRCPTGFTGPKCTQQVC
AGYCANNSTCTVNQGNQPQCRCLPGFLGDRCQYRQCSGYCENFGTCQM
AADGSRQCRCTAYFEGSRCEVNKCSRCLEGACVVNKQSGDVTCNCTDG
RVAPSCLTCVGHCSNGGSCTMNSKMMPECQCPPHMTGPRCEEHVFSQQ
QPGHIASILIPLLLLLLVLVAGVVFWYKRRVQGAKGFQHQRMTNGAM
NVEIGNPTYKMYEGGEPDDVGGLLDADFALDPDKPTNFTNPVYATLYM
GGHGSRHSLASTDEKRELLGRGPEDEIGDPLA
```

```
LRP2:
>gi|126012573|ref|NP_004516.2| low density
lipoprotein-related protein 2 [Homo sapiens]
                                       (SEQ ID NO: 20)
MDRGPAAVACTLLLALVACLAPASGQECDSAHFRCGSGHCIPADWRCD
GTKDCSDDADEIGCAVVTCQQGYFKCQSEGQCIPNSWVCDQDQDCDDG
SDERQDCSQSTCSSHQITCSNGQCIPSEYRCDHVRDCPDGADENDCQY
PTCEQLTCDNGACYNTSQKCDWKVDCRDSSDEINCTEICLHNEFSCGN
GECIPRAYVCDHDNDCQDGSDEHACNYPTCGGYQFTCPSGRCIYQNWV
CDGEDDCKDNGDEDGCESGPHDVHKCSPREWSCPESGRCISIYKVCDG
ILDCPGREDENNTSTGKYCSMTLCSALNCQYQCHETPYGGACFCPPGY
IINHNDSRTCVEFDDCQIWGICDQKCESRPGRHLCHCEEGYILERGQY
CKANDSFGEASIIFSNGRDLLIGDIHGRSFRILVESQNRGVAVGVAFH
YHLQRVFWTDTVQNKVFSVDINGLNIQEVLNVSVETPENLAVDWVNNK
TYLVETKVNRIDMVNLDGSYRVTLITENLGHPRGIAVDPTVGYLFFSD
WESLSGEPKLERAFMDGSNRKDLVKTKLGWPAGVTLDMISKRVYWVDS
RFDYIETVTYDGIQRKTVVHGGSLIPHPFGVSLFEGQVFFTDWTKMAV
LKANKFTETNPQVYYQASLRPYGVTVYHSLRQPYATNPCKDNNGGCEQ
VCVLSHRTDNDGLGFRCKCTFGFQLDTDERHCIAVQNFLIFSSQVAIR
GIPFTLSTQEDVMVPVSGNPSFFVGIDFDAQDSTIFFSDMSKHMIFKQ
KIDGTGREILAANRVENVESLAFDWISKNLYWTDSHYKSISVMRLADK
TRRTVVQYLNNPRSVVVHPFAGYLFFTDWFRPAKIMRAWSDGSHLLPV
INTTLGWPNGLAIDWAASRLYWVDAYFDKIEHSTFDGLDRRRLGHIEQ
MTHPFGLAIFGEHLFFTDWRLGAIIRVRKADGGEMTVIRSGIAYILHL
KSYDVNIQTGSNACNQPTHPNGDCSHFCFPVPNFQRVCGCPYGMRLAS
NHLTCEGDPTNEPPTEQCGLFSFPCKNGRCVPNYYLCDGVDDCHDNSD
EQLCGTLNNTCSSSAFTCGHGECIPAHWRCDKRNDCVDGSDEHNCPTH
APASCLDTQYTCDNHQCISKNWVCDTDNDCGDGSDEKNCNSTETCQPS
QFNCPNHRCIDLSFVCDGKDCVDGSDEVGCVLNCTASQFKCASGDKC
IGVTNRCDGVFDCSDNSDEAGCPTRPPGMCHSDEFQCQEDGICIPNFW
ECDGHPDCLYGSDEHNACVPKTCPSSYFHCDNGNCIHRAWLCDRDNDC
GDMSDEKDCPTQPFRCPSWQWQCLGHNICVNLSVVCDGIFDCPNGTDE
SPLCNGNSCSDFNGGCTHECVQEPFGAKCLCPLGFLLANDSKTCEDID
ECDILGSCSQHCYNMRGSFRCSCDTGYMLESDGRTCKVTASESLLLLV
ASQNKIIADSVTSQVHNIYSLVENGSYIVAVDFDSISGRIFWSDATQG
KTWSAFQNGTDRRVVFDSSIILTETIAIDWVGRNLYWTDYALETIEVS
KIDGSHRTVLISKNLTNPRGLALDPRMNEHLLFWSDWGHHPRIERASM
DGSMRTVIVQDKIFWPCGLTIDYPNRLLYFMDSYLDYMDFCDYNGHHR
RQVIASDLIIRHPYALTLFEDSVYWTDRATRRVMRANKWHGGNQSVVM
YNIQWPLGIVAVHPSKQPNSVNPCAFSRCSHLCLLSSQGPHFYSCVCP
SGWSLSPDLLNCLRDDQPFLITVRQHIIFGISLNPEVKSNDAMVPIAG
IQNGLDVEFDDAEQYIYWVENPGEIHRVKTDGTNRTVFASISMVGPSM
```

NLALDWISRNLYSTNPRTQSIEVLTLHGDIRYRKTLIANDGTALGVF
PIGITVDPARGKLYWSDQGTDSGVPAKIASANMDGTSVKTLFTGNLEH
LECVTLDIEEQKLYWAVTGRGVIERGNVDGTDRMILVHQLSHPWGIAV
HDSFLYYTDEQYEVIERVDKATGANKIVLRDNVPNLRGLQVYHRRNAA
ESSNGCSNNMNACQQICLPVPGGLFSCACATGFKLNPDNRSCSPYNSF
IVVSMLSAIRGFSLELSDHSETMVPVAGQGRNALHVDVDVSSGFIYWC
DFSSSVASDNAIRRIKPDGSSLMNIVTHGIGENGVRGIAVDWVAGNLY
FTNAFVSETLIEVLRINTTYRRVLLKVTVDMPRHIVVDPKNRYLFWAD
YGQRPKIERSFLDCTNRTVLVSEGIVTPRGLAVDRSDGYVYWVDDSLD
IIARIRINGENSEVIRYGSRYPTPYGITVFENSIIWVDRNLKKIFQAS
KEPENTEPPTVIRDNINWLRDVTIFDKQVQPRSPAEVNN<u>NPCLENNGG</u>
<u>CSHLC</u>FALPGLHTPKCDCAFGTLQSDGKNCAISTENFLIFALSNSLRS
LHLDPENHSPPFQTINVERTVMSLDYDSVSDRIYFTQNLASGVGQISY
ATLSSGIHTPTVIASGIGTADGIAFDWITRRIYYSDYLNQMINSMAED
GSNRTVIARVPKPRAIVLDPCQGYLYWADWDTHAKIERATLGGNFRVP
IVNSSLVMPSGLTLDYEEDLLYWVDASLQRIERSTLTGVDREVIVNAA
VHAFGLTLYGQYIYWTDLYTQRIYRANKYDGSGQIAMTTNLLSQPRGI
NTVVKNQKQQCNNPCEQFNGGCSHICAPGPNGAECQCPHEGNWYLANN
RKHCIVDNGERCGASSFTCSNGRCISEEWKCDNDNCGDGSDEMESVC
ALHTCSPTAFTCANGRCVQYSYRCDYYNDCGDGSDEAGCLFRDCNATT
EFMCNNRRCIPREFICNGVDNCHDNNTSDEKNCPDRTCQSGYTKCHNS
NICIPRVYLCDGDNDCGDNSDENPTYCTTHTCSSSEFQCASGRCIPQH
WYCDQETDCFDASDEPASCGHSERTCLADEFKCDGGRCIPSEWICDGD
NDCGDMSDEDKRHQCQNQNCSDSEFLCVNDRPPDRRCIPQSWVCDGDV
DCTDGYDENQNCTRRTCSENEFTCGYGLCIPKIFRCDRHNDCGDYSDE
RGCLYQTCQQNQFTCQNGRCISKTFVCDEDNDCGDGSDELMHLCHTPE
PTCPPHEFKCDNGRCIEMMKLCNHLDDCLDNSDEKGCGINECHDPSIS
GCDHNCTDTLTSFYCSCRPGYKLMSDKRTCVDIDECTEMPFVCSQKCE
NVIGSYICKCAPGYLREPDGKTCRQNSNIEPYLIFSNRYYLRNLTIDG
YFYSLILEGLDNVVALDFDRVEKRLYWIDTQRQVIERMELNKTNKETI
INHRLPAAESLAVDWVSRKLYWLDARLDGLFVSDLNGGHRRMLAQHCV
DANNTFCFDNPRGLALHPQYGYLYWADWGHRAYIGRVGMDGTNKSVII
STKLEWPNGITIDYTNDLLYWADAHLGYIEYSDLEGHHRHTVYDGALP
HPFAITIFEDTIYWTDWNTRTVEKGNKYDGSNRQTLVNTTHRPFDIHV
YHPYRQPIVSNPCGTNNGGCSHLCLIKPGGKGFTCECPDDFRTLQLSG
STYCMPMCSSTQFLCANNEKCIPIWWKCDGQKDCSDGSDELALCPQRF
CRLGQFQCSDGNCTSPQTLCNAHQNCPDGSDEDRLLCENHHCDSNEWQ
CANKRCIPESWQCDTENDCEDNSDEDSSHCASRTCRPGQFRCANGRCI
PQAWKCDVDNDCGDHSDEPIEECMSSAHLCDNFTEFSCKTNYRCIPKW
AVCNGVDDCRDNSDEQGCEERTCHPVGDFRCKNHHCIPLRWQCDGQND
CGDNSDEENCAPRECTESEFRCVNQQCIPSRWICDHYNDCGDNSDERD

CEMRTCHPEYFQCTSGHCVHSELKCDGSADCLDASDEADCPTRFPDGA
YCQATMFECKNHVCIPPYWKCDGDDDCGDGSDEELHLCLDVPCNSPNR
ERCDNNRCIYSHEVCNGVDDCGDGTDETEEHCRKPTPKPCTEYEYKCG
NGHCIPHDNVCDDADDCGDWSDELGCNKGKERTCAENICEQNCTQLNE
GGFICSCTAGFETNVEDRTSCLDINECEQFGTCPQHCRNTKGSYECVC
ADGFTSMSDRPGKRCAAEGSSPLLLLPDNVRIRKYNLSSERFSEYLQD
EEYIQAVDYDWDPKDIGLSVVYYTVRGEGSRFGAIKRAYIPNFESGRN
NLVQEVDLKLKYVMQPDGIAVDWVGRHIYWSDVKNKRIEVAKLDGRYR
KWLISTDLDQPAAIAVNPKLGLMFWTDWGKEPKIESAWMNGEDRNILV
FEDLGWPTGLSIDYLNNDRIYWSDFKEDVIETIKYDGTDRRVIAKEAM
NPYSLDIFEDQLYWISKEKGEVWKQNKFGQGKKEKTLVVNPWLTQVRI
FHQLRYNKSVPNLCKQICSHLCLLRPGGYSCACPQGSSFIEGSTTECD
AAIELPINLPPPCRCMHGGNCYFDETDLPKCKCPSGYTGKYCEMAFSK
GISPGTTAVAVLLTILLIVVIGALAIAGFFHYRRTGSLLPALPKLPSL
SSLVKPSENGNGVTFRSGADLNMDIGVSGEGPETAIDRSMAMSEDFVM
EMGKQPIIFENPMYSARDSAVKVVQPIQVTVSENVDNKNYGSPINPSE
IVPETNPTSPAADGTQVTKWNLFKRKSKQTTNFENPIYAQMENEQKES
VAATPPPSPSLPAKPKPPSRRDPTPTYSATEDTFKDTANLVKEDSEV

LRP4:
>gi|157384998|ref|NP_002325.2| low density
lipoprotein receptor-related protein 4
[Homo sapiens]
(SEQ ID NO: 21)
MRRQWGALLLGALLCAHGLASSPECACGRSHFTCAVSALGECTCIPAQ
WQCDGDNDCGDHSDEDGCILPTCSPLDFHCDNGKCIRRSWVCDGDNDC
EDDSDEQDCPPRECEEDEFPCQNGYCIRSLWHCDGDNDCGDNSDEQCD
MRKCSDKEFRCSDGSCIAEHWYCDGDTDCKDGSDEENCPSAVPAPPCN
LEEFQCAYGRCILDIYHCDGDDDCGDWSDESDCSSHQPCRSGEFMCDS
GLCINAGWRCDGDADCDDQSDERNCTTSMCTAEQFRCHSGRCVRLSWR
CDGEDDCADNSDEENCENTGSPQCALDQFLCWNGRCIGQRKLCNGVND
CGDNSDESPQQNCRPRTGEENCNVNNGGCAQKCQMVRGAVQCTCHTGY
RLTEDGHTCQDVNECAEEGYCSQGCTNSEGAFQCWCETGYELRPDRRS
CKALGPEPVLLFANRIDIRQVLPHRSEYTLLLNNLENAIALDFHHRRE
LVFWSDVTLDRILRANLNGSNVEEVVSTGLESPGGLAVDWVHDKLYNT
DSGTSRIEVANLDGAHRKVLLWQNLEKPRAIALHPMEGTIYWTDWGNT
PRIEASSMDGSGRRIIADTHLFWPNGLTIDYAGRRMYWVDAKHHVIER
ANLDGSHRKAVISQGLPHPFAITVFEDSLYWTDWHTKSINSANKFTGK
NQEIIRNKLHFPMDIHTLHPQRQPAGK<u>NRCGDNNGGCTHLCLPSGQNY</u>
<u>TC</u>ACPTGERKISSHACAQSLDKFLLFARRMDIRRISFDTEDLSDDVIP
LADVRSAVALDWDSRDDHVYWTDVSTDTISRAKWDGTGQEVVVDTSLE
SPAGLAIDWVTNKLYWTDAGTDRIEVANTDGSMRTVLIWENLDRPRDI
VVEPMGGYMYWTDWGASPKIERAGMDASGRQVIISSNLTWPNGLAIDY
GSQRLYWADAGMKTIEFAGLDGSKRKVLIGSQLPHPFGLTLYGERIYW -continued TDWQTKSIQSADRLTGLDRETLQENLENLMDIHVFHRRRPPVSTPCAM
ENGGCSHLCLRSPNPSGFSCTCPTGINLLSDGKTCSPGMNSFLIFARR
IDIRMVSLDIPYFADVVVPINITMKNTIAIGVDPQEGKVYWSDSTLHR
ISRANLDGSQHEDIITTGLQTTDGLAVDAIGRKVYWTDTGTNRIEVGN
LDGSMRKVLVWQNLDSPRAIVLYHEMGFMYWTDWGENAKLERSGMDGS
DRAVLINNNLGWPNGLTVDKASSQLLWADAHTERIEAADLNGANRHTL
VSPVQHPYGLTLLDSYIYWTDWQTRSIHRADKGTGSNVILVRSNLPGL
MDMQAVDRAQPLGENKCGSRNGGCSHLCLPRPSGFSCACPTGIQLKGD
GKTCDPSPETYLLFSSRGSIRRISLDTSDHTDVHVPVPELNNVISLDY
DSVDGKVYYTDVFLDVIRRADLNGSNMETVIGRGLKTTDGLAVDWVAR
NLYWTDTGRNTIEASRLDGSCRKVLINNSLDEPRAIAVFPRKGYLFWT
DWGHIAKIERANLDGSERKVLINTDLGWPNGLTLDYDTRRIYWVDAHL
DRIESADLNGKLRQVLVSHVSHPFALTQQDRWIYWTDWQTKSIQRVDK
YSGRNKETVLANVEGLMDIIVVSPQRQTGTNACGVNNGGCTHLCFARA
SDFVCACPDEPDSRPCSLVPGLVPPAPRATGMSEKSPVLPNTPPTTLY
SSTTRTRTSLEEVEGRCSERDARLGLCARSNDAVPAAPGEGLHISYAI
GGLLSILLILVVIAALMLYRHKKSKFTDPGMGNLTYSNPSYRTSTQEV
KIEAIPKPAMYNQLCYKKEGGPDHNYTKEKIKIVEGICLLSGDDAEWD
DLKQLRSSRGGLLRDHVCMKTDTVSIQASSGSLDDTETEQLLQEEQSE
CSSVHTAATPERRGSLPDTGWKHERKLSSESQV SCUBE3:
>gi|31377568|ref|NP_689966.2| signal peptide,
CUB domain, EGF-like 3 [Homo sapiens]
(SEQ ID NO: 22)
MGSGRVPGLCLLVLLVHARAAQYSKAAQDVDECVEGTDNCHIDAICQN
TPRSYKCICKSGYTGDGKHCKDVDECEREDNAGCVHDCVNIPGNYRCT
CYDGFHLAHDGHNCLDVDECAEGNGGCQQSCVNMMGSYECHCREGFFL
SDNQHTCIQRPEEGMNCMNKNHGCAHICRETPKGGIACECRPGFELTK
NQRDCKLTCNYGNGGCQHTCDDTEQGPRCGCHIKFVLHTDGKTCIETC
AVNNGGCDSKCHDAATGVHCTCPVGFMLQPDRKTCKDIDECRLNNGGC
DHICRNTVGSFECSCKKGYKLLINERNCQDIDECSFDRTCDHICVNTP
GSFQCLCHRGYLLYGITHCGDVDECSINRGGCRFGCINTPGSYQCTCP
AGQGRLHWNGKDCTEPLKCQGSPGASKAMLSCNRSGKKDTCALTCPSR
ARFLPESENGFTVSCGTPSPRAAPARAGHNGNSTNSNHCHEAAVLSIK
QRASFKIKDAKCRLHLRNKGKTEEAGRITGPGGAPCSECQVTFIHLKC
DSSRKGKGRRARTPPGKEVTRLTLELEAEVRAEETTASCGLPCLRQRM
ERRLKGSLKMLRKSINQDRFLLRLAGLDYELAHKPGLVAGERAEPMES
CRPGQHRAGTKCVSCPQGTYYHGQTEQCVPCPAGTFQEREGQLSCDLC
PGSDAHGPLGATNVTTCAGQCPPGQHSVDGFKPCQPCPRGTYQPEAGR
TLCFPCGGGLTTKHEGAISFQDCDTKVQCSPGHYYNTSIHRCIRCAMG
SYQPDFRQNFCSRCPGNTSTDEDGSTSVAQCKNRQCGGELGEFTGYIE
SPNYPGNYPAGVECIWNINPPPKRKILIVVPEIFLPSEDECGDVLVMR
KNSSPSSITTYETCQTYERPIAFTARSRKLWINFKTSEANSARGFQIP
YVTYDEDYEQLVEDIVRDGRLYASENHQEILKDKKLIKAFFEVLAHPQ
NYFKYTEKHKEMLPKSFIKLLRSKVSSFLRPYK LRP5:
>gi|119709832|ref|NP_002326.2| low density
lipoprotein receptor-related protein 5
[Homo sapeins]
(SEQ ID NO: 23)
MEAAPPGPPWPLLLLLLLLALCGCPAPAAASPLLLFANRRDVRLVDA
GGVKLESTIVVSGLEDAAAVDFQFSKGAVYWTDVSEEAIKQTYLNQTG
AAVQNVVISGLVSPDGLACDWVGKKLYWTDSETNRIEVANLNGTSRKV
LFWQDLDQPRAIALDPAHGYMYWTDWGETPRIERAGMDGSTRKIIVDS
DIYWPNGLTIDLEEQKLYWADAKLSFIHRANLDGSFRQKVVEGSLTHP
FALTLSGDTLYWTDWQTRSIHACNKRTGGKRKEILSALYSPMDIQVLS
QERQPFFHTRCEEDNGGCSHLCLLSPSEPFYTCACPTGVQLQDNGRTC
KAGAEEVLLLARRTDLRRISLDTPDFTDIVLQVDDIRHAIAIDYDPLE
GYVYWTDDEVRAIRRAYLDGSGAQTLVNTEINDPDGIAVDWVARNLYW
TDTGTDRIEVTRLNGTSRKILVSEDLDEPRAIALHPVMGLMYWTDWGE
NPKIECANLDGQERRVLVNASLGWPNGLALDLQEGKLYWGDAKTDKIE
VINVDGTKRRTLLEDKLPHIFGFTLLGDFIYWTDWQRRSIERVHKVKA
SRDVIIDQLPDLMGLKAVNVAKVVGTNPCADRNGGCSHLCFFTPHATR
CGCPIGLELLSDMKTCIVPEAFLVFTSRAAIHRISLETNNNDVAIPLT
GVKEASALDFDVSNNHIYWTDVSLKTISRAFMNGSSVEHVVEFGLDYP
EGMAVDWMGKNLYWADTGTNRIEVARLDGQFRQVLVWRDLDNPRSLAL
DPTKGYIYWTEWGGKPRIVRAFMDGTNCMTLVDKVGRANDLTIDYADQ
RLYWTDLDTNMIESSNMLGQERVVIADDLPHPFGLTQYSDYIYWTDWN
LHSIERADKTSGRNRTLIQGHLDFVMDILVEHSSRQDGLNDCMHNNGQ
CGQLCLAIPGGHRCGCASHYTLDPSSRNCSPPTTFLLFSQKSAISRMI
PDDQHSPDLILPLHGLRNVKAIDYDPLDKFIYWVDGRQNIKRAKDDGT
QPFVLTSLSQGQNPDRQPHDLSIDIYSRTLFWTCEATNTINVHRLSGE
AMGVVLRGDRDKPRAIVVNAERGYLYFTNMQDRAAKIERAALDGTERE
VLFTTGLIRPVALVVDNTLGKLFWVDADLKRIESCDLSGANRLTLEDA
NIVQPLGLTILGKHLYWIDRQQQMIERVEKTTGDKRTRIQGRVAHLTG
IHAVEEVSLEEFSAHPCARDNGGCSHICIAKGDGTPRCSCPVHLVLLQ
NLLTCGEPPTCSPDQFACATGEIDCIPGAWRCDGFPECDDQSDEEGCP
VCSAAQFPCARGQCVDLRLRCDGEADCQDRSDEADCDAICLPNQFRCA
SGQCVLIKQQCDSFPDCIDGSDELMCEITKPPSDDSPAHSSAIGPVIG
IILSLFVMGGVYFVCQRVVCQRYAGANGPFPHEYVSGTPHVPLNFIAP
GGSQHGPFTGIACGKSMMSSVSLMGGRGGVPLYDRNHVTGASSSSSSS
TKATLYPPILNPPPSPATDPSLYNMDMFYSSNIPATARPYRPYIIRGM
APPTTPCSTDVCDSDYSASRWKASKYYLDLNSDPYPPPPTPHSQYL
SAEDSCPPSPATERSYFHLFPPPPSPCTDSS MEGF6:
>gi|110347457|ref|NP_001400.3| EGF-like-domain,
multiple 3 [Homo sapiens]
(SEQ ID NO: 24)
MSFLEEARAAGRAVVLALVLLLLPAVPVGASVPPRPLLPLQPGMPHVC

AEQELTLVGRRQPCVQALSHTVPVWKAGCGWQAWCVGHERRTVYYMGY

RQVYTTEARTVLRCCRGWMQQPDEEGCLSAECSASLCFHGGRCVPGSA

QPCHCPPGFQGPRCQYDVDECRTHNGGCQHRCVNTPGSYLCECKPGFR

LHTDSRTCLAINSCALGNGGCQHHCVQLTITRHRCQCRPGFQLQEDGR

HCVRRSPCANRNGSCMHRCQVVRGLARCECHVGYQLAADGKACEDVDE

CAAGLAQCAHGCLNTQGSFKCVCHAGYELGADGRQCYRIEMEIV<u>NSCE

ANNGGCSHGCSHTSAGPLCTC</u>PRGYELDTDQRTCIDVDDCADSPCCQQ

VCTNNPGGYECGCYAGYRLSADGCGCEDVDECASSRGGCEHHCTNLAG

SFQCSCEAGYRLHEDRRGCSPLEEPMVDLDGELPFVRPLPHIAVLQDE

LPQLFQDDDVGADEEEAELRGEHTLTEKEVCLDDSFGHDCSLTCDDCR

NGGTCLLGLDGCDCPEGWTGLICNETCPPDTFGKNCSFSCSCQNGGTC

DSVTGACRCPPGVSGTNCEDGCPKGYYGKHCRKKCNCANRGRCHRLYG

ACLCDPGLYGRECHLTCPPWAFGPGCSEECQCVQPHTQSCDKRDGSCS

CKAGFRGERCQAECELGYFGPGCWQACTCPVGVACDSVSGECGKRCPA

GFQGEDCGQECPVGTFGVNCSSSCSCGGAPCHGVTGQCRCPPGRTGED

CEADCPEGRWGLGCQEICPACQHAARCDPETGACLCLPGFVGSRCQDV

CPAGWYGPSCQTRCSCANDGHCHPATGHCSCAPGWTGFSCQRACDTGH

WGPDCSHPCNCSAGHGSCDAISGLCLCEAGYVGPRCEQQCPQGHFGPG

CEQRCRCQHGAACDHVSGACTCPAGWRGTFCEHACPAGFFGLDCRSAC

NCTAGAACDAVNGSCLCPAGRRGPRCAETCPAHTYGHNCSQACACFNG

ASCDPVHGQCHCAPGWMGPSCLQACPAGLYGDNCRHSCLCQNGGTCDP

VSGHCACPEGWAGLACEKECLPRDVRAGCRHSGGCLNGGLCDPHTGRC

LCPAGWTGDKCQSPCLRGWFGEACAQRCSCPPGAACHHVTGACRCPPG

FTGSSGCEQACPPGSFGEDCAQMCQCPGENPACHPATGTCSCAAGYHGP

SCQQRCPPGRYGPGCEQLCGCLNGGSCDAATGACRCPTGFLGTDCNLT

CPQGRFGPNCTHVCGCGQGAACDPVTGTCLCPPGRAGVRCERGCPQNR

FGVGCEHTCSCRNGGLCHASNGSCSCGLGWTGRHCELACPPGRYGAAC

HLECSCHNNSTCEPATGTCRCGPGFYGQACEHPCPPGFHGAGCQGLCW

CQHGAPCDPISGRCLCPAGFEGHFCERGCEPGSFGEGCHQRCDCDGGA

PCDPVTGLCLCPPGRSGATCNLDCRRGQFGPSCTLHCDCGGGADCDPV

SGQCHCVDGYMGPTCREGGPLRLPENPSLAQGSAGTLPASSRPTSRSG

GPARH

LRP6:
>gi|148727288|ref|NP_002327.2| low density
lipoprotein receptor-related protein 6
[Homo sapiens]
(SEQ ID NO: 25)
MGAVLRSLLACSFCVLLRAAPLLLYANRRDLRLVDATNGKENATIVVG

GLEDAAAVDFVFSHGLIYWSDVSEEAIKRTEFNKTESVQNVVVSGLLS

PDGLACDWLGEKLYWTDSETNRIEVSNLDGSLRKVLFWQELDQPRAIA

LDPSSGDMYWTDWGEVPKIERAGMDGSSRFIIINSEIYWPNGLTLDYE

EQKLYWADAKLNFIHKSNLDGINRQAVVKGSLPHPFALTLFEDILYWI

DWSTHSILACNKYTGEGLREIHSDIFSPMDIHAFSQQRQPNATNPCGI

DNGGCSHLCLMSPVKPFYQCACPIGVKLLENGKICKDGATELLLLARR

IDLRRISLDTPDFTDIVLQLEDIRHAIAIDYDPVEGYIYWIDDEVRAI

RRSFIDGSGSQFVVTAQIAHPDGIAVDWVARNLYWTDIGTDRIEVIRL

NGTMRKILISEDLEEPRAIVLDPMVGYMYWIDWGEIPKIERAALDGSD

RVVLVNTSLGWPNGLALDYDEGKIYWGDAKTDKIEVMNIDGIGRRVLV

EDKIPHIFGFTLLGDYVYWIDWQRRSIERVHKRSAEREVIIDQLPDLM

GLKAINVHRVIGS<u>NPCAEENGGCSHLCLYRPQGLRCAC</u>PIGFELISDM

KICIVPEAFLLFSRRADIRRISLETNNNNVAIPLIGVKEASALDFDVI

DNRIYWIDISLKTISRAFMNGSALEHVVEFGLDYPEGMAVDWLGKNLY

WADTGINRIEVSKLDGQHRQVLVWKDLDSPRALALDPAEGEMYWIEWG

GKPKIDRAAMDGSERTTLVPNVGRANGLTIDYAKRRLYWIDLDINLIE

SSNMLGLNREVIADDLPHPFGLIQYQDYIYWIDWSRRSIERANKTSGQ

NRIIIQGHLDYVMDILVEHSSRQSGWNECASSNGHCSHLCLAVPVGGF

VCGCPAHYSLNADNRICSAPTIFLLFSQKSAINRMVIDEQQSPDIILP

IHSLRNVRAIDYDPLDKQLYWIDSRQNMIRKAQEDGSQGFTVVVSSVP

SQNLEIQPYDLSIDIYSRYIYWICEATNVINVIRLDGRSVGVVLKGEQ

DRPRAVVVNPEKGYMYFINLQERSPKIERAALDGTEREVLFFSGLSKP

IALALDSRLGKLFWADSDLRRIESSDLSGANRIVLEDSNILQPVGLIV

FENWLYWIDKQQQMIEKIDMIGREGRIKVQARIAQLSDIHAVKELNLQ

EYRQHPCAQDNGGCSHICLVKGDGTIRCSCPMHLVLLQDELSCGEPPT

CSPQQFTCFTGEIDCIPVAWRCDGFTECEDHSDELNCPVCSESQFCA

SGQCIDGALRCNGDANCQDKSDEKNCEVLCLIDQFRCANGQCIGKHKK

CDHNVDCSDKSDELDCYPTEEPAPQATNTVGSVIGVIVTIFVSGTVYF

ICQRMLCPRMKGDETMINDYVVHGPASVPLGYVPHPSSLSGSLPGMS

RGKSMISSLSIMGGSSGPPYDRAHVTGASSSSSSSIKGTYFPAILNPP

PSPATERSHYTMEFGYSSNSPSTHRSYSYRPYSYRHFAPPTTPCSIDV

CDSDYAPSRRMTSVATAKGYISDLNYDSEPVPPPPTPRSQYLSAEENY

ESCPPSPYTERSYSHHLYPPPPSPCTDSS

LRP1B:
>gi|93102379|ref|NP_061027.2| low density
lipoprotein-related protein 1B precursor
[Homo sapiens]
(SEQ ID NO: 26)
MSEFLLALLTLSGLLPIARVLTVGADRDQQLCDPGEFLCHDHVICVSQ

SWLCDGDPDCPDDSDESLDTCPEEVEIKCPLNHIACLGTNKCVHLSQL

CNGVLDCPDGYDEGVHCQELLSNCQQLNCQYKCIMVRNSTRCYCEDGF

EITEDGRSCKDQDECAVYGTCSQTCRNTHGSYTCSCVEGYLMQPDNRS

CKAKIEPTDRPPILLIANFETIEVFYLNGSKMAILSSVNGNEIHTLDF

IYNEDMICWIESRESSNQLKCIQITKAGGLIDEWTINILQSEHNVQQM

AIDWLTRNLYFVDHVGDRIFVCNSNGSVCVTLIDLELHNPKAIAVDPI

AGKLFFTDYGNVAKVERCDMDGMNRTRIIDSKTEQPAALALDLVNKLV
YWVDLYLDYVGVVDYQGKNRHIVIQGRQVRHLYGITVFEDYLYAINSD
NYNIVRINRFNGTDIHSLIKIENAWGIRIYQKRIQPIVRSHACEVDPY
GMPGGCSHICLLSSSYKTRICRCRIGFNLGSDGRSCKRPKNELFLFYG
KGRPGIVRGMDLNIKIADEYMIPIENLVNPRALDFHAETNYIYEADTT
SFLIGRQKIDGTERETILKDDLDNVEGIAVDWIGNNLYWTNDGHRKTI
NVARLEKASQSRKTLLEGEMSHPRGIVVDPVNGWMYWTDWEEDEIDDS
VGRIEKAWMDGENRQIFVTSKMLWPNGLTLDFHTNTLYWCDAYYDHIE
KVEINGTHRKIVYSGRELNHPFGLSHHGNYVFWTDYMNGSIFQLDLIT
SEVTLLRHERPPLFGLQIYDPRKQQGD<u>NMCRVNNGGCSTLCLAIPGGR</u>
<u>VC</u>ACADNQLLDENGTTCTFNPGEALPHICKAGEFRCKNRHCIQARWKC
DGDDDCLDGSDEDSVNCFNHSCPDDQFKCQNNRCIPKRWLCDGANDCG
SNEDESNQTCTARTCQVDQFSCGNGRCIPRAWLCDREDDCGDQTDEMA
SCEFPTCEPLTQFVCKSGRCISSKWHCDSDDDCGDGSDEVGCVHSCFD
NQFRCSSGRCIPGHWACDGDNDCGDFSDEAQINCTKEEIHSPAGCNGN
EFQCHPDGNCVPDLWRCDGEKDCEDGSDEKGCNGTIRLCDHKTKFSCW
STGRCINKAWVCDGDIDCEDQSDEDDCDSFLCGPPKHPCANDTSVCLQ
PEKLCNGKKDCPDGSDEGYLCDECSLNNGGCSNHCSVVPGRGIVCSCP
EGLQLNKDNKTCEIVDYCSNHLKCSQVCEQHKHTVKCSCYEGWKLDVD
GESCTSVDPFEAFIIFSIRHEIRRIDLHKRDYSLLVPGLRNTIALDFH
FNQSLLYWTDVVEDRIYRGKLSESGGVSAIEVVVEHGLATPEGLTVDW
IAGNIYWIDSNLDQIEVAKLDGSLRTTLIAGAMEHPRAIALDPRYGIL
FWTDWDANFPRIESASMSGAGRKTIYKDMKTGAWPNGLIVDHFEKRIV
WIDARSDAIYSALYDGINMIEIIRGHEYLSHPFAVSLYGSEVYWTDWR
TNTLSKANKWTGQNVSVIQKTSAAQFDLQIYHPSRQPQAPNPCAANDG
KGPCSHMCLINHNRSAACACPHLMKLSSDKKTCYEMKKELLYARRSEI
RGVDIDNPYFNFITAFTVPDIDDVTVIDFDASEERLYWTDIKTQTIKR
AFINGTGLETVISRDIQSIRGLAVDWVSRNLYWISSEFDETQINVARL
DGSLKTSIIHGIDKPQCLAAHPVRGKLYWTDGNTINMANMDGSNSKIL
FQNQKEPVGLSIDYVENKLYWISSGNGTINRCNLDGGNLEVIESMKEE
LTKATALTIMDKKLWWADQNLAQLGTCSKRDGRNPTILRNKTSGVVHM
KVYDKEAQQGSNSCQLNNGGCSQLCLPTSETTRTCMCTVGYYLQKNRM
SCQGIESFLMYSVHEGIRGIPLEPSDKMDALMPISGTSFAVGIDFHAE
NDTIYWTDMGENKISRAKRDQTWKEDTIINGLGRVEGIAVDWIAGNIY
WTDHGFNLIEVARLNGSFRYVIISQGLDQPRSIAVHPEKGLLFWTEWG
QMPCIGKARLDGSEKVVLVSMGIAWPNGISIDYEENKLYWCDARTDKI
ERIDLEIGGNREMVLSGSNVDMESVAVEGAYIYWSDRAHANGSVRRGH
KNDATETITMRTGLGVNLKEVKIENRVREKGTNVCARDNGGCKQLCLY
RGNSRRTCACAHGYLAEDGVTCLRHEGYLLYSGRTILKSIHLSDETNL
NSPIRPYENPRYFKNVIALAFDYNQRRKGINRIFYSDAHEGNIQLIKD

NWEDRQVIVENVGSVEGLAYHRAWDTLYWISSTTSSITRHTVDQTRPG
AFDREAVITMSEDDHPHVLALDECQNLMFWTNWNEQHPSIMRSTLTGK
NAQVVVSTDILTPNGLTIDYRAEKLYFSDGSLGKIERCEYDGSQRHVI
VKSGPGTELSLAVYDNYIFWSDWGRRAILRSNKYTGGDTKILRSDIPH
QPMGIIAVANDTNSCELSPCALLNGGCHDLCLLTPNGRVNCSCRGDRI
LLEDNRCVTKNSSCNAYSEFECGNGECIDYQLTCDGIPHCKDKSDEKL
LYCENRSCRRGFKPCYNRRCIPHGKLCDGENDCGDNSDELDCKVSTCA
TVEFRCADGTCIPRSARCNQNIDCADASDEKNCNNTDCTHEYKLGVKT
TGFIRCNSTSLCVLPTWICDGSNDCGDYSDELKCPVQNKHKCEENYFS
CPSGRCILNTWICDGQKDCEDGRDEFHCDSSCSWNQFACSAQKCISKH
WICDGEDDCGDGLDESDSICGAITCAADMFSCQGSRACVPRHWLCDGE
RDCPDGSDELSTAGCAPNNTCDENAFMCHNKVCIPKQFVCDHDDDCGD
GSDESPQCGYRQCGTEEFSCADGRCLLNTQWQCGDFDCPDHSDEAPL
NPKCKSAEQSCNSSFFMCKNGRCIPSGGLCDNKDDCGDGSDERNCHIN
ECLSKKVSGCSQDCQDLPVSYKCKCWPGFQLKDDGKTCVDIDECSSGF
PCSQQCINTYGTYKCLCTDGYEIQPDNPNGCKSLSDEEPFLILADHHE
IRKISTDGSNYTLLKQGLNNVIAIDFDYREEFIYWIDSSRPNGSRINR
MCLNGSDIKVVHNTAVPNALAVDWIGKNLYWSDTEKRIIEVSKLNGLY
PTILVSKRLKFPRDLSLDPQAGYLYWIDCCEYPHIGRVGMDGTNQSVV
IETKISRPMALTIDYVNRRLYWADENHIEFSNMDGSHRHKVPNQDIPG
VIALTLFEDYIYWTDGKTKSLSRAHKTSGADRLSLIYSWHAITDIQVY
HSYRQPDVSKHL<u>CMINNGGCSHLC</u>LLAPGKTHTCACPTNFYLAADNRT
CLSNCTASQFRCKTDKCIPFWWKCDTVDDCGDGSDEPDDCPEFRCQPG
REQCGTGLCALPAFICDGENDCGDNSDELNCDTHVOLSGQFKCTKNQK
CIPVNLRCNGQDDCGDEEDERDCPENSCSPDYFQCKTTKHCISKLWVC
DEDPDCADASDEANCDKKTCGPHEFQCKNNNCIPDHWRCDSQNDCSDN
SDEENCKPQTCTLKDFLCANGDCVSSRFWCDGDFDCADGSDERNCETS
CSKDQFRCSNGQCIPAKWKCDGHEDCKYGEDEKSCEPASPTCSSRETI
CASDGCISASLKCNGEYDCADGSDEMDCVTECKEDQFRCKNKAHCIPI
RWLCDGIHDCVDGSDEENCERGGNICRADEFLCNNSLCKLHFWVCDGE
DDCGDNSDEAPDMCVKFLCPSTRPHRCRNNRICLQSEQMCNGIDECGD
NSDEDHCGGKLTYKARPCKKDEFACSNKKCIPMDLQCDRLDDCGDGSD
EQGCRIAPTEYTCEDNVNPCGDDAYCNQIKTSVFCRCKPGFQRNMKNR
QCEDLNECLVFGTCSHQCINVEGSYKCVCDQNFQERNNTCIAEGSEDQ
VLYIANDTDILGFIYPENYSGDHQQISHIEHNSRITGMDVYYQRDMII
WSTQFNPGGIFYKRIHGREKRQANSGLICPEFKRPRDIAVDWVAGNIY
WTDHSRMHWFSYYTTHWTSLRYSINVGQLNGPNCTRLLTNMAGEPYAI
AVNPKRGMMYWITVGDHSHIEEAAMDGTLRRILVQKNLQRPTGLAVDY
FSERIYWADFELSIIGSVLYDGSNSVVSVSSKQGLLHPHRIDIFEDYI
YGAGPKNGVFRVQKFGHGSVEYLALNIDKTKGVLISHRYKQLDLPNPC
LDLACEFLCLLNPSGATCVCPEGKYLINGTCNDDSLLDDSCKLTCENG

GRCILNEKGDLRCHCWPSYSGERCEVNHCSNYCQNGGTCVPSVLGRPT

CSCALGFTGPNCGKTVCEDFCQNGGTCIVTAGNQPYCHCQPETTGDRC

QTYVCHHYCVNSESCTIGDDGSVECVCPTRYEGPKCEVDKCVRCHGGH

CIINKDSEDIFCNCTNGKIASSCQLCDGYCYNGGTCQLDPETNVPVCL

CSTNWSGTQCERPAPKSSKSDHISTRSIAIIVPLVLLVTLITTLVIGL

VLCKRKRRTKTIRRQPIINGGINVEIGNPSYNMYEVDHDHNDGGLLDP

GFMIDPTKARYIGGGPSAFKLPHTAPPIYLNSDLKGPLTAGPTNYSNP

VYAKLYMDGQNCRNSLGSVDERKELLPKKIEIGIRETVA

PROS1:
>gi|4506117|ref|NP_000304.1| protein S, alpha
[Homo sapiens]
(SEQ ID NO: 27)
MRVLGGRCGAPLACLLLVLPVSEANLLSKQQASQVLVRKRRANSLLEE

TKQGNLERECIEELCNKEEAREVFENDPETDYFYPKYLVCLRSFQTGL

ETAARQSTNAYPDLRSCVNAIPDQCSPLPCNEDGYMSCKDGKASFTCT

CKPGWQGEKCEFDINECKDPSNINGGCSQICDNTPGSYHCSCKNGFVM

LSNKKDCKDVDECSLKPSICGTAVCKNIPGDFECECPEGYRYNLKSKS

CEDIDECSENMCAQLCVNYPGGYTCYCDGKKGFKLAQDQKSCEVVSVC

LPLNLDTKYELLYLAEQFAGVVLYLKERLPEISRFSAEFDERTYDSEG

VILYAESIDHSAWLLIALRGGKIEVQLKNEHTSKITTGGDVINNGLWN

MVSVEELEHSISIKIAKEAVMDINKPGPLFKPENGLLETKVYFAGFPR

KVESELIKPINPRLDGCIRSWNLMKQGASGIKEIIQEKQNKHCLVTVE

KGSYYPGSGIAQFHIDYNNVSSAEGWHVNVTLNIRPSTGTGVMLALVS

GNNTVPFAVSLVDSTSEKSQDILLSVENTVIYRIQALSLCSDQQSHLE

FRVNRNNLELSTPLKIETISHEDLQRQLAVLDKAMKAKVATYLGGLPD

VPFSATPVNAFYNGCMEVNINGVQLDLDEAISKHNDIRAHSCPSVWKK

TKNS

GAS6:
>gi|4557617|ref|NP_000811.1| growth arrest-
specific 6 [Homo sapiens]
(SEQ ID NO: 28)
MAPSLSPGPAALRRAPQLLLLLLAAECALAALLPAREATQFLRPRQRR

AFQVFEEAKQGHLERECVEELCSREEAREVFENDPETDYFYPRYLDCI

NKYGSPYTKNSGFATCVQNLPDQCTPNPCDRKGTQACQDLMGNFFCLC

KAGWGGRLCDKDVNECSQENGGCLQICHNKPGSFHCSCHSGFELSSDG

RTCQDIDECADSEACGEARCKNLPGSYSCLCDEGFAYSSQEKACRDVD

ECLQGRCEQVCNSPGSYTCHCDGRGGLKLSQDMDTCEDILPCVPFSV

AKSVKSLYLGRMFSGTPVIRLRFKRLQPTRLVAEFDFRTFDPEGILLF

AGGHQDSTWIVLALRAGRLELQLRYNGVGRVTSSGPVINHGMWQTISV

EELARNLVIKVNRDAVMKIAVAGDLFQPERGLYHLNLTVGGIPFHEKD

LVQPINPRLDGCMRSWNWLNGEDTTIQETVKVNTRMQCFSVTERGSFY

PGSGFAFYSLDYMRTPLDVGTESTWEVEVVAHIRPAADTGVLFALWAP

DLRAVPLSVALVDTHSTKKLKKQLVVLAVEHTALALMEIKVCDGQEHV

VTVSLRDGEATLEVDGTRGQSEVSAAQLQERLAVLERHLRSPVLTFAG

GLPDVPVTSAPVTAFYRGCMTLEVNRRLLDLDEAAYKHSDITAHSCPP

VEPAAA

TLL1:
>gi|22547221|ref|NP_036596.3| tolloid-like 1
[Homo sapiens]
(SEQ ID NO: 29)
MGLGTLSPRMLVWLVASGIVFYGELWVCAGLDYDYTFDGNEEDKTETI

DYKDPCKAAVFWGDIALDDEDLNIFQIDRTIDLTQNPFGNLGHTTGGL

GDHAMSKKRGALYQLIDRIRRIGFGLEQNNTVKGKVPLQFSGQNEKNR

VPRAATSRTERIWPGGVIPYVIGGNFTGSQRAMFKQAMRHWEKHTCVT

FIERSDEESYIVFTYRPCGCCSYVGRRGNGPQAISIGKNCDKEGIVVH

ELGHVIGEWHEHTRPDRDNHVTIIRENIQPGQEYNFLKMEPGEVNSLG

ERYDFDSIMHYARNTFSRGMFLDTILPSRDDNGIRPAIGQRTRLSKGD

IAQARKLYRCPACGETLQESNGNLSSPGFPNGYPSYTHCIWRVSVTPG

EKIVLNFTTMDLYKSSLCWYDYIEVRDGYWRKSPLLGRFCGDKLPEVL

TSTDSRMWIEFRSSSNWVGKGFAAVYEAICGGEIRKNEGQIQSPNYPD

DYRPMKECVWKITVSESYHVGLTFQSFEIERHDNCAYDYLEVRDGTSE

NSPLIGRFCGYDKPEDIRSTSNTLWMKFVSDGTVNKAGFAANFEKEED

ECAKPDRGGCEQRCLNTLGSYQCACEPGYELGPDRRSCEAACGGLLTK

LNGTITTPGWPKEYPPNKNCVWQVVAPTQYRISVKFEFFELEGNEVCK

YDYVEIWSGLSSESKLHGKFCGAEVPEVITSQFNNMRIEFKSDNTVSK

KGFKAHFFSDKDECSKDNGGCQHECVNTMGSYMCQCRNGFVLHDNKHD

CKEAECEQKIHSPSGLITSPNWPDKYPSRKECTWEISATPGHRIKLAF

SEFEIEQHQECAYDHLEVFDGETEKSPILGRLCGNKIPDPLVATGNKM

FVRFVSDASVQRKGFQATHSTECGGRLKAESKPRDLYSHAQFGDNNYP

GQVDCEWLLVSERGSRLELSFQTFEVEEEADCGYDYVELFDGLDSTAV

GLGRFCGSGPPEETYSIGDSVLIHFHTDDTINKKGFHIRYKSIRYPDT

THTKK

NID1:
>gi|115298674|ref|NP_002499.2| nidogen 1 precursor
[Homo sapiens]
(SEQ ID NO: 30)
MLASSSRIRAAWTRALLLPLLLAGPVGCLSRQELFPFGPGQGDLELED

GDDFVSPALELSGALRFYDRSDIDAVYVTTNGIIATSEPPAKESHPGL

EPPTFGAVAPFLADLDTTDGLGKVYYREDLSPSITQRAAECVHRGFPE

ISFQPSSAVVVTWESVAPYQGPSRDPDQKGKRNTFQAVLASSDSSSYA

IFLYPEDGLQFHTTFSKKENNQVPAVVAFSQGSVGFLWKSNGAYNIFA

NDRESVENLAKSSNSGQQGVWVFEIGSPATTNGVVPADVILGTEDGAE

YDDEDEDYDLATTRLGLEDVGTTPFSYKALRRGGADTYSVPSVLSPRR

AATERPLGPPTERTRSFQLAVETFHQQHPQVIDVDEVEETGVVFSYNT

DSRQTCANNRHQCSVHAECRDYATGFCCSCVAGYTGNGRQCVAEGSPQ

RVNGKVKGRIFVGSSQVPIVFENTDLHSYVVMNHGRSYTAISTIPETV

GYSLLPLAPVGGIIGWMFAVEQDGFKNGESITGGEFTRQAEVTFVGHP

GNLVIKQRFSGIDEHGHLTIDTELEGRVPQIPFGSSVHIEPYTELYHY

STSVITSSSTREYTVTEPERDGASPSRIYTYQWRQTITFQECVHDDSR

PALPSTQQLSVDSVFVLYNQEEKILRYALSNSIGPVREGSPDALQNPC

YIGTHGCDTNAACRPGPRTQFTCECSIGFRGDGRTCYDIDECSEQPSV

CGSHTICNNHPGTFRCECVEGYQFSDEGTCVAVVDQRPINYCETGLHN

CDIPQRAQCIYTGGSSYTCSCLPGFSGDGQACQDVDECQPSRCHPDAF

CYNTPGSFTCQCKPGYQGDGERCVPGEVEKTRCQHEREHILGAAGATD

PQRPIPPGLFVPECDAHGHYAPTQCHGSTGYCWCVDRDGREVEGTRTR

PGMTPPCLSTVAPPIHQGPAVPTAVIPLPPGTHLLFAQTGKIERLPLE

GNTMRKTEAKAFLHVPAKVIIGLAFDCVDKMVYWTDITEPSIGRASLH

GGEPTTIIRQDLGSPEGIAVDHLGRNIFWTDSNLDRIEVAKLDGTQRR

VLFETDINNPRGIVTDSVRGNLYWTDWNRDNPKIETSYMDGTNRRILV

QDDLGLPNGLTFDAFSSQLCWVDAGTNRAECLNPSQPSRRKALEGLQY

PFAVTSYGKELYFTDWKMNSVVALDLAISKETDAFQPHKQTRLYGITT

ALSQCPQGH<u>NYCSVNNGGCTHLC</u>LATPGSRTCRCPDNTLGVDCIEQK

TLL2:
>gi|6912724|ref|NP_036597.1| tolloid-like 2
[Homo sapiens]
(SEQ ID NO: 31)
MPRATALGALVSLLLLLPLPRGAGGLGERPDATADYSELDGEEGTEQQ

LEHYHDPCKAAVFWGDIALDEDDLKLFHIDKARDWTKQTVGATGHSTG

GLEEQASESSPDTTAMDTGTKEAGKDGRENTTLLHSPGTLHAAAKTFS

PRVRRATTSRTERIWPGGVIPYVIGGNFTGSQRAIFKQAMRHWEKHTC

VTFIERTDEESFIVESYRTCGCCSYVGRRGGGPQAISIGKECDKEGIV

AHELGHVVGEWHEHTRPDRDQHVTIIRENIQPGQEYNFLKMEAGEVSS

LGETYDFDSIMHYARNITSRGVFLDTILPRQDDNGVRPTIGQRVRLSQ

GDIAQARKLYKCPACGETLQDTTGNFSAPGFPNGYPSYSHCVWRISVT

PGEKIVLNFTSMDLFKSRLCWYDYVEVRDGYWRKAPLLGRFCGDKIPE

PLVSTDSRLWVEFRSSSNILGKGFFAAYEATCGGDMNKDAGQIQSPNY

PDDYRPSKECVWRITVSEGFHVGLTFQAFEIERHDSCAYDYLEVRDGP

TEESALIGHFCGYEKPEDVKSSSNRLWMKFVSDGSINKAGFAANFEKE

VDECSWPDHGGCEHRCVNTLGSYKCACDPGYELAADKKMCEVACGGFI

TKLNGTITSPGWPKEYPTNKNCVWQVVAPAQYRISLQFEVFELEGNDV

CKYDEVEVRSGLSPDAKLHGRFCGSETPEVITSQSNNMRVEFKSDNTV

SKRGFRAHFFSDK<u>DECAKDNGGCQHECVNTFGSYLC</u>RCRNGYWLHENG

HDCKEAGCAHKISSVEGTLASPNWPDKYPSRRECTWNISSTAGHRVKL

TFNEFEIEQHQECAYDHLEMYDGPDSLAPILGRFCGSKKPDPTVASGS

SMFLRFYSDASVQRKGFQAVHSTECGGRLKAEVQTKELYSHAQFGDNN

YPSEARCDWVIVAEDGYGVELTERTFEVEEEADCGYDYMEAYDGYDSS

APRLGRFCGSGPLEETYSAGDSLMIRERTDDTINKKGFHARYTSTKFQ

DALHMKK

EGF:
>gi|166362728|ref|NP_001954.2| epidermal growth
factor (beta-urogastrone) [Homo sapiens]
(SEQ ID NO: 32)
MLLTLIILLPVVSKFSFVSLSAPQHWSCPEGTLAGNGNSTCVGPAPFL

IFSHGNSIFRIDTEGTNYEQLVVDAGVSVIMDFHYNEKRIYWVDLERQ

LLQRVFLNGSRQERVCNIEKNVSGMAINWINEEVIWSNQQEGIITVTD

MKGNNSHILLSALKYPANVAVDPVERFIFWSSEVAGSLYRADLDGVGV

KALLETSEKITAVSLDVLDKRLFWIQYNREGSNSLICSCDYDGGSVHI

SKEPTQHNLFAMSLFGDRIFYSTWKMKTIWIANKHTGKDMVRINLHSS

FVPLGELKVVHPLAQPKAEDDTWEPEQKLCKLRKGNCSSTVCGDQLQS

HLCMCAEGYALSRDRKYCEDVNECAFWNHGCTLGCKNTPGSYYCTCPV

GFVLLPDGKRCHQLVSCPRNVSECSHDCVLTSEGPLCFCPEGSVLERD

GKTCSGCSSPDNGGCSQLCVPLSPVSWECDCFPGYDLQLDEKSCAASG

PQPFLLFANSQDIRHMHFDGTDYGTLLSQQMGMVYALDHDPVENKIYF

AHTALKWIERANMDGSQRERLIEEGVDVPEGLAVDWIGRRFYWIDRGK

SLIGRSDLNGKRSKIITKENISQPRGIAVHPMAKRLFWTDTGINPRIE

SSSLQGLGRLVIASSDLIWPSGITIDFLTDKLYWCDAKQSVIEMANLD

GSKRRRLTQNDVGHPFAVAVFEDYVWFSDWAMPSVMRVNKRTGKDRVR

LQGSMLKPSSLVVVHPLAKPGADP<u>CLYQNGGCEHIC</u>KKRLGTAWCSCR

EGFMKASDGKTCLALDGHQLLAGGEVDLKNQVTPLDILSKTRVSEDNI

TESQHMLVAEIMVSDQDDCAPVGCSMYARCISEGEDATCQCLKGFAGD

GKLCSDIDECEMGVPVCPPASSKCINTEGGYVCRCSEGYQGDGIHCLD

IDECQLGEHSCGENASCTNTEGGYTCMCAGRLSEPGLICPDSTPPPHL

REDDHHYSVRNSDSECPLSHDGYCLHDGVCMYIEALDKYACNCVVGYI

GERCQYRDLKWWELRHAGHGQQQKVIVVAVCVVVLVMLLLLSLWGAHY

YRTQKLLSKNPKNPYEESSRDVRSRRPADTEDGMSSCPQPWFVVIKEH

QDLKNGGQPVAGEDGQAADGSMQPTSWRQEPQLCGMGTEQGCWIPVSS

DKGSCPQVMERSEHMPSYGTQTLEGGVEKPHSLLSANPLWQQRALDPP

HQMELTQ

Fibrillin 2:
>gi|66346695|ref|NP_001990.2| fibrillin 2
precursor [Homo sapiens]
(SEQ ID NO: 33)
MGRRRRLCLQLYFLWLGCVVLWAQGTAGQPQPPPPKPPRPQPPPQQVR

SATAGSEGGFLAPEYREEGAAVASRVRRRGQQDVLRGPNVCGSRFHSY

CCPGWKTLPGGNQCIVPICRNSCGDGFCSRPNMCTCSSGQISSTCGSK

SIQQCSVRCMNGGTCADDHCQCQKGYIGTYCGQPVCENGCQNGGRCIG

PNRCACVYGFTGPQCERDYRTGPCFTQVNNQMCQGQLTGIVCTKTLCC

ATIGRAWGHPCEMCPAQPQPCRRGFIPNIRTGACQDVDECQAIPGICQ

GGNCINTVGSFECRCPAGHKQSETTQKCEDIDECSIIPGICETGECSN

TVGSYFCVCPRGYVTSTDGSRCIDQRTGMCFSGLVNGRCAQELPGRMT

KMQCCCEPGRCWGIGTIPEACPVRGSEEYRRLCMDGLPMGGIPSGAGS

RPGGTGGNGFAPSGNGNGYGPGGTGFIPIPGGNGFSPGVGGAGVGAGG

-continued

QGPIITGLTILNQTIDICKHHANLCLNGRCIPTVSSYRCECNMGYKWA
NGDCIDVDECTSNPCTNGDCVNTPGSYYCKCHAGFQRTPTKQACIDID
ECIQGVLCKNGRCVNTDGSFQCICNAGFELTTDGKNCVDHDECTTTNM
CLNGMCINEDGSFKCICKPGFVLAPNGRYCTDVDECQTPGICMNGHCI
NSEGSFRCDCPPGLAVGMDGRVCVDTHMRSTCYGGIKKGVCVRPFPGA
VTKSECCCANPDYGFGEPCQPCPAKNSAEFHGLCSSGVGITVDGRDIN
ECALDPDICANGICENLRGSYRCNCNSGYEPDASGRNCIDIDECLVNR
LLCDNGLCRNTPGSYSCTCPPGYVFRTETETCEDINECESNPCVNGAC
RNNLGSFNCECSPGSKLSSTGLICIDSLKGTCWLNIQDSRCEVNINGA
TLKSECCATLGAAWGSPCERCELDTACPRGLARIKGVTCEDVNECEVF
PGVCPNGRCVNSKGSFHCECPEGLTLDGTGRVCLDIRMEQCYLKWDED
ECIHPVPGKERMDACCCAVGAAWGTECEECPKPGTKEYETLCPRGAGF
ANRGDVLTGRPFYKDINECKAFPGMCTYGKCRNTIGSFKCRCNSGFAL
DMEERNCTDIDECRISPDLCGSGICVNTPGSFECECFEGYESGFMMMK
NCMDIDECERNPLLCRGGTCVNTEGSFQCDCPLGHELSPSREDCVDIN
ECSLSDNLCRNGKCVNMIGTYQCSCNPGYQATPDRQGCTDIDECMIMN
GGCDTQCTNSEGSYECSCSEGYALMPDGRSCADIDECENNPDICDGGQ
CTNIPGEYRCLCYDGFMASMDMKTCIDVNECDLNSNICMFGECENTKG
SFICHCQLGYSVKKGTTGCTDVDECEIGAHNCDMHASCLNIPGSFKCS
CREGWIGNGIKCIDLDECSNGTHQCSINAQCVNTPGSYRCACSEGFTG
DGFTCSDVDECAENINLCENGQCLNVPGAYRCECEMGFTPASDSRSCQ
DIDECSFQNICVFGTCNNLPGMFHCICDDGYELDRTGGNCTDIDECAD
PINCVNGLCVNTPGRYECNCPPDFQLNPTGVGCVDNRVGNCYLKFGPR
GDGSLSCNTEIGVGVSRSSCCCSLGKAWGNPCETCPPVNSTEYYTLCP
GGEGFRPNPITIILEDIDECQELPGLCQGGNCINTFGSFQCECPQGYY
LSEDTRICEDIDECFAHPGVCGPGTCYNTLGNYTCICPPEYMQVNGGH
NCMDMRKSFCYRSYNGTTCENELPFNVTKRMCCCTYNVGKAWNKPCEP
CPTPGTADEKTICGNIPGFTEDIHTGKAVDIDECKEIPGICANGVCIN
QIGSFRCECPTGFSYNDLLLVCEDIDECSNGDNLCQRNADCINSPGSY
RCECAAGFKLSPNGACVDRNECLEIPNVCSHGLCVDLQGSYQCICHNG
FKASQDQTMCMDVDECERHPCGNGTCKNTVGSYNCLCYPGFELTHNND
CLDIDECSSFFGQVCRNGRCFNEIGSFKCLCNEGYELTPDGKNCIDTN
ECVALPGSCSPGTCQNLEGSFRCICPPGYEVKSENCIDINECDEDPNI
CLEGSCTNTPGGFQCLCPPGFVLSDNGRRCEDTRQSFCFTNFENGKCS
VPKAFNTTKAKCCCSKMPGEGWGDPCELCPKDDEVAFQDLCPYGHGTV
PSLHDTREDVNECLESPGICSNGQCINTDGSFRCECPMGYNLDYTGVR
CVDTDECSIGNPCGNGTCTNVIGSFECNCNEGFEPGPMMNCEDINECA
QNPLLCAFRCMNTEGSYECTCPIGYALREDQKMCKDLDECAEGLHDCE
SRGMMCKNLIGTFMCICPPGMARRPDGEGCVDENECRTKPGICENGRC
VNIIGSYRCECNEGFQSSSSGTECLDNRQGLCFAEVLQTICQMASSSR
NLVTKSECCCDGGRGWGHQCELCPLPGTAQYKKICPHGPGYTTDGRDI
DECKVMPNLCTNGQCINTMGSFRCFCKVGYTTDISGTSCIDLDECSQS
PKPCNYICKNTEGSYQCSCPRGYVLQEDGKTCKDLDECQTKQHNCQFL
CVNTLGGETCKCPPGFTQHHTACIDNNECGSQPSLCGAKGICQNTPGS
FSCECQRGFSLDATGLNCEDVDECDGNHRCQHGCQNILGGYRCGCPQG
YIQHYQWNQCVDENECSNPNACGSASCYNTLGSYKCACPSGFSFDQFS
SACHDVNECSSSKNPCNYGCSNTEGGYLCGCPPGYYRVGQGHCVSGMG
ENKGQYLSLDTEVDEENALSPEACYECKINGYSKKDSRQKRSIHEPDP
TAVEQISLESVDMDSPVNMKENLSHLGSKEHILELRPAIQPLNNHIRY
VISQGNDDSVERIHQRNGLSYLHTAKKKLMPGTYTLEITSIPLYKKKE
LKKLEESNEDDYLLGELGEALRMRLQIQLY

Fibrillin 1:
>gi|24430141|ref|NP_000129.21| fibrillin 1 precursor [*Homo sapiens*]

(SEQ ID NO: 34)

MRRGRLLEIALGFTVLLASYTSHGADANLEAGNVKETRASRAKRRGGG
GHDALKGPNVCGSRYNAYCCPGWKTLPGGNQCIVPICRHSCGDGFCSR
PNMCTCPSGQIAPSCGSRSIQHCNIRCMNGGSCSDDHCLCQKGYIGTH
CGQPVCESGCLNGGRCVAPNRCACTYGFTGPQCERDYRTGPCFTVISN
QMCQGQLSGIVCTKTLCCATVGRAWGHPCEMCPAQPHPCRRGFIPNIR
TGACQDVDECQAIPGLCQGGNCINTVGSFECKCPAGHKLNEVSQKCED
IDECSTIPGICEGGECTNTVSSYFCKCPPGFYTSPDGTRCIDVRPGYC
YTALTNGRCSNQLPQSITKMQCCCDAGRCWSPGVTVAPEMCPIRATED
FNKLCSVPMVIPGRPEYPPPPLGPIPPVLPVPPGFPPGPQIPVPRPPV
EYLYPSREPPRVLPVNVTDYCQLVRYLCQNGRCIPTPGSCRCECNKGF
QLDLRGECIDVDECEKNPCAGGECINNQGSYTCQCRAGYQSTLTRTEC
RDIDECLQNGRICNNGRCINTDGSFHCVCNAGFHVTRDGKNCEDMDEC
SIRNMCLNGMCINEDGSFKCICKPGFQLASDGRYCKDINECETPGICM
NGRCVNTDGSYRCECFPGLAVGLDGRVCVDTHMRSTCYGGYKRGQCIK
PLFGAVTKSECCCASTEYAFGEPCQPCPAQNSAEYQALCSSGPGMTSA
GSDINECALDPDICPNGICENLRGTYKCICNSGYEVDSTGKNCVDINE
CVLNSLLCDNGQCRNTPGSFVCTCPKGFIYKPDLKTCEDIDECESSPC
INGVCKNSPGSFICECSSESTLDPTKTICIETIKGTCWQTVIDGRCEI
NINGATLKSQCCSSLGAAWGSPCTLCQVDPICGKGYSRIKGTQCEDID
ECEVFPGVCKNGLCVNTRGSFKCQCPSGMTLDATGRICLDIRLETCFL
RYEDEECTLPIAGRHRMDACCCSVGAAWGTEECEECPMRNTPEYEELC
PRGPGFATKEITNGKPFFEKDINECKMIPSLCTHGKCRNTIGSFKCRCD
SGFALDSEERNCTDIDECRISPDLCGRGQCVNTPGDFECKCDEGYESG
FMMMKNCMDIDECQRDPLLCRGGVCHNTEGSYRCECPPGHQLSPNISA
CIDINECELSAHLCPNGRCVNLIGKYQCACNPGYHSTPDRLFCVDIDE
CSIMNGGCETFCTNSEGSYECSCQPGFALMPDQRSCTDIDECEDNPNI
CDGGQCTNIPGEYRCLCYDGFMASEDMKTCVDVNECDLNPNICLSGTC
ENTKGSFICHCDMGYSGKKGKTGCTDINECEIGAHNCGKHAVCTNTAG

-continued

SFKCSCSPGWIGDGIKCTDLDECSNGTHMCSQHADCKNTMGSYRCLCK
EGYTGDGFTCTDLDECSENLNLCGNGQCLNAPGGYRCECDMGFVPSAD
GKACEDIDECSLPNICVFGTCHNLPGLFRCECEIGYELDRSGGNCTDV
NECLDPTTCISGNCVNTPGSYICDCPPDFELNPTRVGCVDTRSGNCYL
DIRPRGDNGDTACSNEIGVGVSKASCCCSLGKAWGTPCEMCPAVNTSE
YKILCPGGEGFRPNPITVILEDIDECQELPGLCQGGKCINTFGSFQCR
CPTGYYLNEDTRVCDDVNECETPGICGPGTCYNTVGNYTCICPPDYMQ
VNGGNNCMDMRRSLCYRNYYADNQTCDGELLFNMTKKMCCCSYNIGRA
WNKPCEQCPIPSTDEFATLCGSQRPGFVIDIYTGLPVDIDECREIPGV
CENGVCINMVGSFRCECPVGFEYNDKLLVCEDIDECQNGPVCQRNAEC

INTAGSYRCDCKPGYRFTSTGQCNDRNECQEIPNICSHGQCIDTVGSF

YCLCHTGFKTNDDQTMCLDINECERDACGNGTCRNTIGSFNCRCNHGF

ILSHNNDCIDVDECASGNGNLCRNGQCINTVGSFQCQCNEGYEVAPDG

RTCVDINECLLEPRKCAPGTCQNLDGSYRCICPPGYSLQNEKCEDIDE

CVEEPEICALGTCSNTEGSFKCLCPEGFSLSSSGRRCQDLRMSYCYAK

FEGGKCSSPKSRNHSKQECCCALKGEGWGDPCELCPTEPDEAFRQICP

YGSGIIVGPDDSAVDMDECKEPDVCKHGQCINTDGSYRCECPFGYILA

GNECVDTDECSVGNPCGNGTCKNVIGGFECTCEEGFEPGPMMTCEDIN

ECAQNPLLCAFRCVNTYGSYECKCPVGYVLREDRRMCKDEDECEEGKH

DCTEKQMECKNLIGTYMCICGPGYQRRPDGEGCVDENECQTKPGICEN

GRCLNTRGSYTCECNDGFTASPNQDECLDNREGYCFTEVLQNMCQIGS

SNRNPVTKSECCCDGGRGWGPHCEICPFQGTVAFKKLCPHGRGFMTNG

ADIDECKVIHDVCRNGECVNDRGSYHCICKTGYTPDITGTSCVDLNEC

NQAPKPCNFICKNTEGSYQCSCPKGYILQEDGRSCKDLDECATKQHNC

QFLCVNTIGGFTCKCPPGFTQHHTSCIDNNECTSDINLCGSKGICQNT

PGSFTCECQRGFSLDQTGSSCEDVDECEGNHRCQHGCQNIIGGYRCSC

PQGYLQHYQWNQCVDENECLSAHICGGASCHNTLGSYKCMCPAGFQYE

QFSGGCQDINECGSAQAPCSYGCSNTEGGYLCGCPPGYFRIGQGHCVS

GMGMGRGNPEPPVSGEMDDNSLSPEACYECKINGYPKRGRKRRSTNET

DASNIEDQSETEANVSLASWDVEKTAIFAFNISHVSNKVRILELLPAL

TTLTNHNRYLIESGNEDGFFKINQKEGISYLHETKKKPVAGTYSLQIS

STPLYKKKELNQLEDKYDKDYLSGELGDNLKMKIQVLLH

Fibrillin 3:
>gi|56237021|ref|NP_115823.3| fibrillin 3 precursor [*Homo sapiens*]

(SEQ ID NO: 35)

MTLEGLYLARGPLARLLLAWSALLCMAGGQGRWDGALEAAGPGRVRRR

GSPGILQGPNVCGSRFHAYCCPGWRTFPGRSQCVVPICRRACGEGFCS

QPNLCTCADGTLAPSCGVSRGSGCSVSCMNGGTCRGASCLCQKGYTGT

VCGQPICDRGCHNGGRCIGPNRCACVYGFMGPQCERDYRTGPCFGQVG

PEGCQHQLTGLVCTKALCCATVGRAWGLPCELCPAQPHPCRRGFIPNI

HTGACQDVDECQAVPGLCQGGSCVNMVGSFHCRCPVGHRLSDSSAACE

DYRAGACFSVLEGGRCAGDLAGHYTRRQCCCDRGRCWAAGPVPELCPP

-continued

RGSNEFQQLCAQRLPLLPGHPGLFPGLLGFGSNGMGPPLGPARLNPHG

SDARGIPSLGPGNSNIGTATLNQTIDICRHFTNLCLNGRCLPTPSSYR

CECNVGYTQDVRGECIDVDECTSSPCHHGDCVNIPGTYHCRCYPGFQA

TPTRQACVDVDECIVSGGLCHLGRCVNTEGSFQCVCNAGFELSPDGKN

CVDHNECATSTMCVNGVCLNEDGSFSCLCKPGFLLAPGGHYCMDIDEC

QTPGICVNGHCTNTEGSFRCQCLGGLAVGTDGRVCVDTHVRSTCYGAI

EKGSCARPFPGTVTKSECCCANPDHGFGEPCQLCPAKDSAEFQALCSS

GLGITTDGRDINECALDPEVCANGVCENLRGSYRCVCNLGYEAGASGK

DCTDVDECALNSLLCDNGWCQNSPGSYSCSCPPGFHFWQDTEICKDVD

ECLSSPCVSGVCRNLAGSYTCKCGPGSRLDPSGTFCLDSTKGTCWLKI

QESRCEVNLQGASLRSECCATLGAAWGSPCERCEIDPACARGFARMTG

VTCDDVNECESFPGVCPNGRCVNTAGSFRCECPEGLMLDASGRLCVDV

RLEPCFLRWDEDECGVTLPGKYRMDVCCCSIGAVWGVECEACPDPESL

EFASLCPRGLGFASRDFLSGRPFYKDVNECKVFPGLCTHGTCRNTVGS

FHCACAGGFALDAQERNCTDIDECRISPDLCGQGTCVNTPGSFECECF

PGYESGFMLMKNCMDVDECARDPLLCRGGTCTNTDGSYKCQCPPGHEL

TAKGTACEDIDECSLSDGLCPHGQCVNVIGAFQCSCHAGFQSTPDRQG

CVDINECRVQNGGCDVHCINTEGSYRCSCGQGYSLMPDGRACADVDEC

EENPRVCDQGHCTNMPGGHRCLCYDGFMATPDMRTCVDVDECDLNPHI

CLHGDCENTKGSFVCHCQLGYMVRKGATGCSDVDECEVGGHNCDSHAS

CLNIPGSFSCRCLPGWVGDGFECHDLDECVSQEHRCSPRGDCLNVPGS

YRCTCRQGFAGDGFECEDRDECAENVDLCDNGQCLNAPGGYRCECEMG

FDPTEDHRACQDVDECAQGNLCAFGSCENLPGMFRCICNGGYELDRGG

GNCTDINECADPVNCINGVCINTPGSYLCSCPQDFELNPSGVGCVDTR

AGNCFLETHDRGDSGISCSAEIGVGVTRASCCCSLGRAWGNPCELCPM

ANTTEYRTLCPGGEGFQPNRITVILEDIDECQELPGLCQGGDCVNTEG

SFQCECPPGYHLSEHTRICEDIDECSTHSGICGPGTCYNTLGNYTCVC

PAEYLQVNGGNNCMDMRKSVCFRHYNGTCQNELAFNVTRKMCCCSYNI

GQAWNRPCEACPTPISPDYQILCGNQAPGFLTDIHTGKPLDIDECGEI

PAICANGICINQIGSFRCECPAGFNYNSILLACEDVDECGSRESPCQQ

NADCINIPGSYRCKCTRGYKLSPGGACVGRNECREIPNVCSHGDCMDT

EGSYMCLCHRGFQASADQTLCMDIDECDRQPCGNGTCKNIIGSYNCLC

FPGFVVTHNGDCVDFDECTTLVGQVCRFGHCLNTAGSFHCLCQDGFEL

TADGKNCVDTNECLSLAGTCLPGTCQNLEGSFRCICPPGFQVQSDHCI

DIDECSEEPNLCLEGTCTNSPGSFQCLCPPGFVLSDNGHRCEDTRQSF

CETRFEAGKCSVPKAENTTKTRCCCSKRPGEGWGDPCELCPQEGSAAF

QELCPFGHGAVPGPDDSREDVNECAENPGVCTNGVCVNTDGSFRCECP

FGYSLDFTGINCVDTDECSVGHPCGQGTCTNVIGGFECACADGFEPGL

MMTCEDIDECSLNPLLCAFRCHNTEGSYLCTCPAGYTLREDGAMCRDV

DECADGQQDCHARGMECKNLIGTFACVCPPGMRPLPGSGEGCTDDNEC

-continued
HAQPDLCVNGRCVNTAGSFRCDCDEGFQPSPTLTECHDIRQGPCFAEV
LQTMCRSLSSSSEAVTRAECCCGGGRGWGPRCELCPLPGTSAYRKLCP
HGSGYTAEGRDVDECRMLAHLCAHGECINSLGSFRCHCQAGYTPDATA
TTCLDMDECSQVPKPCTFLCKNTKGSFLCSCPRGYLLEEDGRTCKDLD
ECTSRQHNCQFLCVNTVGAFTCRCPPGFTQHHQACEDNDECSAQPGPC
GAHGHCHNTPGSFRCECHQGFTLVSSGHGCEDVNECDGPHRCQHGCQN
QLGGYRCSCPQGFTQHSQWAQCVDENECALSPPTCGSASCRNTLGGFR
CVCPSGEDFDQALGGCQEVDECAGRRGPCSYSCANTPGGFLCGCPQGY
FRAGQGHCVSGLGESPGPQDTPDKEELLSSEACYECKINGLSPRDRPR
RSAHRDHQVNLATLDSEALLTLGLNLSHLGRAERILELRPALEGLEGR
IRYVIVRGNEQGFERMHHLRGVSSLQLGRRRPGPGTYRLEVVSHMAGP
WGVQPEGQPGPWGQALRLKVQLQLL LTBP3:
>gi|18497288|ref|NP_066548.2| latent transforming
growth factor beta binding protein 3
[Homo sapiens]
(SEQ ID NO: 36)
MPGPRGAAGGLAPEMRGAGAAGLLALLLLLLLLLGLGGRVEGGPAGE
RGAGGGGALARERFKVVFAPVICKRTCLKGQCRDSCQQGSNMTLIGEN
GHSTDTLTGSGERVVVCPLPCMNGGQCSSRNQCLCPPDFTGRFCQVPA
GGAGGGTGGSGPGLSRTGALSTGALPPLAPEGDSVASKHAIYAVQVIA
DPPGPGEGPPAQHAAFLVPLGPGQISAEVQAPPPVVNVRVHHPPEASV
QVHRIESSNAESAAPSQHLLPHPKPSHPRPPTQKPLGRCFQDTLPKQP
CGSNPLPGLTKQEDCCGSIGTAWGQSKCHKCPQLQYTGVQKPGPVRGE
VGADCPQGYKRLNSTHCQDINECAMPGVCRHGDCLNNPGSYRCVCPPG
HSLGPSRTQCIADKPEEKSLCFRLVSPEHQCQHPLTTRLTRQLCCCSV
GKAWGARCQRCPTDGTAAFKEICPAGKGYHILTSHQTLTIQGESDFSL
FLHPDGPPKPQQLPESPSQAPPPEDTEEERGVTTDSPVSEERSVQQSH
PTATTTPARPYPELISRPSPPTMRWFLPDLPPSRSAVEIAPTQVTETD
ECRLNQNICGHGECVPGPPDYSCHCNPGYRSHPQHRYCVDVNECEAEP
CGPGRGICMNTGGSYNCHCNRGYRLHVGAGGRSCVDLNECAKPHLCGD
GGFCINFPGHYKCNCYPGYRLKASRPPVCEDIDECRDPSSCPDGKCEN
KPGSFKCIACQPGYRSQGGGACRDVNECAEGSPCSPGWCENLPGSFRC
TCAQGYAPAPDGRSCLDVDECEAGDVCDNGICSNTPGSFQCQCLSGYH
LSRDRSHCEDIDECDFPAACIGGDCINTNGSYRCLCPQGHRLVGGRKC
QDIDECSQDPSLCLPHGACKNLQGSYVCVCDEGFTPTQDQHGCEEVEQ
PHHKKECYLNFDDTVECDSVLATNVTQQECCCSLGAGWGDHCEIYPCP
VYSSAEFHSLCPDGKGYTQDNNIVNYGIPAHRDIDECMLFGSEICKEG
KCVNTQPGYECYCKQGFYYDGNLLECVDV<u>DECLDESNCRNGVCENTRG</u>
<u>GYRC</u>ACTPPAEYSPAQRQCLSPEEMERAPERRDVCWSQRGEDGMCAGP
LAGPALTFDDCCCRQGRGWGAQCRPCPPRGAGSHCPTSQSESNSFWDT
SPLLLGKPPRDEDSSEEDSDECRCVSGRCVRPGGAVCECPGGFQLDA -continued
SRARCVDIDECRELNQRGLLCKSERCVNTSGSFRCVCKAGFARSRPHG
ACVPQRRR Laminin alpha 4:
>gi|157419124|ref|NP_001098676.1| laminin, alpha
4 isoform 1 precursor [Homo sapiens]
(SEQ ID NO: 37)
MALSSAWRSVLPLWLLWSAACSRAASGDDNAFPFDIEGSSAVGRQDPP
ETSEPRVALGRLPPAAEKCNAGFFHTLSGECVPCDCNGN<u>NECLDGSG</u>
<u>YCVHCQRNTTGEHC</u>EKCLDGYIGDSIRGAPQFCQPCPCPLPHLANFAE
SCYRKNGAVRCICNENYAGPNCERCAPGYYGNPLLIGSTCKKCDCSGN
SDPNLIFEDCDEVTGQCRNCLRNTTGFKCERCAPGYYGDARIAKNCAV
CNCGGGPCDSVTGECLEEGFEPPTGMDCPTISCDKCVWDLTDALRLAA
LSIEEGKSGVLSVSSGAAAHRHVNEINATIYLLKTKLSERENQYALRK
IQINNAENTMKSLLSDVEELVEKENQASRKGQLVQKESMDTINHASQL
VEQAHDMRDKIQEINNKMLYYGEEHELSPKEISEKLVLAQKMLEEIRS
RQPPFFTQRELVDEEADEAYELLSQAESWQRLHNETRTLFPVVLEQLDD
YNAKLSDLQEALDQALNYVRDAEDMNRATAARQRDHEKQQERVREQME
VVNMSLSTSADSLTTPRLTLSELDDIIKNASGIYAEIDGAKSELQVKL
SNLSNLSHDLVQEAIDHAQDLQQEANELSRKLHSSDMNGLVQKALDAS
NVYENIVNYVSEANETAEFALNTTDRIYDAVSGIDTQIIYHKDESENL
LNQARELQAKAESSSDEAVADTSRRVGGALARKSALKTRLSDAVKQLQ
AAERGDAQQRLGQSRLITEEANRTTMEVQQATAPMANNLTNWSQNLQH
FDSSAYNTAVNSARDAVRNLTEVVPQLLDQLRTVEQKRPASNVSASIQ
RIRELIAQTRSVASKIQVSMMFDGQSAVEVHSRTSMDDLKAFTSLSLY
MKPPVKRPELTETADQFILYLGSKNAKKEYMGLAIKNDNLVYVYNLGT
KDVEIPLDSKPVSSWPAYESIVKIERVGKHGKVFLTVPSLSSTAEEKF
IKKGEFSGDDSLLDLDPEDTVFYVGGVPSNFKLPTSLNLPGFVGCLEL
ATLNNDVISLYNEKHIYNMDPSTSVPCARDKLAFTQSRAASYFFDGSG
YAVVRDITRRGKFGQVTRFDIEVRTPADNGLILLMVNGSMFFRLEMRN
GYLHVFYDFGFSGGPVHLEDTLKKAQINDAKYHEISIIYHNDKKMILV
VDRRHVKSMDNEKMKIPFTDIYIGGAPPEILQSRALRAHLPLDINFRG
CMKGFQFQKKDFNLLEQTETLGVGYGGPEDSLISRRAYENGQSFIASI
QKISFEDGFEGGFNFRTLQPNGLLFYYASGSDVESISLDNGTVIMDVK
GIKVQSVDKQYNDGLSHEVISSVSPTRYELIVDKSRVGSKNPTKGKIE
QTQASEKKFYFGGSPISAQYANFTGCISNAYFTRVDRDVEVEDFQRYT
EKVHTSLYECPIESSPLFLLHKKGKNLSKPKASQNKKGGKSKDAPSWD
PVALKLPERNTPRNSHCHLSNSPRAIEHAYQYGGTANSRQEFEHLKGD
FGAKSQFSIRLRTRSSHGMIFYVSDQEENDFMTLFLAHGRLVYMFNVG
HKKLKIRSQEKYNDGLWHDVIFIRERSSGRLVIDGLRVLEESLPPTEA
TWKIKGPIYLGGVAPGKAVKNVQINSIYSFSGCLSNLQLNGASITSAS
QTFSVTPCFEGPMETGTYFSTEGGYVVLDESFNIGLKFEIAFEVRPRS
SSGTLVHGHSVNGEYLNVHMKNGQVIVKVNNGIRDFSTVTPKQSLCD -continued

GRWHRITVIRDSNVVQLDVDSEVNHVVGPLNPKPIDHREPVFVGGVPE

SLLTPRLAPSKPFTGCIRHFVIDGHPVSFSKAALVSGAVSINSCPAA stabilin 2:
>gi|61743980|ref|NP_060034.9|stabilin 2 precursor
[Homo sapiens]
(SEQ ID NO: 38)
MMLQHLVIFCLGLVVQNFCSPAETTGQARRCDRKSLLTIRTECRSCAL

NLGVKCPDGYTMITSGSVGVRDCRYTFEVRTYSLSLPGCRHICRKDYL

QPRCCPGRWGPDCIECPGGAGSPCNGRGSCAEGMEGNGTCSCQEGFGG

TACETCADDNLFGPSCSSVCNCVHGVCNSGLDGDGTCECYSAYTGPKC

DKPIPECAALLCPENSRCSPSTEDENKLECKCLPNYRGDGKYCDPINP

CLRKICHPHAHCTYLGPNRHSCTCQEGYRGDGQVCLPVDPCQINFGNC

PTKSTVCKYDGPGQSHCECKEHYQNFVPGVGCSMTDICKSDNPCHRNA

NCTTVAPGRTECICQKGYVGDGLTCYGNIMERLRELNTEPRGKWQGRL

TSFISLLDKAYAWPLSKLGPFTVLLPTDKGLKGENVNELLVDNKAAQY

FVKLHIIAGQMNIEYMNNTDMFYTLTGKSGEIFNSDKDNQIKLKLHGG

KKKVKIIQGDIIASNGLLHILDRAMDKLEPTFESNNEQTIMTMLQPRY

SKFRSLLEETNLGHALDEDGVGGPYTIFVPNNEALNNMKDGTLDYLLS

PEGSRKLLELVRYHIVPFTQLEVATLISTPHIRSMANQLIQFNTTDNG

QILANDVAMEEIEITAKNGRIYTLTGVLIPPSIVPILPHRCDETKREM

KLGTCVSCSLVYWSRCPANSEPTALFTHRCVYSGRFGSLKSGCARYCN

ATVKIPKCCKGFYGPDCNQCPGGESNPCSGNGQCADSLGGNGTCICEE

GFQGSQCQFCSDPNKYGPRCNKKCLCVHGTCNNRIDSDGACLTGTCRD

GSAGRLCDKQTSACGPYVQFCHIHATCEYSNGTASCICKAGYEGDGTL

CSEMDPCTGLTPGGCSRNAECIKTGTGTHTCVCQQGWTGNGRDCSEIN

NCLLPSAGGCHDNASCLYVGPGQNECECKKGFRGNGIDCEPITSCLEQ

TGKCHPLASCQSTSSGVWSCVCQEGYEGDGFLCYGNAAVELSFLSEAA

IFNRWINNASLQPTLSATSNLTVLVPSQQATEDMDQDEKSFWLSQSNI

PALIKYHMLLGTYRVADLQTLSSSDMLATSLQGNFLHLAKVDGNITIE

GASIVDGDNAATNGVIHIINKVLVPQRRLTGSLPNLLMRLEQMPDYSI

FRGYIIQYNLANAIEAADAYTVFAPNNNAIENYIREKKVLSLEEDVLR

YHVVLEEKLLKNDLHNGMHRETMLGESYFLSFFLHNDQLYVNEAPINY

TNVATDKGVIHGLGKVLEIQKNRCDNNDTTIIRGRCRTCSSELTCPFG

TKSLGNEKRRCIYTSYFMGRRTLFIGCQPKCVRTVITRECCAGFFGPQ

CQPCPGNAQNVCFGNGICLDGVNGTGVCECGEGFSGTACETCTEGKYG

IHCDQACSCVHGRCNQGPLGDGSCDCDVGWRGVHCDNATTEDNCNGTC

HTSANCLTNSDGTASCKCAAGFQGNGTICTAINACEISNGGCSAKADC

KRTTPGRRVCTCKAGYTGDGIVCLEINPCLENHGGCDKNAECTQTGPN

QAACNCLPAYTGDGKVCTL<u>INVCLTKNGGCSEFAIC</u>NHTGQVERTCTC

KPNYIGDGFTCRGSIYQELPKNPKTSQYFFQLQEHFVKDLVGPGPFTV

FAPLSAAFDEEARVKDWDKYGLMPQVLRYHVVACHQLLLENLKLISNA

TSLQGEPIVISVSQSTVYINNKAKIISSDIISTNGIVHIIDKLLSPKN

LLITPKDNSGRILQNLTTLATNNGYIKFSNLIQDSGLLSVITDPIHTP

VTLFWPTDQALHALPAEQQDFLFNQDNKDKLKEYLKFHVIRDAKVLAV

DLPTSTAWKTLQGSELSVKCGAGRDIGDLFLNGQTCRIVQRELLFDLG

VAYGIDCLLIDPTLGGRCDTFTTFDASGECGSCVNTPSCPRWSKPKGV

KQKCLYNLPFKRNLEGCRERCSLVIQIPRCCKGYFGRDCQACPGGPDA

PCNNRGVCLDQYSATGECKCNTGFNGTACEMCWPGRFGPDCLPCGCSD

HGQCDDGITGSGQCLCETGWTGPSCDTQAVLPAVCTPPCSAHATCKEN

NTCECNLDYEGDGITCTVVDECKQDNGGCAKVARCSQKGTKVSCSCQK

GYKGDGHSCTEIDPCADGLNGGCHEHATCKMTGPGKHKCECKSHYVGD

GLNCEPEQLPIDRCLQDNGQCHADAKCVDLHFQDTTVGVEHLRSPLGQ

YKLTEDKAREACANEAATMATYNQLSYAQKAKYHLCSAGWLETGRVAY

PTAFASQNCGSGVVGIVDYGPRPNKSEMWDVECYRMKDVNCTCKVGYV

GDGESCSGNLLQVLMSEPSLTNFLTEVLAYSNSSARGRAFLEHLTDLS

IRGTLFVPQNSGLGENETLSGRDIEHHLANVSMFFYNDLVNGTTLQTR

LGSKLLITASQDPLQPTETRFVDGRAILQWDIFASNGIIHVISRPLKA

PPAPVTLTHTGLGAGIFFAIILVTGAVALAAYSYFRINRRTIGFQHFE

SEEDINVAALGKQQPENISNPLYESTTSAPPEPSYDPFTDSEERQLEG

NDPLRTL

NOTCH2
>gi|24041035|ref|NP_077719.2| notch 2
preproprotein [Homo sapiens]
(SEQ ID NO: 39)
MPALRPALLWALLALWLCCAAPAHALQCRDGYEPCVNEGMCVTYHNGT

GYCKCPEGFLGEYCQHRDPCEKNRCQNGGTCVAQAMLGKATCRCASGF

TGEDCQYSTSHPCFVSRPCLNGGTCHMLSRDTYECTCQVGFTGKECQW

TDACLSHPCANGSTCTTVANQFSCKCLTGFTGQKCETDVNECDIPGHC

QHGGTCLNLPGSYQCQCPQGFTGQYCDSLYVPCAPSPCVNGGTCRQTG

DFTFECNCLPGFEGSTCERNIDDCPNHRCQNGGVCVDGVNTYNCRCPP

QWTGQFCTEDVDECLLQPNACQNGGTCANRGGYGVCVCNGWSGDDCS

ENIDDCAFASCTPGSTCIDRVASFSCMCPEGKAGLLCHLDDACISNPC

HKGALCDTNPLNGQYICTCPQGYKGADCTEDVDECAMANSNPCEHAGK

CVNTDGAFHCECLKGYAGPRCEMDINECHSDPCQNDATCLDKIGGFTC

LCMPGFKGVHCELEINECQSNPCVNNGQCVDKVNRFQCLCPPGFTGPV

CQIDIDDCSSTPCLNGAKCIDHPNGYECQCATGFTGVLCEENIDNCDP

DPCHHGQCQDGIDSYTCICNPGYMGAICSDQIDECYSSPCLNDGRCID

LVNGYQCNCQPGTSGVNCEINFDDCASNPCIHGICMDGINRYSCVCSP

GFTGQRCNIDIDECASNPCRKGATCINGVNGFRCICPEGPHHPSCYSQ

VNECLSNPCIHGNCTGGLSGYKCLCDAGWVGINCEVDK<u>NECLSNPCQN
GGTCDNLVNGYRC</u>TCKKGFKGYNCQVNIDECASNPCLNQGTCFDDISG

YTCHCVLPYTGKNCQTVLAPCSPNPCENAAVCKESPNFESYTCLCAPG

WQGQRCTIDIDECISKPCMNHGLCHNTQGSYMCECPPGFSGMDCEEDI

DDCLANPCQNGGSCMDGVNTESCLCLPGFTGDKCQTDMNECLSEPCKN

GGTCSDYVNSYTCKCQAGEDGVHCENNINECTESSCFNGGTCVDGINS

```
FSCLCPVGFTGSFCLHEINECSSHPCLNEGTCVDGLGTYRCSCPLGYT
GKNCQTLVNLCSRSPCKNKGTCVQKKAESQCLCPSGWAGAYCDVPNVS
CDIAASRRGVLVEHLCQHSGVCINAGNTHYCQCPLGYTGSYCEEQLDE
CASNPCQHGATCSDFIGGYRCECVPGYQGVNCEYEVDECQNQPCQNGG
TCIDLVNHFKCSCPPGTRGLLCEENIDDCARGPHCLNGGQCMDRIGGY
SCRCLPGFAGERCEGDINECLSNPCSSEGSLDCIQLTNDYLCVCRSAF
TGRHCETFVDVCPQMPCLNGGTCAVASNMPDGFICRCPPGFSGARCQS
SCGQVKCRKGEQCVHTASGPRCFCPSPRDCESGCASSPCQHGGSCHPQ
RQPPYYSCQCAPPFSGSRCELYTAPPSTPPATCLSQYCADKARDGVCD
EACNSHACQWDGGDCSLTMENPWANCSSPLPCWDYINNQCDELCNTVE
CLFDNFECQGNSKTCKYDKYCADHFKDNHCDQGCNSEECGWDGLDCAA
DQPENLAEGTLVIVVLMPPEQLLQDARSFLRALGTLLHTNLRIKRDSQ
GELMVYPYYGEKSAAMKKQRMTRRSLPGEQEQEVAGSKVFLEIDNRQC
VQDSDHCFKNTDAAAALLASHAIQGTLSYPLVSVVSESLTPERTQLLY
LLAVAVVIILFIILLGVIMAKRKRKHGSLWLPEGFTLRRDASNHKRRE
PVGQDAVGLKNLSVQVSEANLIGTGTSEHWVDDEGPQPKKVKAEDEAL
LSEEDDPIDRRPWTQQHLEAADIRRTPSLALTPPQAEQEVDVLDVNVR
GPDGCTPLMLASLRGGSSDLSDEDEDAEDSSANIITDLVYQGASLQAQ
TDRTGEMALHLAARYSRADAAKRLLDAGADANAQDNMGRCPLHAAVAA
DAQGVFQILIRNRVTDLDARMNDGTTPLILAARLAVEGMVAELINCQA
DVNAVDDHGKSALHWAAAVNNVEATLLLLKNGANRDMQDNKEETPLFL
AAREGSYEAAKILLDHFANRDITDHMDRLPRDVARDRMHHDIVRLLDE
YNVTPSPPGTVLTSALSPVICGPNRSELSLKHTPMGKKSRRPSAKSTM
PTSLPNLAKEAKDAKGSRRKKSLSEKVQLSESSVTLSPVDSLESPHTY
VSDTTSSPMITSPGILQASPNPMLATAAPPAPVHAQHALSFSNLHEMQ
PLAHGASTVLPSVSQLLSHHHIVSPGSGSAGSLSRLHPVPVPADWMNR
MEVNETQYNEMFGMVLAPAEGTHPGIAPQSRPPEGKHITTPREPLPPI
VTFQLIPKGSIAQPAGAPQPQSTCPPAVAGPLPTMYQIPEMARLPSVA
FPTAMMPQQDGQVAQTILPAYHPFPASVGKYPTPPSQHSYASSNAAER
TPSHSGHLQGEHPYLTPSPESPDQWSSSSPHSASDWSDVTTSPTPGGA
GGGQRGPGTHMSEPPHNNMQVYA

Cubilin:
>gi|126091152|ref|NP_001072.2|cubilin
[Homo sapiens]
                                            (SEQ ID NO: 40)
MMNMSLPFLWSLLTLLIFAEVNGEAGELELQRQKRSINLQQPRMATER
GNLVFLTGSAQNIEFRTGSLGKIKLNDEDLSECLHQIQKNKEDIIELK
GSAIGLPQNISSQIYQLNSKLVDLERKFQGLQQTVDKKVCSSNPCQNG
GTCLNLHDSFFCICPPQWKGPLCSADVNECEIYSGTPLSCQNGGTCVN
TMGSYSHCHCPPETYGPQCASKYDDCEGGSVARCVHGICEDLMREQAGE
PKYSCVCDAGWMFSPNSPACTLDRDECSFQPGPCSTLVQCFNTQGSFY
CGACPTGWQGNGYICEDINECEINNGGCSVAPPVECVNTPGSSHCQAC
PPGYQGDGRVCTLTDICSVSNGGCHPDASCSSTLGSLPLCTCLPGYTG NGYGPNGCVQLSNICLSHPCLNGQCIDTVSGYFCKCDSGWTGVNCTEN
INECLSNPCLNGGTCVDGVDSFSCECTRLWTGALCQVPQQVCGESLSG
INGSFSYRSPDVGYVHDVNCFWVIKTEMGKVLRITFTFFRLESMDNCP
HEFLQVYDGDSSSAFQLGRFCGSSLPHELLSSDNALYFHLYSEHLRNG
RGETVRWETQQPECGGILTGPYGSIKSPGYPGNYPPGRDCVWIVVTSP
DLLVTFTFGTLSLEHHDDCNKDYLEIRDGPLYQDPLLGKFCTTFSVPP
LQTTGPFARIHFHSDSQISDQGFHITYLTSPSDLRCGGNYTDPEGELF
LPELSGPFTHTRQCVYMMKQPQGEQIQINFTHVELQCQSDSSQNYIEV
RDGETLLGKVCGNGTISHIKSITNSVWIRFKIDASVEKASFRAVYQVA
CGDELTGEGVIRSPFFPNVYPGERTCRWTIHQPQSQVILLNFTVFEIG
SSAHCETDYVEIGSSSILGSPENKKYCGTDIPSFITSVYNFLYVTFVK
SSSTENHGFMAKFSAEDLACGEILTESTGTIQSPGHPNVYPHGINCTW
HILVQPNHLIHLMFETFHLEFHYNCTNDYLEVYDTDSETSLGRYCGKS
IPPSLTSSGNSLMLVFVTDSDLAYEGFLINYEAISAATACLQDYTDDL
GTFTSPNFPNNYPNNWECIYRITVRTGQLIAVHFTNFSLEEAIGNYYT
DFLEIRDGGYEKSPLLGIFYGSNLPPTIISHSNKLWLKFKSDQIDTRS
GFSAYWDGSSTGCGGNLTTSSGTFISPNYPMPYYESSECYWWLKSSHG
SAFELEFKDFHLEHHPNCTLDYLAVYDGPSSNSHLLTQLCGDEKPPLI
RSSGDSMFIKLRTDEGQQRGFKAEYRQTCENVVIVNQTYGILESIGY
PNPYSENQHCNWTIRATTGNTVNYTFLAFDLEHHINCSTDYLELYDGP
RQMGRYCGVDLPPPGSTTSSKLQVLLLTDGVGRREKGFQMQWFVYGCG
GELSGATGSFSSPGFPNRYPPNKECIWYIRTDPGSSIQLTIHDFDVEY
HSRCNFDVLEIYGGPDFHSPRIAQLCTQRSPENPMQVSSTGNELAIRE
KTDLSINGRGENASWQAVTGGCGGIFQAPSGEIHSPNYPSPYRSNTDC
SWVIRVDRNHRVLLNFTDFDLEPQDSCIMAYDGLSSTMSRLARTCGRE
QLANPIVSSGNSLFLRFQSGPSRQNRGFRAQFRQACGGHILTSSFDTV
SSPRFPANYPNNQNCSWITQAQPPLNHITLSFTHFELFRSTTCARDFV
EILDGGHEDAPLRGRYCGTDMPHPITSFSSALTLRFVSDSSISAGGFH
TTVTASVSACGGTFYMAEGIFNSPGYPDIYPPNVECVWNIVSSPGNRL
QLSFISFQLEDSQDCSRDFVEIREGNATGHLVGRYCGNSFPLNYSSIV
GHTLWVRFISDGSGSGTGFQATFMKIFGNDNIVGTHGKVASPFWPENY
PHNSNYQWTVNVNASHVVHGRILEMDIEEIQNCYYDKLRIYDGPSIHA
RLIGAYCGTQTESFSSTGNSLTFHFYSDSSISGKGFLLEWFAVDAPDG
VLPTIAPGACGGFLRTGDAPVELFSPGWPDSYSNRVDCTWLIQAPDST
VELNILSLDIESHRTCAYDSLVIRDGDNNLAQQLAVLCGREIPGPIRS
TGEYMEIRFTSDSSVIRAGENASFHKSCGGYLHADRGIITSPKYPETY
PSNENCSWHVLVQSGLTIAVHFEQPFQIPNGDSSCNQGDYLVERNGPD
ICSPPLGPPGGNGHFCGSHASSTLFTSDNQMFVQFISDHSNEGQGFKI
KYEAKSLACGGNVYIHDADSAGYVISPNHPHNYPPHADCIWILAAPPE
TRIQLQFEDREDIEVTPNCTSNYLELRDGVDSDAPILSKFCGTSLPSS
```

QWSSGEVMYLRERSDNSPTHVGFKAKYSIAQCGGRVPGQSGVVESIGH
PTLPYRDNLECEWHLQGLSGHYLTISFEDFNLQNSSGCEKDEVEIWDN
HTSGNILGRYCGNTIPDSIDTSSNTAVVRFVTDGSVTASGFRERFESS
MEECGGDLQGSIGIFTSPNYPNPNPHGRICEWRITAPEGRRITLMENN
LRLATHPSCNNEHVIVENGIRSNSPQLEKLCSSVNVSNEIKSSGNIMK
VIFFIDGSRPYGGETASYTSSEDAVCGGSLPNIPEGNFTSPGYDGVRN
YSRNLNCEWILSNPNQGNSSISIHFEDFYLESHQDCAFDVLEFRVGDA
DGPLMWRLCGPSKPILPLVIPYSQVWIHFVTNERVEHIGFHAKYSFTD
CGGIQIGDSGVITSPNYPNAYDSLTHCSSLLEAPQGHTITLTFSDFDI
EPHTTCAWDSVIVRNGGSPESPIIGQYCGNSNPRTIQSGSNQLVVTFN
SDHSLQGGGFYATWNTQTLGCGGIFHSDNGTIRSPHWPQNFPENSRCS
WTAITHKSKHLEISFDNNFLIPSGDGQCQNSFVKVWAGTEEVDKALLA
TGCGNVAPGPVITPSNIFTAVFQSQEAPAQGFSASFVSRCGSNFTGPS
GYIISPNYPKQYDNNMNCTYVIEANPLSVVELTFVSFHLEARSAVTGS
CVNDGVHIIRGYSVMSTPFATVCGDEMPAPLTIAGPVLLNFYSNEQIT
DFGFKFSYRIISCGGVFNFSSGIITSPAYSYADYPNDMHCLYTITVSD
DKVIELKFSDFDVVPSTSCSHDYLAIYDGANTSDPLLGKFCGSKRPPN
VKSSNNSMELVFKTDSFQTAKGWKMSFRQTLGPQQGCGGYLTGSNNTF
ASPDSDSNGMYDKNENCVWIIIAPVNKVIHLTFNTFALEEAASTRQRCL
YDYVKLYDGDSENANLAGTFCGSTVPAPFISSGNFLTVQFISDLTLER
EGFNATYTIMDMPCGGTYNATWTPQNISSPNSSDPDVPFSICTWVIDS
PPHQQVKITVWALQLTSQDCTQNYLQLQDSPQGHGNSRFQFCGRNASA
VPVFYSSMSTAMVIEKSGVVNRNSRMSFTYQIADCNRDYHKAFGNERS
PGWPDNYDNDKDCTVTLTAPQNHTISLFFHSLGIENSVECRNDFLEVR
NGSNSNSPLEGKYCGTLLPNPVFSQNNELYLRFKSDSVTSDRGYEIIW
TSSPSGCGGTLYGDRGSFTSPGYPGTYPNNTYCEWVLVAPAGRLVTIN
FYFISIDDPGDCVQNYLTLYDGPNASSPSSGPYCGGDTSIAPEVASSN
QVFIKEHADYARRPSAFRETWDS

DNER:
>gi|116235485|ref|NP_620711.3| delta-notch-like
EGF repeat-containing transmembrane
[Homo sapiens]
(SEQ ID NO: 41)
MQPRRAQAPGAQLLPALALLLLLGAGPRGSSLANPVPAAPLSAPGPC
AAQPCRNGGVCTSRPEPDPQHPAPAGEPGYSCTCPAGISGANCQLVAD
PCASNPCHHGNCSSSSSSSSDGYLCICNEGYEGPNCEQALPSLPATGW
TESMAPRQLQPVPATQEPDKILPRSQATVTLPTWQPKTGQKVVEMKWD
QVEVIPDIACGNASSNSSAGGRLVSFEVPQNTSVKIRQDATASLILLW
KVTATGFQQCSLIDGRSVTPLQASGGLVELEEMLALGNNHFIGFVNDS
VTKSIVALRLTVVKVSTCVPGESHANDLECSGKGKCTTKPSEATESC
TCEEQYVGTFCEEYDACQRKPCQNNASCIDANEKQDGSNFTCVCLPGY
TGELCQSKIDYCILDPCRNGATCISSLSGFICQCPEGYFGSACEEKVD
PCASSPCQNNGTCYVDGVHFTCNCSPGFTGPTCAQLIDFCALSPCAHG TCRSVGTSYKCLCDPGYHGLYCEEEYNECLSAPCLNAATCRDLVNGYE
CVCLAEYKGTHCELYKDPCANVSCLNGATCDSDGLNGTCICAPGFTGE
ECDIDINECDSNPCHHGGSCLDQPNGYNCHCPHGWVGANCEIHLQWKS
GHMAESLINMPRHSLYIIIGALCVAFILMLIILIVGICRISRIEYQGS
SRPAYEEFYNCRSIDSEFSNAIASIRHAREGKKSRPAMYDVSPIAYED
YSPDDKPLVTLIKTKDL Jagged 1:
>gi|4557679|ref|NP_000205.1| jagged 1 precursor
[Homo sapiens]
(SEQ ID NO: 42)
MRSPRTRGRSGRPLSELLALLCALRAKVCGASGQFELEILSMQNVGE
LQNGNCCGGARNPGDRKCTRDECDTYFKVCLKEYQSRVTAGGPCSEGS
GSTPVIGGNTFNLKASRGNDRNRIVLPFSFAWPRSYTLLVEAWDSSND
TVQPDSIIEKASHSGMINPSRQWQTLKQNTGVAHFEYQIRVTCDDYYY
GEGCNKFCRPRDDFFGHYACDQNGNKTCMEGWMGPECNRAICRQGCSP
KHGSCKLPGDCRCQYGWQGLYCDKCIPHPGCVHGICNEPWQCLCETNW
GGQLCDKDLNYCGTHQPCLNGGICSNIGPDKYQCSCPEGYSGPNCEIA
EHACLSDPCHNRGSCKETSEGFECECSPGWTGPTCSTNIDDCSPNNCS
HGGTCQDLVNGFKCVCPPQWTGKTCQLDANECEAKPCVNAKSCKNLIA
SYYCDCLPGWMGQNCDININDCLGQCQNDASCRDLVNGYRCICPPGYA
GDHCERDIDECASNPCLNGGHCQNEINRFQCLCPTGFSGNLCQLDIDY
CEPNPCQNGAQCYNRASDYFCKCPEDYEGKNCSHLKDHCRTTPCEVID
SCIVAMASNDTPEGVRYISSNVCGPHGKCKSQSGGKFTCDCNKGFTGT
YCHENINDCESNPCRNGGICIDGVNSYKCICSDGWEGAYCETNINDCS
QNPCHNGGTCRDLVNDFYCDCKNGWKGKTCHSRDSQCDEATCNNGGTC
YDEGDAFKCMCPGGWEGTTCNIARNSSCLPNPCHNGGTCVVNGESFTC
VCKEGWEGPICAQNTNDCSPHPCYNSGTCVDGDNWYRCECAPGFAGPD
CRININECQSSPCAFGATCVDEINGYRCVCPPGHSGAKCQEVSGRPCI
TMGSVIPDGAKWDDDCNTCQCLNGRIACSKVWCGPRPCLLHKGHSECP
SGQSCIPILDDQCFVHPCTGVGECRSSSLQPVKTKCTSDSYYQDNCAN
ITFTFNKEMMSPGLTTEHICSELRNLNILKNVSAEYSIYIACEPSPSA
NNEIHVAISAEDIRDDGNPIKEITDKIIDLVSKRDGNSSLIAAVAEVR
VQRRPLKNRTDELVPLESSVLIVAWICCLVTAFYWCLRKRRKPGSHTH
SASEDNTTNNVREQLNQIKNPIEKHGANTVPIKDYENKNSKMSKIRTH
NSEVEEDDMDKHQQKARFAKQPAYTLVDREEKPPNGTPTKHPNWTNKQ
DNRDLESAQSLNRMEYIV 5'-3' exonuclease 2
>gi|18860916|ref|NP_036387.2| 5'-3'
exoribonuclease 2 [Homo sapiens]
(SEQ ID NO: 43)
MGVPAFFRWLSRKYPSIIVNCVEEKPKECNGVKIPVDASKPNPNDVEF
DNLYLDMNGIIHPCTHPEDKPAPKNEDEMMVAIFEYIDRLFSIVRPRR
LLYMAIDGVAPRAKMNQQRSRRFRASKEGMEAAVEKQRVREEILAKGG
FLPPEEIKERFDSNCITPGIEFMDNLAKCLRYYIADRLNNDPGWKNLT
VILSDASAPGEGEHKIMDYIRRQRAQPNHDPNTHHCLCGADADLIMLG -continued

LATHEPNFTIIREEFKPNKPKPCGLCNQFGHEVKDCEGLPREKKGKHD

ELADSLPCAEGEFIFLRLNVLREYLERELTMASLPFTFDVERSIDDWV

FMCFFVGNDFLPHLPSLEIRENAIDRLVNIYKNVVHKIGGYLTESGYV

NLQRVQMIMLAVGEVEDSIFKKRKDDEDSFRRRQKEKRKRMKRDQPAF

TPSGILTPHALGSRNSPGSQVASNPRQAAYEMRMQNNSSPSISPNTSF

TSDGSPSPLGGIKRKAEDSDSEPEPEDNVRLWEAGWKQRYYKNKFDVD

AADEKFRRKVVQSYVEGLCWVLRYYYQGCASWKWYYPFHYAPFASDFE

GIADMPSDFEKGTKPFKPLEQLMGVFPAASGNFLPPSWRKLMSDPDSS

IIDFYPEDFAIDLNGKKYAWQGVALLPFVDERRLRAALEEVYPDLIPE

ETRRNSLGGDVLEVGKHHPLHDFILELYQTGSTEPVEVPPELCHGIQG

KESLDEEAILPDQIVCSPVPMLRDLTQNTVVSINFKDPQFAEDYIFKA

VMLPGARKPAAVLKPSDWEKSSNGRQWKPQLGFNRDRRPVHLDQAAFR

TLGHVMPRGSGTGIYSNAAPPPVTYQGNLYRPLLRGQAQIPKLMSNMR

PQDSWRGPPPLFQQQRFDRGVGAEPLLPWNRMLQTQNAAFQPNQYQML

AGPGGYPPRRDDRGGRQGYPREGRKYPLPPPSGRYNWN

ZNF569:
>gi|38570117|ref|NP_689697.2| zinc finger protein
569 [Homo sapiens]
(SEQ ID NO: 44)
MTESQGTVIFKDVAIDFTQEEWKRLDPAQRKLYRNVMLENYNNLITVG

YPFTKPDVIFKLEQEEEPWVMEEEVLRRHWQGEIWGVDEHQKNQDRLL

RQVEVKFQKTLTEEKGNECQKKFANVFPLNSDFFPSRH<u>NLYEYDLFGK</u>

<u>CLEHNFDCHNNVKCLMRKEHCEYNEPVKSYGNSSSHFVITPFKCNHCG</u>

<u>KGFNQTLDLI</u>RHLRIHTGEKPYECSNCRKAFSHKEKLIKHYKIHSREQ

SYKCNECGKAFIKMSNLIRHQRIHTGEKPYACKECEKSFSQKSNLIDH

EKIHTGEKPYECNECGKAFSQKQSLIAHQKVHTGEKPYACNECGKAFP

RIASLALHMRSHTGEKPYKCDKCGKAFSQFSMLIIHVRIHTGEKPYEC

NECGKAFSQSSALTVHMRSHTGEKPYECKECRKAFSHKKNFITHQKIH

TREKPYECNECGKAFIQMSNLVRHQRIHTGEKPYICKECGKAFSQKSN

LIAHEKIHSGEKPYECNECGKAFSQKQNFITHQKVHIGEKPYDCNECG

KAFSQIASLTLHLRSHTGEKPYECDKCGKAFSQCSLLNLHMRSHIGEK

PYVCNECGKAFSQRTSLIVHMRGHTGEKPYECNKCGKAFSQSSSLTIH

IRGHTGEKPFDCSKCGKAFSQISSLILHMRKHTGEKPYHCIECGKAFS

QKSHLVRHQRIHTH

FLJ36157 (s2s40):
>gnl|human.nt.rep.ntnoaa.fasta|1274182_f1_0
(76..5241)
(SEQ ID NO: 45)
VPPGGSSVCTAVGSCELVQRGPSGPAPGHMRRPPPLGPITASGPEGNV

RNLQKRQAPGPGAAGGCGPEAGGCRENKQKRRMVARATPGRGEVESDK

SVAASGAGKAARRQVEGRRGPVSPSDSSDPRGLEAAKEAELPLQTERH

TKEKRKVTEASSDDPQPGLDLVRKESLISSESFQTVECLQSLGKESII

EGIKRRIRNKKLKSLENPPLKITENEATQNIKVEFQDELYKNIPKYSC

NILSPEVENNSVLKLRDCNCEPHSKGCNDENNLPYKP<u>DGGCMHVAENF</u>

SKKENLRSLAEKSDTNSIPQLLQTEENVMGVNKLLPEESDLYQSKING

LLSCLQHEKNKYSIEESSVGRKPRKRMKLSEKADETVTEMNFSNEYNK

SELMLQENQMIADGKEAETKSPLNVLRKVSHNTVSLMDHLLSVPETVE

KETSSEHHVNAVFQKTIEPLLKEETENASEPLGYESMASKEDEKSMKS

FIGKSPNEYHIERRSSREDLRSASEELKLSCQRTIPMIGKRTWPYYSC

ARISAWCWKKASLPESSYFLRGSQESCRQVDVPKHQINQTHLTDSKLL

LQSSLTETNTESSSKEKLDSNSNCLSSVSAVEPTLMVIKEPIIKDDKK

IKSEELSRRGSEVISNTTEDTQLTSETQSLIGNKKKARGNLIKLNLTA

TSKDGQEANNSAGKTIHRKACIAQQTFIVPDLVKILNTGRLTNEKIPL

LKNKSEKRKEVNAKSSEREAYSPLELLDNLSGADVRQNRSKENVSMMM

LGPQTLSIRNSVTPVQASSDSFYNKKSYSISPSFTKQGNNSKPSNHVS

EPGNIVSNKEVASLTVENNAFSCDPGYVEKSPSFCCNEQETFRPVSSE

VRGRKITKNESEVGFPDILKAYEDDVLLIDVIQDDPDLEGVSNEGELS

FTSEVPKISQEPNVAGEHQSTDSKYMETPVKKEPSDDLRELPVLDCGW

IKPDICASNSAESEIKRDPKDVNTSLGEVANETSENETLGDFSEQIKG

SDLDEKHRFTDKVITKEEKENIYEVCKSKDSRNADFMVGECQFAVPVP

KPLCLLVPPLNLSGRQEDTILNTWMNDERFLGKHSVLKLQNPETCEIF

KREKNVGVFQKSLGLMIPYKYCKFHENTLRGCERPLCKFAHVPEQGDE

KVCMDVFKKYININELCLLQRAVNIFMEYYRKFPPGVYFDLQVLNDLL

NSLLKHCLLKEVFQIVNLSIMVKMLPSLKILLNIFEYVATMKLRNAVP

ALIDIFCKLVEAGMVLDPEHENYIVKLLYQVQASKQEITAVLEMKSRL

QMRRFKKNWKCDLDSALNKLEHCKEKGDWTKLGKLYINVKMGCEKFAD

FQTFCACIAETLIKNYEDERPDIPFCEFAETVSKDPQNSKVDKGVLGR

IGISAMYFYHKLLQWSKGRKVLEKLYELKIHFISLKGLIGPEKLASRC

QIVNVAAEIFLKSGSLDGAIWVMRESEWIINTPLWPCDRLDVLNRHNL

LCTIAHEILAKSLYRQTFEVLQNLPGFQNSQETVEVSQYSLLFNKLLG

SCIESSSLGMSSSVAEFMISKSIPIDFSFLRRLITSLGRSRLWLKARA

HYKSALSLGCYPPLEGNLYRKLLLIPSYLSEIEMLLAIEIFMVSNASS

IQSPGTSTQILQIVLKRCEDNQSRSNDDYQAAVERLIMAARISDPKLF

VKHMTVNVNKEQVYSLEHCSALKWLKENMKWAGKVWLFSNH

The scope of the present invention includes compositions (e.g., pharmaceutical compositions) comprising any of the EGF-A domain polypeptides identified in table 1 (except any demonstrated in vitro or in vivo not to actually bind to PCSK9) as well as methods of treatment comprising administration of said polypeptides as discussed herein is a manner similar to that of matrilin-2. Such EGF-A domains appear, e.g., in SCUBE2, OIT3, SCUBE1, LRP1, LRP2, LRP4/LRP10, SCUBE3, LRP5, MEGF6/EGFL3, LRP6, LRP1B, PROS1, GAS6, TLL1, NID1, TLL2, EGF, fibrilin 1, fibrilin 2, fibrilin 3, LTBP3, laminin apha 4, stabilin 2, NOTCH2NL, cubilin, DNER, jagged 1,5'-3' exoribonuclease 2, ZNF569 and FLJ36157.

The scope of the present invention includes compositions (e.g., pharmaceutical compositions) comprising ApoER2 EGF-A domain NECLDNNGGCSHVCNDLKIGYEC (SEQ ID NO: 50) or VLDLR EGF-A domain NECLDNNGGCSH-VCNDLKIGYEC (SEQ ID NO: 51) as well as methods of treatment comprising administration of said polypeptides as discussed herein is a manner similar to that of matrilin-2.

In vitro binding assay: Four proteins, including matrilin-2, were purchased to test for PCSK9 binding and Matrilin-2 was found to bind PCSK9 in a dose-dependent manner. These tests were performed as follows:

An Amplified Luminescent Proximity Homogeneous Assay (ALPHA, Perkin-Elmer; Waltham, Mass.) screen capable of detecting the interaction between PCSK9-FLAG and a putative binding partner was established and optimized following manufacturer's guidelines. The PCSK9-FLAG construct used had the following amino acid sequence:

Leader:
MGTVSSRRSWWPLPLLLLLLLLLGPAGARA

Pro domain (remains associated with mature protein-non covalently bound):
QEDEDGDYEELVLALRSEEDGLAEAPEHGTTATFHRCAKDPWRLPGTY

VVVLKEETHLSQSERTARRLQAQAARRGYLTKILHVEHGLLPGFLVKM

SGDLLELALKLPHVDYIEEDSSVFAQ

Catalytic and C-term domains with appended FLAG tag (in bold text):
(SEQ ID NO: 46)
SIPWNLERITPPRYRADEYQPPDGGSLVEVYLLDTSIQSDHREIEGRV

MVTDFENVPEEDGTRFHRQASKCDSHGTHLAGVVSGRDAGVAKGASMR

SLRVLNCQGKGTVSGTLIGLEFIRKSQLVQPVGPLVVLLPLAGGYSRV

LNAACQRLARAGVVLVTAAGNFRDDACLYSPASAPEVITVGATNAQDQ

PVTLGTLGTNFGRCVDLFAPGEDIIGASSDCSTCFVSQSGTSQAAAHV

AGIAAMMLSAEPELTLAELRQRLIHFSAKDVINEAWFPEDQRVLTPNL

VAALPPSTHGAGWQLFCRTVWSAHSGPTRMATAVARCAPDEELLSCSS

FSRSGKRRGERMEAQGGKLVCRAHNAFGGEGVYAIARCCLLPQANCSV

HTAPPAEASMGTRVHCHQQGHVLTGCSSHWEVEDLGTHKPPVLRPRGQ

PNQCVGHREASIHASCCHAPGLECKVKEHGIPAPQEQVTVACEEGWTL

TGCSALPGTSHVLGAYAVDNTCVVRSRDVSTTGSTSEGAVTAVAICCR

SRHLAQASQELQDYKDDDDK

This technique requires that "donor" and "acceptor" beads be brought into proximity via protein-protein interaction, resulting in increased luminescence. Receptor binding to PCSK9 was determined as follows: 5 ml of His-tagged recombinant matrilin-2 at the appropriate concentrations was incubated with 2.5 ml PCSK9-FLAG (1.4 mg/ml, 30 min). To express the His-tagged matrilin-2, a DNA sequence encoding the mature human Matrilin-2, short isoform (Arg 24-Arg 937) (Accession # AAH10444; 000339; Muratoglu, S. et al., 2000, Cytogenet. Cell Genet. 90:323-327) was fused to the signal peptide from human CD33 at the amino-terminus and to a polyhistidine tag at the carboxy-terminus. The chimeric protein was expressed in a mouse myeloma cell line, NS0. (R&D Systems Catalog Number: 3044-MN). 2.5 ml of biotinylated anti-Flag-M2 antibody (1.8 mg/ml) was then added and the mixture incubated for 1 hour. 5 ml of streptavidin donor beads and nickel chelate acceptor beads (1:1 mixture) was then added and the assay was incubated overnight in the dark. AlphaScreen signal (counts per second) was analyzed by using an ALPHASCREEN capable ENVISION microplate reader (Perkin-Elmer). All data points were determined in triplicate. Assays were carried out in buffer containing 25 mM HEPES, 0.1 M NaCl, pH 7.4, 0.1% BSA and all reactions were at 23° C. The data generated in these experiments are set forth in Table 2.

TABLE 2

Matrilin-2 binds PCSK9 in a dose-dependent manner

| log [Matrilin] uM | ALPHASCREEN Signal | Standard Deviation |
|---|---|---|
| −0.4317983 | 212627 | 2548 |
| −0.9089195 | 221834 | 3028 |
| −1.386041 | 54018 | 1634 |
| −1.863162 | 14061 | 1131 |
| −2.340283 | 10107 | 469 |
| −2.817405 | 12869 | 412 |
| −3.294526 | 18752 | 495 |
| −3.771647 | 20154 | 220 |

The following proteins were not found to bind to PCSK9: THBD (thrombomodulin) and BMP1 (bone morphogenetic protein 1)

These data confirmed that the matrilin-2 peptide identified in the sequence-based search for PCSK9 interacting proteins actually bound PCSK9.

Example 2

Matrilin-2 Inhibits LDL Receptor Binding to PCSK9

This example demonstrates that matrilin-2 peptide inhibits binding of PCSK9 to LDL receptor, in vitro, in a concentration-dependent manner.

LDL receptor binding to PCSK9 was determined as follows: 5 ml of recombinant receptor at the appropriate concentrations was incubated with 2.5 ml PCSK9-FLAG (1.4 mg/ml, 30 minutes). 2.5 ml of biotinylated anti-Flag-M2 antibody (1.8 mg/ml) was then added and the mixture incubated for 1 hour. 5 ml of streptavidin donor bead and nickel chelate acceptor bead (1:1 mixture) was then added and the assay incubated overnight in the dark. ALPHASCREEN signal (counts per second) was analyzed by using an ALPHASCREEN capable ENVISION microplate reader (Perkin-Elmer; Waltham, Mass.). All data points were determined in triplicate. Assays were carried out in buffer containing 25 mM HEPES, 0.1 M NaCl, pH7.4, 0.1% BSA and all reactions were at 23° C.

The inhibition assays were determined similarly with slight adjustments to assay volumes and protein concentrations. Briefly, 5 ml of 1.25 mg/ml of PCSK9-Flag and 1.25 mg/ml of His-tagged LDL receptor was incubated with 2.5 ml of inhibitor (matrilin-2 peptide; full length, recombinant) at the appropriate concentrations for 30 minutes followed by the addition of 2.5 ml of anti-Flag-BioM2 (1.8 mg/ml) and a 1 hour incubation. All subsequent steps were the same as above. The data generated in the inhibition assays are set forth below in Table 3.

TABLE 3

Concentration-dependent inhibition of PCSK9 binding to LDLR by recombinant matrilin-2 peptide.

| [mat] nM | % inhibition |
|---|---|
| 34 | 50.7 |
| 11 | 36.0 |
| 3.8 | 17.1 |
| 1.3 | 5.2 |

TABLE 3-continued

Concentration-dependent inhibition of PCSK9 binding to LDLR by recombinant matrilin-2 peptide.

| [mat] nM | % inhibition |
|---|---|
| 0.42 | −0.4 |
| 0.14 | 0.1 |

Data are expressed as percent inhibition relative to maximum signal achieved in the absence of added matrilin-2. "mat" is matrilin-2 peptide.

Example 3 hMatrilin-2/hPCSK9 Interaction ProFound Pull-Down PolyHistidine Assay

These experiments demonstrated that human PCSK9 bound to poly-His fused human matrilin and to poly-His fused human LDL receptor in vitro. In vitro interactions between the two pairs of proteins were performed, then the bound, complexed proteins were analyzed by Western blot. The Western blot analysis demonstrated the presence of both PCSK9/matrilin and PCSK9/LDL receptor in the samples analyzed.

Following the protocol of PROFOUND Pull-Down Poly-His Protein:Protein Interaction Kit (Pierce, Cat.#21277; PIERCE, Rockford, Ill. 61105), equilibrated immobilized cobalt chelate resin column and collected the flow-through wash solution as the Agarose gel control sample. As the purified bait protein, 50 ug of His-tagged human-Matrlin-2 (R&D systems, Cat.#3044-MN/CF) was applied to the equilibrated cobalt chelate column, and incubated at 4° C. for overnight with gentle rocking motion for immobilizing of the His-tagged bait protein to the column. Collected unbound hMatrlin-2 as the bait flow-through sample by centrifuge at 1,250×g for 30 seconds. After washing, applied 50 ug of purified human-PCSK9 as the prey protein to the column and incubated at 4° C. for 2 hours by gentle rocking. Collected the unbound hPCSK9 as the prey flow-through samples by 1,250×g centrifugation. After washing, hMatrilin-2-hPCSK9 (as the Bait-Prey sample) was eluted from the column with 250 ul elution buffer (5 minute incubation) by centrifuge at 1,250×g. All of the samples were placed on ice for same day Western bolts. The samples were Western blotted with goat anti-hMatrilin-2 pAb (R&D, Cat.#AF3044, see blot), or blotted with mixture of anti-hMatrilin-2 and sheep anti-hPCSK9 pAb (R&D, Cat#AF3888; see blot); or blotted with anti-hPCSK9 pAb alone (see blot). The blots were detected by ODYSSEY Infrared imaging system with anti-Goat IRDye 800CW second Ab (LI-COR, Cat.#926-32214).

Figure 1:
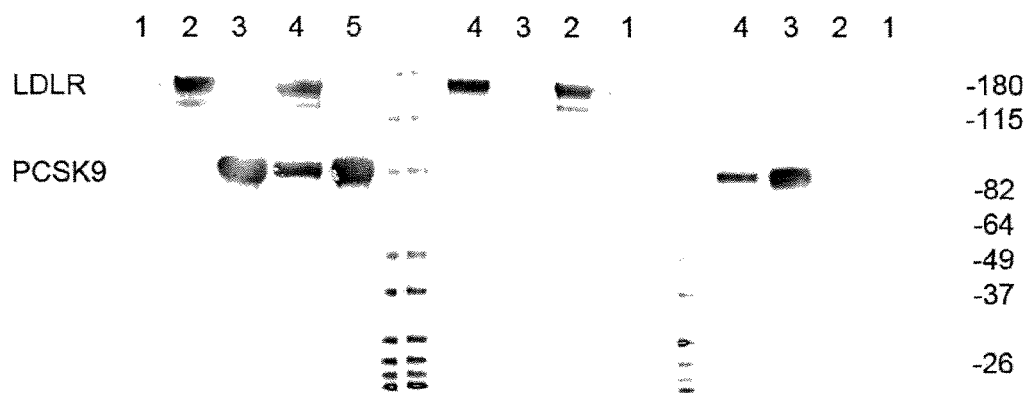
FIG. 1. Pull-Down PolyHis hLDLR-hPCSK9 interaction Western Blot Samples. Samples in each numbered lane are summarized below.

A summary of the results of these experiments is set forth below in Table 4 and in FIGS. 1 and 2.

TABLE 4

Immuno-precipitation Western Blot confirmation of His-tagged hLDLR, and hMatrilin-2 specific binding with hPCSK9

| Interaction tested | Specific binding with hPCSK9 |
|---|---|
| human LDLR/human PCSK9 | Yes |
| human Matrilin-2/human PCSK9 | Yes |

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. A method for reducing total cholesterol level, low density lipoprotein cholesterol level, apolipoprotein B level, total cholesterol/high density lipoprotein ratio or low density lipoprotein/high density lipoprotein ratio, comprising administering to a patient with a disorder of cholesterol or lipid homeostasis, a therapeutically effective amount of a composition comprising matrilin-2 polypeptide comprising the amino acid sequence selected from the group consisting of SEQ ID NO: 1, amino acids 24-956 of SEQ ID NO: 2 and SEQ ID NO: 2.

2. The method of claim 1, wherein the matrilin-2 polypeptide binds specifically to a Proprotein Convertase Subtilisin/kexin 9 (PCSK9) catalytic domain in SEQ ID NO: 46 or to a domain of PCSK9 which interacts with an LDL receptor EGF-A domain.

3. The method of claim 1, wherein the matrilin-2 polypeptide is administered with another chemotherapeutic agent.

4. The method of claim 3, wherein the chemotherapeutic agent is selected from the group consisting of ezetimibe and simvastatin.

5. The method of claim 1, wherein the polypeptide is fused to an immunoglobulin.

6. The method of claim 5, wherein the immunoglobulin is a γ1 or γ4 or monomeric variant thereof.

7. The method of claim 6 wherein the immunoglobulin comprises an amino acid sequence selected from the group consisting of SEQ ID NOs: 5-9.

8. The method of claim 1, wherein the matrilin-2 polypeptide comprises the amino acid sequence of SEQ ID NO: 1.

9. The method of claim 1, wherein the matrilin-2 polypeptide comprises amino acids 24-956 of SEQ ID NO: 2.

10. A method for treating hypercholesterolemia, comprising administering to a patient with the disorder of cholesterol or lipid homeostasis, a therapeutically effective amount of a composition comprising matrilin-2 polypeptide comprising the amino acid sequence selected from the group consisting of SEQ ID NO: 1, amino acids 24-956 of SEQ ID NO: 2 and SEQ ID NO: 2.

11. The method of claim 10, wherein the matrilin-2 polypeptide binds specifically to a Proprotein Convertase Subtilisin/kexin (PCSK9) catalytic domain in SEQ ID NO: 46 or to a domain of PCSK9 which interacts with an LDL receptor EGF-A domain.

12. The method of claim 10, wherein the matrilin-2 polypeptide is administered with another chemotherapeutic agent.

13. The method of claim 12, wherein the chemotherapeutic agent is selected from the group consisting of ezetimibe and simvastatin.

14. The method of claim 10, wherein the polypeptide is fused to an immunoglobulin.

15. The method of claim 14, wherein the immunoglobulin is a γ1 or γ4 or monomeric variant thereof.

16. The method of claim 15 wherein the immunoglobulin comprises an amino acid sequence selected from the group consisting of SEQ ID NOs: 5-9.

17. The method of claim 10, wherein the matrilin-2 polypeptide comprises the amino acid sequence of SEQ ID NO: 1.

18. The method of claim 10, wherein the matrilin-2 polypeptide comprises amino acids 24-956 of SEQ ID NO: 2.

* * * * *